US007968321B1

(12) United States Patent
Green et al.

(10) Patent No.: US 7,968,321 B1
(45) Date of Patent: Jun. 28, 2011

(54) ETHANOL PRODUCTION BY MICROORGANISMS

(75) Inventors: Brian Green, Cambridge, MA (US); Nikos Reppas, Cambridge, MA (US); Dan Robertson, Cambridge, MA (US)

(73) Assignee: Joule Unlimited, Inc., Cambridge, MA (US)

( * ) Notice: Subject to any disclaimer, the term of this patent is extended or adjusted under 35 U.S.C. 154(b) by 0 days.

(21) Appl. No.: 13/054,470

(22) PCT Filed: Sep. 3, 2009

(86) PCT No.: PCT/US2009/055949
§ 371 (c)(1), (2), (4) Date: Jan. 21, 2011

(87) PCT Pub. No.: WO2010/044960
PCT Pub. Date: Apr. 22, 2010

Related U.S. Application Data

(60) Provisional application No. 61/184,757, filed on Jun. 5, 2009, provisional application No. 61/121,532, filed on Dec. 10, 2008, provisional application No. 61/106,543, filed on Oct. 17, 2008.

(30) Foreign Application Priority Data

Mar. 3, 2009 (WO) ................ PCT/US2009/035937

(51) Int. Cl.
*C12P 7/06* (2006.01)
*C12P 1/00* (2006.01)
*C12N 1/00* (2006.01)

(52) U.S. Cl. .......................... 435/161; 435/41; 435/243

(58) Field of Classification Search ........................ None
See application file for complete search history.

(56) References Cited

U.S. PATENT DOCUMENTS

| | | | |
|---|---|---|---|
| 4,720,457 | A | 1/1988 | Armstrong et al. |
| 5,162,516 | A | 11/1992 | Ingram et al. |
| 5,304,475 | A | 4/1994 | Kim et al. |
| 6,306,639 | B1 | 10/2001 | Woods et al. |
| 6,429,006 | B1 | 8/2002 | Porro et al. |
| 6,632,631 | B1 | 10/2003 | Shuster et al. |
| 6,699,696 | B2 | 3/2004 | Woods et al. |
| 7,026,527 | B2 | 4/2006 | Falco et al. |
| 7,122,331 | B1 | 10/2006 | Eisenreich et al. |
| 2005/0014241 | A1 | 1/2005 | Chen |
| 2005/0124010 | A1 | 6/2005 | Short et al. |
| 2005/0239179 | A1 | 10/2005 | Skraly et al. |
| 2008/0176304 | A1 | 7/2008 | Lee |
| 2010/0003739 | A1 | 1/2010 | Duhring et al. |
| 2010/0330637 | A1 | 12/2010 | Lee |
| 2011/0008861 | A1 | 1/2011 | Berry et al. |

FOREIGN PATENT DOCUMENTS

| | | |
|---|---|---|
| WO | WO 2007/084477 | 1/2007 |
| WO | WO 2007/136762 | 11/2007 |
| WO | WO 2007/139925 | 12/2007 |
| WO | WO 2009/062190 | 5/2009 |
| WO | WO 2009/098089 | 8/2009 |
| WO | WO 2009/105714 | 8/2009 |
| WO | WO 2010/044960 | 4/2010 |

OTHER PUBLICATIONS

Cho, H. et al., "*Escherichia coli* Thioesterase I, Molecular Cloning and Sequencing of the Structural Gene and Identification as a Periplasmic Enzyme," *The Journal of Biological Chemistry*, May 5, 1993, pp. 9238-9245, vol. 268, No. 13.
Cohen, R. et al., "Functional expression of rat GLUT 1 glucose transporter in *Dictyostelium discoideum,*" *Biochem. J.*, 1996, pp. 971-975, vol. 315.
Deng, M. et al. "Ethanol Synthesis by Genetic Engineering in Cyanobacteria," *Applied and Environmental Microbiology*, Feb. 1999, pp. 523-528, vol. 65, No. 2.
Frigaard, N-U. et al., "Gene Inactivation in the Cyanobacterium *Synechococcus* sp. PCC 7002 and the Green Sulfur Bacterium *Chlorobium tepidum* Using in Vitro-made DNA Constructs and Natural Transformation," *Methods in Molecular Biology*, 2004, pp. 325-340, vol. 274.
Genin, S. et al., "*Ralstonia solanacearum*: Secrets of a Major Pathogen Unveiled by Analysis of Its Geneome," *Molecular Plant Pathology*, 2002, pp. 111-118, vol. 3, No. 3.
Ho, N. et al., "Genetically Engineered *Saccharomyces* Yeast Capable of Effective Cofermentation of Glucose and Xylose," *Applied and Environmental Microbiology*, May 1998, pp. 1852-1859, vol. 64, No. 5.
Inokuma, K. et al., "Characterization of Enzymes Involved in the Ethanol Production of *Moorella* sp. HUC22-1," Arch Microbiol, 2007, pp. 37-45, vol. 188.
Iwai, M. et al., "Improved Genetic Transformation of the Thermophilic Cyanobacterium, *Thermosynechococcus elongatus* BP-1," *Plant and Cell Physiology*, 2004, pp. 171-175, vol. 45, No. 2.
Kalnenieks, U. et al., "NADH Dehydrogenase Deficiency Results in Low Respiration Rate and Improved Aerobic Growth of *Zymomonas mobilis,*" *Microbiology*, 2008, pp. 989-994, vol. 154.
Kalnenieks, U. et al., "Respiratory Behaviour of a *Zymomonas mobilis adhB::kan'* Mutant Supports the Hypothesis of Two Alcohol Dehydrogenase Isoenzymes Catalysing Opposite Reactions," *FEBS Letters*, 2006, pp. 5084-5088, vol. 580. Kalscheuer, R. et al., "A Novel Bifunctional Wax Ester Synthase/Acyl-CoA:Diacyglycerol Acyltransferase Mediates Wax Ester and Triacylglycerol Biosynthesis in *Acinetobacter calcoaceticus* ADP1," *The Journal of Biological Chemistry*, 2003, pp. 8075-8082, vol. 278, No. 10.
Kalscheuer, R. et al., "Microdiesel: *Escherichia coli* Engineered for Fuel Production," *Microbiology*, 2006, pp. 2529-2536, vol. 152.
Kimura, A. et al., "A High Temperature-Sensitive Mutant of *Synechococcus* sp. PCC 7002 with Modifications in the Endogenous Plasmid, pAQ1," *Plant and Cell Physiology*, 2002, pp. 217-223, vol. 43, No. 2 (abstract only) [Online] [Retrieved Nov. 28, 2009] Retrieved from the internet <URL:http://pcp.oxfordjournals.org/cgi/content/abstract/43/2/217>.

(Continued)

*Primary Examiner* — Suzanne Noakes
*Assistant Examiner* — Jae W Lee
(74) *Attorney, Agent, or Firm* — Chang B. Hong; Fenwick & West LLP

(57) ABSTRACT

The present disclosure relates to methods and compositions for engineering photoautotrophic organisms to convert carbon dioxide and light into fatty acid esters and other molecules, including biofuels. The molecules are then secreted by the organism into a growth medium.

11 Claims, 38 Drawing Sheets

OTHER PUBLICATIONS

Lloyd, A. et al., "Topology of the *Escherichia coli uhpT* Sugar-Phosphate Transporter Analyzed by Using Tn*phoA* Fusions," *Journal of Bacteriology*, Apr. 1990, pp. 1688-1693, vol. 172, No. 4.

Marrakchi, H. et al., "Mechanistic Diversity and Regulation of Type II Fatty Acid Synthesis," *Biochemical Society Transactions*, 2002, pp. 1050-1055, vol. 30, Part 6.

Moon, J. H. et al., "Structures of Iron-Dependent Alcohol Dehydrogenase 2 from *Zymomonas mobilis* ZM4 with and without NAD+ Cofactor," *Journal of Molecular Biology*, 2011, pp. 413-424, vol. 407 (doi:10.1016/j.jmb.2011.01.045).

PCT International Search Report and Written Opinion, PCT Application No. PCT/US2009/035937, Aug. 3, 2009, 15 pages.

PCT International Search Report and Written Opinion, PCT Application No. PCT/US2009/055949, Mar. 15, 2010, seven pages.

Rock, C. et al., "Increased Unsaturated Fatty Acid Production Associated with a Suppressor of the *fabA6*(Ts) Mutation in *Escherichia coli*," *Journal of Bacteriology*, 1996, pp. 5382-5387, vol. 178, No. 18.

United States Office Action, U.S. Appl. No. 12/867,738, Jan. 27, 2011, ten pages.

United States Office Action, U.S. Appl. No. 12/867,738, Mar. 30, 2011, six pages.

U.S. Appl. No. 61/065,292, filed Feb. 8, 2008.

U.S. Appl. No. 12/851,712, filed Aug. 6, 2010.

U.S. Appl. No. 12/368,160, filed Feb. 9, 2009.

U.S. Appl. No. 12/368,060, filed Feb. 9, 2009.

Weisser, P. et al., "Functional Expression of the Glucose Transporter of *Zymomonas mobilis* Leads to Restoration of Glucose and Fructose Uptake in *Escherichia coli* Mutants and Provides Evidence for Its Facilitator Action," *Journal of Bacteriology*, Jun. 1995, pp. 3351-3354, vol. 177, No. 11.

Woodger, F. et al., "Inorganic Carbon Limitation Induces Transcripts Encoding Components of the $CO_2$-Concentrating Mechanism in *Synechococcus* sp. PCC7942 through a Redox-Independent Pathway," *Plant Physiology*, Dec. 2003, pp. 2069-2080, vol. 133, No. 4.

Exemplary Genes for Engineering $CO_2$-fixing, Carbon-based Product-Producing Microorganisms

| Product | *Gene* | Enzyme | *Example organism* | EC # | Reaction |
|---|---|---|---|---|---|
| ethanol | *pdc* | pyruvate decarboxylase | *Zymomonas mobilis* | 4.1.1.1 | pyruvate = acetaldehyde + CO2 |
| | *adhB* | alcohol dehydrogenase | *Zymomonas mobilis* | 1.1.1.1 | acetaldehyde + NADH = ethanol |
| butanol | *phaA* | beta-ketothiolase | *Ralstonia eutropha* | 2.3.1.16 | 2 acetyl-CoA = acetoacetyl-CoA + CoA |
| | *phaB* | acetoacetyl-CoA reductase | *Ralstonia eutropha* | 1.1.1.36 | acetoacetyl-CoA + NADPH = 3-hydroxybutyryl-CoA |
| | *maoC* | enoyl-CoA hydratase | *Escherichia coli* | 4.2.1.{17,55} | 3-hydroxybutyryl-CoA = crotonyl-CoA |
| | *bcd* | butyryl-CoA dehydrogenase | *Clostridium acetobutylicum* | 1.3.99.2 | crotonyl-CoA = butyryl-CoA + NAD(P)H |
| | *pct* | butyrate CoA-transferase | *Ralstonia eutropha* | 2.8.3.1 | butyryl-CoA + acetate = butyrate + acetyl-CoA |
| | *adhE* | aldehyde dehydrogenase | *Escherichia coli* | 1.2.1.{3,4} | butyrate + NADH = butanal |
| | *adhE* | alcohol dehydrogenase | *Escherichia coli* | 1.1.1.{1,2} | butanal + {NADH, NADPH} = 1-butanol |
| octane | *fabH* | acetyl-CoA:ACP transacylase | *Escherichia coli* | 2.3.1.38 | acetyl-CoA + ACP = acetyl-ACP + CoA |
| | *accBCAD* | acetyl-CoA carboxylase | *Escherichia coli* | 6.4.1.2 | acetyl-CoA + ATP + CO2 = malonyl-CoA |
| | *fabD* | malonyl-CoA:ACP transacylase | *Escherichia coli* | 2.3.1.39 | malonyl-CoA + ACP = malonyl-ACP + CoA |
| | *fabB* | 3-ketoacyl-ACP synthase | *Escherichia coli* | 2.3.1.41 | acyl-ACP + malonyl-ACP = CO2 + 3-ketoacyl-ACP |
| | *fabG* | 3-ketoacyl-ACP reductase | *Escherichia coli* | 1.1.1.100 | 3-ketoacyl-ACP + NADPH = 3-hydroxyacyl-ACP |
| | *fabA* | 3-hydroxyacyl-ACP dehydratase | *Escherichia coli* | 4.2.1.60 | 3-hydroxyacyl-ACP = enoyl-ACP |
| | *fabI* | enoyl-ACP reductase | *Escherichia coli* | 1.3.1.{9,10} | enoyl-ACP + {NADH, NADPH} = acyl-ACP |
| | *FAS1* | acyl-ACP hydrolase | *Saccharomyces cerevisiae* | 3.1.2.14 | acyl-ACP = fatty acid + ACP |

FIGURE 1-A

| Product | *Gene* | Enzyme | *Example organism* | EC # | Reaction |
|---|---|---|---|---|---|
| | *(several)* | aldehyde dehydrogenase | *Pseudomonas aeruginosa* | 1.2.1.{3,4} | octanoate + {NADH, NADPH} = octanal |
| | *ADH I* | alcohol dehydrogenase | *Zymomonas mobilis* | 1.1.1.{1,2} | octanal + {NADH, NADPH} = 1-octanol |
| | *alkB* | alkane 1-monooxygenase | *Pseudomonas fluorescens* | 1.14.15.3 | 1-octanol = n-octane + NAD(P)H + O2 |
| terephthalate | *aroF* | 2-dehydro-3-deoxyphosphoheptonate aldolase | *Escherichia coli* | 2.5.1.54 | PEP + D-erythrose-4-P = 3-deoxy-D-arabino-heptulosonate-7-P |
| | *aroB* | 3-dehydroquinate synthase | *Escherichia coli* | 4.2.3.4 | 3-deoxy-D-arabino-heptulosonate-7-P = 3-dehydroquinate |
| | *aroD* | 3-dehydroquinate dehydratase | *Escherichia coli* | 4.2.1.10 | 3-dehydroquinate = 3-dehydro-shikimate |
| | *quiC* | 3-dehydroshikimate dehydratase | *Acinetobacter sp. ADP1* | 4.2.1.n | 3-dehydro-shikimate = protocatechuate |
| | *pcaF* | β-ketoadipyl-CoA synthase | *Rhodococcus sp. RHA1* | 2.3.1.174 | acetyl-CoA + succinyl-CoA = β-ketoadipyl-CoA + CoA |
| | *pcaIJ* | β-ketoadipate CoA-transferase | *Pseudomonas putida* | 2.8.3.6 | β-ketoadipyl-CoA + succinate = β-ketoadipate + succinyl-CoA |
| | *pcaL* | 3-oxoadipate enol-lactone hydrolase | *Rhodococcus sp. RHA1* | 3.1.1.24 | β-ketoadipate = β-ketoadipate enol lactone |
| | *pcaL* | 4-carboxymuconolactone decarboxylase | *Rhodococcus sp. RHA1* | 4.1.1.44 | β-ketoadipate enol lactone + CO2 = γ-carboxy-muconolactone |
| | *pcaB* | γ-carboxy-cis,cis-muconate cycloisomerase | *Rhodococcus sp. RHA1* | 5.5.1.2 | γ-carboxy-muconolactone = β-carboxy-cis,cis-muconate |
| | *pcaGH* | protocatechuate 3,4-dioxygenase | *Rhodococcus sp. RHA1* | 1.13.11.3 | β-carboxy-cis,cis-muconate = protocatechuate |
| | *tpaC* | protocatechuate 1,2-cis-dihydrodiol dehydrogenase | *Rhodococcus sp. RHA1* | 1.3.1.n | protocatechuate + CO2 + NADPH = DDT |

FIGURE 1-B

| Product | *Gene* | Enzyme | *Example organism* | EC # | Reaction |
|---|---|---|---|---|---|
| | *tpaAB* | terephthalate 1,2-dioxygenase | *Rhodococcus sp. RHA1* | 1.14.12.15 | DDT = terephthalate + NADH + O2 |
| 1,3-propanediol | *DAR1* | sn-glycerol-3-P dehydrogenase | *Saccharomyces cerevisiae* | 1.1.1.{8,94} | dihydroxyacetone-P + {NADH, NADPH} = sn-glycerol-3-P |
| | *GPP2* | sn-glycerol-3-phosphatase | *Saccharomyces cerevisiae* | 3.1.3.21 | sn-glycerol-3-P = glycerol |
| | *dhaB1-3* | glycerol dehydratase | *Klebsiella pneumoniae* | 4.2.1.30 | glycerol = 3-hydroxypropanal |
| | *dhaT* | 1,3-propanediol oxidoreductase | *Klebsiella pneumoniae* | 1.1.1.202 | 3-hydroxypropanal + NADH = 1,3-propanediol |
| 1,4-butanediol | *sucD* | succinyl-CoA dehydrogenase | *Clostridium kluyveri* | 1.2.1.n | succinyl-CoA + NADPH = succinic semialdehyde + CoA |
| | *GHBDH* | 4-hydroxybutyrate dehydrogenase | *Arabidopsis thaliana* | 1.1.1.2 | succinic semialdehyde + NADPH = 4-hydroxybutyrate |
| | *gdhA* | glutamate dehydrogenase | *Escherichia coli* | 1.4.1.4 | α-ketoglutarate + NH3 + NADPH = glutamate |
| | *gadA* | glutamate decarboxylase | *Escherichia coli* | 4.1.1.15 | glutamate = 4-aminobutyrate + CO2 |
| | *gabT* | 4-aminobutyrate transaminase | *Escherichia coli* | 2.6.1.19 | 4-aminobutyrate + α-ketoglutarate = glutamate + succinic semialdehyde |
| | *aldH* | aldehyde dehydrogenase | *Escherichia coli* | 1.1.1.n | 4-hydroxybutyrate + NADH = 4-hydroxybutanal |
| | *dhaT* | 1,3-propanediol oxidoreductase | *Klebsiella pneumoniae* | 1.1.1.202 | 4-hydroxybutanal + NADH = 1,4-butanediol |
| PHB | *phaA* | beta-ketothiolase | *Ralstonia eutropha* | 2.3.1.16 | 2 acetyl-CoA = acetoacetyl-CoA + CoA |
| | *phaB* | acetoacetyl-CoA reductase | *Ralstonia eutropha* | 1.1.1.36 | acetoacetyl-CoA + NADPH = 3-hydroxybutyryl-CoA |
| | *phaC* | PHA synthase | *Ralstonia eutropha* | none | 3-hydroxybutyryl-CoA = PHB + CoA |
| acrylate | *paaF* | enoyl-CoA hydratase | *Escherichia coli* | 4.2.1.17 | 3-hydroxypropionyl-CoA = acryloyl-CoA |
| | *pct* | acrylate CoA-transferase | *Ralstonia eutropha* | 2.8.3.n | acryloyl-CoA + acetate = acrylate + acetyl-CoA |

FIGURE 1-C

| Product | *Gene* | Enzyme | *Example organism* | EC # | Reaction |
|---|---|---|---|---|---|
| ε-caprolactone | *fabH* | acetyl-CoA:ACP transacylase | *Escherichia coli* | 2.3.1.38 | acetyl-CoA + ACP = acetyl-ACP + CoA |
| | *accBCAD* | acetyl-CoA carboxylase | *Escherichia coli* | 6.4.1.2 | acetyl-CoA + ATP + CO2 = malonyl-CoA |
| | *fabD* | malonyl-CoA:ACP transacylase | *Escherichia coli* | 2.3.1.39 | malonyl-CoA + ACP = malonyl-ACP + CoA |
| | *fabB* | 3-ketoacyl-ACP synthase | *Escherichia coli* | 2.3.1.41 | acyl-ACP + malonyl-ACP = CO2 + 3-ketoacyl-ACP |
| | *fabG* | 3-ketoacyl-ACP reductase | *Escherichia coli* | 1.1.1.100 | 3-ketoacyl-ACP + NADPH = 3-hydroxyacyl-ACP |
| | *fabA* | 3-hydroxyacyl-ACP dehydratase | *Escherichia coli* | 4.2.1.60 | 3-hydroxyacyl-ACP = enoyl-ACP |
| | *fabI* | enoyl-ACP reductase | *Escherichia coli* | 1.3.1.{9,10} | enoyl-ACP + {NADH, NADPH} = acyl-ACP |
| | *FAS1* | acyl-ACP hydrolase | *Saccharomyces cerevisiae* | 3.1.2.14 | acyl-ACP = fatty acid + ACP |
| | *alkB* | fatty-acid monooxygenase | *Pseudomonas oleovorans* | 1.14.15.3 | fatty acid + NADPH + O2 = ω-hydroxyalkanoate |
| | | 1,6-lactonase | | 3.1.1.n | 6-hydroxyhexanoate = ε-caprolactone |
| isoprene | *dxs* | 1-deoxy-D-xylulose-5-phosphate synthase | *Escherichia coli* | 2.2.1.7 | pyruvate + D-glyceraldehyde-3-P = 1-deoxy-D-xylulose-5-P + CO2 |
| | *dxr* | 1-deoxy-D-xylulose-5-phosphate reductoisomerase | *Escherichia coli* | 1.1.1.267 | 1-deoxy-D-xylulose-5-P + NADPH = 2-C-methyl-D-erythritol-4-P |
| | *ispD* | 2-C-methyl-D-erythritol 4-phosphate cytidylyltransferase | *Escherichia coli* | 2.7.7.60 | CTP + 2-C-methyl-D-erythritol 4-P = 4-(cytidine-5'-PP)-2-C-methyl-D-erythritol |
| | *ispE* | 4-(cytidine 5'-diphospho)-2-C-methyl-D-erythritol kinase | *Escherichia coli* | 2.7.1.148 | ATP + 4-(cytidine-5'-PP)-2-C-methyl-D-erythritol = 2-P-4-(cytidine 5'-PP)-2-C-methyl-D-erythritol |
| | *ispF* | 2-C-methyl-D-erythritol 2,4-cyclodiphosphate synthase | *Escherichia coli* | 4.6.1.12 | 2-P-4-(cytidine 5'-PP)-2-C-methyl-D-erythritol = 2-C-methyl-D-erythritol-2,4-cyclo-PP + CMP |

FIGURE 1-D

| Product | Gene | Enzyme | Example organism | EC # | Reaction |
|---|---|---|---|---|---|
| | ispG | 4-hydroxy-3-methylbut-2-en-1-yl diphosphate synthase | Escherichia coli | 1.17.4.3 | 2-C-methyl-D-erythritol-2,4-cyclo-PP = (E)-4-hydroxy-3-methylbut-2-en-1-yl-PP |
| | ispH | 4-hydroxy-3-methylbut-2-enyl diphosphate reductase | Escherichia coli | 1.17.1.2 | (E)-4-hydroxy-3-methylbut-2-en-1-yl-PP + NADPH = isopentenyl-PP + NADP |
| | ispH | 4-hydroxy-3-methylbut-2-enyl diphosphate reductase | Escherichia coli | 1.17.1.2 | (E)-4-hydroxy-3-methylbut-2-en-1-yl-PP + NADPH = dimethylallyl-PP + NADP |
| | idi | isopentenyl-diphosphate Δ-isomerase | Escherichia coli | 5.3.3.2 | dimethylallyl-PP = isopentenyl-PP |
| rubber | (nc) | rubber cis-polyprenylcistransferase | Hevea brasiliensis | 2.5.1.20 | isopentenyl-PP = rubber |
| lactate | ldhA | lactate dehydrogenase | Escherichia coli | 1.1.1.28 | D-lactate = NADH + pyruvate |
| DHA | dhaK | DHA kinase | Citrobacter freundii | 2.7.1.29 | dihydroxyacetone-P = dihydroxyacetone + ATP |
| 3-hydroxypropionate | accBCAD | acetyl-CoA carboxylase | Escherichia coli | 6.4.1.2 | acetyl-CoA + ATP + CO2 = malonyl-CoA |
| | (nc) | bifunctional malonyl-CoA reductase | Chloroflexus aurantiacus | 1.2.1.18, 1.1.1.59 | malonyl-CoA + 2 NADPH = 3-hydroxypropionate + CoA |
| γ-valerolactone | (nc) | 2-oxobutyrate synthase | Clostridium pasteurianum | 1.2.7.2 | propionyl-CoA + CO2 + 2 Fdred = 2-oxobutanoate + CoA + 2 FDox |
| | (nc) | 2-ethylmalate synthase | Saccharomyces cerevisiae | 2.3.3.6 | 2-oxobutanoate + acetyl-CoA = (R)-2-ethylmalate + CoA |
| | | aconitase analog | | | (R)-2-ethylmalate = 3-carboxy-4-hydroxypentanoate |
| | | isocitrate dehydrogenase analog | | | 3-carboxy-4-hydroxypentanoate = levulinate |
| | ler | acetoacetyl-CoA reductase analog | Ralstonia eutropha | | levulinate + NAD(P)H = 4-hydroxypentanoate |

FIGURE 1-E

| Product | *Gene* | Enzyme | *Example organism* | EC # | Reaction |
|---|---|---|---|---|---|
| | *(nc)* | 1,4-lactonase | *Rattus norvegicus* | 3.1.1.25 | 4-hydroxypentanoate = γ-valerolactone |
| | *accBCAD* | acetyl-CoA carboxylase | *Escherichia coli* | 6.4.1.2 | acetyl-CoA + ATP + CO2 = malonyl-CoA |
| | *(nc)* | bifunctional malonyl-CoA reductase | *Chloroflexus aurantiacus* | 1.2.1.18, 1.1.1.59 | malonyl-CoA + 2 NADPH = 3-hydroxypropionate + CoA |
| | *paaF* | enoyl-CoA hydratase | *Escherichia coli* | 4.2.1.17 | 3-hydroxypropionyl-CoA = acryloyl-CoA |
| | *At3G06810* | acyl-CoA dehydrogenase | *Arabidopsis thaliana* | 1.3.99.3 | acryloyl-CoA + FADH2 = propionyl-CoA |
| | *bktB* | beta-ketothiolase | *Ralstonia eutropha* | 2.3.1.16 | propionyl-CoA + acetyl-CoA = 3-ketovaleryl-CoA + CoA |
| | *phaB* | acetoacetyl-CoA reductase | *Ralstonia eutropha* | 1.1.1.36 | 3-ketovaleryl-CoA + NADPH = (R)-3-hydroxyvaleryl-CoA |
| | *crt* | 3-hydroxybutyryl-CoA dehydratase | *Xanthomonas axonopodis* | 4.2.1.55 | (R)-3-hydroxyvaleryl-CoA = 3-pentenoyl-CoA |
| | *abfD* | vinylacetyl-CoA Δ-isomerase | *Clostridium difficile* | 5.3.3.3 | 3-pentenoyl-CoA = 4-hydroxypentanoyl-CoA |
| | *orfZ* | 4-hydroxybutyryl-CoA transferase | *Clostridium kluyveri* | 2.8.3.n | 4-hydroxypentanoyl-CoA + acetate = acetyl-CoA + 4-hydroxypentanoate |
| | *(nc)* | 1,4-lactonase | *Rattus norvegicus* | 3.1.1.25 | 4-hydroxypentanoate = γ-valerolactone |
| lysine | *aspC* | aspartate aminotransferase | *Escherichia coli* | 2.6.1.1 | oxaloacetate + L-glutamate = L-aspartate + α-ketoglutarate |
| | *lysC* | aspartate kinase | *Escherichia coli* | 2.3.3.14 | L-aspartate + ATP = L-aspartyl-4-P |
| | *asd* | aspartate semialdehyde dehydrogenase | *Escherichia coli* | 1.2.1.11 | L-aspartate-semialdehyde = NADPH + L-aspartyl-4-phosphate |
| | *dapA* | dihydrodipicolinate synthase | *Escherichia coli* | 4.2.1.52 | pyruvate + L-aspartate-semialdehyde = L-2,3-dihydrodipicolinate |
| | *dapB* | dihydrodipicolinate reductase | *Escherichia coli* | 1.3.1.26 | L-2,3-dihydrodipicolinate + NADPH = tetrahydrodipicolinate |
| | *dapD* | tetrahydrodipicolinate succinylase | *Escherichia coli* | 2.3.1.117 | tetrahydrodipicolinate + succinyl-CoA = N-succinyl-2-amino-6-ketopimelate + CoA |

FIGURE 1-F

| Product | *Gene* | Enzyme | *Example organism* | EC # | Reaction |
|---|---|---|---|---|---|
| | *argD* | N-succinyldiaminopimelate-aminotransferase | *Escherichia coli* | 2.6.1.17 | L-glutamate + N-succinyl-2-amino-6-ketopimelate = α-ketoglutarate + N-succinyl-L,L-2,6-diaminopimelate |
| | *dapE* | N-succinyl-L-diaminopimelate desuccinylase | *Escherichia coli* | 3.5.1.18 | N-succinyl-L,L-2,6-diaminopimelate = L,L-diaminopimelate + succinate |
| | *dapF* | diaminopimelate epimerase | *Escherichia coli* | 5.1.1.7 | L,L-diaminopimelate = meso-diaminopimelate |
| | *lysA* | diaminopimelate decarboxylase | *Escherichia coli* | 4.1.1.20 | meso-diaminopimelate = L-lysine + CO2 |
| | *At4g33680* | LL-diaminopimelate aminotransferase | *Arabidopsis thaliana* | 2.6.1.83 | tetrahydrodipicolinate + α-ketoglutarate = L,L-diaminopimelate + L-glutamate (replaces 2.3.1.117-2.6.1.17-3.5.1.18) |
| | *LYS21* | homocitrate synthase | *Saccharomyces cerevisiae* | 2.3.3.14 | acetyl-CoA + α-ketoglutarate = homocitrate + CoA |
| | *LYS4, LYS3* | homoaconitase | *Saccharomyces cerevisiae* | 4.2.1.36 | homocitrate = homo-cis-aconitate = homoisocitrate |
| | *LYS12, LYS11, LYS10* | homoisocitrate dehydrogenase | *Saccharomyces cerevisiae* | 1.1.1.87 | homoisocitrate = 2-oxoadipate + CO2 + NADH |
| | *ARO8* | 2-aminoadipate transaminase | *Saccharomyces cerevisiae* | 2.6.1.39 | 2-oxoadipate + L-glutamate = L-2-aminoadipate + α-ketoglutarate |
| | *LYS2, LYS5* | 2-aminoadipate reductase | *Saccharomyces cerevisiae* | 1.2.1.31 | L-2-aminoadipate + NAD(P)H = L-2-aminoadipate 6-semialdehyde |
| | *LYS9, LYS13* | aminoadipate semialdehyde-glutamate reductase | *Saccharomyces cerevisiae* | 1.5.1.10 | L-glutamate + L-2-aminoadipate 6-semialdehyde + NADPH = N6-(L-1,3-Dicarboxypropyl)-L-lysine + NADP |
| | *LYS1* | lysine-2-oxoglutarate reductase | *Saccharomyces cerevisiae* | 1.5.1.7 | N6-(L-1,3-dicarboxypropyl)-L-lysine = L-lysine + α-ketoglutarate + NADH |

FIGURE 1-G

| Product | Gene | Enzyme | Example organism | EC # | Reaction |
|---|---|---|---|---|---|
| serine | *serA* | phosphoglycerate dehydrogenase | *Escherichia coli* | 1.1.1.95 | 3-P-D-glycerate = 3-phosphonooxypyruvate + NADH |
| | *serC* | phosphoserine transaminase | *Escherichia coli* | 2.6.1.52 | ortho-P-L-serine + α-ketoglutarate = 3-phosphonooxypyruvate + L-glutamate |
| | *serB* | phosphoserine phosphatase | *Escherichia coli* | 3.1.3.3 | ortho-P-L-serine = L-serine |
| aspartate | *aspC* | aspartate aminotransferase | *Escherichia coli* | 2.6.1.1 | oxaloacetate + L-glutamate = L-aspartate + α-ketoglutarate |
| sorbitol | *galM* | aldose-1-epimerase | *Escherichia coli* | 5.1.3.3 | D-β-glucose = D-α-glucose |
| | *GRE3* | polyol dehydrogenase | *Saccharomyces cerevisiae* | 1.1.1.21 | D-α-glucose + NADPH = D-sorbitol |
| ascorbate | *PGI1* | alpha-D-glucose-6-phosphate ketol-isomerase | *Arabidopsis thaliana* | 5.3.1.9 | D-α-glucose-6-P = β-D-fructose-6-P |
| | *DIN9* | D-Mannose-6-phosphate ketol-isomerase | *Arabidopsis thaliana* | 5.3.1.8 | β-D-fructose-6-P = D-mannose-6-P |
| | *ATPMM* | D-Mannose 6-phosphate 1,6-phosphomutase | *Arabidopsis thaliana* | 5.4.2.8 | D-mannose-6-P = D-mannose-1-P |
| | *CYT1* | mannose-1-phosphate guanylyltransferase | *Arabidopsis thaliana* | 2.7.7.22 | D-mannose-1-P = GDP-mannose |
| | *GME* | GDP-mannose 3,5-epimerase | *Arabidopsis thaliana* | 5.1.3.18 | GDP-mannose = GDP-L-galactose |
| | *VTC2* | galactose-1-phosphate guanylyltransferase | *Arabidopsis thaliana* | 2.7.n.n | GDP-L-galactose = L-galactose-1-P |
| | *VTC4* | L-galactose 1-phosphate phosphatase | *Arabidopsis thaliana* | 3.1.3.n | L-galactose-1-P = L-galactose |
| | *At4G33670* | L-galactose dehydrogenase | *Arabidopsis thaliana* | 1.1.1.122 | L-galactose = L-1,4-galactonolactone + NADH |
| | *ATGLDH* | L-galactonolactone oxidase | *Saccharomyces cerevisiae* | 1.3.3.12 | L-1,4-galactonolactone + O2 = ascorbate + H2O2 |
| | *katE* | catalase | *Escherichia coli* | 1.11.1.6 | 2 H2O2 = O2 |

FIGURE 1-H

| Product | Gene | Enzyme | Example organism | EC # | Reaction |
|---|---|---|---|---|---|
| cephalosporin | *LYS21* | homocitrate synthase | *Saccharomyces cerevisiae* | 2.3.3.14 | acetyl-CoA + α-ketoglutarate = homocitrate + CoA |
| | *LYS4, LYS3* | homoaconitase | *Saccharomyces cerevisiae* | 4.2.1.36 | homocitrate = homo-cis-aconitate = homoisocitrate |
| | *LYS12, LYS11, LYS10* | homoisocitrate dehydrogenase | *Saccharomyces cerevisiae* | 1.1.1.87 | homoisocitrate = 2-oxoadipate + CO2 + NADH |
| | *ARO8* | 2-aminoadipate transaminase | *Saccharomyces cerevisiae* | 2.6.1.39 | 2-oxoadipate + L-glutamate = L-2-aminoadipate + α-ketoglutarate |
| | *serA* | phosphoglycerate dehydrogenase | *Escherichia coli* | 1.1.1.95 | 3-P-D-glycerate = 3-phosphonooxypyruvate + NADH |
| | *serC* | phosphoserine transaminase | *Escherichia coli* | 2.6.1.52 | ortho-P-L-serine + α-ketoglutarate = 3-phosphonooxypyruvate + L-glutamate |
| | *serB* | phosphoserine phosphatase | *Escherichia coli* | 3.1.3.3 | ortho-P-L-serine = L-serine |
| | *AtSerat2;1* | serine O-acetyltransferase | *Arabidopsis thaliana* | 2.3.1.30 | acetyl-CoA + L-serine = CoA + O-acetyl-L-serine |
| | *At1G55880* | cysteine synthase | *Arabidopsis thaliana* | 2.5.1.47 | O-acetyl-L-serine = L-cysteine + acetate |
| | *ilvN, ilvB* | acetolactate synthase | *Escherichia coli* | 2.2.1.6 | pyruvate = CO2 + 2-acetolactate |
| | *ilvC* | acetohydroxyacid isomeroreductase | *Escherichia coli* | 1.1.1.86 | 2-acetolactate + NADPH = 2,3-dihydroxyisovalerate |
| | *ilvD* | dihydroxyacid dehydratase | *Escherichia coli* | 4.2.1.9 | 2,3-dihydroxyisovalerate = 2-ketoisovalerate |
| | *ilvE* | valine transaminase | *Escherichia coli* | 2.6.1.42 | 2-ketoisovalerate + L-glutamate = α-ketoglutarate + L-valine |
| | *Ava_1613* | ACV synthetase | *Anabaena variabilis* | 6.3.2.26 | 3 ATP + L-2-aminoadipate + L-cysteine + L-valine = N-[L-5-amino-5-carboxypentanoyl]-L-cysteinyl-D-valine |

FIGURE 1-I

| Product | *Gene* | Enzyme | *Example organism* | EC # | Reaction |
|---|---|---|---|---|---|
| | *Ava_5009* | isopenicillin-N synthase | *Anabaena variabilis* | 1.21.3.1 | N-[L-5-amino-5-carboxypentanoyl]-L-cysteinyl-D-valine + O2 = isopenicillin-N |
| | *cefD* | isopenicillin-N epimerase | *Myxococcus xanthus* | 5.1.1.17 | isopenicillin-N = penicillin-N |
| | *cefEF* | cephalosporin biosynthesis expandase/hydroxylase | *Cephalosporium acremonium* | 1.14.20.1, 1.14.11.26 | penicillin-N + 2 α-ketoglutarate + 2 O2 = deacetylcephalosporin C + 2 succinate + 2 CO2 |
| | *cefG* | deacetylcephalosporin-C acetyltransferase | *Cephalosporium acremonium* | 2.3.1.175 | acetyl-CoA + deacetylcephalosporin C = CoA + cephalosporin C |
| isopentenol | *dxs* | 1-deoxy-D-xylulose-5-phosphate synthase | *Escherichia coli* | 2.2.1.7 | pyruvate + D-glyceraldehyde-3-P = 1-deoxy-D-xylulose-5-P + CO2 |
| | *dxr* | 1-deoxy-D-xylulose-5-phosphate reductoisomerase | *Escherichia coli* | 1.1.1.267 | 1-deoxy-D-xylulose-5-P + NADPH = 2-C-methyl-D-erythritol-4-P |
| | *ispD* | 2-C-methyl-D-erythritol 4-phosphate cytidylyltransferase | *Escherichia coli* | 2.7.7.60 | CTP + 2-C-methyl-D-erythritol 4-P = 4-(cytidine-5'-PP)-2-C-methyl-D-erythritol |
| | *ispE* | 4-(cytidine 5'-diphospho)-2-C-methyl-D-erythritol kinase | *Escherichia coli* | 2.7.1.148 | ATP + 4-(cytidine-5'-PP)-2-C-methyl-D-erythritol = 2-P-4-(cytidine 5'-PP)-2-C-methyl-D-erythritol |
| | *ispF* | 2-C-methyl-D-erythritol 2,4-cyclodiphosphate synthase | *Escherichia coli* | 4.6.1.12 | 2-P-4-(cytidine 5'-PP)-2-C-methyl-D-erythritol = 2-C-methyl-D-erythritol-2,4-cyclo-PP + CMP |
| | *ispG* | 4-hydroxy-3-methylbut-2-en-1-yl diphosphate synthase | *Escherichia coli* | 1.17.4.3 | 2-C-methyl-D-erythritol-2,4-cyclo-PP = (E)-4-hydroxy-3-methylbut-2-en-1-yl-PP |
| | *ispH* | 4-hydroxy-3-methylbut-2-enyl diphosphate reductase | *Escherichia coli* | 1.17.1.2 | (E)-4-hydroxy-3-methylbut-2-en-1-yl-PP + NADPH = isopentenyl-PP |
| | *ispH* | 4-hydroxy-3-methylbut-2-enyl diphosphate reductase | *Escherichia coli* | 1.17.1.2 | (E)-4-hydroxy-3-methylbut-2-en-1-yl-PP + NADPH = dimethylallyl-PP |

FIGURE 1-J

| Product | Gene | Enzyme | Example organism | EC # | Reaction |
|---|---|---|---|---|---|
| | *idi* | Isopentenyl-diphosphate Δ-isomerase | *Escherichia coli* | 5.3.3.2 | dimethylallyl-PP = isopentenyl-PP |
| | | isopentenyl-PP pyrophosphatase | | | isopentenyl-PP = isopentenol |
| | | isopentenol dikinase | | | isopentenyl-PP = isopentenol + ATP |
| | *ERG13* | hydroxymethylglutaryl-CoA synthase | *Saccharomyces cerevisiae* | 2.3.3.10 | acetyl-CoA + acetoacetyl-CoA = (S)-3-hydroxy-3-methylglutaryl-CoA + CoA |
| | *HMG2* | hydroxymethylglutaryl-CoA reductase | *Saccharomyces cerevisiae* | 1.1.1.34 | (R)-mevalonate + CoA = (S)-3-hydroxy-3-methylglutaryl-CoA + 2 NADPH |
| | *ERG12* | mevalonate kinase | *Saccharomyces cerevisiae* | 2.7.1.36 | ATP + (R)-mevalonate = (R)-5-P-mevalonate |
| | *ERG8* | phosphomevalonate kinase | *Saccharomyces cerevisiae* | 2.7.4.2 | ATP + (R)-5-P-mevalonate = (R)-5-PP-mevalonate |
| | *MVD1* | diphosphomevalonate decarboxylase | *Saccharomyces cerevisiae* | 4.1.1.33 | ATP + (R)-5-PP-mevalonate = isopentenyl-PP + CO2 |
| lanosterol | *dxs* | 1-deoxy-D-xylulose-5-phosphate synthase | *Escherichia coli* | 2.2.1.7 | pyruvate + D-glyceraldehyde-3-P = 1-deoxy-D-xylulose-5-P + CO2 |
| | *dxr* | 1-deoxy-D-xylulose-5-phosphate reductoisomerase | *Escherichia coli* | 1.1.1.267 | 1-deoxy-D-xylulose-5-P + NADPH = 2-C-methyl-D-erythritol-4-P |
| | *ispD* | 2-C-methyl-D-erythritol 4-phosphate cytidylyltransferase | *Escherichia coli* | 2.7.7.60 | CTP + 2-C-methyl-D-erythritol 4-P = 4-(cytidine-5'-PP)-2-C-methyl-D-erythritol |
| | *ispE* | 4-(cytidine 5'-diphospho)-2-C-methyl-D-erythritol kinase | *Escherichia coli* | 2.7.1.148 | ATP + 4-(cytidine-5'-PP)-2-C-methyl-D-erythritol = 2-P-4-(cytidine 5'-PP)-2-C-methyl-D-erythritol |
| | *ispF* | 2-C-methyl-D-erythritol 2,4-cyclodiphosphate synthase | *Escherichia coli* | 4.6.1.12 | 2-P-4-(cytidine 5'-PP)-2-C-methyl-D-erythritol = 2-C-methyl-D-erythritol-2,4-cyclo-PP + CMP |

FIGURE 1-K

| Product | *Gene* | Enzyme | *Example organism* | EC # | Reaction |
|---|---|---|---|---|---|
| | *ispG* | 4-hydroxy-3-methylbut-2-en-1-yl diphosphate synthase | *Escherichia coli* | 1.17.4.3 | 2-C-methyl-D-erythritol-2,4-cyclo-PP = (E)-4-hydroxy-3-methylbut-2-en-1-yl-PP |
| | *ispH* | 4-hydroxy-3-methylbut-2-enyl diphosphate reductase | *Escherichia coli* | 1.17.1.2 | (E)-4-hydroxy-3-methylbut-2-en-1-yl-PP + NADPH = isopentenyl-PP |
| | *ispH* | 4-hydroxy-3-methylbut-2-enyl diphosphate reductase | *Escherichia coli* | 1.17.1.2 | (E)-4-hydroxy-3-methylbut-2-en-1-yl-PP + NADPH = dimethylallyl-PP |
| | *idi* | isopentenyl-diphosphate Δ-isomerase | *Escherichia coli* | 5.3.3.2 | dimethylallyl-PP = isopentenyl-PP |
| | *crtE* | geranylgeranyl pyrophosphate synthase | *Synechocystis sp. PCC6803* | 2.5.1.29 | dimethylallyl-PP + 2 isopentenyl-PP = farnesyl-PP |
| | *s110513* | squalene synthase | *Synechocystis sp. PCC6803* | 2.5.1.21 | 2 farnesyl-PP + NADPH = squalene |
| | *ERG1* | squalene monooxygenase | *Saccharomyces cerevisiae* | 1.14.99.7 | squalene + NADPH + O2 = (S)-squalene-2,3-epoxide |
| | *ERG7* | lanosterol synthase | *Saccharomyces cerevisiae* | 5.4.99.7 | (S)-squalene-2,3-epoxide = lanosterol |
| omega-3 DHA | * | acetyl-CoA:ACP transacylase | *Shewanella pneumatophori* | 2.3.1.38 | acetyl-CoA + ACP = acetyl-ACP + CoA |
| * necessary genes are *pfaABCDE*, some of which are multifunctional | * | acetyl-CoA carboxylase | *Escherichia coli* | 6.4.1.2 | acetyl-CoA + ATP + CO2 = malonyl-CoA |
| | * | malonyl-CoA:ACP transacylase | *Escherichia coli* | 2.3.1.39 | malonyl-CoA + ACP = malonyl-ACP + CoA |
| | * | 3-ketoacyl-ACP synthase | *Escherichia coli* | 2.3.1.41 | acyl-ACP + malonyl-ACP = CO2 + 3-ketoacyl-ACP |
| | * | 3-ketoacyl-ACP reductase | *Escherichia coli* | 1.1.1.100 | 3-ketoacyl-ACP + NADPH = 3-hydroxyacyl-ACP |
| | * | 3-hydroxyacyl-ACP dehydratase | *Escherichia coli* | 4.2.1.60 | 3-hydroxyacyl-ACP = enoyl-ACP |
| | * | enoyl-ACP reductase | *Escherichia coli* | 1.3.1.{9,10} | enoyl-ACP + {NADH, NADPH} = acyl-ACP |

FIGURE 1-L

| Product | *Gene* | Enzyme | *Example organism* | EC # | Reaction |
|---|---|---|---|---|---|
| | * | desaturase | *Shewanella pneumatophori* | 1.14.19.n | m:n fatty acid + NADPH + O2 = m:(n+1) fatty acid |
| | *FAS1* | acyl-ACP hydrolase | *Saccharomyces cerevisiae* | 3.1.2.14 | acyl-ACP = fatty acid + ACP |
| lycopene | *dxs* | 1-deoxy-D-xylulose-5-phosphate synthase | *Escherichia coli* | 2.2.1.7 | pyruvate + D-glyceraldehyde-3-P = 1-deoxy-D-xylulose-5-P + CO2 |
| | *dxr* | 1-deoxy-D-xylulose-5-phosphate reductoisomerase | *Escherichia coli* | 1.1.1.267 | 1-deoxy-D-xylulose-5-P + NADPH = 2-C-methyl-D-erythritol-4-P |
| | *ispD* | 2-C-methyl-D-erythritol 4-phosphate cytidylyltransferase | *Escherichia coli* | 2.7.7.60 | CTP + 2-C-methyl-D-erythritol 4-P = 4-(cytidine-5'-PP)-2-C-methyl-D-erythritol |
| | *ispE* | 4-(cytidine 5'-diphospho)-2-C-methyl-D-erythritol kinase | *Escherichia coli* | 2.7.1.148 | ATP + 4-(cytidine-5'-PP)-2-C-methyl-D-erythritol = 2-P-4-(cytidine 5'-PP)-2-C-methyl-D-erythritol |
| | *ispF* | 2-C-methyl-D-erythritol 2,4-cyclodiphosphate synthase | *Escherichia coli* | 4.6.1.12 | 2-P-4-(cytidine 5'-PP)-2-C-methyl-D-erythritol = 2-C-methyl-D-erythritol-2,4-cyclo-PP + CMP |
| | *ispG* | 4-hydroxy-3-methylbut-2-en-1-yl diphosphate synthase | *Escherichia coli* | 1.17.4.3 | 2-C-methyl-D-erythritol-2,4-cyclo-PP = (E)-4-hydroxy-3-methylbut-2-en-1-yl-PP |
| | *ispH* | 4-hydroxy-3-methylbut-2-enyl diphosphate reductase | *Escherichia coli* | 1.17.1.2 | (E)-4-hydroxy-3-methylbut-2-en-1-yl-PP + NADPH = isopentenyl-PP |
| | *ispH* | 4-hydroxy-3-methylbut-2-enyl diphosphate reductase | *Escherichia coli* | 1.17.1.2 | (E)-4-hydroxy-3-methylbut-2-en-1-yl-PP + NADPH = dimethylallyl-PP |
| | *idi* | isopentenyl-diphosphate Δ-isomerase | *Escherichia coli* | 5.3.3.2 | dimethylallyl-PP = isopentenyl-PP |
| | *crtE* | geranylgeranyl pyrophosphate synthase | *Synechocystis sp. PCC6803* | 2.5.1.29 | dimethylallyl-PP + 2 isopentenyl-PP = farnesyl-PP |

FIGURE 1-M

| **Product** | ***Gene*** | **Enzyme** | ***Example organism*** | **EC #** | **Reaction** |
|---|---|---|---|---|---|
| | *crtE* | geranylgeranyl pyrophosphate synthase | *Synechocystis sp. PCC6803* | 2.5.1.29 | isopentenyl-PP + farnesyl-PP = (all trans)-geranylgeranyl-PP |
| | *crtB* | phytoene synthase | *Synechocystis sp. PCC6803* | 2.5.1.32 | 2 geranylgeranyl-PP = phytoene |
| | *crtI* | phytoene oxidoreductase | *Synechocystis sp. PCC6803* | 1.14.99.n | phytoene + 2 NADPH + 2 O2 = ζ-carotene |
| | *crtQ-2* | ζ-carotene oxidoreductase | *Synechocystis sp. PCC6803* | 1.14.99.30 | ζ-carotene + 2 NADPH + 2 O2 = lycopene |
| itaconate | *(nc)* | aconitate decarboxylase | *Aspergillus terreus* | 4.1.1.6 | cis-aconitate = itaconate + CO2 |
| 1,3-butadiene | *sucD* | succinyl-CoA dehydrogenase | *Clostridium kluyveri* | 1.2.1.n | succinyl-CoA + NADPH = succinic semialdehyde + CoA |
| | *GHBDH* | 4-hydroxybutyrate dehydrogenase | *Arabidopsis thaliana* | 1.1.1.2 | succinic semialdehyde + NADPH = 4-hydroxybutyrate |
| | *gdhA* | glutamate dehydrogenase | *Escherichia coli* | 1.4.1.4 | α-ketoglutarate + NH3 + NADPH = glutamate |
| | *gadA* | glutamate decarboxylase | *Escherichia coli* | 4.1.1.15 | glutamate = 4-aminobutyrate + CO2 |
| | *gabT* | 4-aminobutyrate transaminase | *Escherichia coli* | 2.6.1.19 | 4-aminobutyrate + α-ketoglutarate = glutamate + succinic semialdehyde |
| | *aldH* | aldehyde dehydrogenase | *Escherichia coli* | 1.1.1.n | 4-hydroxybutyrate + NADH = 4-hydroxybutanal |
| | *dhaT* | 1,3-propanediol oxidoreductase | *Klebsiella pneumoniae* | 1.1.1.202 | 4-hydroxybutanal + NADH = 1,4-butanediol |
| | | alcohol dehydratase | | 4.2.1.n | 1,4-butanediol = 1,3-butadiene |
| ethylene | | alcohol dehydratase | | 4.2.1.n | ethanol = ethylene |
| propylene | *accBCAD* | acetyl-CoA carboxylase | *Escherichia coli* | 6.4.1.2 | acetyl-CoA + ATP + CO2 = malonyl-CoA |
| | *(nc)* | bifunctional malonyl-CoA reductase | *Chloroflexus aurantiacus* | 1.2.1.18, 1.1.1.59 | malonyl-CoA + 2 NADPH = 3-hydroxypropionate + CoA |
| | *orfZ* | 3-hydroxypropionyl-CoA transferase | *Clostridium kluyveri* | 2.8.3.n | 3-hydroxypropionate + acetyl-CoA = 3-hydroxypropionyl-CoA + acetate |

FIGURE 1-N

| Product | *Gene* | Enzyme | ***Example organism*** | EC # | Reaction |
|---|---|---|---|---|---|
| | | 3-hydroxypropionyl-CoA dehydratase | *Chloroflexus aurantiacus* | 4.2.1.17 | 3-hydroxypropionyl-CoA = acryloyl-CoA |
| | | acryloyl-CoA reductase | *Chloroflexus aurantiacus* | 1.3.1.n | acryloyl-CoA + NADPH = propionyl-CoA |
| | *pct* | propionyl CoA-transferase | *Ralstonia eutropha* | 2.8.3.1 | propionyl-CoA + acetate = acetyl-CoA + propionate |
| | *adhE* | aldehyde dehydrogenase | *Escherichia coli* | 1.2.1.{3,4} | propionate + NADPH = propanal |
| | *adhE* | alcohol dehydrogenase | *Escherichia coli* | 1.1.1.{1,2} | propanal + NADPH = 1-propanol |
| | | alcohol dehydratase | *?* | 4.2.1.n | 1-propanol = propylene |
| Already part of central metabolism | | | | | |
| succinate<br>citrate<br>glutamate<br>malate | | | | | |
| | | | | | |
| | | | | | |
| | | | | | |
| | | | | | |
| | | | | | |
| | | | | | |

FIGURE 1-O

Succinate and derivatives

Fig. 4
n-Alkanes from acyl phosphates
gene to be overexpressed
gene already present
malonyl-ACP
acetyl-ACP
3-ketoacyl-ACP
3-hydroxyacyl-ACP
enoyl-ACP
acyl-ACP
fatB
fatty acid
fabD
acyl-CoA
acr1
fatty aldehyde
cer1
n-alkane
faoT
fatty alcohol
higher fatty acids

FIG. 19

| JCC # | Insert cassette | | | | $OD_{730}$ | IPTG (mM) | mg/L maltose | |
|---|---|---|---|---|---|---|---|---|
| | Insert location | Promoter | Amylase gene | Transporter | | | calculated from GC values | normalized to $OD_{730}$ |
| 724 | glgB | aphII | Gm | MEX1 | 3.66 | 0 | 0 | 0 |
| 725 | glgB | amt2 | Gm | MEX1 | 3.74 | 0 | 0 | 0 |
| 726 | glgB | trc | Gm | MEX1 | 4.56 | 0 | 1.18 | 0.16 |
| 726 | glgB | trc | Gm | MEX1 | 2.8 | 0.5 | 1.23 | 0.91 |
| 727 | glgB | aphII | Gm | setA | 4.47 | 0 | 0 | 0 |
| 728 | glgB | amt2 | Gm | setA | 2.21 | 0 | 0 | 0 |
| 729 | glgB | trc | Gm | setA | 3.76 | 0 | 15.76 | 4.19 |
| 729 | glgB | trc | Gm | setA | 0.78 | 0.5 | 6.23 | 7.98 |
| 730 | restriction | aphII | Gm | MEX1 | 6.89 | 0 | 0 | 0 |
| 731 | restriction | amt2 | Gm | MEX1 | 7.46 | 0 | 0 | 0 |
| 732 | restriction | trc | Gm | MEX1 | 7.24 | 0 | 0 | 0 |
| 732 | restriction | trc | Gm | MEX1 | 2.90 | 0.5 | 0 | 0 |
| 733 | restriction | aphII | Gm | setA | 8.72 | 0 | 0 | 0 |
| 734 | restriction | amt2 | Gm | setA | 9.44 | 0 | 0 | 0 |
| 735 | restriction | trc | Gm | setA | 8.15 | 0 | not tested | |
| 735 | restriction | trc | Gm | setA | 1.48 | 0.5 | 2.96 | 2.00 |
| 736 | glgB | aphII | Bc | MEX1 | 6.65 | 0 | 0 | 0 |
| 737 | glgB | amt2 | Bc | MEX1 | 1.04 | 0 | 0 | 0 |
| 738 | glgB | trc | Bc | MEX1 | 5.11 | 0 | 11.32 | 2.22 |
| 738 | glgB | trc | Bc | MEX1 | 2.07 | 0.5 | 23.19 | 11.20 |
| 739 | glgB | aphII | Bc | setA | 7.88 | 0 | 0 | 0 |
| 740 | restriction | aphII | Bc | MEX1 | 5.86 | 0 | 0 | 0 |
| 741 | restriction | amt2 | Bc | MEX1 | 9.44 | 0 | 0 | 0 |

Growth curve (OD vs Time) of JCC445 and JCC445containing additional adh$A_M$ genes on pAQ7

Ethanol production (mg/L) of JCC445 and
JCC445 containing additional adh genes on pAQ7

Acetaldehyde production (mg/L) of JCC445 and JCC445 containing additional adh genes on pAQ7

SEQUENCE LISTING

```
<160> NUMBER OF SEQ ID NOS: 29

<210> SEQ ID NO 1
<211> LENGTH: 1200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgtgggaaa ctaagattaa tatcaacgaa gtccgtgaga tccgcgcgaa aaccaccgtt     60

tactttggtg ttggtgctat caagaaaatt gatgatatcg ctcgcgagtt caaagaaaaa    120

ggttacgatc gcatcatcgt gatcaccggt aaaggcgctt acaaagcgac cggtgcatgg    180

gaatacatcg tgcctgctct gaacaaaaac cagattacgt atatccatta tgatcaggtg    240

accccgaacc cgaccgtaga tcaggttgac gaagcgacca aacaggcccg tgaatttggc    300

gctcgcgcag tactggctat tggtggcggt tccccgatcg acgcagccaa atctgtggcg    360

gtgctgctgt cttatccgga caaaaacgct cgtcagctgt accagctgga gtttaccccg    420

gtaaaagcag cgccgatcat cgccatcaac ctgacccacg gtacgggcac cgaagcggac    480

cgcttcgcgg ttgtatctat cccggagaag gcctacaaac cggctatcgc ttacgattgc    540

atctacccgc tgtactctat tgacgacccg gctctgatgg ttaaactgcc gagcgaccag    600

acggcgtacg ttagcgtgga tgccctgaac catgttgttg aagctgcgac ctccaaagtt    660

gcatctccgt acactattat cctggcaaaa gaaacggtcc gtctcatcgc acgctacctg    720

cctcaggccc tgtctcaccc tgcagacctg accgcgcgtt attacctcct gtatgcctct    780

ctgatcgccg gtattgcgtt tgataacggc ctgctgcatt tcacccacgc actggaacac    840

ccgctgtctg ccgtgaaacc tgaactggct catggcctgg gtctgggtat gctcctgcct    900

gcggtagtta aacaaattta tccggctacc ccggaggtac tggcggaaat cctggaacca    960

atcgtaccgg atctgaaagg cgttccgggc gaggctgaga aagcggcgtc tggcgtggcg   1020

aaatggctgg ctggtgcagg catcactatg aaactgaaag acgcgggttt ccaggctgaa   1080

gatatcgcgc gtctgaccga cctggccttc accactccat ccctggaact cctgctgtct   1140

atggcaccag taactgctga tcgtgagcgt gtgaaagcaa tttaccagga cgcattttga   1200

<210> SEQ ID NO 2
<211> LENGTH: 399
```

<212> TYPE: PRT
<213> ORGANISM: Moorella sp.

<400> SEQUENCE: 2

```
Met Trp Glu Thr Lys Ile Asn Ile Asn Glu Val Arg Glu Ile Arg Ala
1               5                   10                  15

Lys Thr Thr Val Tyr Phe Gly Val Gly Ala Ile Lys Lys Ile Asp Asp
            20                  25                  30

Ile Ala Arg Glu Phe Lys Glu Lys Gly Tyr Asp Arg Ile Ile Val Ile
        35                  40                  45

Thr Gly Lys Gly Ala Tyr Lys Ala Thr Gly Ala Trp Glu Tyr Ile Val
    50                  55                  60

Pro Ala Leu Asn Lys Asn Gln Ile Thr Tyr Ile His Tyr Asp Gln Val
65                  70                  75                  80

Thr Pro Asn Pro Thr Val Asp Gln Val Asp Glu Ala Thr Lys Gln Ala
                85                  90                  95

Arg Glu Phe Gly Ala Arg Ala Val Leu Ala Ile Gly Gly Gly Ser Pro
            100                 105                 110

Ile Asp Ala Ala Lys Ser Val Ala Val Leu Leu Ser Tyr Pro Asp Lys
        115                 120                 125

Asn Ala Arg Gln Leu Tyr Gln Leu Glu Phe Thr Pro Val Lys Ala Ala
    130                 135                 140

Pro Ile Ile Ala Ile Asn Leu Thr His Gly Thr Gly Thr Glu Ala Asp
145                 150                 155                 160

Arg Phe Ala Val Val Ser Ile Pro Glu Lys Ala Tyr Lys Pro Ala Ile
                165                 170                 175

Ala Tyr Asp Cys Ile Tyr Pro Leu Tyr Ser Ile Asp Asp Pro Ala Leu
            180                 185                 190

Met Val Lys Leu Pro Ser Asp Gln Thr Ala Tyr Val Ser Val Asp Ala
        195                 200                 205

Leu Asn His Val Val Glu Ala Ala Thr Ser Lys Val Ala Ser Pro Tyr
    210                 215                 220

Thr Ile Ile Leu Ala Lys Glu Thr Val Arg Leu Ile Ala Arg Tyr Leu
225                 230                 235                 240

Pro Gln Ala Leu Ser His Pro Ala Asp Leu Thr Ala Arg Tyr Tyr Leu
                245                 250                 255

Leu Tyr Ala Ser Leu Ile Ala Gly Ile Ala Phe Asp Asn Gly Leu Leu
            260                 265                 270

His Phe Thr His Ala Leu Glu His Pro Leu Ser Ala Val Lys Pro Glu
        275                 280                 285

Leu Ala His Gly Leu Gly Leu Gly Met Leu Leu Pro Ala Val Val Lys
    290                 295                 300

Gln Ile Tyr Pro Ala Thr Pro Glu Val Leu Ala Glu Ile Leu Glu Pro
305                 310                 315                 320

Ile Val Pro Asp Leu Lys Gly Val Pro Gly Glu Ala Glu Lys Ala Ala
                325                 330                 335

Ser Gly Val Ala Lys Trp Leu Ala Gly Ala Gly Ile Thr Met Lys Leu
            340                 345                 350

Lys Asp Ala Gly Phe Gln Ala Glu Asp Ile Ala Arg Leu Thr Asp Leu
        355                 360                 365

Ala Phe Thr Thr Pro Ser Leu Glu Leu Leu Leu Ser Met Ala Pro Val
    370                 375                 380

Thr Ala Asp Arg Glu Arg Val Lys Ala Ile Tyr Gln Asp Ala Phe
385                 390                 395
```

<210> SEQ ID NO 3
<211> LENGTH: 3821
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
gcggccgcgg gggggggggg gaaagccacg ttgtgtctca aaatctctga tgttacattg 60
cacaagataa aaatatatca tcatgaacaa taaaactgtc tgcttacata aacagtaata 120
caaggggtca tatggcggat actctgctga ttctgggtga ttctctgtct gcaggctacc 180
gtatgtccgc ctccgcggcc tggccagctc tgctgaatga taagtggcag tctaagacgt 240
ccgttgtgaa cgcatccatc tctggcgaca cgagccagca gggcctggcc cgtctgcctg 300
cactgctgaa acagcaccaa ccgcgctggg tcctggtgga gctgggcggt aacgacggtc 360
tgcgcggctt ccagccgcag cagaccgaac agactctgcg tcagattctg caggacgtga 420
aagctgctaa cgcggaaccg ctgctgatgc agattcgtct gccagcgaac tatggccgcc 480
gttacaacga agcgttctct gcaatctacc caaaactggc gaaagagttt gacgtcccgc 540
tgctgccgtt cttcatggag gaagtatacc tgaaaccgca gtggatgcaa gatgacggca 600
tccacccgaa ccgtgatgcg cagccgttca tcgctgactg gatggcgaag caactgcagc 660
cgctggtaaa ccacgattcc taattaaaga tctgtagtag gatccatgta gggtgaggtt 720
atagctatga agaaagtttg gctgaaccgt tatccggcag atgtaccgac tgaaattaac 780
ccagatcgtt accagtccct ggttgacatg ttcgaacagt ccgtggctcg ctacgccgat 840
cagcctgctt tcgtcaacat gggtgaggta atgacctttc gcaaactgga ggagcgttcc 900
cgtgctttcg cggcatacct gcagcagggt ctgggcctga agaaaggcga ccgcgtggcc 960
ctgatgatgc cgaacctgct gcaatatcct gtggcgctgt tcggtatcct gcgtgctggt 1020
atgatcgttg tcaatgttaa ccctctgtat acccctcgtg aactggagca ccagctgaat 1080
gactctggtg cgtctgctat cgttatcgtt tccaatttcg cacatacgct ggagaaagtg 1140
gttgataaaa ccgcagtgca gcatgtcatt ctgactcgca tgggtgacca gctgtccacc 1200
gctaaaggta ctgtagtcaa cttcgttgtg aaatacatta agcgcctggt tccgaaatac 1260
cacctgccag atgcaattag ctttcgctct gcactgcata acggttaccg tatgcagtac 1320
gtaaaaccag agctggtgcc ggaagacctg gcctttctgc agtataccgg cggcaccacc 1380
ggcgtggcaa agggcgcgat gctgacccat cgtaacatgc tggcgaacct ggagcaggtt 1440
aacgcaacgt acggcccgct gctgcacccg ggtaaagaac tggtagttac ggcactgcct 1500
ctgtatcaca tctttgcact gacgatcaac tgtctgctgt tcattgaact gggtggtcag 1560
aacctgctga tcaccaaccc gcgtgacatt ccgggcctgg taaaagagct ggctaagtac 1620
ccgttcaccg ccattactgg cgtaaacact ctgtttaacg cgctgctgaa caacaaagag 1680
tttcagcagc tggacttctc tagcctgcac ctgagcgctg gcggtggcat gccggttcag 1740
caggttgtgg cagagcgttg ggtgaaactg accggccagt atctgctgga gggttatggt 1800
ctgaccgagt gtgcaccgct ggtcagcgtt aacccgtatg atattgatta ccactctggt 1860
tctattggtc tgccggttcc gtccacggaa gccaaactgg tggacgatga cgacaacgaa 1920
gtacctccgg gccagccggg tgagctgtgt gtcaagggtc cgcaggttat gctgggctac 1980
tggcagcgcc cggacgccac cgacgaaatc attaaaaacg gttggctgca taccggtgat 2040
atcgctgtaa tggacgaaga aggtttcctg cgtatcgtgg accgtaagaa agatatgatt 2100
ctggtgagcg gtttcaacgt gtacccgaac gaaattgagg acgtagttat gcaacaccct 2160
ggcgtgcagg aggtggcagc cgtgggcgtg ccgtccggtt cttctggtga ggctgtgaaa 2220
atctttgtcg ttaaaaagga cccgtccctg accgaagaat ctctggtgac gttttgccgc 2280
cgtcaactga ctggctacaa agtgccgaaa ctggtcgagt tccgcgatga gctgccaaaa 2340
tctaacgtgg gtaagatcct gcgccgcgag ctgcgtgacg aggcacgtgg caaagttgac 2400
aataaagcat aaccgcgtag gaggacagct atgcgcccac ttcatccgat cgatttcatt 2460
ttcctgtccc tggagaaacg ccagcagccg atgcacgtag gtggtctgtt cctgttccag 2520
atcccggata acgctccgga cacctttatt caggacctgg tgaacgatat ccgtatctcc 2580
aagtctattc cggttccgcc gttcaacaac aagctgaacg gtctgttctg ggacgaagac 2640
gaggagttcg atctggatca ccatttccgt catattgcgc tgccgcaccc gggtcgcatc 2700
cgtgagctgc tgatttacat ctctcaggaa cacagcactc tcctcgatcg cgctaaacct 2760
ctgtggactt gcaacatcat tgaaggtatc gagggtaacc gtttcgccat gtacttcaag 2820
attcatcatg cgatggtgga tggtgtggcg ggtatgcgtc tgattgagaa aagcctgtcc 2880
catgatgtta ctgaaaagag catcgtaccg ccgtggtgcg ttgagggcaa acgtgctaaa 2940
cgcctgcgtg aaccgaagac cggcaaaatt aagaaaatca tgtctggtat taaatctcag 3000
ctccaggcca ccccgaccgt tattcaagaa ctgtctcaga cggtcttcaa agacatcggc 3060
cgtaatccgg accacgtttc ctctttccag gcgccgtgct ccatcctcaa ccagcgtgtg 3120
tcttcttctc gtcgtttcgc agcacagagc tttgacctgg accgtttccg caacatcgcc 3180
aaatctctga acgtgaccat taacgacgtt gtcctggctg tgtgtagcgg tgctctgcgc 3240
gcttatctga tgtctcataa ctctctgcca tccaaaccgc tgatcgctat ggtcccagca 3300
agcatccgca acgatgattc tgatgtgtcc aaccgtatta ctatgattct ggccaacctc 3360
gctactcaca aagacgaccc tctgcagcgt ctggaaatca tccgccgctc cgtccagaac 3420
tctaaacagc gttttaaacg catgacttcc gaccagattc tgaactattc tgcggttgta 3480
tacggcccgg ctggtctgaa cattatcagc ggtatgatgc cgaaacgtca ggcttttaac 3540
ctggtaatca gcaacgttcc tggcccgcgt gagccgctgt actggaacgg cgcaaaactg 3600
gacgcactgt acccggcttc catcgttctg gatggccagg ctctgaacat cactatgacc 3660
tcttacctgg acaaactgga agtaggtctg atcgcgtgtc gcaatgcact gccgcgcatg 3720
cagaacctgc tgacccacct ggaggaggaa atccagctgt ttgagggcgt tatcgccaaa 3780
caggaagata tcaaaacggc gaactaacca tggttgaatt c 3821

<210> SEQ ID NO 4
<211> LENGTH: 1448
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
ggccgctcac tgcccgcttt ccagtcggga aacctgtcgt gccagctgca ttaatgaatc 60
ggccaacgcg cggggagagg cggtttgcgt attgggcgcc agggtggttt ttcttttcac 120
cagtgagacg ggcaacagct gattgccctt caccgcctgg ccctgagaga gttgcagcaa 180
gcggtccacg ctggtttgcc ccagcaggcg aaaatcctgt ttgatggtgg ttgacggcgg 240
gatataacat gagctgtctt cggtatcgtc gtatcccact accgagatat ccgcaccaac 300
gcgcagcccg gactcggtaa tggcgcgcat tgcgcccagc gccatctgat cgttggcaac 360
cagcatcgca gtgggaacga tgccctcatt cagcatttgc atggtttgtt gaaaaccgga 420
catggcactc cagtcgcctt cccgttccgc tatcggctga atttgattgc gagtgagata 480
tttatgccag ccagccagac gcagacgcgc cgagacagaa cttaatgggc ccgctaacag 540
cgcgatttgc tggtgaccca atgcgaccag atgctccacg cccagtcgcg taccgtcttc 600
atgggagaaa ataatactgt tgatgggtgt ctggtcagag acatcaagaa ataacgccgg 660
aacattagtg caggcagctt ccacagcaat ggcatcctgg tcatccagcg gatagttaat 720
gatcagccca ctgacgcgct gcgcgagaag attgtgcacc gccgctttac aggcttcgac 780
gccgcttcgt tctaccatcg acaccaccac gctggcaccc agttgatcgg cgcgagattt 840
aatcgccgcg acaatttgcg acggcgcgtg cagggccaga ctggaggtgg caacgccaat 900
cagcaacgac tgtttgcccg ccagttgttg tgccacgcgg ttgggaatgt aattcagctc 960
cgccatcgcc gcttccactt tttcccgcgt tttcgcagaa acgtggctgg cctggttcac 1020
cacgcgggaa acggtctgat aagagacacc ggcatactct gcgacatcgt ataacgttac 1080
tggtttcata ttcaccaccc tgaattgact ctcttccggg cgctatcatg ccataccgcg 1140
aaaggttttg caccattcga tggtgtcaac gtaaatgcat gccgcttcgc cttccaattg 1200
gactgcacgg tgcaccaatg cttctggcgt caggcagcca tcggaagctg tggtatggct 1260
gtgcaggtcg taaatcactg cataattcgt gtcgctcaag gcgcactccc gttctggata 1320 atgtttttg cgccgacatc ataacggttc tggcaaatat tctgaaatga gctgttgaca 1380
attaatcatc cggctcgtat aatgtgtgga attgtgagcg gataacaatt tcacacagga 1440
aacagcat 1448

<210> SEQ ID NO 5
<211> LENGTH: 4255
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5
ttagaaaaac tcatcgagca tcaaatgaaa ctgcaattta ttcatatcag gattatcaat 60
accatatttt tgaaaaagcc gtttctgtaa tgaaggagaa aactcaccga ggcagttcca 120
taggatggca agatcctggt atcggtctgc gattccgact cgtccaacat caatacaacc 180
tattaatttc ccctcgtcaa aaataaggtt atcaagtgag aaatcaccat gagtgacgac 240
tgaatccggt gagaatggca aaagtttatg catttctttc cagacttgtt caacaggcca 300
gccattacgc tcgtcatcaa aatcactcgc atcaaccaaa ccgttattca ttcgtgattg 360
cgcctgagcg aggcgaaata cgcgatcgct gttaaaagga caattacaaa caggaatcga 420
gtgcaaccgg cgcaggaaca ctgccagcgc atcaacaata ttttcacctg aatcaggata 480
ttcttctaat acctggaacg ctgtttttcc ggggatcgca gtggtgagta accatgcatc 540
atcaggagta cggataaaat gcttgatggt cggaagtggc ataaattccg tcagccagtt 600
tagtctgacc atctcatctg taacatcatt ggcaacgcta cctttgccat gtttcagaaa 660
caactctggc gcatcgggct tcccatacaa gcgatagatt gtcgcacctg attgcccgac 720
attatcgcga gcccatttat acccatataa atcagcatcc atgttggaat ttaatcgcgg 780
cctcgacgtt tcccgttgaa tatggctcat attcttcctt tttcaatatt attgaagcat 840
ttatcagggt tattgtctca tgagcggata catatttgaa tgtatttaga aaaataaaca 900

```
aataggggtc agtgttacaa ccaattaacc aattctgaac attatcgcga gcccatttat    960
acctgaatat ggctcataac accccttgtt tgcctggcgg cagtagcgcg gtggtcccac   1020
ctgaccccat gccgaactca gaagtgaaac gccgtagcgc cgatggtagt gtggggactc   1080
cccatgcgag agtagggaac tgccaggcat caaataaaac gaaaggctca gtcgaaagac   1140
tgggcctttc gcccgggcta attagggggt gtcgcccttc tgaagtgggg cctgcaggct   1200
ctcaccaaag attcacctgt tagagctact caacatccat cagttcttaa aaccaggggt   1260
gacattcacc ggggcgagcc ttgaagggtt caaggaaaat tgtttgcggt atgccaagcc   1320
gatcaagtgg attcttggca gaacgatcac cgacaaaatg agcccgctcg aaattgctca   1380
ggcgctccta ggcaagcttg accggaaatt ggaatacaag ggcgctttg gatcgcggga    1440
taaccgtcag cgggtctatg aggcgatcgc ccctaacgat cagcgcgaaa aggtctttgc   1500
tcattggtta cagcgtgacc aagcaaaatt aggggccgtg tccaacccct gtataaatag   1560
atttattcag gaggcttaga cccgtgatcg agcggccgct catatgtaac aggaattcgg   1620
ttactagttt ttaattaacg aatccatgtg ggagtttatt cttgacacag atatttatga   1680
tataataact gagtaagctt aacataagga ggaaaaacta atgttacgca gcagcaacga   1740
tgttacgcag cagggcagtc gccctaaaac aaagttaggt ggctcaagta tgggcatcat   1800
tcgcacatgt aggctcggcc ctgaccaagt caaatccatg cgggctgctc ttgatctttt   1860
cggtcgtgag ttcggagacg tagccaccta ctcccaacat cagccggact ccgattacct   1920
cgggaacttg ctccgtagta agacattcat cgcgcttgct gccttcgacc aagaagcggt   1980
tgttggcgct ctcgcggctt acgttctgcc caagtttgag cagccgcgta gtgagatcta   2040
tatctatgat ctcgcagtct ccggcgagca ccggaggcag ggcattgcca ccgcgctcat   2100
caatctcctc aagcatgagg ccaacgcgct tggtgcttat gtgatctacg tgcaagcaga   2160
ttacggtgac gatcccgcag tggctctcta tacaaagttg ggcatacggg aagaagtgat   2220
gcactttgat atcgacccaa gtaccgccac ctaggcgcgc cgcaaggcac aatgtctttc   2280
tcttatgcac agatggggac tggaaaccac acgcacaatt cccttaaaaa gcaaccgcaa   2340
aaaataacca tcaaaataaa actggacaaa ttctcatgtg ttcttctcaa tttccacact   2400
gtttatccac aggaaattaa ggggctgtag cgttggtgct acagaataaa tgtagggatc   2460
gcccatagct ttattgctag ccacagtgct atggggaaaa ggaaaagaaa aaataccacc   2520
atgaatgggg gtgtcaaatc ttttggatac tgtaaaatga tagagacttt cttaggcgat   2580
cccatgacga ctagaccgaa taagaattta aaatcagcga gcgcggttcg ttttccccca   2640
ctcatgtaca gcgcggctac taaaaaagcc aatgagcaag gcttaaattt cagcgactat   2700
atccgggagc ttgttttacg agatttgctc gaagtctata acaatgatga ggcggatcaa   2760
gatgctgcct aaacacgaga aaaccccggc cggccaacgt caaaagggcg acacaaaatt   2820
tattctaaat gcataataaa tactgataac atcttatagt ttgtattata ttttgtatta   2880
tcgttgacat gtataatttt gatatcaaaa actgattttc cctttattat tttcgagatt   2940
tattttctta attctcttta acaaactaga aatattgtat atacaaaaaa tcataaataa   3000
tagatgaata gtttaattat aggtgttcat caatcgaaaa agcaacgtat cttatttaaa   3060
gtgcgttgct tttttctcat ttataaggtt aaataattct catatatcaa gcaaagtgac   3120
aggcgccctt aaatattctg acaaatgctc tttccctaaa ctcccccat aaaaaaaccc    3180
gccgaagcgg gtttttacgt tatttgcgga ttaacgatta ctcgttatca gaaccgccca   3240
gggggcccga gcttaagact ggccgtcgtt ttacaacaca gaaagagttt gtagaaacgc   3300
```

-continued aaaaaggcca tccgtcaggg gccttctgct tagtttgatg cctggcagtt ccctactctc 3360
gccttccgct tcctcgctca ctgactcgct gcgctcggtc gttcggctgc ggcgagcggt 3420
atcagctcac tcaaaggcgg taatacggtt atccacagaa tcaggggata acgcaggaaa 3480
gaacatgtga gcaaaaggcc agcaaaaggc caggaaccgt aaaaaggccg cgttgctggc 3540
gtttttccat aggctccgcc cccctgacga gcatcacaaa aatcgacgct caagtcagag 3600
gtggcgaaac ccgacaggac tataaagata ccaggcgttt ccccctggaa gctccctcgt 3660
gcgctctcct gttccgaccc tgccgcttac cggatacctg tccgcctttc tcccttcggg 3720
aagcgtggcg ctttctcata gctcacgctg taggtatctc agttcggtgt aggtcgttcg 3780
ctccaagctg ggctgtgtgc acgaaccccc cgttcagccc gaccgctgcg ccttatccgg 3840
taactatcgt cttgagtcca acccggtaag acacgactta tcgccactgg cagcagccac 3900
tggtaacagg attagcagag cgaggtatgt aggcggtgct acagagttct tgaagtggtg 3960
ggctaactac ggctacacta gaagaacagt atttggtatc tgcgctctgc tgaagccagt 4020
taccttcgga aaaagagttg gtagctcttg atccggcaaa caaaccaccg ctggtagcgg 4080
tggttttttt gtttgcaagc agcagattac gcgcagaaaa aaaggatctc aagaagatcc 4140
tttgatcttt tctacggggt ctgacgctca gtggaacgac gcgcgcgtaa ctcacgttaa 4200
gggattttgg tcatgagctt gcgccgtccc gtcaagtcag cgtaatgctc tgctt 4255

<210> SEQ ID NO 6
<211> LENGTH: 1038
<212> TYPE: DNA
<213> ORGANISM: Ralstonia solanacearum

<400> SEQUENCE: 6
atgaccgatc tgacgacatt ccatttgccc gaacgcatta ccaacacgga agcccaccgc 60
gagctcgggc aggccatggt caaggcgtgg cgaacggacg gcattttcca gatcacttta 120
tcgaaacccc aggaacagac cacggacgag gctttcgcgg aaagccggca atttttctcg 180
caggatttcg aaaccaagag ccgccatgtc agcgcgctca cctacagcgg ctatatcgct 240
tcgcgcgagg aagtcacggc cggcgaggcg gactattccg agatcttcac gatctgcccg 300
gacatcggcc tggaggatgc ccgcgtgcgg gaaaacctgc cgtgccacgg cccggtgccc 360
tggcccggcg cggcctatcg ggatcgcatg aaggccttca tgggcatgct cggcacgttc 420
ggcgagcgcc tgctccagct catcgcgctg ggcctcgacc tggacgacat ggacacgttc 480
acccgcctga cccaggacgg ctggcaccat atgcgcgtgc tgcgcttccc cacggtgcag 540
tcgtcggaga acgcgcgggg catcggggcg cataccgact acggcatgct cgtcatcgcg 600
gcgcaggacg atgtgggcgg cctgtatgtc cgcccgccga tcgagggcga acggcgcaac 660
cgcaactggc tgccatcgga aagcaccgcg ggggtgtacg agcatgacga cggctggaac 720
ttcatcaagc cgatgcccgc cgtgctgacg gtcttccccg gcgacttcct gcaattcctg 780
acgggcggcc atctgctgtc gacgccgcac aaggtccgcc tgaacacgcg cgagcgcttt 840
gccatggcct acttccatga gccgaacttc gacgcgtggg tcgagcccct ggaggcggac 900
gccgccgtgg cccccatcca ctacggcacg cacttcacca acatgttcat gcgctgctac 960
ccgaagcgca tcaccacccg gcggatcatg gagaacgggc tgctggacaa gctgcccacg 1020
ctgagcgaac tggcctag 1038

<210> SEQ ID NO 7
<211> LENGTH: 1038

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7
atgactgatc tgactacttt tcacctgccg gagcgtatta ctaacactga agctcatcgt 60
gaactgggtc aggctatggt gaaggcttgg cgtactgatg gtattttcca gatcaccctg 120
agcaaaccgc aggaacaaac gaccgatgag gcttttgcag aatctcgtca atttttcagc 180
caggacttcg aaacgaagtc tcgtcatgtg agcgcactga cctactctgg ttacatcgcg 240
tctcgtgagg aagtgactgc aggtgaagcg gactactctg aaatcttcac catttgtcct 300
gatatcggcc tggaagatgc gcgtgtacgt gaaaacctgc cgtgtcacgg cccggttccg 360
tggccgggtg cggcataccg tgatcgtatg aaagcattta tgggtatgct gggtactttt 420
ggcgagcgcc tgctgcaact catcgctctg ggtctggatc tcgatgatat ggataccttc 480
acccgtctga ctcaggacgg ttggcaccac atgcgtgttc tccgtttccc aacggtacag 540
tcctccgaaa acgctcgcgg tatcggcgcc cacacggact acggcatgct ggttatcgcg 600
gctcaggacg acgtgggcgg tctgtacgtt cgtccgccga tcgagggcga acgtcgcaac 660
cgcaattggc tcccgtctga gtctactgca ggcgtttacg aacatgacga tggttggaac 720
ttcatcaaac cgatgccagc tgtactgact gttttcccgg gcgatttcct gcagtttctg 780
accggtggtc atctgctgtc caccccgcac aaggttcgtc tgaacacccg cgaacgtttc 840
gcaatggctt actttcacga gccgaacttt gacgcttggg tggagccgct ggaggctgac 900
gcagccgttg cgccaatcca ctacggcacc catttcacca acatgttcat gcgctgctat 960
ccgaaacgta ttaccacgcg ccgtattatg gaaaatggcc tgctggataa actgccgacc 1020
ctgtctgagc tggcgtag 1038

<210> SEQ ID NO 8
<211> LENGTH: 1982
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
ggccatgtag gccggcctgg tgcgctatgc cgaatttttc tggcagttga atgatcaaca 60
aattttgccc tacttcaatc ggggggccaa tggcattgat ggtaccctat caacggcttt 120
gggcattgca gagaatcatt cgcctgctgt gttactgacg ggggatctcg ctctcctcca 180
cgatatcaat ggctttttga cattatcaaa atttactggc tccctgacga ttattgtgat 240
caataaccaa ggcggcggca tctttgaaat gttacccatc gccgaagaaa aagatatttt 300
tgaggattat tttgcgacgc cccaaaccgt tgaattttct aaagtatgcg atttatatgg 360
cattgaatat caggcgatcc aaaccaaagc tgatctgatg caaacctgtg ctatcttgcc 420
acccagggga gtacggctat tggaagtcaa aacaaaccgt aaccaagcga tgacttggct 480
gaaagattta ttccaaggtt ttcaaagtca tttttaaggc gcgccttaga agaactcatc 540
cagcagacgg tagaaggcaa tgcgctgaga atccggcgct gcgataccgt acagcaccag 600
gaaacggtca gcccattcac cacccagttc ttctgcaata tcgcgggtag cgagggcgat 660
atcctgatag cgatcagcta cacccagacg gccacagtca ataaaaccag agaagcggcc 720
gttttccacc ataatgtttg gcagacaagc gtcgccatgc gttaccacca ggtcttcgcc 780
gtccggcatg cgggctttca gacgtgcaaa cagttccgcc ggtgcgaggc cctggtgctc 840
ttcatccagg tcgtcctgat caaccagacc cgcttccata cgagtgcgtg cacgttcaat 900
acggtgttta gcctgatggt caaacgggca agttgccggg tccagggtgt gcagacggcg 960
catcgcgtcc gccatgatgg aaactttttc tgccggagcg aggtggctgc tcagcagatc 1020
ctgacccgga acttcaccca gcagcagcca atcgcgaccg gcttcagtaa ctacgtccag 1080
aactgccgcg cacggaacac cagtcgtcgc gagccaggac agacgggccg cttcgtcctg 1140
cagttcgttc agtgcgccgg acaggtcggt tttcacaaac agaaccggac gaccctgtgc 1200
agacagacgg aaaaccgctg catcgctaca gccaatagtc agctgagccc agtcgtaacc 1260
aaacaggcgt tccacccaag cagccggaga accagcatgc aggccatctt gttcaatcat 1320
actcttcctt tttcaatatt attgaagcat ttatcagggt tattgtctca tgagcggata 1380
catatttgaa tgtatttaga aaaataaaca aataggggtt taattaaaaa ctagtgaatt 1440
cctgttacat atgacgcggc cgcctatccg ggaattttgt ccctaagaaa ttgctggatt 1500
tcggcctgat aaaggtgggg attttcgagc atcgggaagt gtcccacctg ggtatttca 1560 atgtactgaa agtttgggtt aagggcgatc gccctttttcg ccatggccgc cggaataatt 1620
tgatcttttt ccccggcgag gaacagggtc ggacattgga tattgcgaaa tgcctggggc 1680
aagcgggtca ccatcatttc attcaccgaa gctagcaggg tgccagcggc ggcgcgatta 1740
tcagcgctca aaaaatcctc caggaattgc cgccgttctg tgggcgcaat cggttgctgc 1800
aaaaaacggg cgatcgccaa ccgatccagc cccggtacct gacgcaacca cggaaaccgt 1860
aggcgcacaa tggtgccagc aattttctga aacgtcccaa aggcgcgggc atcatattca 1920
aaaatcccgt tgcagttcaa aatggcccgg tctaggcgtt gggcctgcag gccagtgagg 1980
cc 1982

<210> SEQ ID NO 9
<211> LENGTH: 4892
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
ggcctcactg gcctgcaggg tcctgttgcg ccgtttcccc gttagtacga taaattttgt 60
tggctgctgc cgttgtgagg aaaacatgac tttctggctt cagttcgaga tccagagata 120
ggcgatcgcc gccgacaatg ccccctgccg tgtggagcaa gaccgtgtga caaactcgat 180
ttccttccgg ataaaaaggc cgctggatgc gaaacggcgc ttgggtaaaa cagcgttgca 240
tttccgtctt gccctggcgt tgcccgtaaa ttaagcccac cttgccgtgc cagggctgcg 300
ctttgtgaat cacctgttgt tgatcttgca tttttgtctg aaattgatgg gattaggggg 360
actaaaaatt actgccaaaa cagcccccag cagcagtcta ttttttcgat catcccactg 420
atccgggcag acccaacggc gatcgccaaa tattttgttc ctaaaacaat ggagcaaaca 480
aacctcaaga atcctaatca cacttccgcc cccgtatagg cggccgccaa ttggaaggcg 540
aagcggcatg catttacgtt gacaccatcg aatggtgcaa aacctttcgc ggtatggcat 600
gatagcgccc ggaagagagt caattcaggg tggtgaatat gaaaccagta acgttatacg 660
atgtcgcaga gtatgccggt gtctcttatc agaccgtttc ccgcgtggtg aaccaggcca 720
gccacgtttc tgcgaaaacg cgggaaaaag tggaagcggc gatggcggag ctgaatacat 780

-continued

```
tcccaaccgc gtggcacaac aactggcggg caaacagtcg ttgctgattg gcgttgccac    840
ctccagtctg gccctgcacg cgccgtcgca aattgtcgcg gcgattaaat ctcgcgccga    900
tcaactgggt gccagcgtgg tggtgtcgat ggtagaacga agcggcgtcg aagcctgtaa    960
agcggcggtg cacaatcttc tcgcgcaacg cgtcagtggg ctgatcatta actatccgct   1020
ggatgaccag gatgccattg ctgtggaagc tgcctgcact aatgttccgg cgttatttct   1080
tgatgtctct gaccagacac ccatcaacag tattattttc tcccatgaag acggtacgcg   1140
actgggcgtg gagcatctgg tcgcattggg tcaccagcaa atcgcgctgt tagcgggccc   1200
attaagttct gtctcggcgc gtctgcgtct ggctggctgg cataaatatc tcactcgcaa   1260
tcaaattcag ccgatagcgg aacgggaagg cgactggagt gccatgtccg gttttcaaca   1320
aaccatgcaa atgctgaatg agggcatcgt tcccactgcg atgctggttg ccaacgatca   1380
gatggcgctg ggcgcaatgc gcgccattac cgagtccggg ctgcgcgttg gtgcggatat   1440
ctcggtagtg ggatacgacg ataccgaaga cagctcatgt tatatcccgc cgtcaaccac   1500
catcaaacag gattttcgcc tgctggggca aaccagcgtg gaccgcttgc tgcaactctc   1560
tcagggccag gcggtgaagg gcaatcagct gttgcccgtc tcactggtga aaagaaaaac   1620
caccctggcg cccaatacgc aaaccgcctc tccccgcgcg ttggccgatt cattaatgca   1680
gctggcacga caggtttccc gactggaaag cgggcagtga gcgcaacgca attaatgtga   1740
gttagcgcga attgatctgg tttgacagct tatcatcgag ctcgactgca cggtgcacca   1800
atgcttctgg cgtcaggcag ccatcggaag ctgtggtatg gctgtgcagg tcgtaaatca   1860
ctgcataatt cgtgtcgctc aaggcgcact cccgttctgg ataatgtttt ttgcgccgac   1920
atcataacgg ttctggcaaa tattctgaaa tgagctgttg acaattaatc atccggctcg   1980
tataatgtgt ggaattgtga gcggataaca atttcacaca ggaaacagca tatgaagccg   2040
gttaaggcgg cagcggcgga aggtggtgac acggcgggcg atgccaaggt gggttttctg   2100
gcaaagtacc cgtggctggt cacgggtttt ttcttcttta tgtggtactt cctgaatgtg   2160
atttttaaca tcctgaacaa gaagatttac aactactttc cgtacccgta tttcgtcagc   2220
gtcatccacc tgttcgttgg cgtggtgtac tgcctgatca gctggtccgt tggtctgccg   2280
aaacgtgctc ctattgactc taatctgctg aaagtcctga tcccggtggc agtctgccac   2340
gcgctgggcc atgtcacttc taatgtttcg tttgcagcgg ttgccgtttc ttttacgcac   2400
accatcaagg cgctggaacc gttctttaac gcagcagcca gccagttcat catgggtcaa   2460
tctattccga ttacgctgtg gctgagcctg gcaccggttg tcctgggtgt tgctatggcc   2520
agcctgaccg agctgtcttt caactggttg ggcttcatct ccgcgatgat ttcgaacatt   2580
agctttacct atcgtagcat tttcagcaag aaagctatga ccgatatgga cagcaccaac   2640
gtgtacgcct atattagcat cattgctctg tttgtgtgta tccctccggc gattatcgtt   2700
gagggtccaa agctgctgaa ccacggtttt gccgatgcta ttgcgaaagt gggcatgacg   2760
aaatttatca gcgatctgtt ctgggtgggc atgttctacc acctgtacaa tcaactggcg   2820
acgaacacgc tggaacgcgt ggccccgctg acccatgcgg tgggcaacgt gctgaaacgt   2880
gtttttgtca ttggtttttc cattgtcatc ttcggcaaca aaatcagcac tcagacgggt   2940
atcggtaccg gtattgcgat cgccggcgtt gcgatgtata gcattattaa ggcaaagatt   3000
gaggaggaaa aacgtcaagg caaaaaggcc tcatgataag aattcggttt tccgtcctgt   3060
cttgattttc aagcaaacaa tgcctccgat ttctaatcgg aggcatttgt ttttgtttat   3120
tgcaaaaaca aaaaatattg ttacaaattt ttacaggcta ttaagcctac cgtcataaat   3180
```

-continued aatttgccat ttactagttt ttaattaacc agaaccttga ccgaacgcag cggtggtaac 3240
ggcgcagtgg cggttttcat ggcttgttat gactgttttt ttggggtaca gtctatgcct 3300
cgggcatcca agcagcaagc gcgttacgcc gtgggtcgat gtttgatgtt atggagcagc 3360
aacgatgtta cgcagcaggg cagtcgccct aaaacaaagt taaacatcat gagggaagcg 3420
gtgatcgccg aagtatcgac tcaactatca gaggtagttg gcgtcatcga gcgccatctc 3480
gaaccgacgt tgctggccgt acatttgtac ggctccgcag tggatggcgg cctgaagcca 3540
cacagtgata ttgatttgct ggttacggtg accgtaaggc ttgatgaaac aacgcggcga 3600
gctttgatca acgacctttt ggaaacttcg gcttcccctg gagagagcga gattctccgc 3660
gctgtagaag tcaccattgt tgtgcacgac gacatcattc cgtggcgtta tccagctaag 3720
cgcgaactgc aatttggaga atggcagcgc aatgacattc ttgcaggtat cttcgagcca 3780
gccacgatcg acattgatct ggctatcttg ctgacaaaag caagagaaca tagcgttgcc 3840
ttggtaggtc cagcggcgga ggaactcttt gatccggttc ctgaacagga tctatttgag 3900
gcgctaaatg aaaccttaac gctatggaac tcgccgcccg actgggctgg cgatgagcga 3960
aatgtagtgc ttacgttgtc ccgcatttgg tacagcgcag taaccggcaa aatcgcgccg 4020
aaggatgtcg ctgccgactg ggcaatggag cgcctgccgg cccagtatca gcccgtcata 4080
cttgaagcta gacaggctta tcttggacaa gaagaagatc gcttggcctc gcgcgcagat 4140
cagttggaag aatttgtcca ctacgtgaaa ggcgagatca ccaaggtagt cggcaaataa 4200
tgtctaacaa ttcgttcaag ccgacgccgc ttcgcggcgc ggcttaactc aagcgttaga 4260
tgcactaagc acataattgc tcacagccaa actatcaggt caagtctgct tttattattt 4320
ttaagcgtgc ataataagcc ctacacaaat tgggagatat atcatgaggc gcgcctgggt 4380
tcttatccaa cacactttga gtacattttg agatcaaaca gctcagtcat ccctgggaaa 4440
tatgtgccca aagcctgaac caaggcccca acaattccca gggaagtcgc taccatggta 4500
ggcaagtttc tcctttgtcc gtgcctatgg atgcctttag tccctatcca cctgagtgga 4560
tcaaaaatgc gagccacgcc ctcagtttcc attgtcctag ctgtgaagcg ctcccccatg 4620
atgcgaaacg ggcttggtta aatcgctatg cccccgtgac cgatgcgctg caccgtcgcc 4680
gctggcagga gttttatgaa tgtcaatgcg gcaccgtttg gtgggcctgg agtagcgatc 4740 gcccccccgtc tcgctaccaa acaaatgacc ggggtgaaaa tgacgaattt cggcggggct 4800
tgttttagag aaatcgcgaa agtcttttcc ggggcgatcg ccgcttgccg agggataccc 4860
cttaccatga taatgggccg gcctacatgg cc 4892

<210> SEQ ID NO 10
<211> LENGTH: 6017
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
ggcctcactg gcctgcaggg tcctgttgcg ccgtttcccc gttagtacga taaattttgt 60
tggctgctgc cgttgtgagg aaaacatgac tttctggctt cagttcgaga tccagagata 120
ggcgatcgcc gccgacaatg ccccctgccg tgtggagcaa gaccgtgtga caaactcgat 180
ttccttccgg ataaaaaggc cgctggatgc gaaacggcgc ttgggtaaaa cagcgttgca 240
tttccgtctt gccctggcgt tgcccgtaaa ttaagcccac cttgccgtgc cagggctgcg 300
ctttgtgaat cacctgttgt tgatcttgca tttttgtctg aaattgatgg gattaggggg 360

```
actaaaaatt actgccaaaa cagcccccag cagcagtcta ttttttcgat catcccactg    420
atccgggcag acccaacggc gatcgccaaa tattttgttc ctaaaacaat ggagcaaaca    480
aacctcaaga atcctaatca cacttccgcc cccgtatagg cggccgccaa ttggaaggcg    540
aagcggcatg catttacgtt gacaccatcg aatggtgcaa aacctttcgc ggtatggcat    600
gatagcgccc ggaagagagt caattcaggg tggtgaatat gaaaccagta acgttatacg    660
atgtcgcaga gtatgccggt gtctcttatc agaccgtttc ccgcgtggtg aaccaggcca    720
gccacgtttc tgcgaaaacg cgggaaaaag tggaagcggc gatggcggag ctgaattaca    780
ttcccaaccg cgtggcacaa caactggcgg gcaaacagtc gttgctgatt ggcgttgcca    840
cctccagtct ggccctgcac gcgccgtcgc aaattgtcgc ggcgattaaa tctcgcgccg    900
atcaactggg tgccagcgtg gtggtgtcga tggtagaacg aagcggcgtc gaagcctgta    960
aagcggcggt gcacaatctt ctcgcgcaac gcgtcagtgg gctgatcatt aactatccgc   1020
tggatgacca ggatgccatt gctgtggaag ctgcctgcac taatgttccg gcgttatttc   1080
ttgatgtctc tgaccagaca cccatcaaca gtattatttt ctcccatgaa gacggtacgc   1140
gactgggcgt ggagcatctg gtcgcattgg gtcaccagca aatcgcgctg ttagcgggcc   1200
cattaagttc tgtctcggcg cgtctgcgtc tggctggctg gcataaatat ctcactcgca   1260
atcaaattca gccgatagcg gaacgggaag gcgactggag tgccatgtcc ggttttcaac   1320
aaaccatgca aatgctgaat gagggcatcg ttcccactgc gatgctggtt gccaacgatc   1380
agatggcgct gggcgcaatg cgcgccatta ccgagtccgg gctgcgcgtt ggtgcggata   1440
tctcggtagt gggatacgac gataccgaag acagctcatg ttatatcccg ccgtcaacca   1500
ccatcaaaca ggattttcgc ctgctggggc aaaccagcgt ggaccgcttg ctgcaactct   1560
ctcagggcca ggcggtgaag ggcaatcagc tgttgcccgt ctcactggtg aaaagaaaaa   1620
ccaccctggc gcccaatacg caaaccgcct ctccccgcgc gttggccgat tcattaatgc   1680
agctggcacg acaggtttcc cgactggaaa gcgggcagtg agcgcaacgc aattaatgtg   1740
agttagcgcg aattgatctg gtttgacagc ttatcatcga gctcgactgc acggtgcacc   1800
aatgcttctg gcgtcaggca gccatcggaa gctgtggtat ggctgtgcag gtcgtaaatc   1860
actgcataat tcgtgtcgct caaggcgcac tcccgttctg gataatgttt tttgcgccga   1920
catcataacg gttctggcaa atattctgaa atgagctgtt gacaattaat catccggctc   1980
gtataatgtg tggaattgtg agcggataac aatttcacac aggaaacagc atatgctcta   2040
tatctttgat ttaggtaatg tgattgtcga tatcgacttt aaccgtgtgc tgggagcctg   2100
gagcgattta acgcgtattc cgctggcatc gcttaagaag agttttcaca tgggtgaggc   2160
gtttcatcag catgagcgtg gggaaattag cgacgaagcg ttcgcagagg cgctgtgtca   2220
cgagatggct ctaccgctaa gctacgagca gttctctcac ggctggcagg cggtgtttgt   2280
tgcgctgcgc ccggaagtga tcgccatcat gcataaactg cgtgagcagg ggcatcgcgt   2340
ggtggtgctt tccaatacca accgcctgca taccaccttc tggccggaag aatacccgga   2400
aattcgtgat gctgctgacc atatctatct gtcgcaagat ctggggatgc gcaaacctga   2460
agcacgaatt taccagcatg ttttgcaggc ggaaggtttt tcacccagcg atacggtctt   2520
tttcgacgat aacgccgata atatagaagg agccaatcag ctgggcatta ccagtattct   2580
ggtgaaagat aaaaccacca tcccggacta tttcgcgaag gtgttatgct catgataaga   2640
attgctcgag ttggatccat gtagggtgag gttatacata tggaaccgtc ctccaagaaa   2700
ctgaccggtc gtctgatgct ggcagttggt ggtgcagtcc tgggctccct gcagttcggc   2760
```

-continued

```
tacaatacgg gcgtgatcaa tgcaccgcag aaggtgatcg aagaatttta caatcagacc   2820
tgggttcatc gttacggtga atccattctg ccaacgaccc tgacgactct gtggagcctg   2880
tcggttgcga tttttagcgt tggtggtatg attggcagct ttagcgtggg cctgtttgtt   2940
aatcgtttcg gccgtcgcaa tagcatgctg atgatgaatc tgctggcatt tgttagcgcg   3000
gtgctgatgg gctttagcaa actgggcaaa agcttcgaga tgctgatcct gggtcgtttt   3060
attattggtg tttactgtgg tctgaccacg ggctttgttc cgatgtacgt gggtgaagtt   3120
tctccgactg cgctgcgtgg cgcgctgggc accctgcacc agctgggcat tgttgtgggt   3180
atcctgattg cgcaggtgtt cggtctggac agcattatgg gtaacaagga tctgtggccg   3240
ctgctgctga gcattatctt tatcccggca ctgctgcagt gcattgtttt gccgttttgt   3300
ccggagagcc cgcgtttcct gctgattaac cgcaatgaag agaatcgcgc taagagcgtg   3360
ttgaagaaac tgcgcggtac ggcggatgtc acccacgatc tgcaagagat gaaggaagag   3420
agccgtcaga tgatgcgtga gaagaaagtt acgattctgg agctgtttcg ctccccggca   3480
taccgtcaac cgatcttgat tgccgttgtg ttgcagctgt cccagcagct gagcggtatt   3540
aatgccgtgt tctactatag caccagcatc ttcgagaagg caggtgtcca gcagccggtt   3600
tatgcaacca tcggcagcgg cattgtgaac accgcattca cggtggttag cttgttcgtt   3660
gtggagcgtg ctggccgtcg tactctgcac ctgatcggtc tggcgggtat ggcgggttgt   3720
gcgattctga tgaccatcgc actggctctg ctggagcagc tgccgtggat gagctatctg   3780
tccattgtgg cgatttttgg cttcgttgcc ttctttgagg ttggtccggg tccgattccg   3840
tggttcattg ttgcagaact gttcagccag ggtccgcgtc cggcagccat cgccgttgct   3900
ggtttttcta attggacgtc taacttcatc gtgggcatgt gcttccaata tgtggaacag   3960
ctgtgtggcc catacgtgtt tatcattttt accgtcttgt tggttctgtt ttttatcttc   4020
acctatttca aggtgccgga aactaagggt cgcacgtttg acgaaattgc gagcggcttc   4080
cgtcaaggtg gcgcgagcca gagcgacaaa acgccggagg agttgtttca tccgctgggt   4140
gcggacagcc aggtgtcatg ataagaattc ggttttccgt cctgtcttga ttttcaagca   4200
aacaatgcct ccgatttcta atcggaggca tttgtttttg tttattgcaa aaacaaaaaa   4260
tattgttaca aatttttaca ggctattaag cctaccgtca taaataattt gccatttact   4320
agtttttaat taaccagaac cttgaccgaa cgcagcggtg gtaacggcgc agtggcggtt   4380
ttcatggctt gttatgactg tttttttggg gtacagtcta tgcctcgggc atccaagcag   4440
caagcgcgtt acgccgtggg tcgatgtttg atgttatgga gcagcaacga tgttacgcag   4500
cagggcagtc gccctaaaac aaagttaaac atcatgaggg aagcggtgat cgccgaagta   4560
tcgactcaac tatcagaggt agttggcgtc atcgagcgcc atctcgaacc gacgttgctg   4620
gccgtacatt tgtacggctc cgcagtggat ggcggcctga agccacacag tgatattgat   4680
ttgctggtta cggtgaccgt aaggcttgat gaaacaacgc ggcgagcttt gatcaacgac   4740
cttttggaaa cttcggcttc ccctggagag agcgagattc tccgcgctgt agaagtcacc   4800
attgttgtgc acgacgacat cattccgtgg cgttatccag ctaagcgcga actgcaattt   4860
ggagaatggc agcgcaatga cattcttgca ggtatcttcg agccagccac gatcgacatt   4920
gatctggcta tcttgctgac aaaagcaaga gaacatagcg ttgccttggt aggtccagcg   4980
gcggaggaac tctttgatcc ggttcctgaa caggatctat ttgaggcgct aaatgaaacc   5040
ttaacgctat ggaactcgcc gcccgactgg gctggcgatg agcgaaatgt agtgcttacg   5100
ttgtcccgca tttggtacag cgcagtaacc ggcaaaatcg cgccgaagga tgtcgctgcc   5160
```

-continued gactgggcaa tggagcgcct gccggcccag tatcagcccg tcatacttga agctagacag 5220
gcttatcttg gacaagaaga agatcgcttg gcctcgcgcg cagatcagtt ggaagaattt 5280
gtccactacg tgaaaggcga gatcaccaag gtagtcggca aataatgtct aacaattcgt 5340
tcaagccgac gccgcttcgc ggcgcggctt aactcaagcg ttagatgcac taagcacata 5400
attgctcaca gccaaactat caggtcaagt ctgcttttat tatttttaag cgtgcataat 5460
aagccctaca caaattggga gatatatcat gaggcgcgcc tgggttctta tccaacacac 5520
tttgagtaca ttttgagatc aaacagctca gtcatccctg ggaaatatgt gcccaaagcc 5580
tgaaccaagg ccccaacaat tcccagggaa gtcgctacca tggtaggcaa gtttctcctt 5640
tgtccgtgcc tatggatgcc tttagtccct atccacctga gtggatcaaa aatgcgagcc 5700
acgccctcag tttccattgt cctagctgtg aagcgctccc ccatgatgcg aaacgggctt 5760
ggttaaatcg ctatgccccc gtgaccgatg cgctgcaccg tcgccgctgg caggagtttt 5820
atgaatgtca atgcggcacc gtttggtggg cctggagtag cgatcgcccc ccgtctcgct 5880
accaaacaaa tgaccggggt gaaaatgacg aatttcggcg gggcttgttt tagagaaatc 5940
gcgaaagtct tttccggggc gatcgccgct tgccgaggga taccccttac catgataatg 6000
ggccggccta catggcc 6017

<210> SEQ ID NO 11
<211> LENGTH: 5960
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
ggcctcactg gcctgcaggg tcctgttgcg ccgtttcccc gttagtacga taaattttgt 60
tggctgctgc cgttgtgagg aaaacatgac tttctggctt cagttcgaga tccagagata 120
ggcgatcgcc gccgacaatg ccccctgccg tgtggagcaa gaccgtgtga caaactcgat 180
ttccttccgg ataaaaaggc cgctggatgc gaaacggcgc ttgggtaaaa cagcgttgca 240
tttccgtctt gccctggcgt tgcccgtaaa ttaagcccac cttgccgtgc cagggctgcg 300
ctttgtgaat cacctgttgt tgatcttgca tttttgtctg aaattgatgg gattaggggg 360
actaaaaatt actgccaaaa cagcccccag cagcagtcta ttttttcgat catcccactg 420
atccgggcag acccaacggc gatcgccaaa tattttgttc ctaaaacaat ggagcaaaca 480
aacctcaaga atcctaatca cacttccgcc cccgtatagg cggccgccaa ttggaaggcg 540
aagcggcatg catttacgtt gacaccatcg aatggtgcaa aacctttcgc ggtatggcat 600
gatagcgccc ggaagagagt caattcaggg tggtgaatat gaaaccagta acgttatacg 660
atgtcgcaga gtatgccggt gtctcttatc agaccgtttc ccgcgtggtg aaccaggcca 720
gccacgtttc tgcgaaaacg cgggaaaaag tggaagcggc gatggcggag ctgaattaca 780
ttcccaaccg cgtggcacaa caactggcgg gcaaacagtc gttgctgatt ggcgttgcca 840
cctccagtct ggccctgcac gcgccgtcgc aaattgtcgc ggcgattaaa tctcgcgccg 900
atcaactggg tgccagcgtg gtggtgtcga tggtagaacg aagcggcgtc gaagcctgta 960
aagcggcggt gcacaatctt ctcgcgcaac gcgtcagtgg gctgatcatt aactatccgc 1020
tggatgacca ggatgccatt gctgtggaag ctgcctgcac taatgttccg gcgttatttc 1080
ttgatgtctc tgaccagaca cccatcaaca gtattatttt ctcccatgaa gacggtacgc 1140

-continued

```
gactgggcgt ggagcatctg gtcgcattgg gtcaccagca aatcgcgctg ttagcgggcc   1200
cattaagttc tgtctcggcg cgtctgcgtc tggctggctg gcataaatat ctcactcgca   1260
atcaaattca gccgatagcg gaacgggaag gcgactggag tgccatgtcc ggttttcaac   1320
aaaccatgca aatgctgaat gagggcatcg ttcccactgc gatgctggtt gccaacgatc   1380
agatggcgct gggcgcaatg cgcgccatta ccgagtccgg gctgcgcgtt ggtgcggata   1440
tctcggtagt gggatacgac gataccgaag acagctcatg ttatatcccg ccgtcaacca   1500
ccatcaaaca ggattttcgc ctgctggggc aaaccagcgt ggaccgcttg ctgcaactct   1560
ctcagggcca ggcggtgaag ggcaatcagc tgttgcccgt ctcactggtg aaaagaaaaa   1620
ccaccctggc gcccaatacg caaaccgcct ctccccgcgc gttggccgat tcattaatgc   1680
agctggcacg acaggtttcc cgactggaaa gcgggcagtg agcgcaacgc aattaatgtg   1740
agttagcgcg aattgatctg gtttgacagc ttatcatcga gctcgactgc acggtgcacc   1800
aatgcttctg gcgtcaggca gccatcggaa gctgtggtat ggctgtgcag gtcgtaaatc   1860
actgcataat tcgtgtcgct caaggcgcac tcccgttctg gataatgttt tttgcgccga   1920
catcataacg gttctggcaa atattctgaa atgagctgtt gacaattaat catccggctc   1980
gtataatgtg tggaattgtg agcggataac aatttcacac aggaaacagc atatgctcta   2040
tatctttgat ttaggtaatg tgattgtcga tatcgacttt aaccgtgtgc tgggagcctg   2100
gagcgattta acgcgtattc cgctggcatc gcttaagaag agttttcaca tgggtgaggc   2160
gtttcatcag catgagcgtg gggaaattag cgacgaagcg ttcgcagagg cgctgtgtca   2220
cgagatggct ctaccgctaa gctacgagca gttctctcac ggctggcagg cggtgtttgt   2280
tgcgctgcgc ccggaagtga tcgccatcat gcataaactg cgtgagcagg ggcatcgcgt   2340
ggtggtgctt tccaatacca accgcctgca taccaccttc tggccggaag aatacccgga   2400
aattcgtgat gctgctgacc atatctatct gtcgcaagat ctggggatgc gcaaacctga   2460
agcacgaatt taccagcatg ttttgcaggc ggaaggtttt tcacccagcg atacggtctt   2520
tttcgacgat aacgccgata atatagaagg agccaatcag ctgggcatta ccagtattct   2580
ggtgaaagat aaaaccacca tcccggacta tttcgcgaag gtgttatgct catgataaga   2640
attgctcgag ttggatccat gtagggtgag gttatacata tgagcagcga atctagccag   2700
ggtctggtta cccgtctggc tttgattgcg gcgattggtg gtctgctgtt cggctacgac   2760
agcgcggtga tcgctgcgat tggtacccct gtcgatatcc actttattgc tccgcgccat   2820
ctgagcgcga cggcggctgc gagcctgagc ggtatggtgg tggttgcggt gctggttggt   2880
tgcgttaccg gtagcctgct gagcggttgg attggtattc gtttcggtcg ccgtggcggc   2940
ctgctgatga gcagcatctg tttcgtggca gcgggttttg gtgctgcgct gacggaaaag   3000
ttgtttggca cgggtggcag cgccttgcaa attttctgtt tcttccgctt cctggctggc   3060
ttgggtatcg gtgttgttag cacgctgacg ccgacgtaca tcgccgaaat tgcaccgccg   3120
gacaaacgcg gtcaaatggt cagcggtcag cagatggcga ttgtgaccgg cgccttgacg   3180
ggttatatct ttacctggct gctggcgcac tttggcagca tcgactgggt caatgcgagc   3240
ggctggtgct ggtccccggc atccgaaggt ttgatcggta tcgcttttct gctgctgttg   3300
ctgacggcgc ctgacacccc gcactggctg gttatgaaag gccgccatag cgaggccagc   3360
aagattctgg cgcgtctgga gccgcaggca gacccgaatc tgacgatcca aaagattaag   3420
gcgggtttcg ataaagcgat ggataaatct agcgcgggtc tgtttgcgtt tggtatcacc   3480
gtcgtttttg cgggcgttag cgtcgcagcg ttccagcaac tggtgggtat caacgcagtg   3540
```

-continued

```
ctgtattatg cgccgcagat gttccagaac ctgggcttcg gtgcggacac cgcgttgctg   3600
cagaccattt ctatcggtgt ggtgaatttc attttcacga tgattgcaag ccgcgtggtc   3660
gatcgctttg gccgcaagcc tctgctgatc tggggtgcgc tgggtatggc ggcgatgatg   3720
gcggttctgg gctgctgttt ctggttcaag gttggtggtg ttctgccgct ggcgagcgtt   3780
ctgttgtata ttgcggtgtt tggtatgagc tggggtccgg tctgttgggt cgtcctgagc   3840
gaaatgtttc cgtcgtctat caaaggtgcc gcgatgccta ttgcggtcac cggccagtgg   3900
ctggcgaaca ttctggtcaa tttcctgttt aaagtggctg atggtagccc ggccttgaat   3960
cagacgttca atcatggttt ctcctatctg gtcttcgccg cgctgagcat cctgggtggc   4020
ttgattgtgg cccgttttgt gccggagacg aagggccgtt cgttggacga aatcgaagaa   4080
atgtggcgtt cccaaaagtc atgataagaa ttcggttttc cgtcctgtct tgattttcaa   4140
gcaaacaatg cctccgattt ctaatcggag gcatttgttt ttgtttattg caaaaacaaa   4200
aaatattgtt acaaattttt acaggctatt aagcctaccg tcataaataa tttgccattt   4260
actagttttt aattaaccag aaccttgacc gaacgcagcg gtggtaacgg cgcagtggcg   4320
gttttcatgg cttgttatga ctgttttttt ggggtacagt ctatgcctcg ggcatccaag   4380
cagcaagcgc gttacgccgt gggtcgatgt ttgatgttat ggagcagcaa cgatgttacg   4440
cagcagggca gtcgccctaa aacaaagtta aacatcatga gggaagcggt gatcgccgaa   4500
gtatcgactc aactatcaga ggtagttggc gtcatcgagc gccatctcga accgacgttg   4560
ctggccgtac atttgtacgg ctccgcagtg gatggcggcc tgaagccaca cagtgatatt   4620
gatttgctgg ttacggtgac cgtaaggctt gatgaaacaa cgcggcgagc tttgatcaac   4680
gaccttttgg aaacttcggc ttcccctgga gagagcgaga ttctccgcgc tgtagaagtc   4740
accattgttg tgcacgacga catcattccg tggcgttatc cagctaagcg cgaactgcaa   4800
tttggagaat ggcagcgcaa tgacattctt gcaggtatct tcgagccagc cacgatcgac   4860
attgatctgg ctatcttgct gacaaaagca agagaacata gcgttgcctt ggtaggtcca   4920
gcggcggagg aactctttga tccggttcct gaacaggatc tatttgaggc gctaaatgaa   4980
accttaacgc tatggaactc gccgcccgac tgggctggcg atgagcgaaa tgtagtgctt   5040
acgttgtccc gcatttggta cagcgcagta accggcaaaa tcgcgccgaa ggatgtcgct   5100
gccgactggg caatggagcg cctgccggcc cagtatcagc ccgtcatact tgaagctaga   5160
caggcttatc ttggacaaga agaagatcgc ttggcctcgc gcgcagatca gttggaagaa   5220
tttgtccact acgtgaaagg cgagatcacc aaggtagtcg gcaaataatg tctaacaatt   5280
cgttcaagcc gacgccgctt cgcggcgcgg cttaactcaa gcgttagatg cactaagcac   5340
ataattgctc acagccaaac tatcaggtca agtctgcttt tattattttt aagcgtgcat   5400
aataagccct acacaaattg ggagatatat catgaggcgc gcctgggttc ttatccaaca   5460
cactttgagt acattttgag atcaaacagc tcagtcatcc ctgggaaata tgtgcccaaa   5520
gcctgaacca aggccccaac aattcccagg gaagtcgcta ccatggtagg caagtttctc   5580
ctttgtccgt gcctatggat gcctttagtc cctatccacc tgagtggatc aaaaatgcga   5640
gccacgccct cagtttccat tgtcctagct gtgaagcgct cccccatgat gcgaaacggg   5700
cttggttaaa tcgctatgcc cccgtgaccg atgcgctgca ccgtcgccgc tggcaggagt   5760
tttatgaatg tcaatgcggc accgtttggt gggcctggag tagcgatcgc cccccgtctc   5820
gctaccaaac aaatgaccgg ggtgaaaatg acgaatttcg gcggggcttg ttttagagaa   5880
atcgcgaaag tcttttccgg ggcgatcgcc gcttgccgag ggataccccct taccatgata   5940
```

atgggccggc ctacatggcc 5960

<210> SEQ ID NO 12
<211> LENGTH: 1641
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12
atgaagaatc aattccagta ttgttgtatt gttattttga gcgttgttat gctgtttgtg 60
agcctgctga ttccgcaagc gtcctccgca gcggttaatg gtaagggcat gaacccagac 120
tataaggctt acctgatggc accgctgaaa aagatcccag aggttacgaa ttgggaaacc 180
ttcgaaaatg acctgcgttg ggcgaaacaa aacggctttt atgcaatcac ggttgacttc 240
tggtggggcg acatggagaa aaacggcgac cagcaatttg acttcagcta tgcacagcgc 300
ttcgcgcagt ctgtgaaaaa tgcgggtatg aagatgattc cgatcatcag cactcatcaa 360
tgcggtggta atgttggcga tgattgcaac gtgccgatcc cgagctgggt ctggaatcaa 420
aaatccgacg actccctgta ctttaaaagc gaaaccggta cggttaataa agaaaccctg 480
aacccgctgg cgagcgacgt gatccgtaag gagtacggcg agctgtatac tgcgttcgca 540
gccgcaatga agccgtataa ggacgttatc gcgaaaattt acttgtccgg tggtccggct 600
ggtgagctgc gctacccgag ctatacgacg agcgatggca cgggctatcc aagccgtggt 660
aaatttcagg catataccga gttcgctaag agcaaattcc gtctgtgggt gctgaacaag 720
tacggcagcc tgaacgaggt caataaggca tggggcacca aactgattag cgagctggca 780
atcctgccac cgtccgacgg cgagcaattc ctgatgaatg gttacctgag catgtatggc 840
aaagattact tggaatggta ccagggcatt ctggagaatc acaccaagct gattggtgaa 900
ttggcgcata atgccttcga cacgaccttc caggtcccga tcggcgcgaa gattgcgggt 960
gtgcactggc agtacaacaa cccgaccatt cctcacggtg ctgaaaaacc ggctggttac 1020
aatgactata gccatctgct ggatgcattc aaaagcgcta agctggacgt cacctttacg 1080
tgtctggaaa tgaccgacaa gggcagctac ccggaatata gcatgccgaa gacgctggtg 1140
caaaacattg cgacgctggc gaacgagaaa ggcatcgtgc tgaatggcga gaacgctctg 1200
agcattggta atgaagagga atataagcgt gttgcggaga tggcattcaa ctacaatttc 1260
gcgggcttta ccctgctgcg ttaccaggac gtgatgtata ataacagcct gatgggtaaa 1320
ttcaaggact tgctgggcgt gaccccagtc atgcagacca ttgtggtgaa aaacgtcccg 1380
accacgatcg gtgataccgt ctacatcacc ggtaaccgtg cggagctggg tagctgggat 1440
accaaacaat atcctatcca gctgtattat gatagccact ccaacgactg gcgtggcaac 1500
gtcgtgctgc cggcggagcg taacattgaa tttaaggcat ttatcaagtc taaagacggc 1560
accgtgaaaa gctggcagac catccagcaa agctggaacc cggtcccgct gaagaccacc 1620
agccacacca gctcttggta a 1641

<210> SEQ ID NO 13
<211> LENGTH: 546
<212> TYPE: PRT
<213> ORGANISM: Bacillus cereus

<400> SEQUENCE: 13

Met Lys Asn Gln Phe Gln Tyr Cys Cys Ile Val Ile Leu Ser Val Val
1 5 10 15

-continued

```
Met Leu Phe Val Ser Leu Leu Ile Pro Gln Ala Ser Ser Ala Ala Val
            20                  25                  30

Asn Gly Lys Gly Met Asn Pro Asp Tyr Lys Ala Tyr Leu Met Ala Pro
        35                  40                  45

Leu Lys Lys Ile Pro Glu Val Thr Asn Trp Glu Thr Phe Glu Asn Asp
    50                  55                  60

Leu Arg Trp Ala Lys Gln Asn Gly Phe Tyr Ala Ile Thr Val Asp Phe
65                  70                  75                  80

Trp Trp Gly Asp Met Glu Lys Asn Gly Asp Gln Gln Phe Asp Phe Ser
                85                  90                  95

Tyr Ala Gln Arg Phe Ala Gln Ser Val Lys Asn Ala Gly Met Lys Met
            100                 105                 110

Ile Pro Ile Ile Ser Thr His Gln Cys Gly Gly Asn Val Gly Asp Asp
        115                 120                 125

Cys Asn Val Pro Ile Pro Ser Trp Val Trp Asn Gln Lys Ser Asp Asp
    130                 135                 140

Ser Leu Tyr Phe Lys Ser Glu Thr Gly Thr Val Asn Lys Glu Thr Leu
145                 150                 155                 160

Asn Pro Leu Ala Ser Asp Val Ile Arg Lys Glu Tyr Gly Glu Leu Tyr
                165                 170                 175

Thr Ala Phe Ala Ala Ala Met Lys Pro Tyr Lys Asp Val Ile Ala Lys
            180                 185                 190

Ile Tyr Leu Ser Gly Gly Pro Ala Gly Glu Leu Arg Tyr Pro Ser Tyr
        195                 200                 205

Thr Thr Ser Asp Gly Thr Gly Tyr Pro Ser Arg Gly Lys Phe Gln Ala
    210                 215                 220

Tyr Thr Glu Phe Ala Lys Ser Lys Phe Arg Leu Trp Val Leu Asn Lys
225                 230                 235                 240

Tyr Gly Ser Leu Asn Glu Val Asn Lys Ala Trp Gly Thr Lys Leu Ile
                245                 250                 255

Ser Glu Leu Ala Ile Leu Pro Pro Ser Asp Gly Glu Gln Phe Leu Met
            260                 265                 270

Asn Gly Tyr Leu Ser Met Tyr Gly Lys Asp Tyr Leu Glu Trp Tyr Gln
        275                 280                 285

Gly Ile Leu Glu Asn His Thr Lys Leu Ile Gly Glu Leu Ala His Asn
    290                 295                 300

Ala Phe Asp Thr Thr Phe Gln Val Pro Ile Gly Ala Lys Ile Ala Gly
305                 310                 315                 320

Val His Trp Gln Tyr Asn Asn Pro Thr Ile Pro His Gly Ala Glu Lys
                325                 330                 335

Pro Ala Gly Tyr Asn Asp Tyr Ser His Leu Leu Asp Ala Phe Lys Ser
            340                 345                 350

Ala Lys Leu Asp Val Thr Phe Thr Cys Leu Glu Met Thr Asp Lys Gly
        355                 360                 365

Ser Tyr Pro Glu Tyr Ser Met Pro Lys Thr Leu Val Gln Asn Ile Ala
    370                 375                 380

Thr Leu Ala Asn Glu Lys Gly Ile Val Leu Asn Gly Glu Asn Ala Leu
385                 390                 395                 400

Ser Ile Gly Asn Glu Glu Glu Tyr Lys Arg Val Ala Glu Met Ala Phe
                405                 410                 415

Asn Tyr Asn Phe Ala Gly Phe Thr Leu Leu Arg Tyr Gln Asp Val Met
            420                 425                 430

Tyr Asn Asn Ser Leu Met Gly Lys Phe Lys Asp Leu Leu Gly Val Thr
        435                 440                 445
```

-continued

```
Pro Val Met Gln Thr Ile Val Val Lys Asn Val Pro Thr Thr Ile Gly
    450                 455                 460

Asp Thr Val Tyr Ile Thr Gly Asn Arg Ala Glu Leu Gly Ser Trp Asp
465                 470                 475                 480

Thr Lys Gln Tyr Pro Ile Gln Leu Tyr Tyr Asp Ser His Ser Asn Asp
                485                 490                 495

Trp Arg Gly Asn Val Val Leu Pro Ala Glu Arg Asn Ile Glu Phe Lys
            500                 505                 510

Ala Phe Ile Lys Ser Lys Asp Gly Thr Val Lys Ser Trp Gln Thr Ile
        515                 520                 525

Gln Gln Ser Trp Asn Pro Val Pro Leu Lys Thr Thr Ser His Thr Ser
    530                 535                 540

Ser Trp
545


<210> SEQ ID NO 14
<211> LENGTH: 1491
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

atggcgacgt ctgactccaa tatgctgctg aattatgtgc ctgtgtatgt catgttgcct     60

ctgggtgtgg tcaatgtgga caacgttttt gaagatccgg atggtctgaa ggaacaactg    120

ttgcaattgc gtgcggcggg tgtggacggt gttatggtgg atgtgtggtg gggcattatc    180

gagctgaagg gtccgaaaca gtacgactgg cgtgcgtatc gttccctgtt tcagctggtt    240

caggaatgtg gtctgactct gcaggcgatc atgagcttcc atcaatgcgg cggtaacgtt    300

ggtgatatcg tgaatattcc gatcccgcaa tgggttctgg atattggtga atctaaccac    360

gacatcttct atacgaatcg cagcggtacg cgtaataagg aatacctgac cgtcggcgtc    420

gataacgagc cgatttttca tggccgtacc gctattgaga tttacagcga ctacatgaag    480

agcttccgcg aaaatatgag cgacttcctg gagtccggcc tgatcattga cattgaagtt    540

ggcctgggtc cggcaggtga actgcgctac ccgagctacc cgcagagcca aggctgggaa    600

tttccgcgta ttggcgaatt tcaatgctac gataagtatc tgaaagcaga ctttaaagct    660

gcggttgcgc gtgcgggcca tccggaatgg gaactgccag acgacgccgg taagtataac    720

gacgttccgg agagcactgg cttctttaag agcaatggta cgtacgtgac ggaaaagggt    780

aagtttttcc tgacctggta cagcaataag ttgttgaacc acggtgacca gatcctggac    840

gaggcgaata aggcctttct gggttgtaaa gttaaactgg cgatcaaagt gagcggcatt    900

cactggtggt ataaagtgga gaaccacgcc gccgaactga cggccggtta ttacaatctg    960

aatgaccgtg acggctaccg tcctattgcg cgtatgctga gccgccatca cgcaatcctg   1020

aattttacgt gcttggagat gcgtgacagc gaacagccga gcgacgcaaa gtctggcccg   1080

caggaattgg ttcagcaggt cctgagcggc ggctggcgcg aggacattcg cgttgccggc   1140

gaaaatgcac tgccgcgtta cgatgcaacc gcatataatc agatcattct gaatgcgaag   1200

ccgcaaggtg tcaataacaa tggtccgccg aaactgagca tgttcggtgt tacgtatctg   1260

cgtctgagcg acgatctgct gcaaaagtct aatttcaata ttttcaagaa atttgtcttg   1320

aagatgcacg cggaccagga ctattgcgca aatccgcaga aatacaatca cgccattacc   1380

ccgctgaagc cgagcgcacc gaagatcccg attgaggtcc tgttggaagc gaccaaacca   1440
```

accctgccgt ttccgtggct gccggagacg gacatgaagg ttgatggtta a 1491

<210> SEQ ID NO 15
<211> LENGTH: 496
<212> TYPE: PRT
<213> ORGANISM: Gylcine max

<400> SEQUENCE: 15

Met Ala Thr Ser Asp Ser Asn Met Leu Leu Asn Tyr Val Pro Val Tyr
1 5 10 15

Val Met Leu Pro Leu Gly Val Val Asn Val Asp Asn Val Phe Glu Asp
20 25 30

Pro Asp Gly Leu Lys Glu Gln Leu Leu Gln Leu Arg Ala Ala Gly Val
35 40 45

Asp Gly Val Met Val Asp Val Trp Trp Gly Ile Ile Glu Leu Lys Gly
50 55 60

Pro Lys Gln Tyr Asp Trp Arg Ala Tyr Arg Ser Leu Phe Gln Leu Val
65 70 75 80

Gln Glu Cys Gly Leu Thr Leu Gln Ala Ile Met Ser Phe His Gln Cys
85 90 95

Gly Gly Asn Val Gly Asp Ile Val Asn Ile Pro Ile Pro Gln Trp Val
100 105 110

Leu Asp Ile Gly Glu Ser Asn His Asp Ile Phe Tyr Thr Asn Arg Ser
115 120 125

Gly Thr Arg Asn Lys Glu Tyr Leu Thr Val Gly Val Asp Asn Glu Pro
130 135 140

Ile Phe His Gly Arg Thr Ala Ile Glu Ile Tyr Ser Asp Tyr Met Lys
145 150 155 160

Ser Phe Arg Glu Asn Met Ser Asp Phe Leu Glu Ser Gly Leu Ile Ile
165 170 175

Asp Ile Glu Val Gly Leu Gly Pro Ala Gly Glu Leu Arg Tyr Pro Ser
180 185 190

Tyr Pro Gln Ser Gln Gly Trp Glu Phe Pro Arg Ile Gly Glu Phe Gln
195 200 205

Cys Tyr Asp Lys Tyr Leu Lys Ala Asp Phe Lys Ala Ala Val Ala Arg
210 215 220

Ala Gly His Pro Glu Trp Glu Leu Pro Asp Asp Ala Gly Lys Tyr Asn
225 230 235 240

Asp Val Pro Glu Ser Thr Gly Phe Phe Lys Ser Asn Gly Thr Tyr Val
245 250 255

Thr Glu Lys Gly Lys Phe Phe Leu Thr Trp Tyr Ser Asn Lys Leu Leu
260 265 270

Asn His Gly Asp Gln Ile Leu Asp Glu Ala Asn Lys Ala Phe Leu Gly
275 280 285

Cys Lys Val Lys Leu Ala Ile Lys Val Ser Gly Ile His Trp Trp Tyr
290 295 300

Lys Val Glu Asn His Ala Ala Glu Leu Thr Ala Gly Tyr Tyr Asn Leu
305 310 315 320

Asn Asp Arg Asp Gly Tyr Arg Pro Ile Ala Arg Met Leu Ser Arg His
325 330 335

His Ala Ile Leu Asn Phe Thr Cys Leu Glu Met Arg Asp Ser Glu Gln
340 345 350

Pro Ser Asp Ala Lys Ser Gly Pro Gln Glu Leu Val Gln Gln Val Leu
355 360 365

Ser Gly Gly Trp Arg Glu Asp Ile Arg Val Ala Gly Glu Asn Ala Leu
    370                 375                 380

Pro Arg Tyr Asp Ala Thr Ala Tyr Asn Gln Ile Ile Leu Asn Ala Lys
385                 390                 395                 400

Pro Gln Gly Val Asn Asn Asn Gly Pro Pro Lys Leu Ser Met Phe Gly
                405                 410                 415

Val Thr Tyr Leu Arg Leu Ser Asp Asp Leu Leu Gln Lys Ser Asn Phe
            420                 425                 430

Asn Ile Phe Lys Lys Phe Val Leu Lys Met His Ala Asp Gln Asp Tyr
        435                 440                 445

Cys Ala Asn Pro Gln Lys Tyr Asn His Ala Ile Thr Pro Leu Lys Pro
    450                 455                 460

Ser Ala Pro Lys Ile Pro Ile Glu Val Leu Leu Glu Ala Thr Lys Pro
465                 470                 475                 480

Thr Leu Pro Phe Pro Trp Leu Pro Glu Thr Asp Met Lys Val Asp Gly
                485                 490                 495

<210> SEQ ID NO 16
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atggagggca aagcaattgc aacttctctg ggtggtgacc gtgttctgat ctttccatgc 60
tccccgcgta gcagcttcgt tttcacctct cgtttgtctt ccttgccgct gaagcgtgcc 120
agcatcggtg gtgcagtgag ctgtagcggt gtcaatggcc tgacccgctg gaatagcatt 180
gtgagcaccc gtcgcctggt cccggtccgc agcatcaata gcgagagcga tagcgacagc 240
gatttcccgc atgagaatca gcaaggtaac ccgggtctgg gtaagtttaa agagtaccaa 300
gaatgggaca gctggaccgc taaattcagc ggcggtgcaa atattccgtt cctgatgctg 360
caattgccgc agatcatcct gaatacgcag aatctgctgg caggtaataa cacggcgctg 420
tcggccgtgc cgtggctggg tatgttgacc ggcctgctgg gtaatctgtc cttgctgagc 480
tatttcgcaa agaagcgtga aaaggaggca gcggtcgttc agaccctggg tgtcgtgtct 540
acgcacattg tgctggcgca gctgactatg gccgaggcga tgccaatcca atacttcgtt 600
gcaaccagcg ctgtcgtgac gatcggtctg attgtgaact gcctgtatta ctttggtaag 660
ctgtccaaga ctgtgtggca actgtgggaa gacgtgatca ccatcggtgg cctgagcgtc 720
ctgccgcaaa ttatgtggtc taccttcgtg cctttggttc caaatagcat cttgccgggt 780
acgaccgcgt tcggtatcgc ggttgctgcg attatcatgg ctcgcaccgg taaactgagc 840
gagaagggcg tgcgttttgt tggttccctg agcggctgga cggccaccct gatgttcatg 900
tggatgccgg ttagccaaat gtggaccaat tttctgaacc cggataacat taaaggtctg 960
agcagcatca ccatgctgct gtccatgatg ggcaacggcc tgatgatccc gcgtgctctg 1020
ttcattcgtg atctgatgtg gctgaccggt tcgttgtggg cgaccttgtt ctacggttac 1080
ggtaatattc tgtgtttgta tctggtgaac tgtaccagcc aaagcttctt tgttgcggca 1140
accatcggcc tgatcagctg gattggcctg gcgctgtggc gcgacgcggt ggcgtacggt 1200
cacaacagcc cgtttcgttc cttgaaagaa ctggtgttcg gtccgtaa 1248

<210> SEQ ID NO 17
<211> LENGTH: 415

```
<212> TYPE: PRT
<213> ORGANISM: Arabidopsis thaliana

<400> SEQUENCE: 17

Met Glu Gly Lys Ala Ile Ala Thr Ser Leu Gly Gly Asp Arg Val Leu
1               5                   10                  15

Ile Phe Pro Cys Ser Pro Arg Ser Ser Phe Val Phe Thr Ser Arg Leu
            20                  25                  30

Ser Ser Leu Pro Leu Lys Arg Ala Ser Ile Gly Gly Ala Val Ser Cys
        35                  40                  45

Ser Gly Val Asn Gly Leu Thr Arg Trp Asn Ser Ile Val Ser Thr Arg
    50                  55                  60

Arg Leu Val Pro Val Arg Ser Ile Asn Ser Glu Ser Asp Ser Asp Ser
65                  70                  75                  80

Asp Phe Pro His Glu Asn Gln Gln Gly Asn Pro Gly Leu Gly Lys Phe
                85                  90                  95

Lys Glu Tyr Gln Glu Trp Asp Ser Trp Thr Ala Lys Phe Ser Gly Gly
            100                 105                 110

Ala Asn Ile Pro Phe Leu Met Leu Gln Leu Pro Gln Ile Ile Leu Asn
        115                 120                 125

Thr Gln Asn Leu Leu Ala Gly Asn Asn Thr Ala Leu Ser Ala Val Pro
    130                 135                 140

Trp Leu Gly Met Leu Thr Gly Leu Leu Gly Asn Leu Ser Leu Leu Ser
145                 150                 155                 160

Tyr Phe Ala Lys Lys Arg Glu Lys Glu Ala Ala Val Val Gln Thr Leu
                165                 170                 175

Gly Val Val Ser Thr His Ile Val Leu Ala Gln Leu Thr Met Ala Glu
            180                 185                 190

Ala Met Pro Ile Gln Tyr Phe Val Ala Thr Ser Ala Val Val Thr Ile
        195                 200                 205

Gly Leu Ile Val Asn Cys Leu Tyr Tyr Phe Gly Lys Leu Ser Lys Thr
    210                 215                 220

Val Trp Gln Leu Trp Glu Asp Val Ile Thr Ile Gly Gly Leu Ser Val
225                 230                 235                 240

Leu Pro Gln Ile Met Trp Ser Thr Phe Val Pro Leu Val Pro Asn Ser
                245                 250                 255

Ile Leu Pro Gly Thr Thr Ala Phe Gly Ile Ala Val Ala Ala Ile Ile
            260                 265                 270

Met Ala Arg Thr Gly Lys Leu Ser Glu Lys Gly Val Arg Phe Val Gly
        275                 280                 285

Ser Leu Ser Gly Trp Thr Ala Thr Leu Met Phe Met Trp Met Pro Val
    290                 295                 300

Ser Gln Met Trp Thr Asn Phe Leu Asn Pro Asp Asn Ile Lys Gly Leu
305                 310                 315                 320

Ser Ser Ile Thr Met Leu Leu Ser Met Met Gly Asn Gly Leu Met Ile
                325                 330                 335

Pro Arg Ala Leu Phe Ile Arg Asp Leu Met Trp Leu Thr Gly Ser Leu
            340                 345                 350

Trp Ala Thr Leu Phe Tyr Gly Tyr Gly Asn Ile Leu Cys Leu Tyr Leu
        355                 360                 365

Val Asn Cys Thr Ser Gln Ser Phe Phe Val Ala Ala Thr Ile Gly Leu
    370                 375                 380

Ile Ser Trp Ile Gly Leu Ala Leu Trp Arg Asp Ala Val Ala Tyr Gly
385                 390                 395                 400
```

```
His Asn Ser Pro Phe Arg Ser Leu Lys Glu Leu Val Phe Gly Pro
                405                 410                 415


<210> SEQ ID NO 18
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

atgatctgga tcatgacgat ggcacgccgt atgaacggtg tctacgccgc ctttatgctg     60

gtggcgttta tgatgggtgt cgccggtgcg ctgcaggcgc caacgctgag cctgtttctg    120

tctcgtgaag tcggtgcgca gccgttctgg attggtttgt tctacacggt taacgcgatc    180

gcaggtattg gtgtgagcct gtggctggct aagcgttccg actcgcaggg tgaccgccgc    240

aaactgatca ttttctgttg cctgatggcg attggtaatg cgctgctgtt tgcgtttaac    300

cgtcattact tgaccttgat cacgtgcggc gttctgctgg cgagcctggc aaacaccgct    360

atgccgcagc tgttcgcgct ggcgcgcgag tatgctgata acagcgcgcg tgaggtggtt    420

atgtttagct cggtgatgcg cgcacagttg tctctggctt gggtcatcgg tccgccgctg    480

gcgttcatgc tggcgttgaa ttatggtttc acggtgatgt tcagcatcgc agccggcatc    540

ttcaccctga gcctggtgtt gattgcattc atgctgccga gcgtcgcgcg cgtggagctg    600

ccgtccgaaa acgccctgag catgcaaggt ggctggcaag attctaatgt tcgtatgctg    660

ttcgtggcaa gcaccctgat gtggacttgc aacacgatgt atatcatcga catgccgctg    720

tggatcagca gcgaactggg tctgccagac aaactggcgg gctttctgat gggtactgcg    780

gcgggtctgg agattccggc aatgatcttg gcgggttatt acgttaagcg ttatggtaaa    840

cgccgcatga tggtcatcgc ggttgcagcg ggcgtgctgt tctatacggg cctgatcttc    900

tttaactccc gtatggccct gatgacgttg caactgttca atgctgtctt cattggcatt    960

gtggcgggca ttggtatgct gtggttccag gacctgatgc cgggtcgtgc tggtgcagcg   1020

acgaccttgt tcaccaattc catttcgacc ggtgtcatcc tggcgggtgt gatccagggt   1080

gcgattgcac agagctgggg tcacttcgca gtgtactggg ttattgcggt tatttccgtg   1140

gttgcgctgt ttctgacggc gaaggttaag gatgtgtaa                          1179


<210> SEQ ID NO 19
<211> LENGTH: 392
<212> TYPE: PRT
<213> ORGANISM: Escherichia coli

<400> SEQUENCE: 19

Met Ile Trp Ile Met Thr Met Ala Arg Arg Met Asn Gly Val Tyr Ala
1               5                   10                  15

Ala Phe Met Leu Val Ala Phe Met Met Gly Val Ala Gly Ala Leu Gln
            20                  25                  30

Ala Pro Thr Leu Ser Leu Phe Leu Ser Arg Glu Val Gly Ala Gln Pro
        35                  40                  45

Phe Trp Ile Gly Leu Phe Tyr Thr Val Asn Ala Ile Ala Gly Ile Gly
    50                  55                  60

Val Ser Leu Trp Leu Ala Lys Arg Ser Asp Ser Gln Gly Asp Arg Arg
65                  70                  75                  80

Lys Leu Ile Ile Phe Cys Cys Leu Met Ala Ile Gly Asn Ala Leu Leu
                85                  90                  95
```

-continued

```
Phe Ala Phe Asn Arg His Tyr Leu Thr Leu Ile Thr Cys Gly Val Leu
            100                 105                 110

Leu Ala Ser Leu Ala Asn Thr Ala Met Pro Gln Leu Phe Ala Leu Ala
        115                 120                 125

Arg Glu Tyr Ala Asp Asn Ser Ala Arg Glu Val Val Met Phe Ser Ser
    130                 135                 140

Val Met Arg Ala Gln Leu Ser Leu Ala Trp Val Ile Gly Pro Pro Leu
145                 150                 155                 160

Ala Phe Met Leu Ala Leu Asn Tyr Gly Phe Thr Val Met Phe Ser Ile
                165                 170                 175

Ala Ala Gly Ile Phe Thr Leu Ser Leu Val Leu Ile Ala Phe Met Leu
            180                 185                 190

Pro Ser Val Ala Arg Val Glu Leu Pro Ser Glu Asn Ala Leu Ser Met
        195                 200                 205

Gln Gly Gly Trp Gln Asp Ser Asn Val Arg Met Leu Phe Val Ala Ser
    210                 215                 220

Thr Leu Met Trp Thr Cys Asn Thr Met Tyr Ile Ile Asp Met Pro Leu
225                 230                 235                 240

Trp Ile Ser Ser Glu Leu Gly Leu Pro Asp Lys Leu Ala Gly Phe Leu
                245                 250                 255

Met Gly Thr Ala Ala Gly Leu Glu Ile Pro Ala Met Ile Leu Ala Gly
            260                 265                 270

Tyr Tyr Val Lys Arg Tyr Gly Lys Arg Arg Met Met Val Ile Ala Val
        275                 280                 285

Ala Ala Gly Val Leu Phe Tyr Thr Gly Leu Ile Phe Phe Asn Ser Arg
    290                 295                 300

Met Ala Leu Met Thr Leu Gln Leu Phe Asn Ala Val Phe Ile Gly Ile
305                 310                 315                 320

Val Ala Gly Ile Gly Met Leu Trp Phe Gln Asp Leu Met Pro Gly Arg
                325                 330                 335

Ala Gly Ala Ala Thr Thr Leu Phe Thr Asn Ser Ile Ser Thr Gly Val
            340                 345                 350

Ile Leu Ala Gly Val Ile Gln Gly Ala Ile Ala Gln Ser Trp Gly His
        355                 360                 365

Phe Ala Val Tyr Trp Val Ile Ala Val Ile Ser Val Val Ala Leu Phe
    370                 375                 380

Leu Thr Ala Lys Val Lys Asp Val
385                 390


<210> SEQ ID NO 20
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

gggggggggg gggaaagcca cgttgtgtct caaaatctct gatgttacat tgcacaagat      60

aaaaatatat catcatgaac aataaaactg tctgcttaca taaacagtaa tacaaggggt     120


<210> SEQ ID NO 21
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 21

```
agagcgttac tgccgatgct aatgctttgc agaagaggat tcattcccct ctttttcagt     60

gtaccgtgca cttcctcgtt ccactagatt ggagcccaaa tatcatcaga gtactgcttt    120

tcccgggccg gcaaattgtg gacaaacagt aacaaaagtt ggcagtgaac aattcattcc    180

ctcctaagat gccatcttga gaaaaatttc acttttccag ggagttgatt tagtataggc    240
```

<210> SEQ ID NO 22
<211> LENGTH: 1439
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

```
ctgcccgctt tccagtcggg aaacctgtcg tgccagctgc attaatgaat cggccaacgc     60

gcggggagag gcggtttgcg tattgggcgc cagggtggtt tttcttttca ccagtgagac    120

gggcaacagc tgattgccct tcaccgcctg gccctgagag agttgcagca agcggtccac    180

gctggtttgc cccagcaggc gaaaatcctg tttgatggtg gttgacggcg ggatataaca    240

tgagctgtct tcggtatcgt cgtatcccac taccgagata tccgcaccaa cgcgcagccc    300

ggactcggta atggcgcgca ttgcgcccag cgccatctga tcgttggcaa ccagcatcgc    360

agtgggaacg atgccctcat tcagcatttg catggtttgt tgaaaaccgg acatggcact    420

ccagtcgcct tcccgttccg ctatcggctg aatttgattg cgagtgagat atttatgcca    480

gccagccaga cgcagacgcg ccgagacaga acttaatggg cccgctaaca gcgcgatttg    540

ctggtgaccc aatgcgacca gatgctccac gcccagtcgc gtaccgtctt catgggagaa    600

aataatactg ttgatgggtg tctggtcaga gacatcaaga aataacgccg gaacattagt    660

gcaggcagct tccacagcaa tggcatcctg gtcatccagc ggatagttaa tgatcagccc    720

actgacgcgc tgcgcgagaa gattgtgcac cgccgcttta caggcttcga cgccgcttcg    780

ttctaccatc gacaccacca cgctggcacc cagttgatcg gcgcgagatt taatcgccgc    840

gacaatttgc gacggcgcgt gcagggccag actggaggtg gcaacgccaa tcagcaacga    900

ctgtttgccc gccagttgtt gtgccacgcg gttgggaatg taattcagct ccgccatcgc    960

cgcttccact ttttcccgcg ttttcgcaga aacgtggctg gcctggttca ccacgcggga   1020

aacggtctga taagagacac cggcatactc tgcgacatcg tataacgtta ctggtttcat   1080

attcaccacc ctgaattgac tctcttccgg gcgctatcat gccataccgc gaaaggtttt   1140

gcaccattcg atggtgtcaa cgtaaatgca tgccgcttcg ccttccaatt ggactgcacg   1200

gtgcaccaat gcttctggcg tcaggcagcc atcggaagct gtggtatggc tgtgcaggtc   1260

gtaaatcact gcataattcg tgtcgctcaa ggcgcactcc cgttctggat aatgtttttt   1320

gcgccgacat cataacggtt ctggcaaata ttctgaaatg agctgttgac aattaatcat   1380

ccggctcgta taatgtgtgg aattgtgagc ggataacaat ttcacacagg aaacagcat    1439
```

<210> SEQ ID NO 23
<211> LENGTH: 687
<212> TYPE: PRT
<213> ORGANISM: Arabidopsis thaliana

<400> SEQUENCE: 23

```
Met Glu Leu Glu Ser Thr Ser Asn Gly Arg Arg Pro Pro Pro Pro Ala
1               5                   10                  15
```

```
Glu Ile Gly Arg Gly Ala Tyr Leu Ala Trp Glu Asp Leu Thr Val Val
            20                  25                  30

Ile Pro Asn Phe Ser Gly Gly Pro Thr Arg Arg Leu Leu Asp Gly Leu
        35                  40                  45

Asn Gly His Ala Glu Pro Gly Arg Ile Met Ala Ile Met Gly Pro Ser
    50                  55                  60

Gly Ser Gly Lys Ser Thr Leu Leu Asp Ser Leu Ala Gly Arg Leu Ala
65                  70                  75                  80

Arg Asn Val Ile Met Thr Gly Asn Leu Leu Leu Asn Gly Lys Lys Ala
                85                  90                  95

Arg Leu Asp Tyr Gly Leu Val Ala Tyr Val Thr Gln Glu Asp Ile Leu
            100                 105                 110

Met Gly Thr Leu Thr Val Arg Glu Thr Ile Thr Tyr Ser Ala His Leu
        115                 120                 125

Arg Leu Ser Ser Asp Leu Thr Lys Glu Glu Val Asn Asp Ile Val Glu
    130                 135                 140

Gly Thr Ile Ile Glu Leu Gly Leu Gln Asp Cys Ala Asp Arg Val Ile
145                 150                 155                 160

Gly Asn Trp His Ser Arg Gly Val Ser Gly Gly Glu Arg Lys Arg Val
                165                 170                 175

Ser Val Ala Leu Glu Ile Leu Thr Arg Pro Gln Ile Leu Phe Leu Asp
            180                 185                 190

Glu Pro Thr Ser Gly Leu Asp Ser Ala Ser Ala Phe Phe Val Ile Gln
        195                 200                 205

Ala Leu Arg Asn Ile Ala Arg Asp Gly Gly Arg Thr Val Val Ser Ser
    210                 215                 220

Ile His Gln Pro Ser Ser Glu Val Phe Ala Leu Phe Asp Asp Leu Phe
225                 230                 235                 240

Leu Leu Ser Ser Gly Glu Thr Val Tyr Phe Gly Glu Ser Lys Phe Ala
                245                 250                 255

Val Glu Phe Phe Ala Glu Ala Gly Phe Pro Cys Pro Lys Lys Arg Asn
            260                 265                 270

Pro Ser Asp His Phe Leu Arg Cys Ile Asn Ser Asp Phe Asp Thr Val
        275                 280                 285

Thr Ala Thr Leu Lys Gly Ser Gln Arg Ile Arg Glu Thr Pro Ala Thr
    290                 295                 300

Ser Asp Pro Leu Met Asn Leu Ala Thr Ser Glu Ile Lys Ala Arg Leu
305                 310                 315                 320

Val Glu Asn Tyr Arg Arg Ser Val Tyr Ala Lys Ser Ala Lys Ser Arg
                325                 330                 335

Ile Arg Glu Leu Ala Ser Ile Glu Gly His His Gly Met Glu Val Arg
            340                 345                 350

Lys Gly Ser Glu Ala Thr Trp Phe Lys Gln Leu Arg Thr Leu Thr Lys
        355                 360                 365

Arg Ser Phe Val Asn Met Cys Arg Asp Ile Gly Tyr Tyr Trp Ser Arg
    370                 375                 380

Ile Val Ile Tyr Ile Val Val Ser Phe Cys Val Gly Thr Ile Phe Tyr
385                 390                 395                 400

Asp Val Gly His Ser Tyr Thr Ser Ile Leu Ala Arg Val Ser Cys Gly
                405                 410                 415

Gly Phe Ile Thr Gly Phe Met Thr Phe Met Ser Ile Gly Gly Phe Pro
            420                 425                 430

Ser Phe Ile Glu Glu Met Lys Val Phe Tyr Lys Glu Arg Leu Ser Gly
```

-continued

```
        435                 440                 445

Tyr Tyr Gly Val Ser Val Tyr Ile Ile Ser Asn Tyr Val Ser Ser Phe
    450                 455                 460

Pro Phe Leu Val Ala Ile Ala Leu Ile Thr Gly Ser Ile Thr Tyr Asn
465                 470                 475                 480

Met Val Lys Phe Arg Pro Gly Val Ser His Trp Ala Phe Phe Cys Leu
                485                 490                 495

Asn Ile Phe Phe Ser Val Ser Val Ile Glu Ser Leu Met Met Val Val
            500                 505                 510

Ala Ser Leu Val Pro Asn Phe Leu Met Gly Leu Ile Thr Gly Ala Gly
        515                 520                 525

Ile Ile Gly Ile Ile Met Met Thr Ser Gly Phe Phe Arg Leu Leu Pro
    530                 535                 540

Asp Leu Pro Lys Val Phe Trp Arg Tyr Pro Ile Ser Phe Met Ser Tyr
545                 550                 555                 560

Gly Ser Trp Ala Ile Gln Gly Ala Tyr Lys Asn Asp Phe Leu Gly Leu
                565                 570                 575

Glu Phe Asp Pro Met Phe Ala Gly Glu Pro Lys Met Thr Gly Glu Gln
            580                 585                 590

Val Ile Asn Lys Ile Phe Gly Val Gln Val Thr His Ser Lys Trp Trp
        595                 600                 605

Asp Leu Ser Ala Ile Val Leu Ile Leu Val Cys Tyr Arg Ile Leu Phe
    610                 615                 620

Phe Ile Val Leu Lys Leu Lys Glu Arg Ala Glu Pro Ala Leu Lys Ala
625                 630                 635                 640

Ile Gln Ala Lys Arg Thr Met Lys Ser Leu Lys Lys Arg Pro Ser Phe
                645                 650                 655

Lys Lys Val Pro Ser Leu Ser Ser Leu Ser Ser Arg Arg His Gln Pro
            660                 665                 670

Leu His Ser Leu Ser Ser Gln Glu Gly Leu Thr Ser Pro Ile Asn
        675                 680                 685


<210> SEQ ID NO 24
<211> LENGTH: 446
<212> TYPE: PRT
<213> ORGANISM: Escherichia coli

<400> SEQUENCE: 24

Met Ser Gln Lys Thr Leu Phe Thr Lys Ser Ala Leu Ala Val Ala Val
1               5                   10                  15

Ala Leu Ile Ser Thr Gln Ala Trp Ser Ala Gly Phe Gln Leu Asn Glu
            20                  25                  30

Phe Ser Ser Ser Gly Leu Gly Arg Ala Tyr Ser Gly Glu Gly Ala Ile
        35                  40                  45

Ala Asp Asp Ala Gly Asn Val Ser Arg Asn Pro Ala Leu Ile Thr Met
    50                  55                  60

Phe Asp Arg Pro Thr Phe Ser Ala Gly Ala Val Tyr Ile Asp Pro Asp
65                  70                  75                  80

Val Asn Ile Ser Gly Thr Ser Pro Ser Gly Arg Ser Leu Lys Ala Asp
                85                  90                  95

Asn Ile Ala Pro Thr Ala Trp Val Pro Asn Met His Phe Val Ala Pro
            100                 105                 110

Ile Asn Asp Gln Phe Gly Trp Gly Ala Ser Ile Thr Ser Asn Tyr Gly
        115                 120                 125

Leu Ala Thr Glu Phe Asn Asp Thr Tyr Ala Gly Gly Ser Val Gly Gly
```

-continued

```
    130                 135                 140

Thr Thr Asp Leu Glu Thr Met Asn Leu Asn Leu Ser Gly Ala Tyr Arg
145                 150                 155                 160

Leu Asn Asn Ala Trp Ser Phe Gly Leu Gly Phe Asn Ala Val Tyr Ala
                165                 170                 175

Arg Ala Lys Ile Glu Arg Phe Ala Gly Asp Leu Gly Gln Leu Val Ala
            180                 185                 190

Gly Gln Ile Met Gln Ser Pro Ala Gly Gln Thr Gln Gln Gly Gln Ala
        195                 200                 205

Leu Ala Ala Thr Ala Asn Gly Ile Asp Ser Asn Thr Lys Ile Ala His
    210                 215                 220

Leu Asn Gly Asn Gln Trp Gly Phe Gly Trp Asn Ala Gly Ile Leu Tyr
225                 230                 235                 240

Glu Leu Asp Lys Asn Asn Arg Tyr Ala Leu Thr Tyr Arg Ser Glu Val
                245                 250                 255

Lys Ile Asp Phe Lys Gly Asn Tyr Ser Ser Asp Leu Asn Arg Ala Phe
            260                 265                 270

Asn Asn Tyr Gly Leu Pro Ile Pro Thr Ala Thr Gly Gly Ala Thr Gln
        275                 280                 285

Ser Gly Tyr Leu Thr Leu Asn Leu Pro Glu Met Trp Glu Val Ser Gly
    290                 295                 300

Tyr Asn Arg Val Asp Pro Gln Trp Ala Ile His Tyr Ser Leu Ala Tyr
305                 310                 315                 320

Thr Ser Trp Ser Gln Phe Gln Gln Leu Lys Ala Thr Ser Thr Ser Gly
                325                 330                 335

Asp Thr Leu Phe Gln Lys His Glu Gly Phe Lys Asp Ala Tyr Arg Ile
            340                 345                 350

Ala Leu Gly Thr Thr Tyr Tyr Tyr Asp Asp Asn Trp Thr Phe Arg Thr
        355                 360                 365

Gly Ile Ala Phe Asp Asp Ser Pro Val Pro Ala Gln Asn Arg Ser Ile
    370                 375                 380

Ser Ile Pro Asp Gln Asp Arg Phe Trp Leu Ser Ala Gly Thr Thr Tyr
385                 390                 395                 400

Ala Phe Asn Lys Asp Ala Ser Val Asp Val Gly Val Ser Tyr Met His
                405                 410                 415

Gly Gln Ser Val Lys Ile Asn Glu Gly Pro Tyr Gln Phe Glu Ser Glu
            420                 425                 430

Gly Lys Ala Trp Leu Phe Gly Thr Asn Phe Asn Tyr Ala Phe
        435                 440                 445


<210> SEQ ID NO 25
<211> LENGTH: 465
<212> TYPE: PRT
<213> ORGANISM: Pseudomonas putida

<400> SEQUENCE: 25

Met Lys Ile Lys Asn Leu Pro Asn Lys Val Ile Ser Gly Ala Ile Leu
1               5                   10                  15

Gly Ile Ala Ser Ser His Ala Ile Ala Thr Asp Gly Leu Phe Leu Glu
            20                  25                  30

Gly Phe Gly Ala Ile Ser Arg Ser Met Gly Gly Thr Ala Val Ala His
        35                  40                  45

Tyr Val Gly Pro Ala Ser Met Met Val Asn Pro Ala Thr Met Asp Leu
    50                  55                  60

Ser Asp Ser Ala Gly Glu Leu Leu Leu Gly Phe Asp Leu Ile Thr Thr
```

```
65                  70                  75                  80

Asp Ile Gly Ala Thr Asn Pro Glu Thr Gly Gln His Val Ser Ser Ser
                85                  90                  95

Asp His Ser Asn Asn Arg Gly Pro Tyr Val Ala Pro Gln Phe Ala Tyr
            100                 105                 110

Ile His Lys Val Ser Asn Trp Thr Phe Gly Ala Gly Val Phe Ala Gln
        115                 120                 125

Ala Gly Val Gly Val Glu Tyr Gly Asn Asp Ser Phe Leu Ser Arg Gly
    130                 135                 140

Asp Val Gly Gly Lys Gly Tyr Ala Ala Gly Ala Asp Thr Gly Leu Glu
145                 150                 155                 160

Asn Ala Ser Arg Leu Phe Ile Leu Asp Ile Pro Phe Ala Ala Ser Phe
                165                 170                 175

Lys Val Asn Asp Arg Leu Ala Ile Gly Gly Ser Leu Asp Ala Lys Trp
            180                 185                 190

Thr Gly Leu Asn Leu Asp Tyr Leu Leu Gly Met Asn Gln Leu Gly Ser
        195                 200                 205

Leu Ala Gly Asp Gly Arg Ala Ser Gly Ser Leu Met Gly Val Ile Gly
    210                 215                 220

Thr Leu Pro Asp Pro Arg Gly Val His Leu Ser Val Ser Lys Asn Lys
225                 230                 235                 240

Glu Met Ser Ser Gly Val Asp Gly Trp Gly Tyr Ser Ala Arg Leu Gly
                245                 250                 255

Leu Leu Tyr Lys Val Ala Pro Thr Thr Asn Val Gly Val Ser Tyr Met
            260                 265                 270

Phe Lys Ser His Met Asn Asp Leu Lys Gly Lys Gly Thr Val Thr Ala
        275                 280                 285

Val Asp Gly Ile Ala Gly Asn Val Pro Ile Glu Gly Glu Val Arg Phe
    290                 295                 300

Leu Asp Phe Asn Thr Pro Ala Lys Leu Asp Val Gly Ile Ser His Gln
305                 310                 315                 320

Val Thr Asp Lys Trp Leu Ile Ala Phe Asp Val Ser Arg Val Phe Trp
                325                 330                 335

Lys Asp Ala Leu Lys Asp Ile Lys Leu Gly Phe Ala Ser Gly Met Gly
            340                 345                 350

Asp Val Asp Leu Lys Leu Pro Gln Asp Ala Lys Asp Gln Thr Ile Met
        355                 360                 365

Ala Ile Gly Thr Ser Tyr Ser Val Thr Pro Arg Leu Thr Leu Arg Ala
    370                 375                 380

Gly Tyr Arg His Ala Thr Gln Pro Phe Asn Asp Glu Gly Leu Leu Ala
385                 390                 395                 400

Leu Ile Pro Ala Val Leu Gln Asp His Ala Ser Leu Gly Phe Ser Tyr
                405                 410                 415

Gln Leu Ser Lys Ser Gly Arg Phe Asp Ala Ala Tyr Ser His Ala Phe
            420                 425                 430

Lys Glu Ser Met Thr Asn Arg Ser Ala Tyr Asn Thr Ser Ser Pro Val
        435                 440                 445

Lys Ser Ser Ile Ala Gln Asp Asn Phe Val Leu Ala Tyr Asn Tyr Ser
    450                 455                 460

Phe
465
```

<210> SEQ ID NO 26
<211> LENGTH: 3828

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
gccaccacag ccaaattcat cgttaatgtg gacttgccga cgcccccttt tcgactaaca 60
atcgcaattt ttttcataga catttcccac agaccacatc aaattacagc aattgatcta 120
gctgaaagtt taacccactt ccccccagac ccagaagacc agaggcgctt aagcttcccc 180
gaacaaactc aactgaccga gggggaggga gccgtagcgg cgttggtgtt ggcgtaaatg 240
acaggccgag caaagagcga tgagattttc ccgacgattg tcttcgggga tgtaattttt 300
gtggtggacg cttaaggtta aaacagcccg caggtgacga tcaatgcctt tgaccttcac 360
atccgacgga atacaaacca agccacagag ttcacagcgc cagtctgcat cctcttttac 420
ttgtaaggcg atcgcctgcc aatcatcaga atatcgagaa gaatgtttca tctaaaccta 480
gcgccgcaag ataatcctga aatcgctaca gtattaaaaa attctggcca acatcacagc 540
caatactcgg ccgctagtac aaaaagacga ttaaccccat gggtaaaagc aggggagcca 600
ctaaagttca caggtttaca ccgaattttc catttgaaaa gtagtaaatc atacagaaaa 660
caatcatgta aaaattgaat actctaatgg tttgatgtcc gaaaaagtct agtttcttct 720
attcttcgac caaatctatg gcagggcact atcacagagc tggcttaata atttgggaga 780
aatgggtggg ggcggacttt cgtagaacaa tgtagattaa agtaccatat ggtcatgagc 840
cagaaaaccc tgtttacaaa gtctgctctc gcagtcgcag tggcacttat ctccacccag 900
gcctggtcgg caggctttca gttaaacgaa ttttcttcct ctggcctggg ccgggcttat 960
tcaggggaag gcgcaattgc cgatgatgca ggtaacgtca gccgtaaccc cgcattgatt 1020
actatgtttg accgcccgac attttctgcg ggtgcggttt atattgaccc ggatgtaaat 1080
atcagcggaa cgtctccatc tggtcgtagc ctgaaagccg ataacatcgc gcctacggca 1140
tgggttccga acatgcactt tgttgcaccg attaacgacc aatttggttg ggcgcttct 1200 attacctcta actatggtct ggctacagag tttaacgata cttatgcagg cggctctgtc 1260
gggggtacaa ccgaccttga aaccatgaac ctgaacttaa gcggtgcgta tcgcttaaat 1320
aatgcatgga gctttggtct tggtttcaac gccgtctacg ctcgcgcgaa aattgaacgt 1380
ttcgcaggcg atctggggca gttggttgct ggccaaatta tgcaatctcc tgctggccaa 1440
actcagcaag ggcaagcatt ggcagctacc gccaacggta ttgacagtaa taccaaaatc 1500
gctcatctga acggtaacca gtggggcttt ggctggaacg ccggaatcct gtatgaactg 1560
gataaaaata accgctatgc actgacctac cgttctgaag tgaaaattga cttcaaaggt 1620
aactacagca gcgatcttaa tcgtgcgttt aataactacg gtttgccaat tcctaccgcg 1680
acaggtggcg caacgcaatc gggttatctg acgctgaacc tgcctgaaat gtgggaagtg 1740
tcaggttata accgtgttga tccacagtgg gcgattcact atagcctggc ttacaccagc 1800
tggagtcagt tccagcagct gaaagcgacc tcaaccagtg gcgacacgct gttccagaaa 1860
catgaaggct ttaaagatgc ttaccgcatc gcgttgggta ccacttatta ctacgatgat 1920
aactggacct tccgtaccgg tatcgccttt gatgacagcc cagttcctgc acagaatcgt 1980
tctatctcca ttccggacca ggaccgtttc tggctgagtg caggtacgac ttacgcattt 2040
aataaagatg cttcagtcga cgttggtgtt tcttatatgc acggtcagag cgtgaaaatt 2100
aacgaaggcc cataccagtt cgagtctgaa ggtaaagcct ggctgttcgg tactaacttt 2160

-continued

```
aactacgcgt tctgaggaat tcggttttcc gtcctgtctt gattttcaag caaacaatgc   2220

ctccgatttc taatcggagg catttgtttt tgtttattgc aaaaacaaaa aatattgtta   2280

caaattttta caggctatta agcctaccgt cataaataat ttgccattta ctagttttta   2340

attaaacccc tatttgttta tttttctaaa tacattcaaa tatgtatccg ctcatgagac   2400

aataaccctg ataaatgctt caataatatt gaaaaaggaa gagtatgatt gaacaagatg   2460

gcctgcatgc tggttctccg gctgcttggg tggaacgcct gtttggttac gactgggctc   2520

agctgactat tggctgtagc gatgcagcgg ttttccgtct gtctgcacag ggtcgtccgg   2580

ttctgtttgt gaaaaccgac ctgtccggcg cactgaacga actgcaggac gaagcggccc   2640

gtctgtcctg gctcgcgacg actggtgttc cgtgcgcggc agttctggac gtagttactg   2700

aagccggtcg cgattggctg ctgctgggtg aagttccggg tcaggatctg ctgagcagcc   2760

acctcgctcc ggcagaaaaa gtttccatca tggcggacgc gatgcgccgt ctgcacaccc   2820

tggacccggc aacttgcccg tttgaccatc aggctaaaca ccgtattgaa cgtgcacgca   2880

ctcgtatgga agcgggtctg gttgatcagg acgacctgga tgaagagcac cagggcctcg   2940

caccggcgga actgtttgca cgtctgaaag cccgcatgcc ggacggcgaa gacctggtgg   3000

taacgcatgg cgacgcttgt ctgccaaaca ttatggtgga aaacggccgc ttctctggtt   3060

ttattgactg tggccgtctg ggtgtagctg atcgctatca ggatatcgcc ctcgctaccc   3120

gcgatattgc agaagaactg ggtggtgaat gggctgaccg tttcctggtg ctgtacggta   3180

tcgcagcgcc ggattctcag cgcattgcct tctaccgtct gctggatgag ttcttctaag   3240

gcgcgccgaa actgcgccaa gaatagctca cttcaaatca gtcacggttt tgtttagggc   3300

ttgtctggcg attttggtga catagacagt cacagcaaca gtagccacaa aaccaagaat   3360

ccggatcgac cactgggcaa tggggttggc gctggtgctt tctgtgccga gggtcgcaag   3420

atttccggcc agggagccaa tgtagacata catgatggtg ccagggatca tccccacaga   3480

gccgaggaca tagtctttta gggaaacgcc cgtgacccca taggcatagt taagcagatt   3540

aaagggaaat acaggtgaga gacgcgtcag gagaacaatc ttcaggcctt ccttgcccac   3600

agcttcgtcg atggcgcgaa atttcgggtt gtcggcgatt ttttggctca cccattggcg   3660

ggccagataa cgacccacta ggaaagcagc gatcgctcct agggttgcgc caacaaagac   3720

gtaaattgat cctaaagcga caccaaaaac aaccccggct cccaaggtca gaatcgaccc   3780

cggtagaaaa gccaccgtcg ccaccacata aagcaccata aaggcgat                3828
```

```
<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27

taacaccgtg cgtgttgact attttacctc tggcggtgat aatggttgca ggatcctttt     60

gctggaggaa aaccatatg                                                  79


<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 28

ctcgagttgg atcc                                                  14


<210> SEQ ID NO 29
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29

tttcaaaaca ggaattc                                               17
```

ETHANOL PRODUCTION BY MICROORGANISMS

REFERENCE TO SEQUENCE LISTING

The instant application contains a Sequence Listing which has been submitted via EFS-Web and is hereby incorporated by reference in its entirety. Said ASCII copy, created on Oct. 7, 2009, is named "16020_PCT_SL.txt", lists 29 sequences, and is 95 kb in size.

FIELD

The present disclosure relates to methods and compositions for engineering photoautotrophic organisms to convert carbon dioxide and light into fatty acid esters and other molecules which are then secreted by the organism into a growth medium.

BACKGROUND

Photosynthesis is a process by which biological entities utilize sunlight and $CO_2$ to produce sugars for energy. Photosynthesis, as naturally evolved, is an extremely complex system with numerous and poorly understood feedback loops, control mechanisms, and process inefficiencies. This complicated system presents likely insurmountable obstacles to either one-factor-at-a-time or global optimization approaches [Nedbal et al., *Photosynth Res.,* 93(1-3):223-34 (2007); Salvucci et al., *Physiol Plant.,* 120(2):179-186 (2004); Greene et al., *Biochem J.,* 404(3):517-24 (2007)].

Existing photoautotrophic organisms (i.e., plants, algae, and photosynthetic bacteria) are poorly suited for industrial bioprocessing and have therefore not demonstrated commercial viability for this purpose. Such organisms have slow doubling time (3-72 hrs) compared to industrialized heterotrophic organisms such as *Escherichia coli* (20 minutes), reflective of low total productivities. In addition, techniques for genetic manipulation (knockout, over-expression of transgenes via integration or episomic plasmid propagation) are inefficient, time-consuming, laborious, or non-existent.

SUMMARY

The invention described herein identifies pathways and mechanisms to confer direct carbon-based products producing capacity to photoautotrophic organisms. The resultant engineered carbon-based products-producing photoautotrophs uniquely enable the efficient production of carbon-based products directly from carbon dioxide and light, eliminating the time-consuming and expensive processing steps currently required to generate biofuels and biochemicals from biomass sources including corn, sugar cane, miscanthus, cellulose, and others. Accordingly, the novel microorganisms of the invention are capable of synthesizing carbon-based products of interest derived from various biosynthetic pathways by fixing $CO_2$ and are also capable of releasing such products.

Such products range from alcohols such as ethanol, propanol, isopropanol, butanol, fatty alcohols, fatty acid esters, wax esters; hydrocarbons and alkanes such as propane, octane, diesel, JP8; polymers such as terephthalate, 1,3-propanediol, 1,4-butanediol, polyols, PHA, PHB, acrylate, adipic acid, ε-caprolactone, isoprene, caprolactam, rubber; commodity chemicals such as lactate, DHA, 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, HPA, lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-ADCA/cephalosporin, erythromycin, polyketides, statins, paclitaxel, docetaxel, terpenes, peptides, steroids, omega fatty acids and other such suitable products of interest. Such products are useful in the context of fuels, biofuels, industrial and specialty chemicals, additives, as intermediates used to make additional products, such as nutritional supplements, neutraceuticals, polymers, paraffin replacements, personal care products and pharmaceuticals. These compounds can also be used as feedstock for subsequent reactions for example transesterification, hydrogenation, catalytic cracking via either hydrogenation, pyrolisis, or both or epoxidations reactions to make other products.

A method of selecting and using various organisms to directly convert sunlight and carbon dioxide into carbon-based products is also disclosed. In one aspect of the invention, a method is provided to introduce an engineered nucleic acid sequence encoding one or more proteins capable of $CO_2$ fixation to produce and, in some examples, excrete or secrete carbon-based products of interest, such as ethanol, ethylene, hydrocarbons, ethyl esters and methyl esters. A salient feature provided herein is that the microorganisms can produce various carbon-based products of interest preferably in commercial scale without the need for a renewable carbon-based intermediate or source, such as biomass, as a starting material.

To produce at least one of the desired carbon-based products of interest such as hydrocarbons, various organisms capable of $CO_2$ fixation, such as those capable of photosynthesis or in the alternative, organisms engineered to fix $CO_2$ are used. For example, photoautotrophic organisms include eukaryotic plants and algae, as well as prokaryotic cyanobacteria, green-sulfur bacteria, green non-sulfur bacteria, purple sulfur bacteria, and purple non-sulfur bacteria.

In one aspect, a host cell capable of $CO_2$ fixation is engineered to produce a carbon-based product having a desired number of carbons. Preferably the host cell produces various carbon-based products of interests in commercial scale.

In other examples a modified host cell is one that is genetically modified with an exongenous nucleic acid sequence encoding a single protein involved in a biosynthetic pathway involved in product or intermediate production. In other embodiments, a modified host cell is one that is genetically modified with exongenous nucleic acid sequences encoding two or more proteins involved in a biosynthetic pathway involved in product or intermediate production, for example, the first and second enzymes in a biosynthetic pathway.

In another aspect, the present invention provides a host cell capable of $CO_2$ fixation that produces ethylene. The host can include an exogenous nucleic acid encoding an ethylene forming enzyme, efe. The ethylene forming enzyme, efe, can include a *Ralstonia* ethylene forming enzyme.

In one embodiment, such a carbon-based product of interest is ethanol. In a preferred embodiment, the host cell produces commercial yields of ethanol. Also provided is a method of using the organisms to directly convert sunlight, water and carbon dioxide directly into ethanol in commercial scale. A method of monetizing the ethanol produced as well as the carbon dioxide taken up in association with the production of ethanol is additionally disclosed.

In some aspects, ethanol production is optimized by channeling carbon away from glycogen and toward pyruvate, etc.

during light exposure. Normally glycogen is formed in the light and it is consumed for reducing power in the dark. In one embodiment, glycogen-synthesis genes are attenuated or knocked out and in other embodiments, glycolytic genes are made constitutive. In other aspects, certain fermentative pathways, such as those leading to acetate, lactate, succinate, etc., if present, are eliminated.

Still in other aspects, if light-dark cycle is to be implemented, glycogen production is optimize during light exposure (as opposed to biomass, etc.) and increased in % of dry cell weight that can be glycogen (i.e., the cell is engineered to defeat any limitation that keeps the cells from swelling full of glycogen). Then, during the dark, ethanol synthesis is allowed to proceed from the accumulated glycogen, having attenuated or knocked out the other fermentative pathways. Furthermore, using a light-dark cycle that matches rates of glycogen synthesis/catabolism such that minimal time is wasted. is disclosed (glycogen doesn't run out and the cells sit unproductively in the dark, or there is too much glycogen to consume completely during the dark period).

In various aspects of the invention, described is a genetically modified photosynthetic organism for sugar production. In certain embodiments, sugars, e.g., glucose, fructose or a combination thereof, are produced. Preferably, the sugars produced are diffused through uniporters or transporters. In other embodiments, sugars are produced by expressing enzymes in a selected host cell producing 3-phosphoglyceraldehyde (3PGAL) and actively transported using transporters. In yet other embodiments, photosynthetic organisms functionally lack cellulose, glycogen, or sucrose synthesis. The resulting photosynthetic products, e.g., sugars produced from the photosynthetic organisms, can be used as feedstock or as a carbon source to produce additional carbon-based products of interest.

In another aspect of the invention, the invention provides engineered photosynthetic organisms for producing maltose. In certain embodiments, the invention provides cloned genes for glycogen hydrolyzing enzymes which allow the engineered cells to hydrolyze glycogen to glucose and/or maltose and transport maltose and glucose from the cell. Enzymes for transporting maltose from the cell include the maltose efflux pump from chloroplast for maltose transport: MEX1; glucose permeases, low and high Km, glucose:H+ symporter, glucose/fructose permease, general sugar:H+ antiporter for glucose transport; and glucose 6-phosphate:Pi antiporter, triose-phosphate:phosphate antiporter for glucose-6-phosphate transport are contemplated transport mechanisms of the present invention.

In another embodiment, hydrocarbons are produced by engineering various organisms capable of $CO_2$ fixation or engineered to fix $CO_2$. In one embodiment, the microorganisms are introduced with one or more exogenous nucleic acid sequences encoding acetyl-CoA:ACP transacylase activity (fabH), acetyl-CoA carboxylase activity (accBCAD), malonyl-CoA:ACP transacylase activity (fabD), 3-ketoacyl-ACP synthase activity (fabB), 3-ketoacyl-ACP reductase activity (fabG), 3-hydroxyacyl-ACP dehydratase activity (fabA), enoyl-ACP reductase activity (fabI), acyl-ACP hydrolase activity (FAS1), aldehyde dehydrogenase activity (adhA, adhB), alcohol dehydrogenase activity (ADH I), alkane 1-monooxygenase activity (alkB).

Additional genes that can be over-expressed for the production of fatty acid derivatives are for example, pdh, panK, aceEF (encoding the EIp dehydrogenase component and the E2p dihydrolipoamide acyltransferase component of the pyruvate and 2-oxoglutarate dehydrogenase complexes, Accessions: NP_414656, NP_414657, EC: 1.2.4.1. 2.3.1.61, 2.3.1.12), accABCD/fabH/fabD/fabG/acpP/fabF (encoding FAS, Accessions: CAD85557, CAD85558, NP_842277, NP_841683, NP_415613, EC: 2.3.1.180, 2.3.1.39, 1.1.1.100, 1.6.5.3, 2.3.1.179), genes encoding fatty-acyl-coA reductases (Accessions: AAC45217, EC 1.2.1.–), UdhA or similar genes (encoding pyridine nucleotide transhydrogenase, Accession: CAA46822, EC: 1.6.1.1) and genes encoding fatty-acyl-coA reductases (Accessions: AAC45217, EC 1.2.1.–).

In contrast to expressing exogenous nucleic acid sequences that allow for the production of fatty acid derivatives, the host can have one or more endogenous genes functionally deleted or attenuated. For example, ackA (EC 2.7.2.1), ackB (EC 2.7.2.1), adhE (EC 1.1.1.1, 1.2.1.10), fabF (EC 2.3.1.179), fabR (accession NP_418398), fadE (EC 1.3.99.3, 1.3.99.–), GST (EC 6.3.2.3), gpsA (EC 1.1.1.94), IdhA (EC 1.1.1.94), pflB (EC 2.3.1.54), plsB (EC 2.3.1.15), poxB (EC 1.2.2.2), pta (EC 2.3.1.8), glutathione synthase (EC 6.3.2.3) and combinations thereof can be at least attenuated.

Such microorganisms can be engineered to produce hydrocarbons or fatty acid of defined carbon chain length, branching, and saturation levels.

In some embodiments, peptides, e.g., thioesterase encoded by the exogenous nucleic acid sequences is expressed to provide homogeneous products, which would decreases the overall cost associated with fermentation and separation.

In some embodiments, the microorganisms include one or more exogenous engineered nucleic acids encoding acyl-CoA synthetase (EC6.2.1.3), thioesterase (EC 3.1.2.14), wax synthase (EC 2.3.1.75), alcohol acetyltransferase (EC 2.3.1.84) or a combination thereof. In other embodiments, the microorganisms include engineered nucleic acids encoding thioesterase (EC 3.1.2.14), acyl-CoA reductase (EC 1.2.1.50), alcohol dehydrogenase (EC 1.1.1.1), fatty alcohol forming acyl-CoA reductase (EC 1.1.1.*) or a combination thereof.

In some embodiments, the microorganisms described herein produce at least 1 mg of carbon-based product of interest, e.g., hydrocarbon per liter of fermentation media. In more preferred embodiments, the microorganisms produce at least 100 mg/L, 500 mg/L, 1 g/L, 5 g/L, 10 g/L, 20 g/L, 25 g/L, 30 g/L, 35 g/L, 40 g/L, 50 g/L, 100 g/L, or 120 g/L of hydrocarbons. In some examples, the hydrocarbon is produced and released from the microorganism and in yet other examples the microorganism is lysed prior to separation of the product.

In some examples, the hydrocarbon includes a carbon chain that is at least 2, 4, 6, 8, 10, 12, 14, 16, 18, 20, 22, 24, 26, 28, 30, 32, or 34 carbons long. In some examples at least 50%, 60%, 70%, 80%, 85%, 90%, or 95% of the hydrocarbon product made contains a carbon chain that is 2, 4, 6, 8, 10, 12, 14, 16, 18, 20, 22, 24, 26, 28, 30, 32, or 34 carbons long. In yet other examples, at least 60%, 70%, 80%, 85%, 90%, or 95% of the fatty acid derivative product contain 1, 2, 3, 4, or 5, points of unsaturation.

Certain biosynthetic pathways can be engineered to make fatty alcohols and wax/fatty acid esters as illustrated in WO 2007/136762 (incorporated by reference in its entirety for all purposes) the conversion of each substrate (acetyl-CoA, malonyl-CoA, acyl-ACP, fatty acid, and acyl-CoA) to each product (acetyl-CoA, malonyl-CoA, acyl-ACP, fatty acid, and acyl-CoA), which can be accomplished using several different polypeptides that are members of the enzyme classes indicated.

Alcohols (short chain, long chain, branched or unsaturated) can be produced by the hosts described herein. Such alcohols can be used as fuels directly or they can be used to create an ester, i.e. the A side of an ester as described above. Such ester alone or in combination with the other fatty acid derivatives described herein are useful a fuels.

Similarly, hydrocarbons produced from the microorganisms described herein can be used as biofuels. Such hydrocarbon based fuels can be designed to contain branch points, defined degrees of saturation, and specific carbon lengths. When used as biofuels alone or in combination with other fatty acid derivatives the hydrocarbons can be additionally combined with additives or other traditional fuels (alcohols, diesel derived from triglycerides, and petroleum based fuels).

In one embodiment, the invention provides an engineered microbial host cell, wherein said engineered host cell comprises one or more engineered nucleic acids, and wherein said engineered host cell is capable of using a minimum amount of light energy to synthesize a carbon-based product of interest directly from carbon dioxide and water, and wherein said carbon-based product of interest is selected from the group consisting of: ethyl ester, methyl ester, sucrose, alcohol, ethanol, propanol, isopropanol, butanol, fatty alcohols, fatty acid ester, wax ester, hydrocarbons, n-alkanes, propane, octane, diesel, JP8, polymers, terephthalate, polyol, 1,3-propanediol, 1,4-butanediol, PHA, PHB, acrylate, adipic acid, ϵcaprolactone, isoprene, caprolactam, rubber, lactate, DHA, 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, HPA, lactic acid, THF, gamma butyrolactone, pyrrolidones, hydroxybutyrate, glutamic acid, levulinic acid, acrylic acid, malonic acid, carotenoid, isoprenoid, itaconic acid, limonene, pharmaceutical or pharmaceutical intermediates, erythromycin 7-ADCA/cephalosporin, polyketides, statin, paclitaxel, docetaxel, terpene, peptide, steroid, and an omega fatty acid.

In another embodiment, the engineered nucleic acid comprised by the host cell encodes an ethylene forming enzyme (Efe) activity. In a related embodiment, the ethylene forming enzyme is selected from *Pseudomonas syringae* pv. *Phaseolicola* D13182, *P. syringae* pv. *Pisi* AF101061 and *Ralstonia solanacearum* AL646053. In another embodiment, the engineered nucleic acid encodes a codon-optimized *Ralstonia* ethylene-forming enzyme. In a related embodiment, the codon optimization is for *Escherichia coli* codon usage. In yet another related embodiment, the engineered nucleic acid is SEQ ID NO. 7.

In certain embodiments, the engineered cell of the invention produces ethylene in an amount greater than about 1 mg, 100 mg, 500 mg, 1 g, 5 g, 10 g, 20 g, 25 g, 30 g, 35 g, 40 g, 50 g, 100 g, 120 g, or 150 g per liter of fermentation medium In certain embodiments, the engineered nucleic acid comprised by the engineered cell of the invention encodes an alcohol dehydrogenase activity. In related embodiments, the alcohol dehydrogenase activity is selected from *Z. mobilis* adhII, *Z. mobilis* adhII TS42 and *Z. mobilis* adhB activity. In another related embodiment, the engineered nucleic acid encodes a NADPH-dependent alcohol dehydrogenase activity. In yet another embodiment, wherein the NADPH-dependent alcohol dehydrogenase activity is *Moorella* sp. HUC22-1 adhA.

In another embodiment, the engineered nucleic acid comprised by the engineered cell of the invention encodes a pyruvate decarboxylase activity. In a related embodiment, the pyruvate decarboxylase activity is selected from *Z. palmae* and *Z. mobilis* pdc activity.

In certain embodiments, the engineered cell of the invention, in culture, is capable of producing ethanol in a yield of at least about 249 mg/L culture medium in 72 hours. In certain other embodiments, the yield is at least about 296 mg/L of ethanol over 72 hours. In still other embodiments, the ethanol yield is between about 2.5 to about 5 g/L culture medium-hr. In other embodiments, the level of acetaldehyde in said culture after 72 hours is less than about 14 mg/L. In other embodiments, the cell in culture produces at least about 36 mg/L of ethanol per OD, or at least about 47 mg/L of ethanol per OD.

In another embodiment, the engineered nucleic acid comprised by the engineered cell of the invention encodes a methionine synthase activity.

In another embodiment, the engineered nucleic acid comprised by the engineered cell of the invention encodes a phosphate transporter activity selected from the group consisting of an *E. coli* sugar phosphate transporter UhpT (NP_418122.1), an *A. thaliana* glucose-6-phosphate transporter GPT1 (AT5G54800.1), and an *A. thaliana* glucose-6-phosphate transporter GPT2 (AT1G61800.1).

In another embodiment, the engineered nucleic acid comprised by the engineered cell of the invention encodes a phosphatase enzyme activity selected from the group consisting of a *H. sapiens* glucose-6-phosphatase G6PC (P35575), an *E. coli* glucose-1-phosphatase Agp (P19926), an *E. cloacae* glucose-1-phosphatase AgpE (Q6EV19), and an *E. coli* acid phosphatase YihX (P0A8Y3).

In another embodiment, the engineered nucleic acid comprised by the engineered cell of the invention encodes a glucose/hexose transporter activity selected from the group consisting of a *H. sapiens* glucose transporter GLUT-1, -3, or -7 (P11166, P11169, Q6PXP3), a *S. cerevisiae* hexose transporter HXT-1, -4, or -6 (P32465, P32467, P39003), and a *Z. mobilis* glucose uniporter Glf (P21906). In a related embodiment, the engineered cell of the invention further comprising an engineered nucleic acid encoding a Glucose/fructose:H+ symporter, a GlcP Bacteria GlcP of *Synechocystis* sp. (P15729), a major glucose (or 2-deoxyglucose) uptake transporter GlcP Q7BEC, a hexose (glucose and fructose) transporter, a PfHT1 of *Plasmodium falciparum* O97467, a Glut-1 transporter, or a Glut-2 transporter.

In another aspect, the engineered cell provided by the invention is attenuated in an enzyme activity selected from the group consisting of: cellulose synthase; glycogen synthase; sucrose phosphate synthase; sucrose phosphorylase; alpha-1,4-glucan lyase; and 1,4-alpha-glucan branching enzyme. In a related aspect, the engineered cell further comprises an engineered nucleic acid encoding a phosphatase or a hexokinase activity.

In yet another embodiment, the invention provides an engineered cell comprising a glycogen hydrolysis activity selected from the group consisting of alpha, beta, gamma amylases; glucoamylase; isoamylase; pullulanase; amylomaltase; amylo-alpha-1,6-glucosidase; phosphorylase kinase; and phosphorylase.

In yet another embodiment, the invention provides an engineered cell capable of producing a sugar or sugar phosphate selected from the group consisting of glucose, glucose-6-phosphate, fructose-6-phosphate, maltose, and maltose phosphate. In a related embodiment, the cell is capable of producing a sugar or sugar phosphate above its endogenous levels and transporting said sugar outside of the cell. In yet another related embodiment, the cell produces a sugar selected from the group of sugars consisting of glucose, maltose, fructose, sucrose, xylose, pentose, rhamnose, and arabinose. In certain aspects, the engineered cell of the invention, in culture, is capable of producing sugar or sugar phosphate in an amount greater than about 1 mg, 100 mg, 500 mg, 1 g, 5 g, 10 g, 20 g, 25 g, 30 g, 35 g, 40 g, 50 g, 100 g, 120 g, or 150 g per liter of fermentation medium.

In yet another embodiment, the engineered cell provided by the invention comprises an engineered nucleic acid encoding an activity selected from the group consisting of an acetyl-CoA acetyltransferase, AtoB, a β-hydroxybutyryl-CoA dehydrogenase, a crotonase, a CoA dehydrogenase, a CoA-acylating aldehyde dehydrogenase (ALDH), and an aldehyde-alcohol dehydrogenase, AdhE. In still another embodiment, the cell comprises an engineered nucleic acid encoding an activity selected from the group consisting of 2-dehydro-3-deoxyphosphoheptonate aldolase, aroF (EC 2.5.1.54), a 3-dehydroquinate synthase, aroB (EC 4.2.3.4), a 3-dehydroquinate dehydratase, aroD (EC 4.2.1.10), a 3-dehydroshikimate dehydratase, quiC (EC 4.2.1.n), a β-ketoadipyl-CoA synthase, pcaF (EC 2.3.1.174), a β-ketoadipate CoA-transferase, pcaIJ (EC 2.8.3.6), a 3-oxoadipate enol-lactone hydrolase, pcaL (EC 3.1.1.24), a 4-carboxymuconolactone decarboxylase, pcaL (EC 4.1.1.44), a γ-carboxy-cis, cis-muconate cycloisomerase, pcaB (EC 5.5.1.2), a protocatechuate 3,4-dioxygenase, pcaGH (EC 1.13.11.3), a protocatechuate 1,2-cis-dihydrodiol dehydrogenase, tpaC (EC 1.3.1.n), and a terephthalate 1,2-dioxygenase, tpaAB (EC 1.14.12.15). In yet another embodiment, the cell comprises an engineered nucleic acid encoding an activity selected from the group consisting of alpha-D-glucose-6-phosphate ketol-isomerase, PGI1 (EC 5.3.1.9), a D-Mannose-6-phosphate ketol-isomerase, din9 (EC 5.3.1.8), a D-Mannose 6-phosphate 1,6-phosphomutase, atpmm (EC 5.4.2.8), a mannose-1-phosphate guanylyltransferase, cyt (EC 2.7.7.22), a GDP-mannose 3,5-epimerase, gme (EC 5.1.3.18), a galactose-1-phosphate guanylyltransferase, VTC2 (EC 2.7.n.n), an L-galactose 1-phosphate phosphatase, VTC4 (EC 3.1.3.n), an L-galactose dehydrogenase, At4G33670 (EC 1.1.1.122), and an L-galactonolactone oxidase, ATGLDH (EC 1.3.3.12).

In another embodiment, the engineered cell provided by the invention comprises an engineered nucleic acid encoding an activity selected from the group consisting of a C-16:1 thioesterase, fatB, a malonyl-CoA:ACP transacylase, fabD, an alcohol reductase, acr1, a decarbonylase, cer1, and a gene listed in Table 11.

In yet another embodiment, the engineered cell provided by the invention comprises an engineered nucleic acid encoding a gene selected from the group consisting of *E. coli* tesA; *E. coli* fadD; and *A. baylyi* wax-dgat.

In certain embodiments, the engineered cell provided by the invention is capable of producing an alkane, alkene, methyl ester or ethyl ester.

In certain other embodiments, the engineered cell provided by the invention comprises an engineered nucleic acid encoding an MEV pathway enzyme. In some embodiments, the MEV pathway enzyme is selected from the group consisting of acetyl CoA thiolase, an HMG CoA synthase, an HMG CoA reductase, a mevalonate kinase, a phosphomevalonate kinase, a mevalonate pyrophosphate decarboxylase, and an IPP isomerase.

In yet another embodiment, the engineered cell provided by the invention comprises an engineered nucleic acid encoding a DXP pathway enzyme. In related embodiments, the DXP pathway enzyme is selected from the group consisting of a 1-deoxy-D-xylulose 5-phosphate synthase, a 1-deoxy-D-xylulose 5-phosphate reductoisomerase, a 4-diphosphocytidyl-2C-methyl-D-erythritol synthase, a 4-diphosphocytidyl 2C-methyl-D-erythritol kinase, a 2C methyl D erythritol 2,4 cyclodiphosphate synthase, a 1 hydroxy 2 methyl 2 (E) butenyl 4 diphosphate synthase, and an isopentyl/dimethylallyl diphosphate synthase.

In yet another embodiment, the engineered cell provided by the invention comprises a nucleic acid encoding an activity selected from the group consisting of a homocitrate synthase, lys21 (EC 2.3.3.14), a homoaconitase, lys4, lys3 (EC 4.2.1.36), a homoisocitrate dehydrogenase, lys12, lys11, lys10 (EC 1.1.1.87), a 2-aminoadipate transaminase, aro8 (EC 2.6.1.39), a phosphoglycerate dehydrogenase, serA (EC 1.1.1.95), a phosphoserine transaminase serC (EC 2.6.1.52), a phosphoserine phosphatase, serB (EC 3.1.3.3), a serine O acetyltransferase, AtSerat2;1 (EC 2.3.1.30), a cysteine synthase, At1G55880 (EC 2.5.1.47), an acetolactate synthase, ilvN, ilvB (EC 2.2.1.6), an acetohydroxyacid isomeroreductase, ilvC (EC 1.1.1.86), a dihydroxyacid dehydratase, ilvD (EC 4.2.1.9), a valine transaminase, ilvE (EC 2.6.1.42), an ACV synthetase, Ava_1613 (EC 6.3.2.26), an isopenicillin N synthase, Ava_5009 (EC 1.21.3.1), converts N [L 5 amino 5 carboxypentanoyl] L cysteinyl D valine and O2 to isopenicillin N, an isopenicillin N epimerase, cefD (EC 5.1.1.17), a cephalosporin biosynthesis expandase/hydroxylase, cefEF (EC 1.14.20.1, 1.14.11.26), and a deacetylcephalosporin C acetyltransferase, cefG (EC 2.3.1.175).

In yet another embodiment, the engineered cell provided by the invention comprises a nucleic acid encoding alcohol dehydratase activity (EC 4.2.1.n). In a related embodiment, the alcohol dehydratase activity is selected from the group of alcohol dehydratases having EC numbers 4.2.1.2, 4.2.1.3, 4.2.1.4, 4.2.1.11, 4.2.1.17, 4.2.1.55, 4.2.1.33, 4.2.1.34, 4.2.1.35, 4.2.1.54, 4.2.1.58, 4.2.1.60, 4.2.1.68, 4.2.1.74, or 4.2.1.79. In yet another embodiment, the alcohol dehydratase is EC 4.2.1.54.

In still other embodiments, the engineered cell provided by the invention is capable of producing a pharmaceutical or an intermediate thereof. In certain related embodiments, the pharmaceutical or intermediate thereof is produced in an amount greater than about 1 mg, 100 mg, 500 mg, 1 g, 5 g, 10 g, 20 g, 25 g, 30 g, 35 g, 40 g, 50 g, 100 g, 120 g, or 150 g per liter of fermentation medium.

In still further embodiments, the engineered cell provided by the invention is capable of producing a carbon-based product of interest comprises a compound selected from the group consisting of an alcohol, ethanol, propanol, isopropanol, butanol, fatty alcohols, fatty acid ester, wax ester, ethyl ester, methyl ester, hydrocarbons, n-alkanes, propane, octane, diesel, JP8, polymers, terephthalate, polyol, 1,3-propanediol, 1,4-butanediol, PHA, PHB, acrylate, adipic acid, ε-caprolactone, isoprene, caprolactam, rubber, lactate, DHA, 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, HPA, lactic acid, THF, gamma butyrolactone, pyrrolidones, hydroxybutyrate, glutamic acid, levulinic acid, acrylic acid, malonic acid, carotenoid, isoprenoid, itaconic acid, limonene, pharmaceutical or pharmaceutical intermediates, erythromycin 7-ADCA/cephalosporin, polyketides, statin, paclitaxel, docetaxel, terpene, peptide, steroid, and an omega fatty acid. In certain embodiments, the isoprenoid produced by the cell is selected from the group consisting of an isoprenoid selected from isopentylpyrophosphate (IPP), dimethylallyl pyrophosphate (DMAP), a monoterpene a sesquiterpene, a diterpene, a triterpene, a tetraterpene, and a polyterpene.

In additional embodiments, the engineered cell provided by the invention comprises an the cell is selected from eukaryotic plants, algae, cyanobacteria, green-sulfur bacteria, green non-sulfur bacteria, purple sulfur bacteria, purple non-sulfur bacteria, extremophiles, yeast, fungi, engineered organisms thereof, and synthetic organisms. In certain related embodiments, the cell is light dependent or fixes carbon. In other related embodiments, the cell has autotrophic activity or photoautotrophic activity. In other embodiments, the cell is photoautotrophic in the presence of light and heterotrophic or mixotrophic in the absence of light. In other related embodiments, the engineered cell is a plant cell selected from the group consisting of *Arabidopsis, Beta, Glycine, Jatropha, Miscanthus, Panicum, Phalaris, Populus, Saccharum, Salix, Simmondsia* and *Zea*. In still other related embodiments, the engineered cell of the invention is an algae and/or cyanobacterial organism selected from the group consisting of *Acanthoceras, Acanthococcus, Acalyochloris, Achnanthes, Achnanthidium, Actinastrum, Actinochloris, Actinocyclus, Actinotaenium, Amphichlysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Claysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostornum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyram-*

*ichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thermosynechococcus, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis*, and *Zygonium*. In yet other related embodiments, the engineered cell provided by the invention is derived from a *Chloroflexus, Chloronema, Oscillochloris, Heliothrix, Herpetosiphon, Roseiflexus*, and *Thermomicrobium* cell; a green sulfur bacteria selected from: *Chlorobium, Clathrochloris*, and *Prosthecochloris*; a purple sulfur bacteria is selected from: *Allochromatium, Chromatium, Halochromatium, Isochromatium, Marichromatium, Rhodovulum, Thermochromatium, Thiocapsa, Thiorhodococcus*, and *Thiocystis*; a purple non-sulfur bacteria is selected from: *Phaeospirillum, Rhodobaca, Rhodobacter, Rhodomicrobium, Rhodopila, Rhodopseudomonas, Rhodothalassium, Rhodospirillum, Rodovibrio*, and *Roseospira*; an aerobic chemolithotrophic bacteria selected from: nitrifying bacteria. *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria, *Hydrogenobacter* sp., iron and manganese-oxidizing and/or depositing bacteria, *Siderococcus* sp., and magnetotactic bacteria, *Aquaspirillum* sp; an archaeobacteria selected from: methanogenic archaeobacteria, *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic sulfur-Metabolizers such as *Thermoproteus* sp., *Pyrodictium* sp., *Sulfolobus* sp., *Acidianus* sp., *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast; and extremophile selected from *Pyrolobus fumarii; Synechococcus lividis*, mesophiles, psychrophiles, *Psychrobacter*, insects, *Deinococcus radiodurans*, piezophiles, barophiles, hypergravity tolerant organisms, hypogravity tolerant organisms, vacuum tolerant organisms, tardigrades, insects, microbes seeds, dessicant tolerant anhydrobiotic organisms, xerophiles, *Artemia salina*, nematodes, microbes, fungi, lichens, salt tolerant organisms halophiles, *halobacteriacea, Dunaliella salina*, pH tolerant organisms, alkaliphilcs, *Natronobacterium, Bacillus firmus* OF4, *Spirulina* spp., acidophiles, *Cyanidium caldarium, Ferroplasma* sp., anaerobes, which cannot tolerate $O_2$, *Methanococcus jannaschii*, microaerophils, which tolerate some $O_2$, *Clostridium*, aerobes, which require $O_2$, gas tolerant organisms, which tolerate pure $CO_2$, *Cyanidium caldarium*, metal tolerant organisms, metalotolerants, *Ferroplasma acidarmanus Ralstonia* sp. CH34.

In yet other embodiments, engineered cell provided by the invention is derived from *Arabidopsis thaliana, Panicum virgatum, Miscanthus giganteus*, and *Zea mays* (plants), *Botryococcus braunii, Chlamydomonas reinhardtii* and *Dunaliela salina* (algae), *Synechococcus* sp. PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus*, and *Rhodopseudomonas palusris* (purple non-sulfur bacteria).

In still other embodiments, the engineered cell provided by the invention is a *Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis* cell.

In certain embodiments, the engineered cell provided by the invention are capable of conducting or regulating at least one metabolic pathway selected from the group consisting of photosynthesis, sulfate reduction, methanogenesis, acetogenesis, reductive TCA cycle, Calvin cycle, 3-HPA cycle and 3HP/4HB cycle.

In certain other embodiments, the invention provides a method for producing carbon-based product of interest or intermediate thereof comprising: introducing one or more engineered nucleic acids into a carbon fixing organism, wherein said engineered host cell is capable of using a minimum amount of light energy to synthesize a carbon-based product of interest directly from carbon dioxide and water, culturing said engineered host cell, then isolating a carbon-based product of interest from said engineered cell or culture medium. In a related embodiment, the cell is cultured in a photobioreactor. In another related embodiment, the carbon-based products of interest are released, permeated or exported from the cell. In yet another related embodiment, the carbon-based product is isolated from the culture medium.

In certain embodiments, the engineered cell provided by the invention is capable of producing a carbon-based product of interest characterized as having $-\delta_p$(‰) of about 63.5 to about 66 and $-D$(‰) of about 37.5 to about 40.

The invention also provides a method for monetizing carbon-based product of interest production and $CO_2$ taken up in association with the production of a carbon-based product of interest by an engineered photoautotrophic organism, comprising: quantifying an amount of said product produced by said engineered photoautotrophic organism; quantifying an amount of $CO_2$ taken up in association with said amount of said product produced; valuing said amount of said product according to a market value; valuing said amount of $CO_2$ taken up in association with said amount of product produced; and monetizing said amounts of said product produced and $CO_2$ taken up in association with said amount of said product produced by selling said amount of said product and selling a $CO_2$ credit into a carbon market.

The invention also provides a method for the biogenic production of ethanol, comprising: culturing an engineered cyanobacterium in a culture medium in the presence of light and CO2, wherein said cyanobacterium comprises at least two copies of a recombinant alcohol dehydrogenase gene, and wherein at least one copy of said recombinant alcohol dehydrogenase gene is extrachromosomal. In certain related embodiments, the expression of at least one copy of said recombinant alcohol dehydrogenase gene is driven by a lambda cI promoter.

In another embodiment, the invention provides a method for increasing the production of ethanol by an engineered cyanobacterium, comprising the step of varying the activity of recombinantly expressed alcohol dehydrogenase and pyruvate decarboxylase in said cyanobacterium. In certain embodiments, the cyanobacterium is a thermophile. In a related embodiment, the activity levels are varied by differentially expressing the enzymes alcohol dehydrogenase and pyruvate decarboxylase. In yet another embodiment, the differential expression is achieved by modulating the strength of a promoter that controls expression of alcohol dehydrogenase or pyruvate decarboxylase. In yet another embodiment, the method of claim 4, wherein said expression of alcohol dehydrogenase is driven by promoters on at least two distinct plasmids, e.g., a plasmid selected from the group of plasmids consisting of AQ1, pAQ3, pAQ4, pAQ5, pAQ6, and pAQ7. In yet another embodiment, the activity is varied by controlling the level of a co-factor required by alcohol dehydrogenase or pyruvate decarboxylase.

In certain embodiments of the method for increasing the production of ethanol by an engineered cyanobacterium, the measured level of acetaldehyde released into said culture medium by said engineered organism is less than about 7 mg/L after approximately 10 days of culture. In certain other embodiments, the cumulative amount of ethanol released into said culture medium by said engineered organism is equal to or greater than about 4 g/L after approximately 380 hours. In yet other embodiments, the measured level of ethanol released into said culture medium by said engineered organism is at least about 1750 mgs/L. In still other embodiments, the measured concentration (mg/ml) of ethanol released into said culture medium by said engineered organism is 100, 200 or 300 fold higher than the measured level of acetaldehyde in said culture medium.

The invention also provides an engineered cyanobacterium comprising alcohol dehydrogenase under the control of the lambda cI promoter. In related embodiments, the engineered cyanobacterium is an engineered *Synechococcus* strain comprising at least two engineered plasmids. For example, the plasmics could be selected from the group consisting of pAQ1, pAQ3, pAQ4, pAQ5, pAQ6, and pAQ7. In related embodiments, the two engineered plasmids separately encode a recombinant alcohol dehydrogenase activity. In yet other related embodiments, the recombinant alcohol dehydrogenase activity is $adhA_M$. In one embodiment, the cyanobacterium lacks a functioning lactate dehydrogenase gene or lactate dehydrogenase enzyme activity. In yet another embodiment, the cyanobacterium is engineered to express a recombinant pyruvate decarboxylase activity in addition to the alcohol dehydrogenase activity. In yet another embodiment, the recombinant pyruvate decarboxylase activity is encoded by one of the least two engineered plasmids encoding the recombinant alcohol dehydrogenase activity.

BRIEF DESCRIPTION OF THE FIGURES

FIG. 1(A-O) provides various genes identified that can be expressed, upregulated, attenuated or knocked out in engineering carbon dioxide fixing microorganisms of the invention in the production of carbon-based products of interest.

FIG. 19 is a table indicating the amounts of maltose found in cell pellet extracts given as mg/L of culture.

DETAILED DESCRIPTION

Abbreviations and Terms

Figure 2:
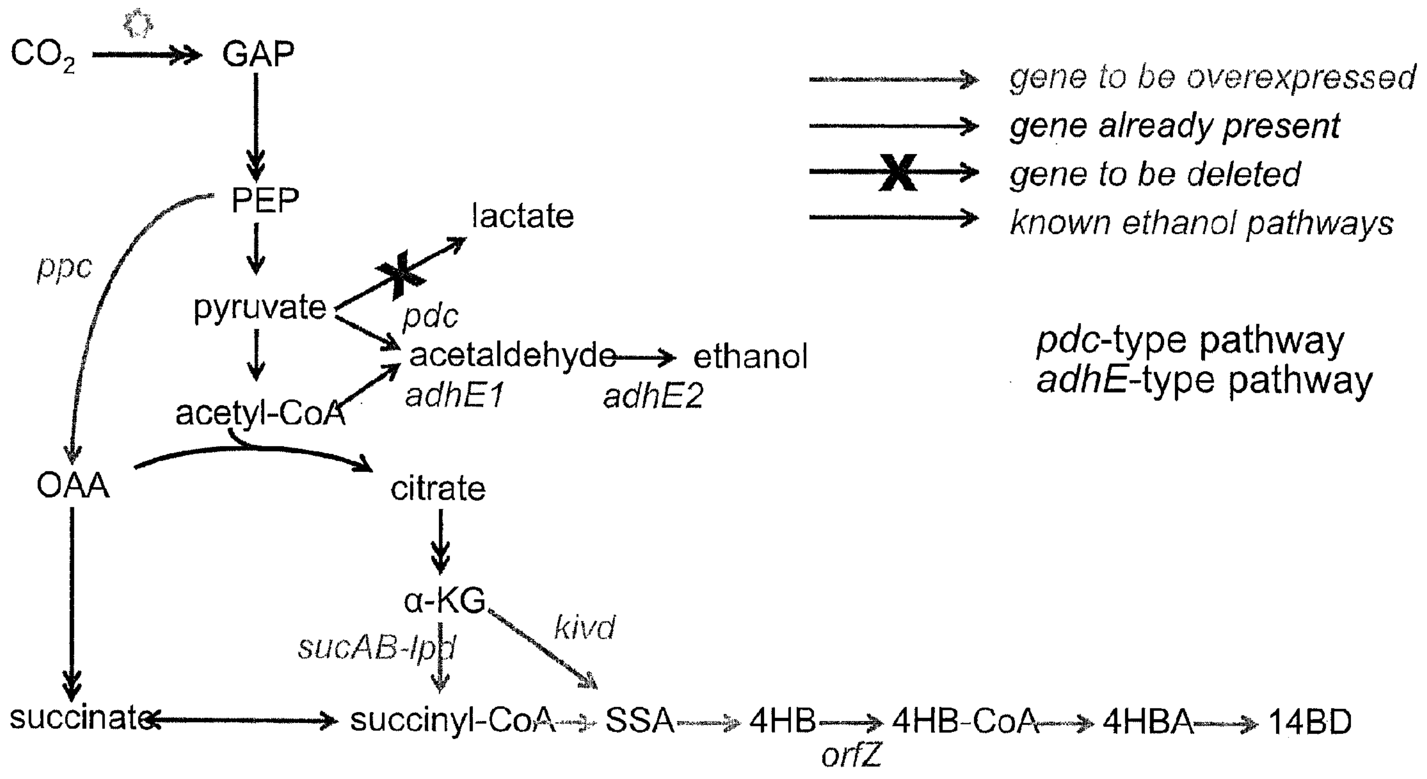
FIG. 2 provides an example of pathways to produce ethanol, succinate and other derivates.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and reference to "comprising the thioesterase" includes reference to one or more thioesterase peptides and equivalents thereof known to those of ordinary skill in the art, and so forth. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Accession Numbers: The accession numbers throughout this description are derived from the NCBI database (National Center for Biotechnology Information) maintained by the National Institute of Health, U.S.A. The accession numbers are as provided in the database on Feb. 1, 2008.

Enzyme Classification Numbers (EC): The EC numbers provided throughout this description are derived from the KEGG Ligand database, maintained by the Kyoto Encyclopedia of Genes and Genomics, sponsored in part by the University of Tokyo. The EC numbers are as provided in the database on Feb. 1, 2008.

Amino acid: Triplets of nucleotides, referred to as codons, in DNA molecules code for amino acid in a peptide. The term codon is also used for the corresponding (and complementary) sequences of three nucleotides in the mRNA into which the DNA sequence is transcribed.

Attenuate: The term as used herein generally refers to a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Attenuation also includes amino acid sequence changes by altering the nucleic acid sequence, placing the gene under the control of a less active promoter, downregulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

"Carbon-based Products of Interest" include alcohols such as ethanol, propanol, isopropanol, butanol, fatty alcohols, fatty acid esters, wax esters; hydrocarbons and alkanes such as propane, octane, diesel, Jet Propellant 8, polymers such as terephthalate, 1,3-propanediol, 1,4-butanediol, polyols, polyhydroxyalkanoates (PHAs), polyhydroxybutyrates (PHBs), acrylate, adipic acid, ε-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypri-onic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodesacetoxycephalosporonic acid, cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

Deletion: The removal of one or more nucleotides from a nucleic acid molecule or one or more amino acids from a protein, the regions on either side being joined together.

DNA: Deoxyribonucleic acid. DNA is a long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached.

Endogenous: As used herein with reference to a nucleic acid molecule and a particular cell or microorganism refers to a nucleic acid sequence or peptide that is in the cell and was not introduced into the cell (or its progentors) using recombinant engineering techniques. For example, a gene that was present in the cell when the cell was originally isolated from nature. A gene is still considered endogenous if the control sequences, such as a promoter or enhancer sequences that activate transcription or translation have been altered through recombinant techniques.

"An enzyme activity": As used herein, the term "an enzyme activity" means that the indicated enzyme (e.g., "an alcohol dehydrogenase activity") has measurable attributes in terms of, e.g., substrate specific activity, pH and temperature optima, and other standard measures of enzyme activity as the activity encoded by a reference enzyme (e.g., alcohol dehydrogenase). Furthermore, the enzyme is at least 90% identical at a nucleic or amino acid level to the sequence of the reference enzyme as measured by a BLAST search.

Exogenous: As used herein with reference to a nucleic acid molecule and a particular cell or microorganism refers to a nucleic acid sequence or peptide that was not present in the cell when the cell was originally isolated from nature. For example, a nucleic acid that originated in a different microorganism and was engineered into an alternate cell using recombinant DNA techniques or other methods for delivering said nucleic acid is exogenous.

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Expression Control Sequence: as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

Overexpression: When a gene is caused to be transcribed at an elevated rate compared to the endogenous transcription rate for that gene. In some examples, overexpression additionally includes an elevated rate of translation of the gene compared to the endogenous translation rate for that gene. Methods of testing for overexpression are well known in the art, for example transcribed RNA levels can be assessed using reverse transcriptase polymerase chain reaction (RT-PCR) and protein levels can be assessed using sodium dodecyl sulfate polyacrylamide gel electrophoresis (SDS-PAGE) analysis. Furthermore, a gene is considered to be overexpressed when it exhibits elevated activity compared to its endogenous activity, which may occur, for example, through reduction in concentration or activity of its inhibitor, or via expression of mutant version with elevated activity. In preferred embodiments, when the host cell encodes an endogenous gene with a desired biochemical activity, it is useful to overexpress an exogenous gene, which allows for more explicit regulatory control in the fermentation and a means to potentially mitigate the effects of central metabolism regulation, which is focused around the native genes explicity.

Downregulation: When a gene is caused to be transcribed at a reduced rate compared to the endogenous gene transcription rate for that gene. In some examples, downregulation additionally includes a reduced level of translation of the gene compared to the endogenous translation rate for that gene. Methods of testing for downregulation are well known to those in the art. For example, the transcribed RNA levels can be assessed using RT-PCR, and protein levels can be assessed using SDS-PAGE analysis.

Knock-out: A gene whose level of expression or activity has been reduced to zero. In some examples, a gene is knocked-out via deletion of some or all of its coding sequence. In other examples, a gene is knocked-out via introduction of one or more nucleotides into its open-reading frame, which results in translation of a non-sense or otherwise non-functional protein product.

Autotroph: Autotrophs (or autotrophic organisms) are organisms that produce complex organic compounds from simple inorganic molecules and an external source of energy, such as light (photoautotroph) or chemical reactions of inorganic compounds.

Hydrocarbon: The term generally refers to a chemical compound that consists of the elements carbon (C), hydrogen (H) and optionally oxygen (O). There are essentially three types of hydrocarbons, e.g., aromatic hydrocarbons, saturated hydrocarbons and unsaturated hydrocarbons such as alkenes, alkynes, and dienes. The term also includes fuels, biofuels, plastics, waxes, solvents and oils. Hydrocarbons encompass biofuels, as well as plastics, waxes, solvents and oils.

"Immiscible" or "Immiscibility" refers to the relative inability of a compound to dissolve in water and is defined by the compounds partition coefficient. The partition coefficient, P, is defined as the equilibrium concentration of compound in an organic phase (in a bi-phasic system the organic phase is usually the phase formed by the fatty acid derivative during the production process, however, in some examples an organic phase can be provided (such as a layer of octane to facilitate product separation) divided by the concentration at equilibrium in an aqueous phase (i.e., fermentation broth). When describing a two phase system the P is usually discussed in terms of logP. A compound with a logP of 10 would partition 10:1 to the organic phase, while a compound of logP of 0.1 would partition 10:1 to the aqueous phase.

Biosynthetic pathway: Also referred to as "metabolic pathway," refers to a set of anabolic or catabolic biochemical reactions for converting (transmuting) one chemical species into another. For example, a hydrocarbon biosynthetic pathway refers to the set of biochemical reactions that convert inputs and/or metabolites to hydrocarbon product-like intermediates and then to hydrocarbons or hydrocarbon products. Anabolic pathways involve constructing a larger molecule from smaller molecules, a process requiring energy. Catabolic pathways involve breaking down of larger: molecules, often releasing energy.

Cellulose: Cellulose $[(C_6H_{10}O_5)_n]$ is a long-chain polymer polysaccharide carbohydrate, of beta-glucose. It forms the primary structural component of plants and is not digestible by humans. Cellulose is a common material in plant cell walls and was first noted as such in 1838. It occurs naturally in almost pure form only in cotton fiber; in combination with lignin and any hemicellulose, it is found in all plant material.

Biofuel: A biofuel is any fuel that derives from a biological source. Biofuel refers to one or more hydrocarbons, one or more alcohols, one or more fatty esters or a mixture thereof. Preferably, liquid hydrocarbons are used.

"Fuel component" is any compound or a mixture of compounds that are used to formulate a fuel composition. There are "major fuel components" and "minor fuel components." A major fuel component is present in a fuel composition by at least 50% by volume; and a minor fuel component is present in a fuel composition by less than 50%. Fuel additives are minor fuel components. The isoprenoid compounds disclosed herein can be a major component or a minor component, by themselves or in a mixture with other fuel components.

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol.

%, less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

Nucleic Acid Molecule: The term encompasses both RNA and DNA molecules including, without limitation, cDNA, genomic DNA, and mRNA and also includes synthetic nucleic acid molecules, such as those that are chemically synthesized or recombinantly produced. The nucleic acid molecule can be double-stranded or single-stranded, circular or linear. If single-stranded, the nucleic acid molecule can be the sense strand or the antisense strand.

Engineered nucleic acid: An "engineered nucleic acid" is a nucleic acid molecule that includes at least one difference from a naturally-occurring nucleic acid molecule. An engineered nucleic acid includes all exogenous modified and unmodified heterologous sequences (i.e., sequences derived from an organism or cell other than that harboring the engineered nucleic acid) as well as endogenous genes, operons, coding sequences, or non-coding sequences, that have been modified, mutated, or that include deletions or insertions as compared to a naturally-occurring sequence. Engineered nucleic acids also include all sequences, regardless of origin, that are linked to an inducible promoter or to another control sequence with which they are not naturally associated.

Suitable fermentation conditions. The term generally refers to fermentation media and conditions adjustable with, pH, temperature, levels of aeration, etc., preferably optimum conditions that allow microorganisms to produce carbon-based products of interest. To determine if culture conditions permit product production, the microorganism can be cultured for about 24 hours to one week after inoculation and a sample can be obtained and analyzed. The cells in the sample or the medium in which the cells are grown are tested for the presence of the desired product.

Isolated: An "isolated" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems. However, "isolated" docs not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g. by homologous recombination) for the native promoter of a gene in the genome of a human cell, such that this gene has an altered expression pattern. This gene would now become "isolated" because it is separated from at least some of the sequences that naturally flank it. A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g. by human intervention. An "isolated nucleic acid" also includes a nucleic acid integrated into a host cell chromosome at a heterologous site, as well as a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. Configurations of separate genes that are transcribed in tandem as a single messenger RNA are denoted as operons. Thus placing genes in close proximity, for example in a plasmid vector, under the transcriptional regulation of a single promoter, constitutes a synthetic operon.

Purified: The term purified does not require absolute purity; rather, it is intended as a relative term. Thus, for example, a purified product preparation, is one in which the product is more concentrated than the product is in its environment within a cell. For example, a purified wax is one that is substantially separated from cellular components (nucleic acids, lipids, carbohydrates, and other peptides) that can accompany it. In another example, a purified wax preparation is one in which the wax is substantially free from contaminants, such as those that might be present following fermentation.

Figure 4:
FIG. 4 provides an example of a pathway for n-alkane and fatty alcohol synthesis.

In one example, a fatty acid ester is purified when at least about 50% by weight of a sample is composed of the fatty acid ester, for example when at least about 60%, 70%, 80%, 85%, 90%, 92%, 95%, 98%, or 99% or more of a sample is composed of the fatty acid ester. Examples of methods that can be used to purify waxes, fatty alcohols, and fatty acid esters are well-known to persons of ordinary skill in the art and are described below. An example of a pathway for n-alkane and fatty alcohol synthesis is provided in FIG. 4.

Detectable: Capable of having an existence or presence ascertained using various analytical methods as described throughout the description or otherwise known to a person skilled in the art.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

The term "recombinant host cell" ("expression host cell," "expression host system," "expression system," or simply "host cell"), as used herein, refers to a cell into which a recombinant vector has been introduced, e.g., a vector comprising acyl-CoA synthase. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

Release: The movement of a compound from inside a cell (intracellular) to outside a cell (extracellular). The movement can be active or passive. When release is active it can be facilitated by one or more transporter peptides and in some examples it can consume energy. When release is passive, it can be through diffusion through the membrane and can be facilitated by continually collecting the desired compound from the extracellular environment, thus promoting further diffusion. Release of a compound can also be accomplished by lysing a cell.

Surfactants: Substances capable of reducing the surface tension of a liquid in which they are dissolved. They are typically composed of a water-soluble head and a hydrocarbon chain or tail. The water soluble group is hydrophilic and can be either ionic or nonionic, and the hydrocarbon chain is hydrophobic. Surfactants are used in a variety of products, including detergents and cleaners, and are also used as auxiliaries for textiles, leather and paper, in chemical processes, in cosmetics and pharmaceuticals, in the food industry and in agriculture. In addition, they can be used to aid in the extraction and isolation of crude oils which are found in hard to access environments or as water emulsions.

There are four types of surfactants characterized by varying uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons and are typically used in shampoos. Non-ionic surfactants are generally used in cleaning products.

Vector: The term "vector" as used herein refers to a nucleic acid molecule capable of transporting another nucleic acid to which it has been linked. One type of vector is a "plasmid," which refers to a circular double-stranded DNA loop into which additional DNA segments may be ligated. Other vectors include cosmids, bacterial artificial chromosomes (BACs) and yeast artificial chromosomes (YACs). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors"). A vector can also include one or more selectable marker genes and other genetic elements known in the art.

Wax: A variety of fatty acid esters which form solids or pliable substances under an identified set of physical conditions. Fatty acid esters that are termed waxes generally have longer carbon chains than fatty acid esters that are not waxes. For example, a wax generally forms a pliable substance at room temperature.

Fatty ester: Includes any ester made from a fatty acid. The carbon chains in fatty acids can contain any combination of the modifications described herein. For example, the carbon chain can contain one or more points of unsaturation, one or more points of branching, including cyclic branching, and can be engineered to be short or long. Any alcohol can be used to form fatty acid esters, for example alcohols derived from the fatty acid biosynthetic pathway, alcohols produced by the production host through non-fatty acid biosynthetic pathways, and alcohols that are supplied in the fermentation broth.

Fatty acid: Includes products or derivatives thereof made in part from the fatty acid biosynthetic pathway of the host organism. The fatty acid biosynthetic pathway includes fatty acid synthase enzymes which can be engineered as described herein to produce fatty acid derivatives, and in some examples can be expressed with additional enzymes to produce fatty acid derivatives having desired carbon chain characteristics. Exemplary fatty acid derivatives include for example, short and long chain alcohols, hydrocarbons, and fatty acid esters including waxes.

General Methods for Engineering Microorganisms to Produce Carbon-Based Products

The methods of the invention are based on principles of metabolic engineering, and uses, e.g., engineered pathways as described in, e.g., WO 2007/136762 and WO 2007/139925 (each of which is incorporated by reference in its entirety for all purposes) to make products from energy captured by photoautotrophic organisms. Generally, carbon-based products of interest are produced by expressing a gene or a set of genes as described in FIG. 1 in a photoautotrophic microorganism, e.g., cyanobacteria, as described herein. Plasmids are constructed to express various proteins that are useful in production of carbon-based products, as described in the Examples herein, e.g., Example 1. The constructs can be synthetically made or made using standard molecular biology methods and all the cloned genes are put under the control of constitutive promoters or inducible promoters. Plasmids containing the genes of interest are transformed into the host and corresponding transformants are selected in LB plate supplemented with antibiotics such as spectinomycin, carbenicillin, etc. Using standard molecular biology techniques, cells in which a nucleic acid molecule has been introduced are transformed to express or over-express desired genes while other nucleic acid molecules are attenuated or functionally deleted. Transformation techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration. Transformants are inoculated into a suitable medium. The samples containing the transformants are grown at suitable temperatures in a shaker until they reach at certain OD. The cells are then spun down at and the cell pellets are suspended. Separation techniques allows for the sample to be subjected to GC/MS analysis. Total yield is determined.

Selected or Engineered Microorganisms for the Production of Carbon-Based Products of Interest Microorganism: Includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

A variety of host organisms can be transformed to produce a product of interest. Photoautotrophic organisms include eukaryotic plants and algae, as well as prokaryotic cyanobacteria, green-sulfur bacteria, green non-sulfur bacteria, purple sulfur bacteria, and purple non-sulfur bacteria.

Suitable organisms include extremophiles that withstand various environmental parameters such as temperature, radiation, pressure, gravity, vacuum, desiccation, salinity, pH, oxygen tension, and chemicals. They include hyperthermophiles, which grow at or above 80° C. such as *Pyrolobus fumarii*; thermophiles, which grow between 60-80° C. such as *Synechococcus lividis*; mesophiles, which grow between 15-60° C. and psychrophiles, which grow at or below 15° C. such as *Psychrobacter* and some insects. Radiation tolerant organisms include *Deinococcus radiodurans*. Pressure tolerant organisms include piezophiles or barophiles which tolerate pressure of 130 MPa. Hypergravity (e.g., >1 g) hypogravity (e.g., <1 g) tolerant organisms are also contemplated. Vacuum tolerant organisms include tardigrades, insects, microbes and seeds. Dessicant tolerant and anhydrobiotic organisms include xerophiles such as *Artemia salina*; nematodes, microbes, fungi and lichens. Salt tolerant organisms include halophiles (e.g., 2-5 M NaCl) *Halobacteriacea* and *Dunaliella salina*. pH tolerant organisms include alkaliphiles such as *Natronobacterium, Bacillus firmus* OF4, *Spirulina* spp. (e.g., pH>9) and acidophiles such as *Cyanidium caldarium, Ferroplasma* sp. (e.g., low pH). Anaerobes, which cannot tolerate $O_2$ such as *Methanococcus jannaschii*; microaerophils, which tolerate some $O_2$ such as *Clostridium* and aerobes, which require $O_2$ are also contemplated. Gas tolerant organisms, which tolerate pure $CO_2$ include *Cyanidium caldarium* and metal tolerant organisms include metalotolerants such as *Ferroplasma acidarmanus* (e.g., Cu, As, Cd, Zn), *Ralstonia* sp. CH34 (e.g., Zn, Co, Cd, Hg, Pb). Gross, Michael. *Life on the Edge: Amazing Creatures Thriving in Extreme Environments*. New York: Plenum (1998) and Seckbach, J. "Search for Life in the Universe with Terrestrial Microbes Which Thrive Under Extreme Conditions." In Cristiano Batalli Cosmovici, Stuart Bowyer, and Dan Werthemier, eds., *Astronomical and Biochemical Origins and the Search for Life in the Universe*, p. 511. Milan: Editrice Compositori (1997).

Plants include but are not limited to the following genera: *Arabidopsis, Beta, Glycine, Jatropha, Miscanthus, Panicum, Phalaris, Populus, Saccharum, Salix, Simmondsia* and *Zea*.

Algae and cyanobacteria include but are not limited to the following genera:

*Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloca, Chloroglocopsis, Chlorogonium, Chlorolobion, Chloromonas, Chlorophyscma, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microco-*

*leus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis*, and *Zygonium*.

Green non-sulfur bacteria include but are not limited to the following genera: *Chloroflexus, Chloronema, Oscillochloris, Heliothrix, Herpetosiphon, Roseiflexus*, and *Thermomicrobium.*

Green sulfur bacteria include but are not limited to the following genera: *Chlorobium, Clathrochloris*, and *Prosthecochloris.*

Purple sulfur bacteria include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis.*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roscospira.*

Aerobic chemolithotrophic bacteria include but are not limited to nitrifying bacteria such as *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligately chemolithotrophic hydrogen bacteria such as *Hydrogenobacter* sp., iron and manganese-oxidizing and/or depositing bacteria such as *Siderococcus* sp., and magnetotactic bacteria such as *Aquaspirillum* sp.

Archaeobacteria include but are not limited to methanogenic archaeobacteria such as *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic Sulfur-Metabolizers such as *Thermoproteus* sp., *Pyrodictium* sp., *Sulfolobus* sp., *Acidianus* sp. and other microorganisms such as, *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast.

HyperPhotosynthetic conversion requires extensive genetic modification; thus, in preferred embodiments the parental photoautotrophic organism can be transformed with exogenous DNA.

Preferred organisms for HyperPhotosynthetic conversion include: *Arabidopsis thaliana, Panicum virgatum, Miscanthus giganteus*, and *Zea mays* (plants), *Botryococcus braunii, Chlamydomonas reinhardtii* and *Dunaliela salina* (algae), *Synechococcus* sp PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus*, and *Rhodopseudomonas palusris* (purple non-sulfur bacteria).

Yet other suitable organisms include synthetic cells or cells produced by synthetic genomes as described in Venter et al. US Pat. Pub. No. 2007/0264688, and cell-like systems or synthetic cells as described in Glass et al. US Pat. Pub. No. 2007/0269862.

Still, other suitable organisms include microorganisms that can be engineered to fix carbon dioxide bacteria such as *Escherichia coli, Acetobacter aceti, Bacillus subtilis*, yeast and fungi such as *Clostridium ljungdahlii, Clostridium thermocellum, Penicillium chrysogenum, Pichia pastoris, Saccharomyces cerevisiae, Schizosaccharomyces pombe, Pseudomonas fluorescens*, or *Zymomonas mobilis*.

A common theme in selecting or engineering a suitable organism is autotrophic fixation of carbon, such as $CO_2$ to products. This would cover photosynthesis and methanogenesis. Acetogenesis, encompassing the three types of $CO_2$ fixation; Calvin cycle, acetyl CoA pathway and reductive TCA pathway is also covered. The capability to use carbon dioxide as the sole source of cell carbon (autotrophy) is found in almost all major groups of prokaryotes. The $CO_2$ fixation pathways differ between groups, and there is no clear distribution pattern of the four presently-known autotrophic pathways. Fuchs, G. 1989. Alternative pathways of autotrophic $CO_2$ fixation, p. 365-382. In H. G. Schlegel, and B. Bowien (ed.), Autotrophic bacteria. Springer-Verlag, Berlin, Germany. The reductive pentose phosphate cycle (Calvin-Bassham-Benson cycle) represents the $CO_2$ fixation pathway in almost all aerobic autotrophic bacteria, for example, the cyanobacteria.

Propagation of Selected Microorganisms

Methods for cultivation of photosynthetic organisms in liquid media and on agarose-containing plates are well known to those skilled in the art (see, e.g., websites associated with ATCC, and with the Institute Pasteur). For example, *Synechococcus* sp. PCC 7002 cells (available from the Pasteur Culture Collection of Cyanobacteria) are cultured in BG-11 medium (17.65 mM NaNO3, 0.18 mM K2HPO4, 0.3 mM MgSO4, 0.25 mM CaCl2, 0.03 mM citric acid, 0.03 mM ferric ammonium citrate, 0.003 mM EDTA, 0.19 mM Na2CO3, 2.86 mg/L H3BO3, 1.81 mg/L MnCl2, 0.222 mg/L ZnSO4, 0.390 mg/L Na2MoO4, 0.079 mg/L CuSO4, and 0.049 mg/L Co(NO3)2, pH 7.4) supplemented with 16 μg/L biotin, 20 mM MgSO4, 8 mM KCl, and 300 mM NaCl (see, e.g., website associated with the Institute Pasteur, and Price G D, Woodger F J, Badger M R, Howitt S M, Tucker L. "Identification of a SulP-type bicarbonate transporter in marine cyanobacteria. *Proc Natl. Acad. Sci*. USA (2004) 101(52): 18228-33). Typically, cultures are maintained at 28° C. and bubbled continuously with 5% CO2 under a light intensity of 120 μmol photons/m2/s. Alternatively, as described in Example 1, *Synechococcus* sp. PCC 7002 cells are cultured in $A^+$ medium as previously described [Frigaard N U et al. (2004) "Gene inactivation in the cyanobacterium *Synechococcus* sp. PCC 7002 and the green sulfur bacterium *Chlorobium tepidum* using in vitro-made DNA constructs and natural transformation," *Methods Mol. Biol.,* 274:325-340].

*Thermosynechococcus elongatus* BP-1 (available from the Kazusa DNAResearch Institute, Japan) is propagated in BG11 medium supplemented with 20 mM TES-KOH (pH 8.2) as previously described [Iwai M, Katoh H, Katayama M, Ikeuchi M. "Improved genetic transformation of the thermophilic cyanobacterium, *Thermosynechococcus elongatus* BP-1." Plant Cell Physiol (2004). 45(2):171-175)]. Typically, cultures are maintained at 50° C. and bubbled continuously with 5% CO2 under a light intensity of 38 μmol photons/m2/s. *T. elongatus* BP-1 can be grown in A medium also as described in Example 2.

*Chlamydomonas reinhardtii* (available from the *Chlamydomonas* Center culture collection maintained by Duke University, Durham, N.C.) are grown in minimal salt medium consisting of 143 mg/L K2HPO4, 73 mg/L KH2PO4, 400 mg/L NH4NO3, 100 mg/L MgSO4-7H2O, 50 mg/L CaCl2-2H20, 1 mL/L trace elements stock, and 10 mL/L 2.0 M MOPS titrated with Tris base to pH 7.6 as described (Geraghty A M, Anderson J C, Spalding M H. "A 36 kilodalton limiting-CO2 induced polypeptide of *Chlamydomonas* is distinct from the 37 kilodalton periplasmic anhydrase." Plant Physiol (1990). 93:116-121). Typically, cultures are maintained at 24° C. and bubbled with 5% CO2 in air, under a light intensity of 60 μmol photons/m2/s.

The above define typical propagation conditions. As appropriate, incubations are performed using alternate media or gas compositions, alternate temperatures (5-75° C.), and/or light fluxes (0-5500 μmol photons/m2/s).

Light is delivered through a variety of mechanisms, including natural illumination (sunlight), standard incandescent, fluorescent, or halogen bulbs, or via propagation in specially-designed illuminated growth chambers (for example Model LI15 Illuminated Growth Chamber (Sheldon Manufacturing, Inc. Cornelius, Oreg.). For experiments requiring specific wavelengths and/or intensities, light is distributed via light emitting diodes (LEDs), in which wavelength spectra and intensity can be carefully controlled (Philips).

Carbon dioxide is supplied via inclusion of solid media supplements (i.e., sodium bicarbonate) or as a gas via its distribution into the growth incubator or media. Most experiments are performed using concentrated carbon dioxide gas, at concentrations between 1 and 30%, which is directly bubbled into the growth media at velocities sufficient to provide mixing for the organisms. When concentrated carbon dioxide gas is utilized, the gas originates in pure form from commercially-available cylinders, or preferentially from concentrated sources including off-gas or flue gas from coal plants, refineries, cement production facilities, natural gas facilities, breweries, and the like.

Transformation of Selected Microorganisms

*Synechococcus* sp. PCC 7002 cells are transformed according to the optimized protocol previously described [Essich E S, Stevens Jr E, Porter R D "Chromosomal Transformation in the Cyanobacterium *Agmenellum quadruplicatum*". J Bacteriol (1990). 172(4):1916-1922]. Cells are grown in Medium A (18 g/L NaCl, 5 g/L MgSO4.7H20, 30 mg/L Na2EDTA, 600 mg/L KCl, 370 mg/L CaCl2.2H2O, 1 g/L NaNO3, 50 mg/L KH2PO4, 1 g/L Trizma base pH 8.2, 4 μg/L Vitamin B12, 3.89 mg/L FeCl3.6H20, 34.3 mg/L H3BO3, 4.3 mg/L MnCl2.4H20, 315 μg/L ZnCl2, 30 μg/L MoO3, 3 μg/L CuSO4.5H20, 12.2 μg/L CoCl2.6H20) [Stevens S E, Patterson C O P, and Myers J. "The production of hydrogen peroxide by green algae: a survey." J. Phycology (1973). 9:427-430] plus 5 g/L of NaNO3 to approximately 108 cells/mL. Nine volumes of cells are mixed with 1 volume of 1-10 μg/mL DNA in 0.15 M NaCl/0.015 M Na3 citrate and incubated at 27-30° C. for 3 hours before addition of 1 volume of DNaseI to a final concentration of 10 μg/mL. The cells are plated in 2.5 mL of 0.6% medium A overlay agar that was tempered at 45° C. and incubated. Cells are challenged with antibiotic by under-laying 2.0 mL of 0.6% medium A agar containing appropriate concentration of antibiotic with a sterile Pasteur pipette. Transformants are picked 3-4 days later. Selections are typically performed using 200 μg/ml kanamycin, 8 μg/ml chloramphenicol, 10 μg/ml spectinomycin on solid media, whereas 150 μg/ml kanamycin, 7 μg/ml chloramphenicol, and 5 μg/ml spectinomycin are employed in liquid media.

*T. elongatus* BP-1 cells are transformed according to the optimized protocol previously described (Iwai M, Katoh H, Katayama M, and Ikeuchi).

*E. coli* are transformed using standard techniques known to those skilled in the art, including heat shock of chemically competent cells and electroporation [Berger and Kimmel, Guide to Molecular Cloning Techniques, Methods in Enzymology volume 152 Academic Press, Inc., San Diego, Calif.; Sambrook et al. (1989) Molecular Cloning—A Laboratory Manual (2nd ed.) Vol. 1-3, Cold Spring Harbor Laboratory, Cold Spring Harbor Press, N.Y.; and Current Protocols in Molecular Biology, F. M. Ausubel et al., eds., Current Protocols, a joint venture between Greene Publishing Associates, Inc. and John Wiley & Sons, Inc., (through and including the 1997 Supplement)].

The biosynthetic pathways as described herein are first tested and optimized using episomal plasmids described above. Non-limiting optimizations include promoter swapping and tuning, ribosome binding site manipulation, alteration of gene order (e.g., gene ABC versus BAC, CBA, CAB, BCA), co-expression of molecular chaperones, random or targeted mutagenesis of gene sequences to increase or decrease activity, folding, or allosteric regulation, expression of gene sequences from alternate species, codon manipulation, addition or removal of intracellular targeting sequences such as signal sequences, and the like.

Each gene or engineered nucleic acid is optimized individually, or alternately, in parallel. Functional promoter and gene sequences are subsequently integrated into the *E. coli* chromosome to enable stable propagation in the absence of selective pressure (i.e., inclusion of antibiotics) using standard techniques known to those skilled in the art.

FIG. 1 lists genes involved in the production of carbon-based products of interest, related to associated pathways, Enzyme Commission (EC) Numbers, exemplary gene names, source organism, GenBank accession numbers, and homologs from alternate sources. When the parental organism encodes a gene with the indicated enzymatic activity, it is useful to overexpress these components or at least attenuate these components as indicated. In one embodiment, the native enzyme sequence is overexpressed or attenuated. In preferred embodiments, it is useful to overexpress or attenuate an exogenous gene, which allows for more explicit regulatory control in the bioprocess and a means to potentially mitigate the effects of central metabolism regulation, which is focused around the native genes explicitly.

Ethanol Production

In one aspect, alcohols such as ethanol, propanol, isopropanol, butanol, fatty alcohols, other such carbon-based products of interest are produced. FIG. 2 provides one pathway to produce ethanol, succinate and derivatives thereof.

To date, current yields of ethanol produced in cyanobacteria are not suited for commercial production at 1.3 mM per $OD_{730}$ per day, as disclosed in WO 2007/084477, or 1.7 μmol of ethanol per mg of chlorophyll per hour, as shown in U.S. Pat. No. 6,699,696.

The present invention, therefore, provides methods to produce a host cell capable of CO2 fixation that produces biofuels, e.g., ethanol at a commercial level, e.g., at between about 50 and 150 g/L in about a 48 hour period. In certain embodiments, the rate of ethanol productivity is in the range of about 2.5 g/L-hr to about 5 g/L-hr. In one embodiment, a host cell capable of CO2 fixation such as a cyanobacterium *Synechococcus* sp. PCC 7002 is engineered to express genes such as pdc and/or adh as disclosed. Such recombinant microorganism encodes PDC activity converting pyruvic acid to acetoaldehyde and/or ADH activity converting acetoaldehyde to ethanol. The transformed microorganism's ability to fix CO2 obviates the need to supplement with either sugars or biomass. Accordingly, the microorganisms of the present invention are attractive alternatives to produce biofuels. The present invention provides the w/v of ethanol to be at least 50, or at least 60 or at least 70 or at least 80 or at least 90 or at least 100 or at least 125 or at least 150 g/L or otherwise produced in commercial scale.

Enzyme Selection & Optimal Enzymes

Currently, fermentative products such as ethanol, butanol, lactic acid, formate, acetate produced in biological organisms employ a NADH-dependent processes. NAD is used to break down glucose or other sugar sources to form NADH. NADH is recycled during fermentation to $NAD^+$ to allow further sugar breakdown, which results in fermentative byproducts. During photosynthesis, however, the cell forms NADPH, which is used mostly for biosynthetic operations in biological organisms, e.g., cell for growth, division, and for building up chemical stores such as glycogen, sucrose, and other macromolecules. Fermentative products are produced in the light, but in small quantities.

Using natural or engineered enzymes that utilize NADPH as a source of reducing power instead of NADH would allow direct use of photosynthetic reducing power towards formation of normally fermentative byproducts. Accordingly, the present invention provides methods for producing fermentative products such as ethanol by expressing NADPH-dependent enzymes. This is an improvement from previous methods of using organisms such as algae to build stores of chemicals, which are subsequently used to make fermentation products at night or the extraneous use of separate organisms. In effect, fermentative products are formed at higher efficiencies directly in the light during photosynthesis. In addition, the obligatory production of macromolecules at high concentration is alleviated during the day, by producing such products directly during the day.

NADPH-dependent enzymes that produce normally fermented products are rare in nature. Accordingly, in certain aspects of the invention, ethanol is produced in organisms expressing or modified to express *Moorella* sp. HUC22-1 or a homolog thereof including at least three alcohol dehydrogenases such as AdhA (NCBI Accession YP_430754). This enzyme has previously shown to preferentially use NADP as a cofactor as opposed to NAD and produce ethanol at high rates from acetaldehyde ["Characterization of enzymes involved in the ethanol production of *Moorella* sp. HUC22-1"]. By co-expressing this gene in selected organisms, such as cyanobacteria, $NADPH_2$ formed during photosynthesis can be used directly to form ethanol in these organisms. Alternatively, enzymes that naturally use NADH can be engineered using established protein engineering techniques to require $NADPH_2$ rather than NADH.

In certain embodiments, NADPH-dependent AdhA from *Moorella* is co-expressed with pyruvate decarboxylase from *Zymomonas mobilis* in cyanobacteria in order to derive an efficient process for ethanol production dependent upon NADPH as a cofactor rather than the traditional NADH. Such transgenic organisms are able to make ethanol using NADPH-dependent processes.

Isolated Polynucleotides

Accordingly, the present invention provides isolated nucleic acid molecules for the adhA gene and variants thereof. The full-length nucleic acid sequence for this gene, encoding the enzyme NADP-dependant alcohol dehydrogenase, EC 1.1.1.2, has been identified and sequenced. SEQ ID NO:1 represents the codon- and expression-optimized coding sequence for the *Moorella* sp. HUC22-1 adhA gene of the present invention.

The present invention provides a nucleic acid molecule comprising or consisting of a sequence which is a codon and expression optimized version of the wild-type adhA gene. In a further embodiment, the present invention provides a nucleic acid molecule and homologs, variants and derivatives of SEQ ID NO:1 comprising or consisting of a sequence which is a variant of the adhA gene having at least 77.1% identity to SEQ TD NO: 1. The nucleic acid sequence can be preferably 78%, 79%, 80%, 81%-85%, 90%-95%, 96%-98%, 99%, 99.9% or even higher identity to SEQ ID NO:1.

In another embodiment, the invention provides a nucleic acid molecule encoding a polypeptide having the amino acid sequence of SEQ ID NO:2.

The present invention also provides nucleic acid molecules that hybridize under stringent conditions to the above-described nucleic acid molecules. As defined above, and as is well known in the art, stringent hybridizations are performed at about 25° C. below the thermal melting point ($T_m$) for the specific DNA hybrid under a particular set of conditions, where the $T_m$ is the temperature at which 50% of the target sequence hybridizes to a perfectly matched probe. Stringent washing is performed at temperatures about 5° C. lower than the $T_m$ for the specific DNA hybrid under a particular set of conditions.

Nucleic acid molecules comprising a fragment of any one of the above-described nucleic acid sequences are also provided. These fragments preferably contain at least 20 contiguous nucleotides. More preferably the fragments of the nucleic acid sequences contain at least 25, 30, 35, 40, 45, 50, 60, 70, 80, 90, 100 or even more contiguous nucleotides.

The nucleic acid sequence fragments of the present invention display utility in a variety of systems and methods. For example, the fragments may be used as probes in various hybridization techniques. Depending on the method, the target nucleic acid sequences may be either DNA or RNA. The target nucleic acid sequences may be fractionated (e.g., by gel electrophoresis) prior to the hybridization, or the hybridization may be performed on samples in situ. One of skill in the art will appreciate that nucleic acid probes of known sequence find utility in determining chromosomal structure (e.g., by Southern blotting) and in measuring gene expression (e.g., by Northern blotting). In such experiments, the sequence fragments are preferably detectably labeled, so that their specific hydridization to target sequences can be detected and optionally quantified. One of skill in the art will appreciate that the nucleic acid fragments of the present invention may be used in a wide variety of blotting techniques not specifically described herein.

It should also be appreciated that the nucleic acid sequence fragments disclosed herein also find utility as probes when immobilized on microarrays. Methods for creating microarrays by deposition and fixation of nucleic acids onto support substrates are well known in the art. Reviewed in DNA Microarrays: A Practical Approach (Practical Approach Series), Schena (ed.), Oxford University Press (1999) (ISBN: 0199637768); Nature Genet. 21(1)(suppl):1-60 (1999); Microarray Biochip: Tools and Technology, Schena (ed.), Eaton Publishing Company/BioTechniques Books Division (2000) (ISBN: 1881299376), the disclosures of which are incorporated herein by reference in their entireties. Analysis of, for example, gene expression using microarrays comprising nucleic acid sequence fragments, such as the nucleic acid sequence fragments disclosed herein, is a well-established utility for sequence fragments in the field of cell and molecular biology. Other uses for sequence fragments immobilized on microarrays are described in Gerhold et al., Trends Biochem. Sci. 24:168-173 (1999) and Zweiger, Trends Biotechnol. 17:429-436 (1999); DNA Microarrays: A Practical Approach (Practical Approach Series), Schena (ed.), Oxford University Press (1999) (ISBN: 0199637768); Nature Genet. 21(1)(suppl):1-60 (1999); Microarray Biochip: Tools and Technology, Schena (ed.), Eaton Publishing Company/BioTechniques Books Division (2000) (ISBN: 1881299376), the disclosures of each of which is incorporated herein by reference in its entirety.

In another embodiment, isolated nucleic acid molecules encoding the NADPH-dependent AdhA polypeptide comprising alcohol dehydrogenase activity are provided. As is well known in the art, enzyme activities can be measured in various ways. For example, the pyrophosphorolysis of OMP may be followed spectroscopically. Grubmeyer et al., J. Biol. Chem. 268:20299-20304 (1993). Alternatively, the activity of the enzyme can be followed using chromatographic techniques, such as by high performance liquid chromatography. Chung and Sloan, J. Chromatogr. 371:71-81 (1986). As another alternative the activity can be indirectly measured by determining the levels of product made from the enzyme activity. These levels can be measured with techniques including aqueous chloroform/methanol extraction as known and described in the art (cf. M. Kates (1986) *Techniques of Lipidology; Isolation, analysis and identification of Lipids*. Elsevier Science Publishers, New York (ISBN: 0444807322)). More modern techniques include using gas chromatography linked to mass spectrometry (Niessen, W. M. A. (2001). *Current practice of gas chromatography—mass spectrometry*. New York, N.Y.: Marcel Dekker. (ISBN: 0824704738)). Additional modern techniques for identification of recombinant protein activity and products including liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G., R. O. Dunn, and M. O. Bagby. 1997. Biodiesel: The use of vegetable oils and their derivatives as alternative diesel fuels. Am. Chem. Soc. Symp. Series 666: 172-208), titration for determining free fatty acids (Komers, K., F. Skopal, and R. Stloukal. 1997. Determination of the neutralization number for biodiesel fuel production. Fett/Lipid 99(2): 52-54), enzymatic methods (Bailer, J., and K. de Hueber. 1991. Determination of saponifiable glycerol in "biodiesel." Fresenius J. Anal. Chem. 340(3): 186), physical property-based methods, wet chemical methods, etc. can be used to analyze the levels and the identity of the product produced by the organisms of the present invention. Other methods and techniques may also be suitable for the measurement of enzyme activity, as would be known by one of skill in the art.

Also provided are vectors, including expression vectors, which comprise the above nucleic acid molecules of the present invention, as described further herein. In a first embodiment, the vectors include the isolated nucleic acid molecules described above. In an alternative embodiment, the vectors of the present invention include the above-described nucleic acid molecules operably linked to one or more expression control sequences. The vectors of the instant invention may thus be used to express an NADPH-dependent AdhA polypeptide comprising alcohol dehydrogenase activity.

Isolated Polypeptides

According to another aspect of the present invention, isolated polypeptides (including muteins, allelic variants, fragments, derivatives, and analogs) encoded by the nucleic acid molecules of the present invention are provided. In one embodiment, the isolated polypeptide comprises the polypeptide sequence corresponding to SEQ ID NO:2. In an alternative embodiment of the present invention, the isolated polypeptide comprises a polypeptide sequence at least 71.1% identical to SEQ ID NO: 2. Preferably the isolated polypeptide of the present invention has 72%, 73%-75%, 76%-80%, 81%-90%, 95%, 96%, 97%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9% or even higher identity to SEQ ID NO: 2.

According to other embodiments of the present invention, isolated polypeptides comprising a fragment of the above-described polypeptide sequences are provided. These fragments preferably include at least 20 contiguous amino acids, more preferably at least 25, 30, 35, 40, 45, 50, 60, 70, 80, 90, 100 or even more contiguous amino acids.

The polypeptides of the present invention also include fusions between the above-described polypeptide sequences and heterologous polypeptides. The heterologous sequences can, for example, include sequences designed to facilitate purification, e.g., histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), and fusions to the IgG Fc region.

Results of Optimal Enzymes

Increased level of ethanol is observed by engineering host cells to have NADPH-dependent alcohol dehydrogenase activity. Methods for producing increased level of ethanol comprise expression of such NADPH-dependent adhA genes as described herein.

Figure 12:
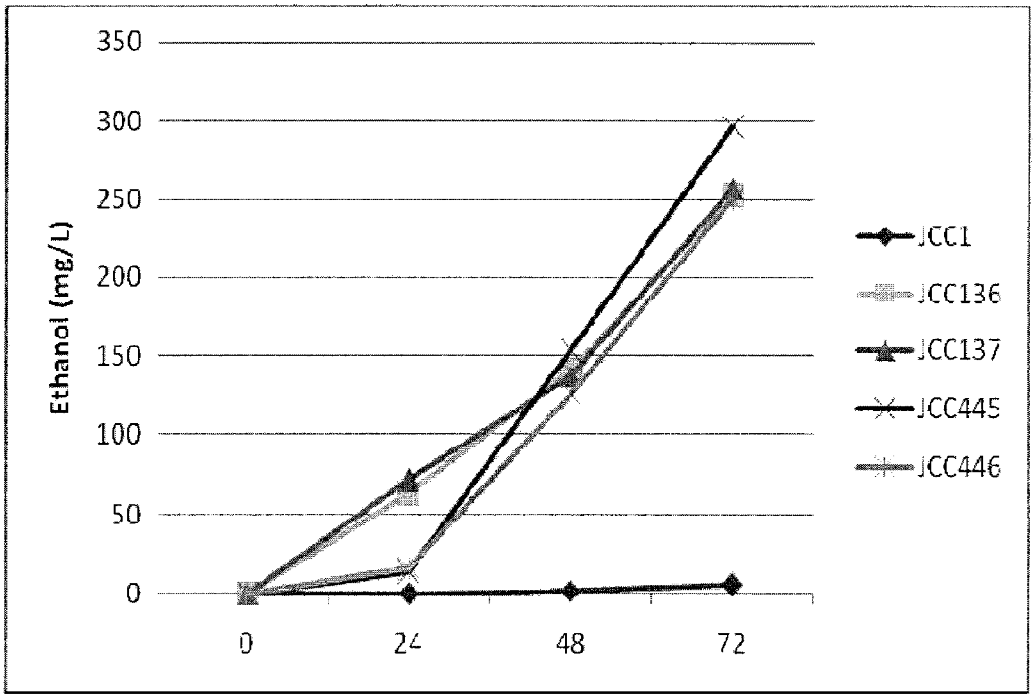
FIG. 12 graphically illustrates ethanol concentrations of cultures in the supernatant over time.

In certain aspects of the invention, increased levels of ethanol are at least about 249 mg/L of ethanol is produced over 72 hours. More preferably, at least about 297 mg/L of ethanol is produced over 72 hours (FIG. 12).

Figure 13:
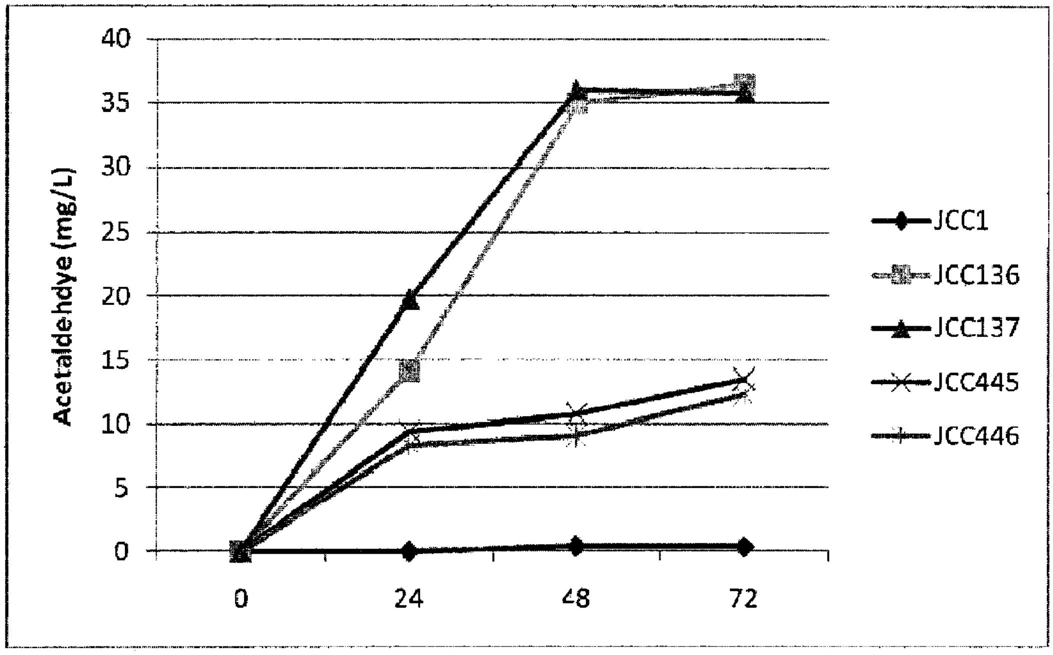
FIG. 13 graphically illustrates acetaldehyde concentrations of cultures in the supernatant over time.

In other aspects of the invention, methods to produce decreased levels of acetaldehyde are disclosed. In preferred embodiments, less than about 14 mg/L of acetaldehyde is produced (FIG. 13).

Figure 14:
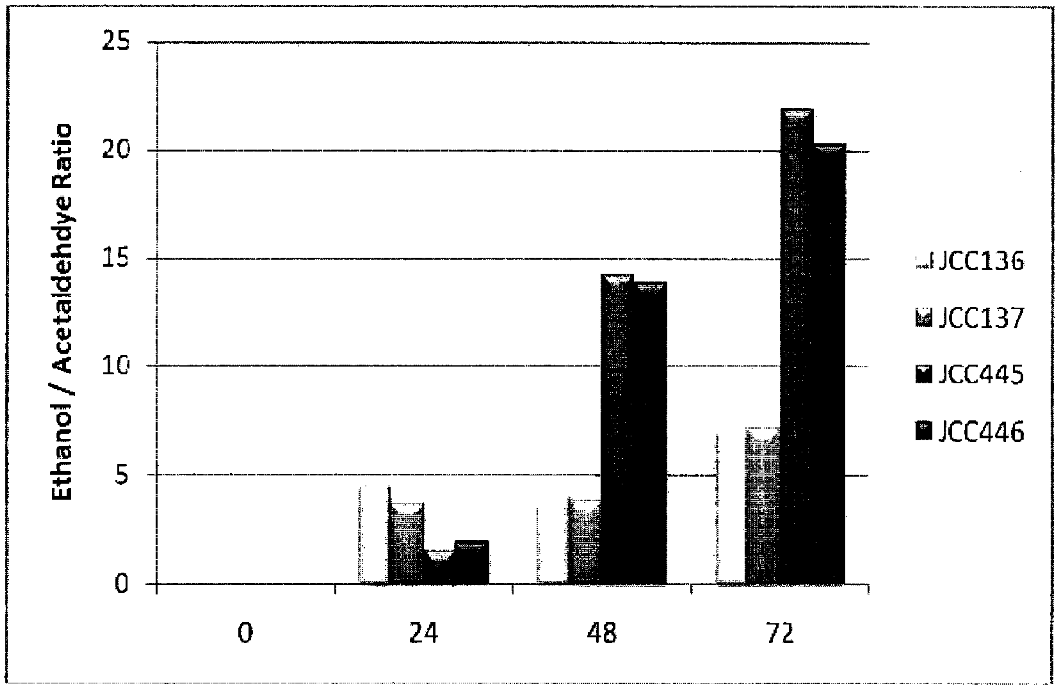
FIG. 14 graphically illustrates ethanol to acetaldehyde ratios of cultures in the supernatant over time.

Still, in other aspects of the invention, methods to produce increased amount of ethanol relative to increased OD is also disclosed. In preferred embodiments, at least about 36 mg/L of ethanol per OD is produced. More preferably, at least about 47 mg/L of ethanol per OD is produced (FIG. 14).

Accordingly, expression of such NADPH-dependent enzymes for generating fermentative products such as ethanol is shown herein to increase levels of ethanol, decrease levels of acetaldehyde and in effect allows for increased ethanol production as a function of OD.

Nutrient Independence

In another aspect, in addition to CO2 and light, photoautotrophic organisms typically require inorganic nutrient sources and vitamins. Required nutrients are generally supplemented to the growth media during bench-scale propagation of such organisms. However, such nutrients are prohibitively expensive in the context of industrial scale bioprocessing.

Vitamin B12 is a vitamin cofactor that facilitates radical-based reaction catalyzation. Many organisms, including *Synechococcus* sp. PCC 7002, require external sources of Vitamin B12 for growth, which is prohibitively expensive in large-scale industrial bioprocessing. In one embodiment, the need for Vitamin B12 is obviated by engineering photoautotrophic cells to express the Vitamin B12 biosynthesis pathway as disclosed in PCT/US2008/083056, filed Nov. 10, 2008. An exemplary biosynthesis pathway found in *Salmonella typhimurium* is overexpressed, including but not limited to the following genes encoding the amino acid sequences set forth in (Uroporphyrin-III C-methyltransferase (CysG), EC 2.1.1.107, locus NP_462380), (Sirohydrochlorin cobaltochelatase (CbiK), EC 4.99.1.3, locus NP_460970), (Precorrin-2 C20 methyltransferase (CbiL), EC 2.1.1.130, locus NP_460969), (Precorrin3B methylase (CbiH), EC 2.1.1.131, locus NP_460972), (Bifunctional CbiG/precorrin methyltransferase (CbiG), locus NP_460973), (Precorrin-4 C11-methyltransferase (CbiF), EC 2.1.1.133, locus NP_460974), (Cobalamin biosynthesis protein (CbiD), locus NP_460977), (NADPH-dependent precorrin-6A reductase (CbiJ), EC 1.3.1.54, locus NP_460971), (Precorrin-6B C5,15-methyltransferase (CbiE), EC 2.1.1.132, locus NP_460976), (Precorrin-6B C12 decarboxylase (CbiT), EC 2.1.1.132, locus NP_460975), (Precorrin-8X-methylmutase (CbiC), EC 5.4.1.2, locus NP_460978), (Cobyrinic acid A,C-diamide synthase (CbiA), EC 6.3.1.–, locus NP_460980), (Cob(I)yrinic acid a,c-diamide adenosyltransferase (BtuR), EC 2.5.1.17, locus NP_460677), (Cobyrinic acid synthase (CbiP), EC 6.3.5.10, locus NP_460964), (Cobyric acid decarboxylase (CobD), EC 4.1.1.81, locus NP_459636), (Adenosylcobinamide-phosphate synthase (CbiB), EC 6.3.1.10, locus NP_460979), (Alpha ribazole-5'-P phosphatase (CobC), EC 3.1.3.73, locus NP_459635), (Cobalamin(5'-phosphate) synthase (CobS), EC 2.7.8.26, locus NP_460962), (Cobinamide phosphate guanylyl transferase (CobU), EC 2.7.7.62, locus NP_460963), and (Nicotinate-nucleotide dimethylbenzimidazole-P phosphoribosyl transferase (CobT), EC 2.4.2.21, locus NP_460961)].

In addition, to allow for cobalt uptake and incorporation into Vitamin B12, the genes encoding the cobalt transporter are overexpressed. The exemplary cobalt transporter protein found in *Salmonella typhimurium* is overexpressed and is encoded by amino acid sequences set forth in (ABC-type Co2+ transport system, permease component (CbiM), locus NP_460968), (ABC-type cobalt transport system, periplasmic component (CbiN), locus NP_460967), and (ABC-type cobalt transport system, permease component (CbiQ), locus NP_461989).

In a preferred embodiment, photoautotrophic organisms are engineered to overexpress Vitamin B12-independent enzymes to obviate the need for this cofactor entirely. In most photoautotrophic organisms, only methionine synthase (EC 2.1.1.13) and class II ribonucleotide reductases require Vitamin B12. An exemplary Vitamin B12 independent methionine synthase (EC 2.1.1.14) from *Thermotoga maritime* is therefore overexpressed, as set forth in PCT/US2008/083,506 (5-methyltetrahydropteroyltriglutamate-homocysteine methyltransferase (MetE), locus NP_229090). In addition, an exemplary class I ribonucleotide reductase (nrdAB) from *Synechocystis* sp. PCC 6803 is overexpressed encoding the amino acids sequences set forth in (Ribonucleoside-diphosphate reductase, alpha subunit (NrdA), locus NP_441654), (Ribonucleoside-diphosphate reductase, beta subunit (NrdB), locus NP_443040).

By engineering an organism with the enzymes listed above and in FIG. 1, a photoethanolgen is produced as described more specifically in Example 3. Accordingly, the present invention provides in a host cell capable of CO2 fixation such as a cyanobacterium *Synechococcus* sp. PCC 7002 that is engineered to express genes such as pdc and/or adh to produce ethanol, the host cell is engineered to be nutrient independent.

Ethanol Production Under Continuous Illumination

Normally, glycogen in microorganisms is formed in the light, to be consumed for reducing power when it is dark. With continuous illumination, however, it may be disadvantageous to accumulate significant amounts of glycogen, which would draw carbon away from the desired pathway(s), especially because there could be no dark period long enough to utilize the glycogen. In certain embodiments to prevent glycogen synthesis during illumination, genes encoding enzyme activities related to glycogen synthesis is attenuated or eliminated entirely, to the extent that the organism continue to be easily maintained in a viable state and be robust in fermentation conditions. Accordingly, the present invention provides microorganism that are at least attenuated in the enzyme activities including, without limitation: glucose-1-phosphate adenylyltransferase (EC 2.7.7.27), glycogen synthase (EC 2.4.1.21 and EC 2.4.1.11), glucose-1-phosphate uridylyltransferase (EC 2.7.7.9), and 1,4-alpha-glucan branching enzyme (EC 2.4.1.18).

In certain aspects for ethanol production, the carbon that is available from $CO_2$ fixation is directed to pyruvate as effectively as possible. Cyanobacteria can synthesize some pyruvate from carbon fixation during illumination, using glyceraldehyde-3-phosphate derived from the Calvin cycle, because they still must make biosynthetic precursors from it. However, they do so only to the extent that they require it for growth. To increase the flux to pyruvate from Calvin cycle intermediates, it is desirable to express constitutively the genes encoding glycolytic enzymes, from the native host or from a non-native host. The choice of genes is made on the basis of whether allosteric regulatory effects are projected to prevent them from exercising their full activities in the expected metabolic context of the host. Constitutivity could be achieved by eliminating transcriptional regulation where it exists, or by expressing the enzymes from constitutive promoters with which they are not normally associated. Accordingly, the present invention provides ethanol-producing microorganisms comprising the enzymes activities including, but without limitation: glyceraldehyde 3-phosphate dehydrogenase (EC 1.2.1.12 or EC 1.2.1.13), phosphoglycerate kinase (EC 2.7.2.3), phosphoglycerate mutase (EC 5.4.2.1), enolase (EC 4.2.1.11), and pyruvate kinase (EC 2.7.1.40).

The present invention also provides additional enzyme activities for the conversion of pyruvate to ethanol. In certain embodiments, such conversion can be carried out by at least four distinct pathways: 1) the pyruvate decarboxylase pathway, 2) the pyruvate dehydrogenase pathway, 3) the pyruvate oxidase pathway, and 4) the pyruvate formate-lyase pathway. The enzyme activities required for the pyruvate decarboxylase pathway are: pyruvate decarboxylase (EC 4.1.1.1) and alcohol dehydrogenase (EC 1.1.1.1 or EC 1.1.1.2). The enzyme activities required for the pyruvate dehydrogenase pathway are: acetaldehyde dehydrogenase (EC 1.2.1.10), and alcohol dehydrogenase (EC 1.1.1.1 or EC 1.1.1.2). The enzyme activities required for the pyruvate oxidase pathway are: pyruvate oxidase (EC 1.2.2.2), acetyl-CoA synthetase (EC 6.2.1.1), acetaldehyde dehydrogenase (EC 1.2.1.10), and alcohol dehydrogenase (EC 1.1.1.1 or EC 1.1.1.2). The enzyme activities required for the pyruvate formate-lyase pathway are: pyruvate formate-lyase (EC 2.3.1.54), formate hydrogen-lyase (no EC number), acetaldehyde dehydrogenase (EC 1.2.1.10), and alcohol dehydrogenase (EC 1.1.1.1 or EC 1.1.1.2). Preferably, one or more of these pathways is expressed constitutively or under some other controlled regulation.

In addition to providing exogenous genes or endogenous genes with novel regulation, the optimization of ethanol production in microorganisms preferably requires the elimination or attenuation of certain host enzyme activities. These include, but are not limited to, pyruvate oxidase (EC 1.2.2.2), D-lactate dehydrogenase (EC 1.1.1.28), acetate kinase (EC 2.7.2.1), phosphate acetyltransferase (EC 2.3.1.8), citrate synthase (EC 2.3.3.1), phosphoenolpyruvate carboxylase (EC 4.1.1.31). The extent to which these manipulations are necessary is determined by the observed byproducts found in the bioreactor or shake-flask. For instance, observation of acetate would suggest deletion of pyruvate oxidase, acetate kinase, and/or phosphotransacetylase enzyme activities. In another example, observation of D-lactate would suggest deletion of D-lactate dehydrogenase enzyme activities, whereas observation of succinate, malate, fumarate, oxaloacetate, or citrate would suggest deletion of citrate synthase and/or PEP carboxylase enzyme activities.

Ethanol Production in Light-Dark Cycle

In alternative embodiments, the present invention is adapted so that the microorganisms are used in systems that are suitable to run with a light-dark cycle, in which several hours of constant illumination are followed by several hours of relative darkness. Using such a cycle, the complete elimination of glycogen synthesis capability may not be a viable strategy, because the cells will require some glycogen to survive the dark period. In this case, one of two alternative strategies can be implemented: 1) attenuation, but not elimination, of glycogen-synthesis enzymes, so that some glycogen is still made during the light phase; or 2) maximization of glycogen production during the light phase.

In one embodiment, the microorganisms are attenuated but not eliminated in glycogen-synthesis enzyme activities. Such methods are implemented by deleting the native glycogen-synthesis gene(s) activities and replacing them with analogs having non-native regulation and expression at a level lower than in the native host.

In another embodiment, the microorganisms maximize glycogen production during the light phase. Such methods are implemented by screening for strains with the highest glycogen content among a collection of wild-type strains or a library of mutants of a particular strain, after such strains have been grown to a suitable cell concentration and subjected subsequently to limitation of a key nutrient such as nitrogen, phosphorus, or potassium. It would be most advantageous to utilize a light-dark cycle such that glycogen is synthesized to the maximum amount possible in terms of dry cell weight during the light cycle, then metabolized to ethanol to near completion as possible during the dark cycle.

During the dark cycle, glycogen is converted to pyruvate by endogenous enzymes, but, as in the case of continuous illumination, these enzymes may be regulated in the host such that the overall conversion proceeds at a suboptimal rate. To increase the rate of this conversion, such regulation is defeated, either by mutagenizing and screening strains for rapid glycogen utilization in the dark or by supplying the host with the necessary enzymes at higher expression levels and/or providing exogenous genes encoding enzymes that are less subject to allosteric regulation than those of the host. Accordingly, the preferred enzyme activities to achieve this effect include those listed above for the conversion of glyceraldehyde-3-phosphate into ethanol, in addition to enzyme activities that convert glycogen to glyceraldehyde-3-phosphate: glycogen phosphorylase (EC 2.4.1.1), phosphoglucomutase (EC 5.4.2.2), glucose-6-phosphate isomerase (EC 5.3.1.9), phosphofructokinase (EC 2.7.1.11), fructose-6-phosphate aldolase (EC 4.1.2.13), and triosephosphate isomerase (EC 5.3.1.1).

In yet another embodiment, at least one cytochrome oxidase activity is attenuated or functionally deleted. Cytochromeoxidases function to transfer electrons to oxygen in the dark. Howitt et al., made deletions of cytochrome oxidases (CtaI, CtaII and Cyd) and were able to get strains that did not respire in the dark but grew normally in the light. (Quinol and Cytochrome Oxidases in the Cyanobacterium *Synechocystis* sp. PCC 6803, [Howitt et al., *Biochemistry* (1998) 37(51):17944-51]. Strains that lacked one oxidase respired at near-wild-type rates, whereas those that lacked both CtaI and Cyd did not respire. The inability to respire in the dark means more fermentative products, including ethanol and perhaps also succinate as well as 1,4-butanediol. Accordingly, the present invention provides a carbon fixing organism, e.g., a cyanobacterium engineered wherein at least one cytochrome oxidase activity is attenuated, which increases production of ethanol, succinate and/or 1,4-butanediol.

Production of Ethylene, Propylene, 1-Butene, 1,3-Butadiene, Acrylic Acid, etc.

In another aspect of the invention, ethylene is produced using an alcohol dehydratase (EC 4.2.1.n), which converts ethanol to ethylene. Accordingly, ethylene is produced by expressing at least one dehydratase activity in a microorganism. While many dehydratases exist in nature, none has been shown to convert ethanol to ethylene (or propanol to propylene, propionic acid to acrylic acid, etc.) by dehydration. There appears to be no purely mechanistic reason that this cannot be the case. Many examples of biological dehydratases exist, as shown in Example 55. Biological dehydrations usually take place adjacent to an activated carbon atom (i.e., one with a substituent group more electron-withdrawing than hydrogen), which helps to reduce the activation energy of the dehydration.

In addition, thermodynamics does not appear to be a barrier. By group contribution methods and by consultation of experimental values in the NIST database, the reaction ethanol→ethylene+$H_2O$ was found to have a $\Delta G°$ of between −0.5 and −1.0 kJ/mol, thus making it mildly spontaneous. The water concentration will be high, but ethylene is a gas and should spontaneously remove itself from the vicinity of the reaction. A reaction such as that catalyzed by EC 4.2.1.54 may be of particular interest, as it generates propenoyl-CoA ($CH_2$=CH—CO—SCoA) from lactoyl-CoA ($CH_3$—CHOH—CO—SCoA). Replacement of —CO—SCoA with —H gives ethylene ($CH_2$=$CH_2$) from ethanol ($CH_3$—$CH_2$OH). Such an enzyme can be used as a starting point for directed evolution. Genes encoding enzymes in the 4.2.1.x group can be identified by searching databases such as GenBank, expressed in any desired host (such as *Escherichia coli*, for simplicity), and that host can be assayed for the ethanol dehydratase activity. A high-throughput screen is especially useful for screening many genes and variants of genes generated by mutagenesis. The ethanol dehydratase gene, after its development to a suitable level of activity, can then be expressed in an ethanologenic organism to enable that organism to produce ethylene. For instance, coexpress native or evolved ethanol dehydratase gene into an organism that already produces ethanol, then test a culture by GC analysis of offgas for ethylene production which is significantly higher than without the added gene. It may be desirable to eliminate ethanol-export proteins from the production organism to prevent ethanol from being secreted into the medium and preventing its conversion to ethylene.

Preferably, a customized high-throughput screen for ethylene production by whole cells is developed, i.e., an adaptation of a colorimetric test such as that described by Lame and Kurz, 1973, Plant Physiol. 51:1074-5. Initially, a group of unmutagenized genes identified by database DNA-sequence searches is tested for activity by expression in a host such as *E. coli*. Those genes enabling ethylene production from ethanol are evolved by mutagenesis (i.e., error-prone PCR, synthetic libraries, chemical mutagenesis, etc.) and subjected to the high-throughput screen.

Figure 3:
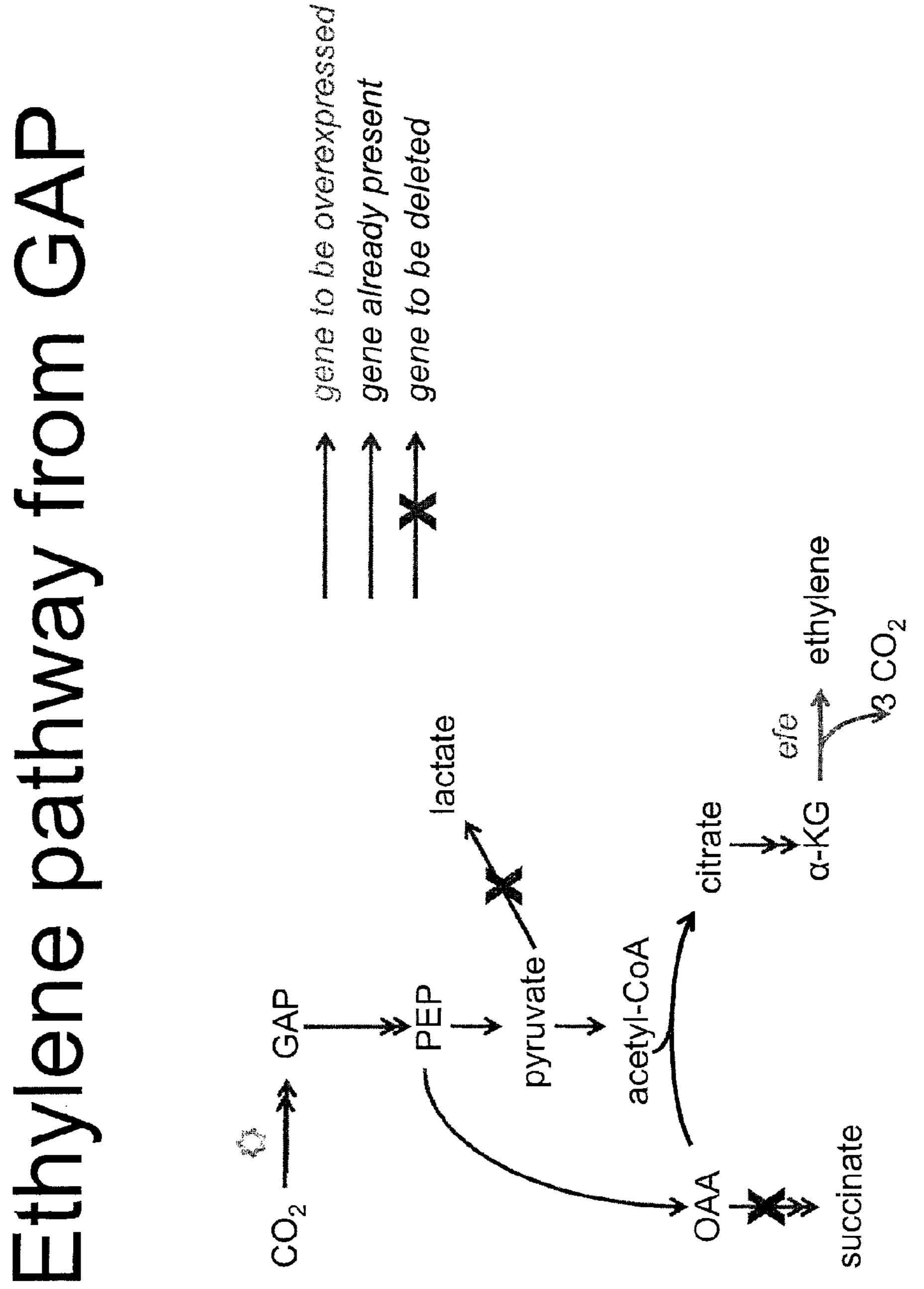
FIG. 3 provides a schematic diagram to produce ethylene from GAP.

Alternatively, genes encoding ethylene-forming enzyme activities (EfE) from various sources are expressed, e.g., *Pseudomonas syringae* pv. *Phaseolicola* (D13182), *P. syringae* pv. *Pisi* (AF101061), *Ralstonia solanacearum* (AL646053). Optimizing production may require further metabolic engineering (improving production of alpha-ketogluterate, recycling succinate as two examples). FIG. 3 depicts ethylene production from the GAP pathway using an EfE.

The production host may be of the genus *Synechococcus, Thermosynechococcus, Synechocystis*, or other photosynthetic microorganism; it may also be a commonly-used industrial organism such as *Escherichia coli, Klebsiella oxytoca*, or *Saccharomyces cerevisiae*, among others disclosed herein.

Production of Fatty Acids

In general, carbon dioxide fixing organisms can be modified to increase the production of acyl-ACP or acyl-CoA, reduce the catabolism of fatty acid derivatives and intermediates, or to reduce feedback inhibition at specific points in the biosynthetic pathway. In addition to modifying the genes described herein additional cellular resources can be diverted to over-produce fatty acids, for example the lactate, succinate and/or acetate pathways can be attenuated, and acetyl-CoA carboxylase (ACC) can be over expressed. The modifications to the production host described herein can be through genomic alterations, extrachromosomal expression systems, or combinations thereof.

Fatty Acid Biosynthetic Pathway

In one embodiment, carbon dioxide fixing organisms such as cyanobacteria can be engineered to express certain fatty acid synthase activities (FAS), which is a group of peptides that catalyze the initiation and elongation of acyl chains (Marrakchi et al., Biochemical Society, 30:1050-1055, 2002). The acyl carrier protein (ACP) and the enzymes in the FAS pathway control the length, degree of saturation and branching of the fatty acids produced, which can be attenuated or over-expressed. Such enzymes include accABCD, FabD, FabH, FabG, FabA, FabZ, Fabl, FabK, FabL, FabM, FabB, and FabF.

For example, carbon dioxide fixing organisms engineered with the fatty acid biosynthetic pathway uses the precursors acetyl-CoA and malonyl-CoA. Host cells engineered to overproduce these intermediates can serve as the starting point for subsequent genetic engineering steps to provide the specific output products such as, fatty acid esters, hydrocarbons, fatty alcohols. Several different modifications can be made, either in combination or individually, to the host cell to obtain increased acetyl CoA/malonyl CoA/fatty acid and fatty acid derivative production. Preferably, to increase acetyl CoA production, pdh, panK, aceEF, (encoding the E1p dehydrogenase component and the E2p dihydrolipoamide acyltransferase component of the pyruvate and 2-oxoglutarate dehydrogenase complexes), fabH/fabD/fabG/acpP/fabF, and in some examples additional nucleic acid encoding fatty-acyl-CoA reductases and aldehyde decarbonylases, all under the control of a constitutive, or otherwise controllable promoter, are expressed. Exemplary Genbank accession numbers for these genes are: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

Genes to be knocked-out or attenuated include fadE, gpsA, ldhA, pflb, adhE, pta, poxB, ackA, and/or ackB by transforming the hosts with conditionally replicative or non-replicative plasmids containing null or deletion mutations of the corresponding genes, or by substituting promoter or enhancer sequences. Exemplary Genbank accession numbers for these genes are; fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430).

The resulting engineered microorganisms can be grown in a desired environment, for example one with limited glycerol (less than 1% w/v in the culture medium). As such, these microorganisms will have increased acetyl-CoA production levels. Malonyl-CoA overproduction can be effected by engineering the microorganism as described above, with nucleic encoding accABCD (acetyl CoA carboxylase, for example accession number AAC73296, EC 6.4.1.2). Fatty acid overproduction can be achieved by further including nucleic acid encoding lipase (for example Accessions numbers CAA89087, CAA98876).

In some cases, acetyl-CoA carboxylase (ACC) is overexpressed to increase the intracellular concentration thereof by at least 2-fold, such as at least 5-fold, or at least 10-fold, for example relative to native expression levels.

In addition, the plsB (for example Accession number AAC77011) D311E mutation can be used to remove limitations on the pool of acyl-CoA.

In addition, over-expression of a sfa gene (suppressor of Fab A, for example Accession number AAN79592) can be included in the production host to increase production of monounsaturated fatty acids (Rock et al, J. Bacteriology 178: 5382-5387, 1996).

Expression of Thioesterase

To engineer a host cell for the production of a homogeneous population of fatty acid derivatives, one or more endogenous genes can be attenuated or functionally deleted and one or more thioesterases can be expressed. For example, C10 fatty acids can be produced by attenuating thioesterase C18 (for example accession numbers AAC73596 and P0ADA1), which uses C18:1-ACP and expressing thioesterase C10 (for example accession number Q39513), which uses C10-ACP, thus, resulting in a relatively homogeneous population of fatty acids that have a carbon chain length of 10. In another example, C14 fatty acid derivatives can be produced by attenuating endogenous thioesterases that produce non-C14 fatty acids and expressing the thioesterase accession number Q39473 (which uses C14-ACP). In yet another example, C12 fatty acid derivatives can be produced by expressing thioesterases that use C12-ACP (for example accession number Q41635) and attenuating thioesterases that produce non-C12 fatty acids. Acetyl CoA, malonyl CoA, and fatty acid overproduction can be verified using methods known in the art, for example by using radioactive precursors, HPLC, and GC-MS subsequent to cell lysis.

Thioesterases can be expressed in the host cell as provided in Example 6. As the above exemplary genes encode preferred amino acid sequences, similar genes can be selected or optimized.

Expression of Acyl-CoA Synthase

In yet another aspect, fatty acids of various lengths can be produced in a host cell engineered by expressing or overexpressing an acyl-CoA synthase peptides (EC 2.3.1.86), which catalyzes the conversion of fatty acids to acyl-CoA. Some acyl-CoA synthase peptides, which are non-specific, accept other substrates in addition to fatty acids.

Fatty Alcohol Forming Peptides

In yet further aspects, hosts cells are engineered to convert acyl-CoA to fatty alcohols by expressing or overexpressing a fatty alcohol forming acyl-CoA reductase (FAR, EC 1.1.1.*), or an acyl-CoA reductases (EC 1.2.1.50) (Example 18) and alcohol dehydrogenase (EC 1.1.1.1) or a combination of the foregoing to produce fatty alcohols from acyl-CoA. Hereinafter fatty alcohol forming acyl-CoA reductase (FAR, EC 1.1.1.*), acyl-CoA reductases (EC 1.2.1.50) and alcohol dehydrogenase (EC 1.1.1.1) are collectively referred to as fatty alcohol forming peptides. Some fatty alcohol forming peptides are non-specific and catalyze other reactions as well, for example some acyl-CoA reductase peptides accept other substrates in addition to fatty acids.

Hydrocarbon-Based Surfactants

To produce surfactants, the host cells, e.g., that demonstrate an innate ability to synthesize high levels of surfactant precursors in the form of lipids and oil is modified to include a first exogenous nucleic acid sequence encoding a protein capable of converting a fatty acid to a fatty aldehyde and a second exogenous nucleic acid sequence encoding a protein capable of converting a fatty aldehyde to an alcohol (See various Examples). In some examples, the first exogenous nucleic acid sequence encodes a fatty acid reductase. In other examples, the second exogenous nucleic acid sequence encodes mammalian microsomal aldehyde reductase or long-chain aldehyde dehydrogenase. In yet another example, the first and second exogenous nucleic acid sequences are from a multienzyme complex from *Arthrobacter* AK 19, *Rhodotorula glutinins, Acinobacler* sp. strain M-1, or *Candida lipolytica*. In one embodiment, the first and second heterologous DNA sequences are from a multienzyme complex from *Acinobacter* sp, strain M-1 or *Candida lipolytica*.

Additional sources of heterologous nucleic acid sequences encoding fatty acid to long-chain alcohol converting proteins that can be used in surfactant production include, but are not limited to, *Mortierella alpina* (ATCC 32222), *Crytococcus curvatus*, (also referred to as *Apiotricum curvatum*), *Alcanivorax jadensis* (T9T=DSM 12718=ATCC 700854), *Acinetobacter* sp. HO1-N, (ATCC 14987) and *Rhodococcus opacus* (PD630 DSMZ 44193).

In one example, the fatty acid derivative is a saturated or unsaturated surfactant product having a carbon atom content limited to between 6 and 36 carbon atoms. In another example, the surfactant product has a carbon atom content limited to between 24 and 32 carbon atoms.

Fatty Esters of Various Lengths

In another aspect, engineered host cells produce various lengths of fatty esters. For example, alcohol O-acetyltransferase peptides (EC 2.3.1.84) is expressed or overexpressed. These peptides catalyze the reaction of acetyl-CoA and an alcohol to form CoA and an acetic ester. In some embodiments, the alcohol O-acetyltransferase peptides are co-expressed with selected thioesterase peptides, FAS peptides and fatty alcohol forming peptides, thus, allowing the carbon chain length, saturation and degree of branching to be controlled. In other embodiments, the bkd operon can be co-expressed to enable branched fatty acid precursors to be produced.

Alcohol O-acetyltransferase peptides catalyze other reactions such that the peptides accept other substrates in addition to fatty alcohols or acetyl-CoA thioester, for example, other alcohols and other acyl-CoA thioesters. Modification of such enzymes and the development of assays for characterizing the activity of a particular alcohol O-acetyltransferase peptides are within the scope of a skilled artisan. Engineered O-acetyltransferases and O-acyltransferases can be created that have new activities and specificities for the donor acyl group or acceptor alcohol moiety.

Alcohol acetyl transferases (AATs, EC 2.3.1.84), which are responsible for acyl acetate production in various plants, can be used to produce medium chain length waxes, such as octyl octanoate, decyl octanoate, decyl decanoate, and the like. Fatty esters, synthesized from medium chain alcohol (such as C6, C8) and medium chain acyl-CoA (or fatty acids, such as C6 or C8) have a relative low melting point. For example, hexyl hexanoate has a melting point of −55° C. and octyl octanoate has a melting point of −18 to −17° C. The low melting points of these compounds make them good candidates for use as biofuels.

In one embodiment, a SAAT gene is co-expressed in a production host ΔfadE with fadD from *E. coli* and acr1 (alcohol reductase from *A. baylyi* ADP1). Octanoic acid is provided in the fermentation media. This results in the production of octyl octanoate. Similarly, when the wax synthase gene from *A. baylyi* ADP1 is expressed in the production host instead of the SAAT gene, octyl octanoate is produced. Medium-chain waxes which have low melting points, such as octyl octanoate and octyl decanoate, are good candidates for biofuel to replace triglyceride-based biodiesel.

A recombinant SAAT gene can be synthesized using DNA 2.0 (Menlo Park, Calif.) based on the published gene sequence (accession number AF 193789) and modified to eliminate the Ncd1 site. The synthesized SAAT gene is cloned in a vector and cotransformed into a host, which carries afadD gene from *E. coli* and acyl gene from *A. baylyi* ADP1. The transformants are grown in LB medium. After induction with antibiotics and the addition of 0.02% of octanoic acid, the culture is continued at 25° C. from 40 hours. After that, 3 mL of acetyl acetate is added to the whole culture and mixed several times. The acetyl acetate phase is analyzed by GC/MS.

Fatty Esters (Biodiesels and Waxes)

Host cells are engineered to produce fatty esters (biodiesels and waxes) from acyl-CoA and alcohols. In some examples, the alcohols are provided in the fermentation media and in other examples the host cells can provide the alcohol as described herein. Structurally, fatty acid esters have an A and a B side, the A side of the ester is used to describe the carbon chain contributed by the alcohol, and the B side of the ester is used to describe the carbon chain contributed by the acyl-CoA. Either chain can be saturated or unsaturated, branched or unbranched. In some embodiments, the engineered host cells produce fatty alcohols or short chain alcohols. In alternative embodiments, the host cell is engineered to produce specific acyl-CoA molecules. As used herein fatty acid esters are esters derived from a fatty acyl-thioester and an alcohol, wherein the A side and the B side of the ester can vary in length independently. Generally, the A side of the ester is at least 1, 2, 3, 4, 5, 6, 7, or 8 carbons in length, while the B side of the ester is 8, 10, 12, 14, 16, 18, 20, 22, 24, or 26 carbons in length. The A side and the B side can be straight chain or branched, saturated or unsaturated.

Increased expression of one or more wax synthases (EC 2.3.1.75) leads to the production of fatty esters, including waxes from acyl-CoA and alcohols (Example 17). As used herein, waxes are long chain fatty acid esters, wherein the A side and the B side of the ester can vary in length independently. Generally, the A side of the ester is at least 8, 10, 12, 14, 16, 18, 20, 22, 24, or 26 carbons in length. Similarly the B side of the ester is at least 8, 10, 12, 14, 16, 18, 20, 22, 24, or 26 carbons in length. The A side and the B side can be mono-, di-, tri-unsaturated. Wax synthase peptides are capable of catalyzing the conversion of an acyl-thioester to fatty esters and some wax synthase peptides will catalyze other reactions for example, accept short chain acyl-CoAs and short chain alcohols to produce fatty esters. Methods to identify wax synthase activity are provided in U.S. Pat. No. 7,118,896, which is herein incorporated by reference.

In other aspects, microorganisms are modified to produce a fatty ester-based biofuel by expressing nucleic acids encoding a wax ester synthase such that is expressed so as to confer upon said microorganism the ability to synthesize a saturated, unsaturated, or branched fatty ester. In some embodiments, the wax ester synthesis proteins include, but are not limited to: fatty acid elongases, acyl-CoA reductases, acyltransferases or wax synthases, fatty acyl transferases, diacylglycerol acyltransferases, acyl-coA wax alcohol acyltransferases, bifunctional wax ester synthase/acyl-CoA:diacylglycerol acyltransferase selected from a multienzyme complex from *Simmondsia chinensis, Acinetobacter* sp. strain ADP1 (formerly *Acinetobacter calcoaceticus* ADP1), *Pseudomonas aeruginosa, Fundibacter jadensis, Arabidopsis thaliana*, or *Alkaligenes eutrophus*. In one embodiment, the fatty acid elongases, acyl-CoA reductases or wax synthases are from a multienzyme complex from *Alkaligenes eutrophus* and other organisms known in the literature to produce wax and fatty acid esters. Additional nucleic acids encoding wax synthesis proteins useful in fatty ester production include, but are not limited to, *Mortierella alpina* (for example ATCC 32222), *Crytococcus curvatus*, (also referred to as *Apiotricum curvatum*), *Alcanivorax jadensis* (for example T9T=DSM 12718=ATCC 700854), *Acinetobacter* sp. HO1-N, (for example ATCC 14987) and *Rhodococcus opacus* (for example PD630, DSMZ 44193).

Fatty esters of various length are produced, for example, the fatty ester product is a saturated or unsaturated fatty ester product having a carbon atom content between 24 and 46 carbon atoms; 24 and 32 carbon atoms; or 14 and 20 carbons. In another embodiment the fatty ester is the methyl ester of C 18:1; ethyl ester of C 16:1; methyl ester of C 16:1; or octadecyl ester of octanol.

In another embodiment, the wax ester synthase from *Acinetobacter* sp. ADP1 at locus AAO17391 (described in Kalscheuer and Steinbuchel, J. Biol. Chem. 278:8075-8082, 2003, herein incorporated by reference) is used. In another example the wax ester synthase from *Simmondsia chinensis*, at locus AAD38041 is used.

Optionally a wax ester exporter such as a member of the FATP family is used to facilitate the release of waxes or esters into the extracellular environment. One example of a wax ester exporter that can be used is fatty acid (long chain) transport protein CG7400-PA, isoform A from *D. melanogaster*, at locus NP_524723.

As described herein, the B side is contributed by a fatty acid produced from de novo synthesis in the host organism. In some instances where the host is additionally engineered to make alcohols, including fatty alcohols, the A side is also produced by the host organism. In yet other examples the A side can be provided in the medium. As described herein, by selecting the desired thioesterase genes the B side, and when fatty alcohols are being made the A side, can be designed to be have certain carbon chain characteristics. These characteristics include points of unsaturation, branching, and desired carbon chain lengths. Exemplary methods of making long chain fatty acid esters, wherein the A and B side are produced by the production host are provided. When both the A and B side are contributed by the production host and they are produced using fatty acid biosynthetic pathway intermediates they will have similar carbon chain characteristics. For example, at least 50%, 60%, 70%, or 80% of the fatty acid esters produced will have A sides and B sides that vary by 6, 4, or 2 carbons in length. The A side and the B side will also display similar branching and saturation levels.

In one embodiment, wax esters are produced by engineering *Synechococcus* sp. PCC 7002 to express a fatty alcohol forming acyl-CoA reductase, thioesterase, and a wax synthase. Thus, the production host produces both the A and the B side of the ester and the structure of both sides is influenced by the expression of the thioesterase gene *A. baylyi* ADP1 (termed WSadp1, accessions AA017391, EC: 2.3.175). The host is transformed and selected in LB plates supplemented with antibiotics such as kanamycin, carbenicillin or spectinomycin. Transformants are inoculated in LB and cultured in a shaker at a suitable temperature. When the cultures reach a preferred OD, an aliquot is transferred into flasks. The culture is then placed into conical tubes and the cells are spun down. The cell pellet is then mixed with ethyl acetate. The ethyl acetate extract is analyzed with GC/MS.

In addition to producing fatty alcohols for contribution to the A side, the host can produce other short chain alcohols such as ethanol, propanol, isopropanol, isobutanol, and butanol for incorporation on the A side using techniques well known in the art. For example, butanol can be made by the host organism. To create butanol-producing cells, host cells can be further engineered to express atoB (acetyl-CoA acetyltransferase) from *E. coli* K12, β-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium fulvum*, and adhE encoding an aldehyde-alcohol dehydrogenase of *Clostridium acetobutylicum* in an expression vector. Similarly, ethanol can be produced in a production host using the methods taught by Kalscheuer et al., Microbiology 152:2529-2536, 2006, which is herein incorporated by reference.

The centane number (CN), viscosity, melting point, and heat of combustion for various fatty acid esters have been characterized in for example, Knothe, Fuel Processing Technology 86:1059-1070, 2005, which is herein incorporated by reference. Using the teachings provided herein a host cell can be engineered to produce any one of the fatty acid esters described in the Knothe, Fuel Processing Technology 86:1059-1070, 2005.

Acyl-ACP, Acyl-CoA to Hydrocarbon

Various microorganisms are known to produce hydrocarbons, such as alkanes, olefins, and isoprenoids. Many of these hydrocarbons are derived from fatty acid biosynthesis. The production of these hydrocarbons can be controlled by controlling the genes associated with fatty acid biosynthesis in the native hosts of some microorganisms. For example, hydrocarbon biosynthesis in the algae *Botryococcus braunii* occurs through the decarbonylation of fatty aldehydes. The fatty aldehydes are produced by the reduction of fatty acyl—thioesters by fatty acyl-CoA reductase. Thus, the structure of the final alkanes can be controlled by engineering *B. braunii* to express specific genes, such as thioesterases, which control the chain length of the fatty acids being channeled into alkane biosynthesis. Expressing the enzymes that result in branched chain fatty acid biosynthesis in *B. braunii* will result in the production of branched chain alkanes. Introduction of genes affecting the production of desaturation of fatty acids will result in the production of olefins. Further combinations of these genes can provide further control over the final structure of the hydrocarbons produced. To produce higher levels of the native or engineered hydrocarbons, the genes involved in the biosynthesis of fatty acids and their precursors or the degradation to other products can be expressed, overexpressed, or attenuated. Each of these approaches can be applied to the production of alkanes in engineered microorganisms such as *Vibrio furnissi* M1 and its functional homologues, which produce alkanes through the reduction of fatty alcohols. Each of these approaches can also be applied to the production of the olefins produced by many strains of *Micrococcus leuteus, Stenotrophomonas maltophilia, Jeogalicoccus* sp. (ATCC8456), and related microorganisms. These microorganisms produce long chain internal olefins that are derived from the head to head condensation of fatty acid precursors. Controlling the structure and level of the fatty acid precursors using the methods described herein will result in formation of olefins of different chain length, branching, and level of saturation.

Examples 9, 10, 11 and 19 provide several alternatives in engineering a microorganism to produce hydrocarbons such as alkane and octane.

Hydrocarbons can also be produced using evolved oxido/reductases for the reduction of primary alcohols. Primary fatty alcohols are known to be used to produce alkanes in microorganisms such as *Vibrio furnissii* M1 (Myong-Ok, J. Bacterial., 187: 1426-1429, 2005). An NAD(P)H dependent oxido/reductase is the responsible catalyst. Synthetic NAD(P)H dependent oxidoreductases can be produced through the use of evolutionary engineering and be expressed in production hosts to produce fatty acid derivatives. One of ordinary skill in the art will appreciate that the process of "evolving" a fatty alcohol reductase to have the desired activity is well known (Kolkman and Stemmer Nat Biotechnol 19:423-8, 2001, Ness et al., Adv Protein Chem. 55:261-92, 2000, Minshull and Stemmer Curr Opin Chem Biol. 3:284-90, 1999, Huisman and Gray Curr Opin Biotechnol August; 13:352-8, 2002, and see U.S. patent publication 2006/0195947). A library of NAD(P)H dependent oxidoreductases is generated by standard methods, such as error-prone PCR, site-specific random mutagenesis, site specific saturation mutagenesis, or site directed specific mutagenesis. Additionally, a library can be created through the "shuffling" of naturally occurring NAD(P)H dependent oxidoreductase encoding sequences. The library is expressed in a suitable host, such as *E. coli*. Individual colonies expressing a different member of the oxido/reductase library is then analyzed for its expression of an oxido/reductase that can catalyze the reduction of a fatty alcohol. For example, each cell can be assayed as a whole cell bioconversion, a cell extract, a permeabilized cell, or a purified enzyme. Fatty alcohol reductases are identified by the monitoring the fatty alcohol dependent oxidation of NAD(P)H spectrophotometrically or fluorometrically. Production of alkanes is monitored by GC/MS, TLC, or other methods. An oxido/reductase identified in this manner is used to produce alkanes, alkenes, and related branched hydrocarbons. This is achieved either in vitro or in vivo. The latter is achieved by expressing the evolved fatty alcohol reductase gene in an organism that produces fatty alcohols, such as those described herein. The fatty alcohols act as substrates for the alcohol reductase which would produce alkanes. Other oxidoreductases can be also engineered to catalyze this reaction, such as those that use molecular hydrogen, glutathione, FADH, or other reductive coenzymes.

Increased Fatty Acid Production

Introduction of heterologous nucleic acid sequences involved in a biosynthetic pathway for the production of hydrocarbons can be done stably or transiently into various host cells using techniques well known in the art, for example, electroporation, calcium phosphate precipitation, DEAE-dextran-mediated transfection, liposome-mediated transfection, conjugation and transduction. For stable transformation, a DNA sequence can further include a selectable marker, such as, antibiotic resistance, for example resistance to neomycin, tetracycline, chloramphenicol, kanamycin and genes that complement auxotrophic deficiencies.

Suitable expression control sequences for use in prokaryotic host cells include, but are not limited to, promoters capable of recognizing the T4, T3, Sp6 and T7 polymerases, the PR and $P_L$ promoters of bacteriophage lambda, the trp, recA, heat shock, and lacZ promoters of *E. coli*, the alpha-amylase and the sigma-specific promoters of *B. subtilis*, the promoters of the bacteriophages of *Bacillus, Streptomyces* promoters, the int promoter of bacteriophage lambda, the bla promoter of the beta-lactamase gene of pBR322, and the CAT promoter of the chloramphenicol acetyl transferase gene. Prokaryotic promoters are reviewed by Glick, J. Ind. Microbiol. 1:277, 1987; Watson et al, MOLECULAR BIOLOGY OF THE GENES 4th Ed., Benjamin Cummins (1987); and Sambrook et al., supra.

Non-limiting examples of suitable eukaryotic promoters for use within an eukaryotic host are viral in origin and include the promoter of the mouse metallothionein I gene (Hamer et al., J. MoI. Appl. Gen. 1:273, 1982); the TK promoter of Herpes virus (McKnight, Cell 31:355, 1982); the SV40 early promoter (Benoist et al, Nature (London) 290: 304, 1981); the Rous sarcoma virus promoter; the cytomegalovirus promoter (Foecking et al, Gene 45:101, 1980); the yeast gal4 gene promoter (Johnston, et al, PNAS (USA) 79:6971, 1982; Silver, et al., PNAS (USA) 81:5951, 1984); and the IgG promoter (Orlandi et al, PNAS (USA) 86:3833, 1989).

In some examples a genetically modified host cell is genetically modified with a heterologous DNA sequence encoding a biosynthetic pathway gene product that is operably linked to a constitutive promoter. Suitable constitutive promoters are known in the art and include, constitutive adenovirus major late promoter, a constitutive MPSV promoter, and a constitutive CMV promoter. Suitable constitutive promoters applicable for *Synechococcus* sp. PCC 7002 include for example, PtacI, P-EM7, Paph2 and PaadA The microbial host cell can be genetically modified with a heterologous nucleic acid sequence encoding a biosynthetic pathway gene product that is operably linked to an inducible promoter. Inducible promoters are well known in the art. Suitable inducible promoters include, but are not limited to promoters that are affected by proteins, metabolites, or chemicals. These include: a bovine leukemia virus promoter, a metallothionein promoter, a dexamethasone-inducible MMTV promoter, a SV40 promoter, a MRP polIII promoter, a tetracycline-inducible CMV promoter (such as the human immediate-early CMV promoter) as well as those from the trp and lac operons.

When a host cell is genetically modified with heterologous nucleic acid sequences encoding two or more proteins involved in a biosynthesis pathway to produce carbon-based products of interest, the nucleic acid sequences can be driven by a single promoter on a single vector or at least one promoter on separate expression vectors.

In some embodiments, the intracellular concentration (e.g., the concentration of the intermediate in the genetically modified host cell) of the biosynthetic pathway intermediate can be increased to further boost the yield of the final product. For example, by increasing the intracellular amount of a substrate (e.g., a primary substrate) for an enzyme that is active in the biosynthetic pathway, and the like.

In some examples the fatty acid or intermediate is produced in the cytoplasm of the cell. The cytoplasmic concentration can be increased in a number of ways, including, but not limited to, binding of the fatty acid to coenzyme A to form an acyl-CoA thioester. Additionally, the concentration of acyl-CoAs can be increased by increasing the biosynthesis of CoA in the cell, such as by over-expressing genes associated with pantothenate biosynthesis (panD) or knocking out the genes associated with glutathione biosynthesis (glutathione synthase).

Carbon Chain Modifications

FIG. 1 provides a description of the various genes that can be modulated to alter the structure of the fatty acid derivative product and the encoded enzymes that can be used alone or in combination to make various fatty acids and hydrocarbons. The products can be produced such that they contain branch points, levels of saturation, and carbon chain length, thus, making these products desirable starting materials for use in many applications. Provided are various carbon-based products of interest produced by the microorganisms.

FIG. 1 also lists enzymes that are directly involved in the synthesis of carbon-based products, including waxes, fatty acid esters and/or fatty alcohols. To increase the production of waxes/fatty acid esters, and fatty alcohols, one or more of the enzymes can be over expressed or mutated to reduce feedback inhibition. Additionally, enzymes that metabolize the intermediates to make nonfatty-acid based products (side reactions) can be functionally deleted or attenuated to increase the flux of carbon through the fatty acid biosynthetic pathway. The Examples provided herein describe how to engineer enzymes in the respective pathways of host organisms to yield engineered organisms that produce carbon-based products of interest.

In other examples, the expression of exongenous FAS genes originating from different species or engineered variants can be introduced into the host cell to result in the biosynthesis of fatty acid metabolites structurally different (in length, branching, degree of unsaturation, etc.) as that of the native host. These heterologous gene products can be also chosen or engineered so that they are unaffected by the natural complex regulatory mechanisms in the host cell and, therefore, function in a manner that is more controllable for the production of the desired commercial product. For example the FAS enzymes from *Bacillus subtilis, Saccharomyces cerevisiae, Streptomyces* spp, *Ralstonia, Rhodococcus, Corynebacteria, Brevibacteria, Mycobacteria*, oleaginous yeast, and the like can be expressed in the production host.

A skilled artisan will appreciate that when a production host is engineered to produce a fatty acid from the fatty acid biosynthetic pathway that contains a specific level of unsaturation, branching, or carbon chain length, the resulting engineered fatty acid can be used in the production of fatty acid derivatives. Hence, fatty acid derivatives generated from the production host can display the characteristics of the engineered fatty acid. For example, a production host can be engineered to make branched, short chain fatty acids. Then, using the teachings provided herein relating to fatty alcohol production (i.e., including alcohol-forming enzymes such as FAR), the production host produces branched, short chain fatty alcohols. Similarly, a hydrocarbon can be produced by engineering a production host to produce a fatty acid having a defined level of branching, unsaturation, and/or carbon chain length, thus, producing a homogenous hydrocarbon population. Moreover, when an unsaturated alcohol, fatty acid ester or hydrocarbon is desired, the fatty acid biosynthetic pathway can be engineered to produce low levels of saturated fatty acids and an additional desaturase can be expressed to lessen the saturated product production.

Saturation

In one aspect, hosts are engineered to produce unsaturated fatty acids by over-expressing fabB, or by growing the host at low temperatures (for example less than 37° C.). FabB has preference to cis-$\delta^3$decenoyl-ACP and results in unsaturated fatty acid production in *E. coli*. Over-expression of FabB results in the production of a significant percentage of unsaturated fatty acids (de Mendoza et al, J. Biol. Chem., 258: 2098-101, 1983). These unsaturated fatty acids can then be used as intermediates in hosts that are engineered to produce fatty acids, such as fatty alcohols, esters, waxes, olefins, alkanes, and the like. One of ordinary skill in the art will appreciate that by attenuating fabA, or over-expressing fabB and expressing specific thioesterases (described below), unsaturated fatty acid derivatives having a desired carbon chain length can be produced. Alternatively, the repressor of fatty acid biosynthesis, FabR (Genbank accession NP_418398), can be deleted, which will also result in increased unsaturated fatty acid production in *E. coli* (Zhang et al., *J. Biol. Chem.* 277: pp. 15558, 2002.). Further increase in unsaturated fatty acids is achieved by over-expression of FabM (trans-2, cis-3-decenoyl-ACP isomerase, Genbank accession DAA05501) and controlled expression of FabK (trans-2-enoyl-ACP reductase II, Genbank accession NP_357969) from *Streptococcus pneumoniae* (Marrakchi et al., *J. Biol. Chem.* 277: 44809, 2002), while deleting *E. coli* Fab I (trans-2-enoyl-ACP reductase, Genbank accession NP_415804). Additionally, to increase the percentage of unsaturated fatty acid esters, the microorganism can also overexpress fabB (encoding β-ketoacyl-ACP synthase I, Accessions: BAA16180, EC:2.3.1.41), Sfa (encoding a suppressor of fabA, Accession: AAC44390) and gnsA and gnsB (both encoding secG null mutant suppressors, a.k.a. cold shock proteins, Accession: ABD18647.1, AAC74076.1) over-expressed. In some examples, the endogenous fabF gene can be attenuated, thus, increasing the percentage of palmitoleate (C 16:1) produced.

Fatty acids can be produced that contain branch points, cyclic moieties, and combinations thereof, using the teachings provided herein (Example 11).

By inserting and expressing one or more exogenous nucleic acid sequences, microorganisms that naturally produce straight fatty acids (sFAs) can be engineered to be capable of fixing carbon dioxide and producing branched chain fatty acids (brFAs). For example, a host such as *E. coli* naturally produces straight fatty acids (sFAs). The host can also engineered to capture light as described in, e.g., PCT/US2008/075899, filed Sep. 10, 2008, or in PCT/US2008/083056, filed Nov. 10, 2008, and several genes can be introduced and expressed that provide branched precursors (bkd operon) and allow initiation of fatty acid biosynthesis from branched precursors (fabH). Additionally, the organism can express genes for the elongation of brFAs (e.g. ACP, FabF). Additionally, or alternatively, the corresponding *E. coli* genes that normally lead to sFAs and would compete with the introduced genes (e.g. FabH, FabF) can be deleted.

The branched acyl-CoAs 2-methyl-buturyl-CoA, isovaleryl-CoA and isobuturyl-CoA are the precursors of brFA. In most brFA-containing microorganisms they are synthesized in two steps (described in detail below) from branched amino acids (isoleucine, leucine and valine) [Kadena, *Microbiol. Rev.* 55: pp. 288, (1991)]. A microorganism can be engineered to produce brFAs, or to overproduce brFAs, by recombinantly expressing or over-expressing one or more of the enzymes in these two steps. In some instances the production host may have an endogenous enzyme that can accomplish one step, in which case only enzymes involved in the second step need to be recombinantly expressed.

The first step in forming branched fatty acids is the production of the corresponding α-keto acids by a branched-chain amino acid aminotransferase. *E. coli* has such an enzyme, IlvE (EC 2.6.1.42; Genbank accession YP_026247). In some examples, a heterologous branched-chain amino acid aminotransferase may not be expressed. However, *E. coli* IlvE or any other branched-chain amino acid aminotransferase, e.g., IlvE from *Lactococcus lactis* (Genbank accession AAF34406), ilvE from *Pseudomonas putida* (Genbank accession NP_745648), or ilvE from *Streptomyces coelicolor* (Genbank accession NP_629657) can be overexpressed in a host microorganism, should the host's aminotransferase reaction turn out to be rate limiting.

The second step, the oxidative decarboxylation of the α-ketoacids to the corresponding branched-chain acyl-CoA, is catalyzed by branched-chain α-keto acid dehydrogenase complexes (bkd; EC 1.2.4.4.) [Denoya et al. J. Bacteriol 177: pp. 3504, (1995)], which consist of E1α/β (decarboxylase), E2 (dihydrolipoyl transacylase) and E3 (dihydrolipoyl dehydrogenase) subunits. These subunits are similar to pyruvate and α-ketoglutarate dehydrogenase complexes. FIG. 1 lists potential bkd genes from several microorganisms that can be expressed in a production host to provide branched-chain acyl-CoA precursors. Basically, every microorganism that possesses brFAs and/or grows on branched-chain amino acids can be used as a source to isolate bkd genes for expression in production hosts such as *E. coli*. Furthermore, *E. coli* naturally has the E3 component (as part of its pyruvate dehydrogenase complex; lpd, EC 1.8.1.4, Genbank accession NP_414658). Therefore, in *E. coli*, only the E1 α/β and E2 bkd genes need be expressed.

In another example, isobuturyl-CoA can be made in a production host, for example in *E. coli* through the coexpression of a crotonyl-CoA reductase (Ccr, EC 1.1.1.9) and isobuturyl-CoA mutase (large subunit IcmA, EC 5.4.99.2; small subunit IcmB, EC 5.4.99.13) (Han and Reynolds J. Bacteriol 179: pp. 5157, 1997). Crotonyl-CoA is an intermediate in fatty acid biosynthesis in *E. coli* and other microorganisms.

In addition to expression of the bkd genes, the initiation of brFA biosynthesis utilizes β-ketoacyl-acyl-carrier-protein synthase III (FabH, EC 2.3.1.41) with specificity for branched chain acyl CoAs (Li et al. J. Bacterial. 187: pp. 3795, 2005). FabH genes that are involved in fatty acid biosynthesis of any brFA-containing microorganism can be expressed in a production host. The Bkd and FabH enzymes from production hosts that do not naturally make brFA may not support brFA production. Bkd and FabH, therefore, may be expressed recombinantly in these hosts. Similarly, if the endogenous level of Bkd and FabH production are not sufficient to produce brFA, these genes can be over-expressed. Additionally, other components of fatty acid biosynthesis machinery can be expressed, including acyl carrier proteins (ACPs) and genes such as β-ketoacyl-acyl-carrier-protein synthase II (fabF, EC 2.3.1.41). In addition to expressing these genes, some genes in the endogenous fatty acid biosynthesis pathway may be attenuated in the production host. For example, in *E. coli* the most likely candidates to interfere with brFA biosynthesis are fabH (Genbank accession # NP_415609) and/or fabF genes (Genbank accession # NP_415613).

As mentioned above, through the combination of expressing genes that support brFA synthesis and alcohol synthesis, branched chain alcohols can be produced. For example, when an alcohol reductase such as AcrI from *Acinetobacter baylyi* ADP1 is coexpressed with a bkd operon, *E. coli* can synthesize isopentanol, isobutanol or 2-methyl butanol. Similarly, when AcrI is coexpressed with ccr/icm genes, *E. coli* can synthesize isobutanol.

In order to convert a production host such as *E. coli* into an organism capable of synthesizing ω-cyclic fatty acids (cyFAs), several genes need to be introduced and expressed that provide the cyclic precursor cyclohexylcarbonyl-CoA (Cropp et al Nature Biotech. 18: pp. 980, 2000). The genes (fabH, ACP and fabF) can then be expressed to allow initiation and elongation of ω-cyclic fatty acids (Example 13). Alternatively, the homologous genes can be isolated from microorganisms that make cyFAs and expressed in *E. coli*.

Expression of the following genes are sufficient to provide cyclohexylcarbonyl-CoA in *E. coli*: ansJ, ansK, ansL, chcA and ansM from the ansatrienin gene cluster of *Streptomyces collinus* [Chen et al., *Eur. J. Biochem.* 261 (1999)] or plmJ, plmK, plmL, chcA and plmM from the phoslactomycin B gene cluster of *Streptomyces* sp. HK803 [Palaniappan et al., *J. Biol. Chem.* 278:35552 (2003)] together with the chcB gene [Patton et al. *Biochem.,* 39:7595 (2000)] from *S. collinus, S. avermitilis* or *S. coelicolor.*

The genes (fabH, ACP and fabF) are sufficient to allow initiation and elongation of ω-cyclic fatty acids, because they can have broad substrate specificity. In the event that coexpression of any of these genes with the ansJKLM/chcAB or pmlJKLM/chcAB genes does not yield cyFAs, fabH, ACP and/or fabF homologs from microorganisms that make cyFAs can be isolated (e.g., by using degenerate PCR primers or heterologous DNA probes) and coexpressed.

Production of Sugars

Industrial production of chemical products from biological organisms is usually accomplished by anaerobic fermentation of sugars such as glucose. Notably, photosynthetic organisms often produce polymers such as glycogen and cellulose made up of glucose monomers in the course of photosynthesis. To produce fermentation products during periods of photosynthesis is challenging as it generally requires the cell to direct flux both towards gluconeogenesis and glycolysis simultaneously. On the other hand, using a day/night cycle to allow carbon buildup and then fermentation of the carbon stores at night is limited by the maximum carbon storage capacities of the cell.

There are at least two major avenues to export sugars into the medium. In one embodiment, sugars and sugar phosphates such as glucose or fructose phosphates or triose phosphates are exported. Triose phosphates include 3-phosphoglyceraldehyde (3PGAL) and dihydroxyacetone-phosphate (DHAP). In this case, a specific transporter is needed, which usually act as an anti-porter with inorganic phosphates.

In another embodiment, in order to export unphosphorylated sugars, such as glucose, in appreciable quantities the cell is engineered to dephosphorylate glucose-phosphate (e.g., phosphatase) in the cell. Diffusion through a transporter allows glucose to exit the cell.

Preferably, to prevent buildup of other storage polymers, these proteins are expressed in cells that are attenuated in their ability to build other storage polymers such as glycogen, starch, sucrose, cellulose, and cyanophycin.

In one aspect of the present invention, to transport 3PGAL directly out of the cells, genes are expressed that encode enzymes to facilitate transport of the photosynthetic products from within the host cell to the culture media. For instance, to export triose-phosphates out of the cell with concomitant import of inorganic phosphate, the following protein is expressed: *A. thaliana* triose-phosphate transporter APE2 (AT5G46110.4) in a host cell of interest, e.g., cyanobacteria.

In another aspect, an antiporter or a transporter is used to transport glucose-6-phosphate or fructose-6-phosphate outside of the cell. For example, to export glucose-6-phosphate out of the cell with concomitant import of inorganic phosphate, one or more of the following proteins are expressed in a photosynthetic organism: (1) *E. coli* sugar phosphate transporter UhpT (NP_418122.1), (2) *A. thaliana* glucose-6-phosphate transporter GPT1 (AT5G54800.1) or (3) *A. thaliana* glucose-6-phosphate transporter GPT2 (AT1G61800.1).

In other embodiments, to facilitate conversion of D-fructose 6-phosphate to D-glucose-6-phosphate, a fructose-6-phosphate isomerase is introduced in the cell. For example, a glucose-6-phosphatase (e.g., GenBank Accession Nos. AAA16222, AAD19898, O43826) is introduced into the cell to convert D-glucose 6-phosphate and $H_{2O}$ to D-glucose and phosphate.

Additionally, a phosphatase enzyme activity introduced into the host cell to dephosphorylate glucose-6-phosphate and/or glucose-1-phosphate within in a photosynthetic organism. In one embodiment, one or more of the following proteins are expressed: (1) *H. sapiens* glucose-6-phosphatase G6PC (P35575), (2) *E. coli* glucose-1-phosphatase Agp (P19926), (3) *E. cloacae* glucose-1-phosphatase AgpE (Q6EV19) and (4) *E. coli* acid phosphatase YihX (P0A8Y3).

To facilitate the diffusive efflux of the glucose made intracellularly via the action of the aforementioned phosphatase(s), one or more of the following permeases are expressed: (1) *H. sapiens* glucose transporter GLUT-1, -3, or -7 (P11166, P11169, Q6PXP3), (2) *S. cerevisiae* hexose transporter HXT-1, -4, or -6 (P32465, P32467, P39003), or (3) *Z. mobilis* glucose uniporter Glf (P21906). In certain embodiments, the following transporters are expressed: 2.A.1.1.32 Glucose/fructose:H+ symporter, GlcP [Zhang et al. (1989)] bacteria GlcP of *Synechocystis* sp. (P15729); 2.A.1.1.35, the major glucose (or 2-deoxyglucose) uptake transporter, GlcP [van Wezel et al., (2005)]; and/or Q7BEC, 2.A.1.1.24 Hexose (Glucose and Fructose) transporter, PfHT1 of *Plasmodium falciparum* sp. O97467. In other embodiments, a glucose transporter, such as the Glut-1 transporter (e.g., GenBank Accession No. 577924) is introduced in the cell in order to facilitate active secretion of glucose form within the cell to the culture media. A diffusive mechanism may involve the native bacterial transporters such as the native glucose transporters which normally let glucose in and/or the mammalian transporters such as Glut-1, Glut-2 for diffusive efflux of glucose. Accordingly, glucose produced as a result of photosynthesis is diffused from within the cells to the culture media.

The genes corresponding to the above proteins are synthetically made and placed downstream of constitutive and/or inducible promoters for expression in the photosynthetic organism. The constructs can then be used to transform the organisms via linkage to a positively selectable marker such as an antibiotic resistance gene. In certain embodiments, the above genes are integrated into the chromosome of the host cell, e.g., cyanobacteria. Preferred integration sites include genomes that are involved in cellulose, glycogen or sucrose synthesis.

Alteration of Cellulose, Glycogen or Sucrose Synthesis

In another aspect of the invention, cells are modified to attenuate, disrupt or delete cellulose, glycogen, sucrose synthesis or a combination thereof as shown in Table 1.

TABLE 1

| Enzyme | Reaction | *Synnechococcus* sp. PCC 7002 Locus |
|---|---|---|
| cellulose synthase (UDP-forming) (EC 2.4.1.12) | UDP-glucose + (1,4-beta-D-glucosyl)n = UDP + (1,4-beta-D-glucosyl)n + 1 | A2118 |
| glycogen synthase e.g., glgA1, glgA2 (EC 2.4.1.21) | ADP-glucose + (1,4-beta-D-glucosyl)n = ADP + (1,4-alpha-D-glucosyl)n + 1 | A1532<br>A2125 |
| sucrose phosphate synthase (EC 2.4.1.14) | UDP-glucose + D-fructose 6-phosphate = UDP + sucrose 6-phosphate | A0888 (spsA) |
| sucrose phosphorylase (EC 3.1.3.24) | sucrose 6-phosphate + H2O = sucrose + phosphate | AmyA (A2022) |
| α-1,4-glucan lyase | Linear alpha-glucan = glucose | |

TABLE 1-continued

| Enzyme | Reaction | *Synnechococcus* sp. PCC 7002 Locus |
|---|---|---|
| (EC 4.2.2.13) | glucose + 1,5-anhydro-D-fructose | |
| glycogen synthase (EC 2.4.1.11) | UDP-glucose + (1,4-alpha-D-glucosyl)n = UDP + (1,4-alpha-D-glucosyl)n + 1 | |
| 1,4-α-glucan branching enzyme (EC 2.4.1.18) | transfers a segment of a 1,4-alpha-D-glucan chain to a primary hydroxy group in a similar glucan chain | A1865 |

Phototrophic fixation of CO2 is followed by the rapid flux of carbon compounds to the creation and maintenance of biomass and to the storage of retrievable carbon in the form of glycogen, cellulose and/or sucrose. Under medium conditions of sufficient nitrogen, glycogen stores can represent 30% of cell mass. Under nitrogen starvation conditions, cells partition more carbon to glycogen creating stores up to 60% of cell mass. Nitrogen limitation can act as a biological control over carbon flux to glycogen.

Glycogen is a polymer of glucose composed of linear alpha 1,4-linkages and branched alpha 1,6-linkages. The polymer is insoluble at degree of polymerization (DP) greater than about 60,000 and forms intracellular granules. Glycogen in synthesized in vivo via a pathway originating from glucose 1-phosphate. Its hydrolysis can proceed through phosphorylation to glucose phosphates; via the internal cleavage of polymer to maltodextrins; via the successive exo-cleavage to maltose; or via the concerted hydrolysis of polymer and maltodextrins to maltose and glucose.

In certain aspects, various routes to engineer metabolism to produce glucose biosynthetically are described. For example, glycogen synthesis can be interrupted, and glucose-1-phosphate or glucose-6-phosphate can be desphosphorylated. Glucose phosphate could be dephosphorylated intracellularly via a cloned or endogenous phosphatase or hexokinase and transported out of the cell via a cloned or endogenous facilitating carrier. Alternatively, the glucose phosphate could be transported and dephosphorylated externally. The glucose phosphate could also be used directly as a fermentation substrate.

In addition to the above, another mechanism is described to produce glucose biosynthetically. In certain embodiments, the present invention provides for cloned genes for glycogen hydrolyzing enzymes to hydrolyze glycogen to glucose and/or maltose and transport maltose and glucose from the cell. Preferred enzymes are set forth below in Table 2. Glucose is transported out by a glucose/hexose transporter. This alternative allows the cell to accumulate glycogen naturally but adds enzyme activities to continuously return it to maltose or glucose units which can be collected as a fermentable product.

There are a number of potential enzyme candidates for glycogen hydrolysis. Enzymes are limited in their mechanisms for hydrolysis of the 1,4- and 1,6-bonds of the glycogen polymer and complete hydrolysis requires an ensemble of enzymes. α-amylases perform an endo-attack on large polymers of glycogen and hydrolysis results in formation of shorter, average DP 13, polymers which are attacked in an exo-fashion by glucoamylase to result in glucose product. Neither of the aforementioned enzymes will attack at the 1,6-branches. Therefore, pullulanases and other amylo-1,6-glycosidases, which in nature perform this hydrolysis, are used to completely hydrolyze glycogen to glucose. An alternative is a β-amylase which performs exo-attack on the large polymer ends and results in release of maltose units. Additionally, there are a number of possibilities for enzymatic dephosphorylation of glucose-6-phosphate including alkaline or acid phosphatases and kinases. The following enzymes listed in Table 2 below have activities specific to sugar or sugar polymer dephosphorylation.

TABLE 2

| Enzymes for hydrolysis of glycogen | | |
|---|---|---|
| Enzyme Name | Enzyme Classification No. | Function |
| α-amylase | EC 3.2.1.1 | endohydrolysis of 1,4-alpha-D-glucosidic linkages in polysaccharides |
| β-amylase | EC 3.2.1.2 | hydrolysis of 1,4-alpha-D-glucosidic linkages in polysaccharides so as to remove successive maltose units from the non-reducing ends of the chains |
| γ-amylase | EC 3.2.1.3 | hydrolysis of terminal 1,4-linked alpha-D-glucose residues successively non-reducing ends of the chains with release of beta-D-glucose |
| glucoamylase | EC 3.2.1.3 | hydrolysis of terminal 1,4-linked alpha-D-glucose residues successively from non-reducing ends of the chains with release of beta-D-glucose |
| isoamylase | EC 3.2.1.68 | hydrolysis of (1−>6)-alpha-D-glucosidic branch linkages in glycogen, amylopectin and their beta-limit dextrins |
| pullulanase | EC 3.2.1.41 | hydrolysis of (1−>6)-alpha-D-glucosidic linkages in pullulan [a linear polymer of alpha-(1−>6)-linked maltotriose units] and in amylopectin and glycogen, and the alpha- and beta-limit dextrins of amylopectin and glycogen |
| amylomaltase: | EC 2.4.1.25; | transfers a segment of a 1,4-alpha-D-glucan to a new position in an acceptor, which may be glucose or a 1,4-alpha-D-glucan (part of yeast debranching system) |

TABLE 2-continued

| Enzymes for hydrolysis of glycogen | | |
|---|---|---|
| Enzyme Name | Enzyme Classification No. | Function |
| amylo-α-1,6-glucosidase | EC 3.2.1.33 | debranching enzyme; hydrolysis of (1->6)-alpha-D-glucosidic branch linkages in glycogen phosphorylase limit dextrin |
| phosphorylase kinase | EC 2.7.11.19 | 2 ATP + phosphorylase b = 2 ADP + phosphorylase a |
| phosphorylase | EC 2.4.1.1 | (1,4-alpha-D-glucosyl)n + phosphate = (1,4-alpha-D-glucosyl)n-1 + alpha-D-glucose-l-phosphate |

Transport/Efflux Gene Products

A number of transport mechanisms are possible. Most bacterial cells have vectorial active transporters to move glucose or maltose into the cell. To accumulate sugars, these mechanisms rely on energy coupling in the form of ATP, proton motive force or gradients of other molecular species, e.g., phosphate. Plant chloroplasts have active mechanisms to facilitate efflux of glucose and maltose to the plant or algal cytoplasm. Accordingly, in certain embodiments, building transporters into the inner membrane may involve targeting and assembly, and vectoriality of the energy coupling mechanism versus solute flux. For instance, maltose efflux pump from chloroplast for maltose transport: MEX1; glucose permeases, low and high Km, glucose:H+ symporter, glucose/fructose permease, general sugar:H+ antiporter for glucose transport; and glucose 6-phosphate:Pi antiporter, triose-phosphate:phosphate antiporter for glucose-6-phosphate transport are contemplated transport mechanisms of the present invention.

There are natural *Chlorella* algal strains that secrete maltose and glucose at appreciable rates. These strains are normally endosymbiotic and, remarkably, when isolated freshly from their hosts excrete almost all of their photosynthate as extracellular monosaccharide, however, almost invariably, they lose this ability soon after being removed.

A few *Chlorella* strains can be grown as axenic cultures (~12 hr doubling time, 30° C.) and still secrete appreciable fractions (5-40%) of their photosynthate almost entirely as either glucose or maltose on nutrient starvation media (akin to glycogen production upon nitrogen starvation). These excretion rates continue in the dark from intracellular stores of photosynthate. Some of the best rates in the literature are described by Fischer et al. 179:251-256 (1989); and Brechignac et al., *Adv. Space Res.* 14:79-88 (1994).

In certain embodiments, the above mentioned rates of sugar production are maintained or, more preferably, exceeded. Operating at a biomass density of 15 g/l (~OD 50), implies a volumetric productivity of ~0.05*15=0.75 g sugar/l/hr.

The fermentation products according to the above aspect of the invention are sugars, which are exported into the media as a result of carbon fixation during photosynthesis. The sugars can be reabsorbed later and fermented, directly separated, or utilized by a co-cultured organism. This approach has several advantages. First, the total amount of sugars the cell can handle is not limited by maximum intracellular concentrations because the end-product is exported to the media. Second, by removing the sugars from the cell, the equilibria of carbon fixation reactions are pushed towards creating more sugar. Third, during photosynthesis, there is no need to push carbon flow towards glycolysis. Fourth, the sugars are potentially less toxic than the fermentation products that would be directly produced.

Accordingly, the invention provides cells which produce metabolic sugars, e.g., glucose, through photosynthesis using light, water and $CO_2$, subsequently converting the sugars into carbon-based products of interest in an efficient, sustainable yield. In certain embodiments, the photosynthetic organisms are genetically modified to produce photosynthetic products such as glucose at amounts greater than 1 mg, 100 mg, 500 mg, 1 g, 5 g, 10 g, 20 g, 25 g, 30 g, 35 g, 40 g, 50 g, 100 g, 120 g, or 150 g per liter of fermentation medium.

The invention also provides engineered photosynthetic organisms that produce other sugars such as sucrose, xylose, pentose, rhamnose, and arabinose according to the same principles. Using such sugars as its primary carbon source, the organism can ferment the sugar and produce carbon-based products of interest, e.g., biofuels such as ethanol (see, e.g., Ho et al., *Appl Environ Microbiol,* 64:1852-1859 (1998), describing use of glucose and xylose for the producing ethanol from cellulosic biomass).

Consolidated Photo-Fermentation

The above aspect of the invention is an alternative to directly producing final carbon-based product of interest as a result of photosynthesis. In this approach, carbon-based products of interest would be produced by leveraging other organisms that are more amenable to making any one particular product while culturing the photosynthetic organism for its carbon source. Consequently, fermentation and production of carbon-based products of interest can occur separately from carbon source production in a photobioreactor.

In one aspect, the methods of producing such carbon-based products of interest include two steps. The first-step includes using photosynthetic organisms to convert carbon dioxide to photosynthetic products such as glucose. The second-step is to use the photosynthetic products as a carbon source for cells that produce carbon-based products of interest. In one embodiment, the two-stage approach comprises a photobioreactor comprising photosynthetic cells; a second reactor comprising cells capable of fermentation; wherein the photosynthetic cells provides a carbon source such as glucose for cells capable of fermentation to produce a carbon-based product of interest. The second reactor may comprise more than one type of microorganism. The resulting carbons-based products of interest are subsequently separated and/or collected.

Preferably, the two-steps are combined into a single-step process whereby the engineered photosynthetic organisms convert light and $CO_2$ directly into glucose and such organisms are capable of producing a variety of carbon-based products of interest.

The present invention also provides methods and compositions for sustained glucose production in photosynthetic organisms wherein these or other organisms that use the sugars are cultured using light, water and $CO_2$ for use as a carbon source to produce carbon-based products of interest. In such embodiments, the host cells are capable of secreting the sugars, such as glucose from within the cell to the culture media in continuous or fed-batch in a bioreactor.

Certain changes in culture conditions of photosynthetic host cells, e.g., cyanobacteria for the production of sugars can be optimized for growth. For example, conditions are optimized for light intensity, light exposure, time of exposure, diurnal cycle, addition of supplements, nutrients, the rate of recirculation and flow rates that maintain a light to dark ratio. As will be apparent to those skilled in the art, the conditions sufficient to achieve optimum growth will vary depending upon location, climate, and other environmental factors, such as the diurnal cycle, light intensity and time of exposure to light. Other adjustments may be required, for example, an organism's ability for carbon uptake. Increased carbon in the form of $CO_2$ may be introduced into a bioreactor by a gas sparger or aeration devices Advantages of consolidated photo-fermentation include a process where there is separation of chemical end products, e.g., glucose, spatial separation between end products (membranes) and time. Additionally, unlike traditional or cellulosic biomass to biofuels production, pretreatment, saccharification and crop plowing are obviated.

The consolidated photo-fermentation process produces continuous products. In preferred embodiments, the process involves direct capture of light to product from engineered front-end organisms to produce various products without the need to lyse the organisms. For instance, the organisms can utilize 3PGAL in the light to make a desired fermentation product, e.g., ethanol. In other embodiments, the organisms can accumulate glycogen in the light and metabolize ethanol in the dark to make more fermentation products. Such end products can be readily secreted as opposed to intracellular products such as oil and cellulose. In yet other embodiments, organisms produce sugars in the light, which are secreted into the media and such sugars are used in the dark during fermentation with the same or different organisms or a combination of both.

Fermentation Conditions

The production and isolation of carbon-based products of interest can be enhanced by employing specific fermentation techniques. One method for maximizing production while reducing costs is increasing the percentage of the carbon that is converted to hydrocarbon products. During normal cellular lifecycles carbon is used in cellular functions including producing lipids, saccharides, proteins, organic acids, and nucleic acids. Reducing the amount of carbon necessary for growth-related activities can increase the efficiency of carbon source conversion to output. This can be achieved by first growing microorganisms to a desired density, such as a density achieved at the peak of the log phase of growth. At such a point, replication checkpoint genes can be harnessed to stop the growth of cells. Specifically, quorum sensing mechanisms [reviewed in Camilli and Bassler, *Science* 311:1113, (2006); Venturi *FEMS Microbio Rev* 30:274-291 (2006); and Reading and Sperandio, *FEMS Microbiol Lett,* 254:1-11, (2006)] can be used to activate genes such as p53, p21, or other checkpoint genes. Genes that can be activated to stop cell replication and growth in *E. coli* include umuDC genes, the over-expression of which stops the progression from stationary phase to exponential growth [Murli et al, *J. of Bact.,* 182:1127, (2000)]. UmuC is a DNA polymerase that can carry out translesion synthesis over non-coding lesions—the mechanistic basis of most UV and chemical mutagenesis. The umuDC gene products are used for the process of translesion synthesis and also serve as a DNA damage checkpoint. UmuDC gene products include UmuC, UmuD, umuD', UmuD'$_2$C, UmuD'$_2$ and UmUD$_2$. Simultaneously, the product-producing genes are activated, thus minimizing the need for replication and maintenance pathways to be used while the fatty acid derivative is being made.

In one aspect, the percentage of input carbons converted to hydrocarbon products is an efficient and inexpensive process. Using carbon dioxide as the carbon source, the oxygen is released in the form of $O_2$, leading to a maximal theoretical metabolic efficiency of ~34% (w/w) (for fatty acid derived products).

This figure, however, changes for other hydrocarbon products and carbon sources. Typical efficiencies in the literature are ~<5%. Engineered microorganisms which produce hydrocarbon products can have greater than 1, 3, 5, 10, 15, 20, 25, and 30% efficiency. In one example microorganisms will exhibit an efficiency of about 10% to about 25%. In other examples, such microorganisms will exhibit an efficiency of about 25% to about 30%, and in other examples such microorganisms will exhibit >30% efficiency.

In some examples where the final product is released from the cell, a continuous process can be employed. In this approach, a reactor with organisms producing fatty acid derivatives can be assembled in multiple ways. In one example, a portion of the media is removed and allowed to separate. Fatty acid derivatives are separated from the aqueous layer, which will in turn, be returned to the fermentation chamber.

In another example, the fermentation chamber will enclose a fermentation that is undergoing a continuous reduction. In this instance, a stable reductive environment would be created. The electron balance would be maintained by the release of oxygen. Efforts to augment the NAD/H and NADP/H balance can also facilitate in stabilizing the electron balance.

The availability of intracellular NADPH can be also enhanced by engineering the production host to express an NADH:NADPH transhydrogenase. The expression of one or more NADH:NADPH transhydrogenase converts the NADH produced in glycolysis to NADPH which enhances the production of fatty acid derivatives.

For large-scale product production, the engineered microorganisms are grown in 10 L, 100 L or larger batches, fermented and induced to express desired products based on the specific genes encoded in plasmids as appropriate. Cells harboring engineered nucleic acids to over-express or attenuate gene products are incubated from a 500 mL seed culture for 10 L fermentations (5 L for 100 L fermentations) in LB media (glycerol free) at 37° C. shaken at >200 rpm until cultures reached a desired OD (typically 16 hours) incubated with kanamycin, ampicillin or the like. Media is treated with continuously supplemented to maintain a 25 mM sodium proprionate at a suitable pH of about 8.0 to activate the engineered in gene systems for production as well as to stop cellular proliferation. Media is continuously supplemented with carbon dioxide. Aliquots of no more than 10% of the total cell volume are removed each hour and allowed to sit unaggitated so as to allow the hydrocarbon product to rise to the surface and undergo a spontaneous phase separation. The hydrocarbon component is then collected and the aqueous phase returned to the reaction chamber. The reaction chamber is operated continuously. For wax ester production, subsequent to isolation, the wax esters are washed briefly in 1 M HCl to split the ester bond, and returned to pH 7 with extensive washing with distilled water.

Production and Release of Fatty Alcohol from Production Host

Also disclosed herein is a system for continuously producing and exporting hydrocarbons out of recombinant host microorganisms via a transport protein. Many transport and efflux proteins serve to excrete a large variety of compounds and can be evolved to be selective for a particular type of fatty acid. Thus, in some embodiments an exogenous nucleic acid sequence encoding an ABC transporter will be functionally expressed by the recombinant host microorganism, so that the microorganism exports the fatty acid into the culture medium. In one example, the ABC transporter is an ABC transporter from *Caenorhabditis elegans, Arabidopsis thalania, Alkaligenes eutrophus* or *Rhodococcus erythropolis* (locus AAN73268). In another example, the ABC transporter is an ABC transporter chosen from CER5 (locuses AtI g51500 or AY734542), AtMRPS, AmiS2 and AtPGP1. In some examples, the ABC transporter is CER5. In yet another example, the CER5 gene is from *Arabidopsis* (locuses AtI g51500, AY734542, At3g21090 and At Ig51460).

The transport protein, for example, can also be an efflux protein selected from: AcrAB, ToIC and AcrEF from *E. coli*, or t111618, H11619 and U10139 from *Thermosynechococcus elongatus* BP-I.

In addition, the transport protein can be, for example, a fatty acid transport protein (FATP) selected from *Drosophila melanogaster, Caenorhabditis elegans, Mycobacterium tuberculosis* or *Saccharomyces cerevisiae* or any one of the mammalian FATPs. The FATPs can additionally be resynthesized with the membranous regions reversed in order to invert the direction of substrate flow. Specifically, the sequences of amino acids composing the hydrophilic domains (or membrane domains) of the protein can be inverted while maintaining the same codons for each particular amino acid. The identification of these regions is well known in the art.

Production hosts can also be selected for their endogenous ability to release fatty acids. The efficiency of product production and release into the fermentation media can be expressed as a ratio of intracellular product to extracellular product. In some examples the ratio can be 5:1, 4:1, 3:1, 2:1, 1:1, 1:2, 1:3, 1:4, or 1:5.

Processing & Separation

The carbon-based products produced by the carbon dioxide fixing organisms during fermentation can be separated from the fermentation media. Known techniques for separating fatty acid derivatives from aqueous media can be employed. One exemplary separation process provided herein is a two-phase (bi-phasic) separation process. This process involves fermenting the genetically-engineered production hosts under conditions sufficient to produce for example, a fatty acid, allowing the fatty acid to collect in an organic phase and separating the organic phase from the aqueous fermentation media. This method can be practiced in both a batch and continuous fermentation setting.

Bi-phasic separation uses the relative immiscibility of fatty acid to facilitate separation. A skilled artisan will appreciate that by choosing a fermentation media and the organic phase such that the fatty acid derivative being produced has a high logP value, even at very low concentrations the fatty acid will separate into the organic phase in the fermentation vessel.

When producing fatty acids by the methods described herein, such products will be relatively immiscible in the fermentation media, as well as in the cytoplasm. Therefore, the fatty acid will collect in an organic phase either intracellularly or extracellularly. The collection of the products in an organic phase will lessen the impact of the fatty acid derivative on cellular function and allows the production host to produce more product.

The fatty alcohols, fatty acid esters, waxes, and hydrocarbons produced as described herein allow for the production of homogeneous compounds with respect to other compounds wherein at least 50%, 60%, 70%, 80%, 90%, or 95% of the fatty alcohols, fatty acid esters, waxes and hydrocarbons produced have carbon chain lengths that vary by less than 4 carbons, or less than 2 carbons. These compounds can also be produced so that they have a relatively uniform degree of saturation with respect to other compounds, for example at least 50%, 60%, 70%, 80%, 90%, or 95% of the fatty alcohols, fatty acid esters, hydrocarbons and waxes are mono-, di-, or tri-unsaturated.

Pathways Associated with Production of Isoprenoids

There are two known biosynthetic pathways that synthesize isopentenyl pyrophosphate ("IPP") and its isomer, dimethylallyl pyrophosphate ("DMAPP"). Eukaryotes other than plants use the mevalonate-dependent ("MEV") isoprenoid pathway exclusively to convert acetyl-coenzyme A ("acetyl-CoA") to IPP, which is subsequently isomerized to DMAPP. Prokaryotes, with some exceptions, use the mevalonate-independent or deoxyxylulose 5-phosphate ("DXP") pathway to produce IPP and DMAPP separately through a branch point. In general, plants use both the MEV and DXP pathways for IPP synthesis.

MEV Pathway: In general, the pathway comprises six steps. In the first step, two molecules of acetyl-coenzyme A are enzymatically combined to form acetoacetyl-CoA. An enzyme known to catalyze this step is, for example, acetyl-CoA thiolase. Examples include without limitation NC_000913 REGION: 232413 L.2325315; *E. coli*, D49362; *Paracoccus denitrificans*, and L20428; *S. cerevisiae.*

In the second step of the MEV pathway, acetoacetyl-CoA is enzymatically condensed with another molecule of acetyl-CoA to form 3-hydroxy-3-methylglutaryl-CoA (HMG-CoA). An enzyme known to catalyze this step is, for example, HMG-CoA synthase. Examples include without limitation NC_001 145 complement 19061 . . . 20536; *S. cerevisiae*, X96617; *S. cerevisiae*, X83882; *A. thaliana*, AB037907; *Kitasatospora griseola*, BT007302; *H. sapiens*, and NC_002758, Locus tag SAV2546, GeneID 1 122571; *S. aureus.*

In the third step, HMG-CoA is enzymatically converted to mevalonate. HMG-CoA reductase is an example of n enzyme known to catalyze this step. Examples from various organisms include, without limitation, NM_206548; *D. melanogaster*, NC_002758, Locus tag SAV2545, GeneID 1122570; *S. aureus*, NM_204485; *Gallus gallus*, AB015627; *Streptomyces* sp. KO 3988, AF542543; *Nicotiana attenuata*, AB037907; *Kitasatospora griseola*, AX128213, providing the sequence encoding a truncated HMGR; *S. cerevisiae*, and NC_001 145: complement 115734 . . . 1 18898; *S. cerevisiae.*

In the fourth step, mevalonate is enzymatically phosphorylated to form mevalonate 5-phosphate. An enzyme known to catalyze this step is, for example, mevalonate kinase. Examples include without limitation L77688; *A. thaliana*, and X55875; *S. cerevisiae.*

In the fifth step, a second phosphate group is enzymatically added to mevalonate 5-phosphate to form mevalonate 5-pyrophosphate. An enzyme known to catalyze this step is, for example, phosphomevalonate kinase. Examples include without limitation AF429385; *Hevea brasiliensis*, NM_006556; *H. sapiens*, and NC_001 145 complement 712315 . . . 713670; *S. cerevisiae.*

In the sixth step, mevalonate 5-pyrophosphate is enzymatically converted into IPP. An enzyme known to catalyze this step is, for example, mevalonate pyrophosphate decarboxylase. Examples include without limitation X97557; *S. cerevisiae*, AF290095; *E. faecium*, and U49260; *H. sapiens.*

If IPP is to be converted to DMAPP using the mevalonate pathway, then a seventh step is required. An enzyme known to catalyze this step is, for example, IPP isomerase. Examples include without limitation NC 000913, 3031087, 3031635; *E. coli*, and AF082326; *Haematococcus pluvialis.*

DXP Pathway: In general, the DXP pathway comprises seven steps In the first step, pyruvate is condensed with D-glyceraldehyde 3-phosphate to make 1-deoxy-D-xylulose-5-phosphate. An enzyme known to catalyze this step is, for example, 1-deoxy-D-xylulose-5-phosphate synthase. Examples include without limitation AF035440; *E. coli*, NC__002947, locus tag PP0527; *P. putida* KT2440, CP000026, locus tag SPA2301; *Salmonella enterica Paratyphi*, see ATCC 9150, NC__007493, locus tag RSP__0254; *Rhodobacter sphaeroides* 2.4.1, NC__005296, locus tag RPA0952; *Rhodopseudomonas palustris* CGA009, (NC__004556, locus tag PD1293; *Xylellafastidiosa Temecu-lal*, and NC__003076, locus tag AT5G11380; *A. thaliana.*

In the second step, 1-deoxy-D-xylulose-5-phosphate is converted to 2C-methyl-D-erythritol-4-phosphate. An enzyme known to catalyze this step is, for example, 1-deoxy-D-xylulose-5-phosphate reductoisomerase. Examples include without limitation AB013300; *E. coli*, AF148852; *A. thaliana*, NC__002947, locus tag PP 1597; *Pseudomonas putida* KT2440, AL939124, locus tag SCO5694; *Streptomyces coelicolor* A3(2), (NC__007493), locus tag RSP__2709; *Rhodobacter sphaeroides* 2.4.1, and NC__007492, locus tag Pfl__1107; *Pseudomonas fluorescens* PfO-1.

In the third step, 2C-methyl-D-erythritol-4-phosphate is converted to 4-diphosphocytidyl-2C-methyl-D-erythritol. An enzyme known to catalyze this step is, for example, 4-diphosphocytidyl-2C-methyl-D-erythritol synthase. Examples include without limitation AF230736; *E. coli*, NC__007493, locus_tag RSP__2835; *Rhodobacter sphaeroides* 2.4.1, NC__003071, locus tag AT2G02500; *A. thaliana*, and NC 002947, locus_tag PP 1614; *P. putida* KT2440).

In the fourth step, 4-diphosphocytidyl-2C-methyl-D-erythritol is converted to 4-diphosphocytidyl-2C-methyl-D-erythritol-2-phosphate. An enzyme known to catalyze this step is, for example, 4-diphosphocytidyl-2C-methyl-D-erythritol kinase. Examples include without limitation AF216300; *E. coli* and NC__007493, locus_tag RSP__1779; *Rhodobacter sphaeroides* 2.4.1).

In the fifth step, 4-diphosphocytidyl-2C-methyl-D-erythritol-2-phosphate is converted to 2C-methyl-D-erythritol 2,4-cyclodiphosphate. An enzyme known to catalyze this step is, for example, 2C-methyl-D-erythritol 2,4-cyclodiphosphate synthase. Examples include without limitation AF230738; *E. coli*, NC__007493, locus_tag RSP__6071; *Rhodobacter sphaeroides* 2.4.1, and NC__002947, locus tag PP1 618; *P. putida* KT2440.

In the sixth step, 2C-methyl-D-erythritol 2,4-cyclodiphosphate is converted to 1-hydroxy-2-methyl-2-(E)-butenyl-4-diphosphate. An enzyme known to catalyze this step is, for example, 1-hydroxy-2-methyl-2-(E)-butenyl-4-diphosphate synthase. Examples include without limitation AY033515; *E. coli*, NC__002947, locus_tag PP0853; *P. putida* KT2440, and NC007493, locus_tag RSP__2982; *Rhodobacter* sphaeroides 2.4.1.

In the seventh step, 1-hydroxy-2-methyl-2-(E)-butenyl-4-diphosphate is converted into either IPP or its isomer, DMAPP. An enzyme known to catalyze this step is, for example, isopentyl/dimethylallyl diphosphate synthase. Examples include without limitation AY062212; *E. coli* and NC__002947, locus_tag PP0606; *P. putida* KT2440.

Isoprenoid Production

Any suitable host cell as described herein may be used in the practice of the present invention. In one embodiment, the host cell is a genetically modified host microorganism in which nucleic acid molecules have been inserted, deleted or modified (i.e., mutated, e.g., by insertion, deletion, substitution, and/or inversion of nucleotides), to either produce the desired isoprenoid compound or starting material, or to increase yields of the desired isoprenoid compound or starting material. In another embodiment, the host cell is capable of being grown in liquid growth medium.

Provided herein is a method to produce isoprenoids in carbon dioxide fixing hosts engineered with the isopentenyl pyrophosphate pathway enzymes. Some examples of isoprenoids include: hemiterpenes (derived from 1 isoprene unit) such as isoprene; monoterpenes (derived from 2 isoprene units) such as myrcene; sesquiterpenes (derived from 3 isoprene units) such as amorpha-4,11-diene; diterpenes (derived from four isoprene units) such as taxadiene; triterpenes (derived from 6 isoprene units) such as squalene; tetraterpenes (derived from 8 isoprenoids) such as β-carotene; and polyterpenes (derived from more than 8 isoprene units) such as polyisoprene. The production of isoprenoids is also described in some detail in the published PCT applications WO2007/139925 and WO/2007/140339.

In one aspect, a host cell producing isoprenoid involves the steps of selecting a host cell that is capable or can be modified to produce an enzymatic pathway for making isopentenyl pyrophosphate wherein the all of the pathway enzymes are under expression control sequences; and culturing the host cells in a medium under suitable conditions for growth. In some embodiments, the pathway is the mevalonate pathway. In other embodiments, the pathway is the DXP pathway.

In some embodiments, "cross talk" (or interference) between the host cells own metabolic processes and those processes involved with the production of IPP are minimized or eliminated entirely. For example, cross talk is minimized or eliminated entirely when the host microorganism relies exclusively on the DXP pathway for synthesizing IPP, and a MEV pathway is introduced to provide additional IPP. Such a host organism would not be equipped to alter the expression of the MEV pathway enzymes or process the intermediates associated with the MEV pathway. Organisms that rely exclusively or predominately on the DXP pathway include, for example, *E. coli.*

In some embodiments, the host cell produces IPP via the MEV pathway, either exclusively or in combination with the DXP pathway. In other embodiments, a host cell's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the host cell produces IPP via the DXP pathway, either exclusively or in combination with the MEV pathway. In other embodiments, a host cell's MEV pathway is functionally disabled so that the host cell produces IPP exclusively through a heterologously introduced DXP pathway. The MEV pathway can be functionally disabled by disabling gene expression or inactivating the function of one or more of the MEV pathway enzymes.

In yet another embodiment, a method for producing an isoprenoid or isoprenoid precursor comprises the steps of (i) performing a fermentation reaction comprising a fermentation medium and a plurality of genetically modified carbon dioxide fixing host cells that produce the isoprenoid under conditions such that (a) the fermentation medium is kept at a temperature lower than that which would provide for a maximum specific growth rate of said host cells; (b) the fermentation medium comprises a carbon dioxide; and/or (c) the fermentation medium comprises a nitrogen source present in an amount that is lower than that which would provide for a maximum specific growth rate of the host cells; (ii) recovering the isoprenoid produced under one or more conditions set forth in (a) through (c). In one aspect, the isoprenoid is produced under at least two of the conditions set forth in (a) through (c). In another aspect, the isoprenoid is produced under all of the conditions set forth in (a) through (c).

In a further aspect of the present invention, compositions and methods are provided for a robust production of isoprenoids by the use of isopentenyl pyrophosphate pathway enzymes that are under the control of at least one heterologous regulator or fermentation conditions, either alone or in combination.

In yet another aspect, a method for producing an isoprenoid involves the steps of (a) selecting or obtaining genetically modified carbon dioxide fixing host cells that comprise an enzymatic pathway for making isopentenyl pyrophosphate wherein all of the pathway enzymes are under control of at least one heterologous transcriptional regulator; and (b) culturing the host cells in a medium under conditions that are suboptimal as compared to conditions that would provide for a maximum specific growth rate for the host cells. In some embodiments, the pathway is the mevalonate pathway. In other embodiments, the pathway is the DXP pathway. In other embodiments, the pathway enzymes are under expression control sequences.

In some embodiments, the pathway comprises a nucleic acid sequence encoding a mevalonate pathway enzyme from a prokaryote having an endogenous mevalonate pathway. Exemplary prokaryotes having an endogenous mevalonate pathway include but are not limited to the genus *Enterococcus*, the genus *Pseudomonas*, and the genus *Staphylococcus*. In one embodiment, the mevalonate pathway enzyme is selected from acetyl-CoA thiolase, HMG-CoA synthase, HMG-CoA reductase, and mevalonate kinase. In another embodiment, the heterologous nucleic acid sequence encodes a Class II HMG-CoA reductase. In other embodiments, host cells such as cyanobacteria are engineered to heterologously express a mevalonate pathway.

In some embodiments, the amount of the isoprenoid compound produced by the host cell is at least 30% by volume based on the total volume of the biofuel.

In another embodiment, the host cells are cultured in a medium wherein the nutrient and/or temperature level is maintained at a level below that which would provide for the maximum specific growth rate for the host cells. In another embodiment, the host cells are cultured in a medium where the carbon source is maintained at a level to provide for less than about 90%, 75%, 50%, 25%, 10%, or anywhere between 90% and 10% of the maximum specific growth rate. In another embodiment, the host cells are cultured in a medium where the nitrogen source is maintained at a level to provide for less than about 90%, 75%, 50%, 25%, 10%, or anywhere between 90% and 10% of the maximum specific growth rate In another embodiment, the host cells are cultured in a medium where the temperature is maintained at a level to provide for less than about 90%, 75%, 50%, 25%, 10% or anywhere between 90% and 10% of the maximum specific growth rate. In another embodiment, the medium temperature is maintained at least about 2° C., 4° C., 5° C., 6° C., 8° C., 10° C., 15° C., or 20° C. below the temperature that would provide for the maximum specific growth rate.

Fuel Compositions

The above compositions produced by the carbon dioxide fixing organisms, carbon-based products, e.g., ethanol, fatty acids, alkanes, isoprenoids can be used as fuel. For example, using the methods described herein fuels comprising relatively homogeneous fatty acid derivatives that have desired fuel qualities can be produced. Such fuels can be characterized by carbon fingerprinting, their lack of impurities when compared to petroleum-derived fuels or bio-diesel derived from triglycerides and, moreover, the fatty-acid-based fuels can be combined with other fuels or fuel additives to produce fuels having desired properties.

Similar to the fuels from fatty acids, the present invention encompasses a fuel composition comprising a fuel component and a bioengineered $C_5$ isoprenoid compound.

In another aspect, the invention encompasses a fuel composition produced by preparing 3-methyl-3-buten-1-ol using a carbon dioxide fixing microorganism, and incorporating the 3-methyl-3-buten-1-ol in a fuel.

In another aspect, the invention encompasses a fuel composition produced by preparing 3-methyl-2-buten-1-ol using a microorganism, and incorporating the 3-methyl-2-buten-1-ol in a fuel.

In another aspect, the invention encompasses a fuel composition produced by preparing 3-methyl-3-buten-1-ol using a microorganism, preparing isoamyl alcohol from the 3-methyl-3-buten-1-ol, and incorporating the isoamyl alcohol in a fuel.

In another aspect, the invention encompasses a fuel composition produced by preparing 3-methyl-2-buten-1-ol using a microorganism, preparing isoamyl alcohol from the 3-methyl-2-buten-1-ol, and incorporating the isoamyl alcohol in a fuel.

In some embodiments, the recombinant host cell is modified to increase an enzymatic conversion of isopentenyl pyrophosphate (IPP), dimethylallyl pyrophosphate (DMAPP), or a combination thereof to an isopentenol.

In certain embodiments, the biofuel comprises 3-methyl-3-buten-1-ol, 3-methyl-2-buten-1-ol, 3-methyl-1-butanol or a combination thereof. In further embodiments, the amount of 3-methyl-3-buten-1-ol, 3-methyl-2-buten-1-ol or 3-methyl-1-butanol is at least about 2%.

Methods of preparing the isoprenoid compound using one or more microorganisms are described in Example 20. In certain embodiments, the fuel composition is produced by preparing 3-methyl-3-buten-1-ol using one or more microorganisms, preparing 3-methyl-1-butanol from 3-methyl-3-buten-1-ol, and incorporating the 3-methyl-1-butanol in the fuel composition. In other embodiments, the fuel composition is produced by preparing 3-methyl-2-buten-1-ol using one or more microorganisms, preparing 3-methyl-1-butanol from 3-methyl-2-buten-1-ol, and incorporating the 3-methyl-1-butanol in the fuel composition.

Impurities

In certain aspects, carbon-based products, e.g., ethanol, fatty acids, alkanes, isoprenoids produced herein contain fewer impurities than are normally associated with biofuels derived from triglycerides, such as fuels derived from vegetable oils and fats. For instance, crude fatty acid biofuels described herein (prior to mixing the fatty acid derivative with other fuels such as petrochemical diesel or bio-diesel) can contain less glycerol (or glycerin) than bio-fuels made from triglycerides, crude biofuel can contain less free alcohol (i.e., alcohol that is used to create the ester) than biodiesel made from triglycerides. Biofuels characteristically have a low concentration of sulfur compared to petroleum-derived diesel.

In one aspect, the crude fatty acid biofuels described herein (prior to mixing the fatty acid derivative with other fuels such as traditional fuels) can contain less transesterification catalyst than petrochemical diesel or bio-diesel. Preferably, the fatty acid derivative can contain less than about 2%, 1.5%, 1.0%, 0.5%, 0.3%, 0.1%, 0.05%, or 0% of a transesterification catalyst, or an impurity resulting from a transesterification catalyst, glycerol, free alcohol or sulfur. Transesterification catalysts include, for example, hydroxide catalysts such as NaOH, KOH, LiOH, and acidic catalysts, such as mineral acid catalysts and Lewis acid catalysts. Catalysts and impurities resulting from transesterification catalysts include, without limitation, tin, lead, mercury, cadmium, zinc, titanium, zirconium, hafnium, boron, aluminum, phosphorus, arsenic, antimony, bismuth, calcium, magnesium, strontium, uranium, potassium, sodium, lithium, and combinations thereof.

The differences in composition of gasoline may require that, in order to produce a uniform product, blending of the products from several component streams may be necessary. The properties of each stream may vary considerably, significantly affecting the product gasoline. The blending process is relatively straightforward, but the determination of the amount of each component to include in a blend is much more difficult.

In certain embodiments, the fuel composition disclosed herein is free or substantially free of a second alcohol wherein the second alcohol is not 3-methyl-3-buten-1-ol, 3-methyl-2-buten-1-ol or a combination thereof. In further embodiments, the second alcohol is methanol, ethanol, n-propanol, isopropanol, n-butanol, iso-butanol, tert-butanol, n-pentanol, sec-pentanol, tert-pentanol, n-hexanol, iso-hexanol, sec-hexanol, tert-hexanol, heptanols, octanols, nonanols, decanols or a combination thereof. In some embodiments, the fuel composition disclosed herein is free or substantially free of an aromatic compound. In other embodiments, the fuel composition disclosed herein is free or substantially free of an alkylamine, fatty acid ester or fatty acid salt.

In certain embodiments, the fuel composition disclosed herein further comprises a petroleum-based fuel in an amount from 1% to 95% by volume, based on the total volume of the fuel composition. In some embodiments, the petroleum-based fuel is gasoline. In further embodiments, the $C_5$ isoprenoid compound is present in an amount from about 1% to about 5% by volume, from about 1% to about 10% by volume, from about 1% to about 12.5% by volume, from about 2.5% to about 12.5% by volume, or from about 5% to about 12.5% by volume, based on the total volume of the fuel composition.

Additives

Generally, fuel additives are used to enhance the performance of a fuel or engine. For example, fuel additives can be used to alter the freezing/gelling point, cloud point, lubricity, viscosity, oxidative stability, ignition quality, octane level, and flash point. A skilled artisan will recognize that the fatty acids described herein can be mixed with other fuels such as bio-diesel derived from triglycerides, various alcohols such as ethanol and butanol, and petroleum-derived products such as gasoline. In some examples, a fatty acid, such as C16:1 ethyl ester or C18:1 ethyl ester, is produced which has a low gel point. This low gel point fatty acid derivative is mixed with bio-diesel made from triglycerides to lessen the overall gelling point of the fuel. Similarly, a fatty acid derivative such as C16:1 ethyl ester or C18:1 ethyl ester can be mixed with petroleum-derived diesel to provide a mixture that is at least and often greater than 5% biodiesel. In some examples, the mixture includes at least 20% or greater of the fatty acid.

For example, a biofuel composition can be made that includes at least about 20%, 30%, 40%, 50%, 60%, 70%, 80%, 85%, 90% or 95% of a fatty acid that includes a carbon chain that is 8:0, 10:0, 12:0, 14:0, 14:1, 16:0, 16:1, 18:0, 18:1, 18:2, 18:3, 20:0, 20:1, 20:2, 20:3, 22:0, 22:1 or 22:3. Such biofuel compositions can additionally include at least one additive selected from a cloud point-lowering additive that can lower the cloud point to less than about 5° C., or 0° C., a surfactant, or a microemulsion, at least about 5%, 10%, 15%, 20%, 30%, 40%, 50%, 60%, 70% or 80%, 85%, 90%, or 95% diesel fuel from triglycerides, petroleum-derived gasoline or diesel fuel from petroleum.

In some embodiments, the biofuel further comprises a petroleum-based fuel, a fuel additive or a combination thereof. In further embodiments, the petroleum-based fuel is a gasoline, jet fuel, kerosene, diesel fuel or a combination thereof.

The amount of the $C_5$ isoprenoid compound or a derivative thereof in the fuel composition disclosed herein may be from 0.5% to 99%, from 0.5% to 98%, from 1% to 97%, from 1% to 96%, from 2% to 95%, from 2% to 90%, from 3% to 85%, or from 5% to 80%, based on the total amount of the fuel composition. In certain embodiments, the $C_5$ isoprenoid or derivative thereof is a $C_5$ cyclic hydrocarbon. The amount of the $C_5$ cyclic hydrocarbon is more than 1%, more than 2%, more than 3%, more than 4%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90% or more than 95%, based on the total amount of the fuel composition. In some embodiments, the amount is in wt. % based on the total weight of the fuel composition. In other embodiments, the amount is in vol. % based on the total volume of the fuel composition. In certain embodiments, the fuel composition is a gasoline fuel composition.

The amount of the petroleum-based fuel component in the fuel composition disclosed herein may be from 0.1% to 99%, from 1% to 95%, from 2% to 90%, from 3% to 85%, from 5% to 80%, from 5% to 70%, from 5% to 60%, or from 5% to 50%, based on the total amount of the fuel composition. In certain embodiments, the amount of the petroleum-based fuel component is less than 95%, less than 90%, less than 85%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than 3%, less than 2%, less than 1% or less than 0.5%, based on the total amount of the fuel composition. In some embodiments, the amount is in wt. % based on the total weight of the fuel composition. In other embodiments, the amount is in vol. % based on the total volume of the fuel composition. In certain embodiments, the fuel composition is a gasoline fuel composition.

In certain embodiments, the fuel additive in the fuel composition disclosed herein is selected from the group consisting of oxygenates, antioxidants, thermal stability improvers, cetane improvers, stabilizers, cold flow improvers, combustion improvers, anti-foams, anti-haze additives, corrosion inhibitors, lubricity improvers, icing inhibitors, injector cleanliness additives, smoke suppressants, drag reducing additives, metal deactivators, dispersants, detergents, demulsifiers, dyes, markers, static dissipaters, biocides and combinations thereof. In further embodiments, the amount of the fuel additive is from about 0.1% to about 20% by weight or volume, based on the total weight or volume of the fuel composition.

The most common jet fuel is a kerosene/paraffin oil-based fuel classified as Jet A-1, which is produced to an internationally standardized set of specifications. In the United States only, a version of Jet A-1 known as Jet A is also used. Another jet fuel that is commonly used in civilian aviation is called Jet B. Jet B is a lighter fuel in the naphtha-kerosene region that is used for its enhanced cold-weather performance Jet A, Jet A-1 and Jet B are specified in ASTM Specification D. 1655-68. Alternatively, jet fuels are classified by militaries around the world with a different system of JP numbers. Some are almost identical to their civilian counterparts and differ only by the amounts of a few additives. For example, Jet A-1 is similar to JP-8 and Jet B is similar to JP-4. Alternatively, jet fuels can also be classified as kerosene or naphtha-type. Some non-limiting examples of kerosene-type jet fuels include Jet A, Jet A1, JP-5 and JP-8. Some non-limiting examples of naphtha-type jet fuels include Jet B and JP-4. Jet A is used in the United States while most of the rest of the world uses Jet A-1. An important difference between Jet A and Jet A-1 is the maximum freezing point. Jet A-1 has a lower maximum freezing temperature of −47° C. while Jet A has a maximum freezing temperature of −40° C. Like Jet A-1, Jet A has a fairly high flash point of minimum 38° C., with an autoignition temperature of 210° C.

The amount of each of the conventional fuel additives in the fuel composition disclosed herein may be from 0.1% to less than 50%, from 0.2% to 40%, from 0.3% to 30%, from 0.4% to 20%, from 0.5% to 15% or from 0.5% to 10%, based on the total amount of the fuel composition. In certain embodiments, the amount of each of the conventional fuel additives is less than 50%, less than 45%, less than 40%, less than 35%, less than 30%, less than 25%, less than 20%, less than 15%, less than 10%, less than 5%, less than 4%, less than 3%, less than 2%, less than 1% or less than 0.5%, based on the total amount of the fuel composition. In some embodiments, the amount is in wt % based on the total weight of the fuel composition. In other embodiments, the amount is in volume % based on the total volume of the fuel composition.

Some conventional fuel additives have been described in "Gasoline: Additives, Emissions, and Performance" by Society of Automotive Engineers, SAE International, 1995 (ISBN: 1560916451), which is incorporated herein by reference. Further, the following U.S. patents disclose various fuel additives that can be employed in embodiments of the invention as additives: U.S. Pat. Nos. 6,054,420; 6,051,039; 5,997,593; 5,997,592; 5,993,498; 5,968,211; 5,958,089; 5,931,977; 5,891,203; 5,882,364; 5,880,075; 5,880,072; 5,855,629; 5,853,436; 5,743,922; 5,630,852; 5,529,706; 5,505,867; 5,492,544; 5,490,864; 5,484,462; 5,321,172; and 5,284,492. The disclosures of all of the preceding U.S. patents are incorporated by reference herein in their entirety for all purposes.

Any oxygenate that increases the weight % of oxygen in the fuel composition disclosed herein can be used. Generally, oxygenates are combustible liquids comprises carbon, hydrogen and oxygen that can be categorized into two classes of organic compounds, i.e., alcohols and ethers. Some non-limiting examples of suitable oxygenates include ethanol, methyl tertiary-butyl ether (MTBE), tertiary-amyl methyl ether (TAME), and ethyl tertiary-butyl ether (ETBE).

Any lubricity improver that increases the fuel lubricity can be used. In some embodiments, one or more lubricity improvers are mixed with the fuel composition disclosed herein. Typically, the concentration of the lubricity improver in the fuel falls in the range of from 1 to 50,000 ppm, preferably about 10 to 20,000 ppm, and more preferably from 25 to 10,000 ppm. Some non-limiting examples of lubricity improver include esters of fatty acids.

Any combustion improver that can increase the mass burning rate of the fuel composition disclosed herein can be used. Some non-limiting examples of combustion improvers include ferrocene(dicyclopentadienyl iron), iron-based combustion improvers (e.g., TURBOTECT™ ER-18 from Turbotect (USA) Inc., Tomball, Tex.), barium-based combustion improvers, cerium-based combustion improvers, and iron and magnesium-based combustion improvers (e.g., TURBOTECT™ 703 from Turbotect (USA) Inc., Tomball, Tex.). The combustion improver may be present in the fuel composition at a concentration of about 0.001 to 1 wt %, based on the total weight of the fuel composition, and in one embodiment from 0.01 to 1% by weight.

In some embodiments, the fuel compositions comprise an antioxidant. Any antioxidant that can prevent the formation of gum depositions on fuel system components caused by oxidation of fuels in storage and/or inhibit the formation of peroxide compounds in certain fuel compositions can be used herein. The antioxidant may be present in the fuel composition at a concentration of about 0.001 to 5 wt %, based on the total weight of the fuel composition, and in one embodiment from 0.01 to 1% by weight.

In other embodiments, the fuel compositions comprise a static dissipater. Static dissipaters reduce the effects of static electricity generated by movement of fuel through high flow-rate fuel transfer systems. The static dissipater may be present in the fuel composition at a concentration of about 0.001 to 5 wt %, based on the total weight of the fuel composition, and in one embodiment from 0.01 to 1% by weight.

In further embodiments, the fuel compositions comprise a corrosion inhibitor. Corrosion inhibitors protect ferrous metals in fuel-handling systems such as pipelines, and fuel storage tanks, from corrosion. In circumstances where additional lubricity is desired, corrosion inhibitors that also improve the lubricating properties of the composition can be used. The corrosion inhibitor may be present in the fuel composition at a concentration of about 0.001 to 5 wt %, based on the total weight of the fuel composition, and in one embodiment from 0.01 to 1% by weight.

In certain embodiments, the fuel composition comprises a fuel system icing inhibitor (also referred to as an anti-icing additive). Fuel system icing inhibitors reduce the freezing point of water precipitated from jet fuels due to cooling at high altitudes and prevent the formation of ice crystals which restrict the flow of fuel to the engine. Certain fuel system icing inhibitors can also act as a biocide. The fuel system icing inhibitor may be present in the fuel composition at a concentration of about 0.001 to 5 wt %, based on the total weight of the fuel composition, and in one embodiment from 0.01 to 1% by weight.

In another set of embodiments, the fuel compositions further comprise a biocide. Biocides are used to combat microbial growth in the fuel composition. The biocide may be present in the fuel composition at a concentration of about 0.001 to 5 wt %, based on the total weight of the fuel composition, and in one embodiment from 0.01 to 1% by weight.

In another set of embodiments, the fuel composition further comprises a metal deactivator. Metal deactivators suppress the catalytic effect some metals, particularly copper, have on fuel oxidation. The metal deactivator may be present in the fuel composition at a concentration of about 0.001 to 5 wt %, based on the total weight of the fuel composition, and in one embodiment from 0.01 to 1% by weight.

In another set of embodiments, the fuel composition further comprises a thermal stability improver. Thermal stability improvers are use to inhibit deposit formation in the high-temperature areas of the aircraft fuel system. The thermal stability improver may be present in the fuel composition at a concentration of about 0.001 to 5 wt %, based on the total weight of the fuel composition, and in one embodiment from 0.01 to 1% by weight.

Volatility is an important property of gasoline and is a necessity to ensure engine starting in cold weather. In winter, volatility is raised and the flash point is lowered by adding the more volatile butanes and pentanes. To prevent vapor lock in warm weather, the amounts of the more volatile constituents are reduced to produce mixtures that will not vaporize in the fuel lines.

Detection and Analysis

Generally, the products of interest produced from the "solar biofactories" described herein can be analyzed by any of the standard analytical methods, e.g., gas chromatography (GC), mass spectrometry (MS) gas chromatography-mass spectrometry (GCMS), and liquid chromatography-mass spectrometry (LCMS), high performance liquid chromatography (HPLC), capillary electrophoresis, Matrix-Assisted Laser Desorption Ionization time-of-flight mass spectrometry (MALDI-TOF MS), nuclear magnetic resonance (NMR), near-infrared (NIR) spectroscopy, viscometry [Knothe et al., *Am. Chem. Soc. Symp. Series,* 666:172-208 (1997)], titration for determining free fatty acids [Komers et al., *Fett/Lipid* 99(2):52-54 (1997)], enzymatic methods [Bailer et al., *J. Anal. Chem.* 340(3):186 (1991)1, physical property-based methods, wet chemical methods, etc.

Carbon Fingerprinting

Biologically-produced carbon-based products, e.g., ethanol, fatty acids, alkanes, isoprenoids, represent a new commodity for fuels, such as alcohols, diesel and gasoline. Such biofuels have not been produced using biomass but use CO2 as its carbon source. These new fuels may be distinguishable from fuels derived form petrochemical carbon on the basis of dual carbon-isotopic fingerprinting. Such products, derivatives, and mixtures thereof may be completely distinguished from their petrochemical derived counterparts on the basis of $^{14}C$ (fM) and dual carbon-isotopic fingerprinting, indicating new compositions of matter.

There are three naturally occurring isotopes of carbon: $^{12}C$, $^{13}C$, and $^{14}C$. These isotopes occur in above-ground-total carbon at fractions of 0.989, 0.011, and $10^{-12}$, respectively. The isotopes $^{12}C$ and $^{13}C$ are stable, while $^{14}C$ decays naturally to $^{14}N$, a beta particle, and an anti-neutrino in a process with a half-life of 5730 years. The isotope $^{14}C$ originates in the atmosphere, due primarily to neutron bombardment of $^{14}N$ caused ultimately by cosmic radiation. Because of its relatively short half-life (in geologic terms), $^{14}C$ occurs at extremely low levels in fossil carbon. Over the course of 1 million years without exposure to the atmosphere, just 1 part in $10^{50}$ will remain $^{14}C$.

The $^{13}C$:$^{12}C$ ratio varies slightly but measurably among natural carbon sources. Generally these differences are expressed as deviations from the $^{13}C$:$^{12}C$ ratio in a standard material. The international standard for carbon is Pee Dee Belemnite, a form of limestone found in South Carolina, with a $^{13}C$ fraction of 0.0112372. For a carbon source a, the deviation of the $^{13}C$:$^{12}C$ ratio from that of Pee Dee Belemnite is expressed as:

$\delta_a=(R_a/R_s)-1$, where $R_a$=$^{13}C$:$^{12}C$ ratio in the natural source, and $R_s$=$^{13}C$:$^{12}C$ ratio in Pee Dee Belemnite, the standard.

For convenience, $\delta_a$ is expressed in parts per thousand, or ‰. A negative value of $\delta_a$ shows a bias toward $^{12}C$ over $^{13}C$ as compared to Pee Dee Belemnite. Table 3 shows $\delta_a$ and $^{14}C$ fraction for several natural sources of carbon.

TABLE 3

$^{13}C$: $^{12}C$ variations in natural carbon sources

| Source | $-\delta_a$ (‰) | References |
|---|---|---|
| Underground coal | 32.5 | Farquhar et al. |
| Fossil fuels | 26 | Farquhar et al. |
| Ocean DIC* | 0-1.5 | Goericke et al., Ivlev |
| Atmospheric CO2 | 6-8 | Ivlev, Farquhar et al. |
| Freshwater DIC* | 6-14 | Dettman et al. |
| Pee Dee Belemnite | 0 | Ivlev |

*DIC = dissolved inorganic carbon

Biological processes often discriminate among carbon isotopes. The natural abundance of $^{14}C$ is very small, and hence discrimination for or against $^{14}C$ is difficult to measure. Biological discrimination between $^{13}C$ and $^{12}C$, however, is well-documented. For a biological product p, we can define similar quantities to those above:

$\delta_p=(R_p/R_s)-1$, where $R_p$=$^{13}C$:$^{12}C$ ratio in the biological product, and $R_s$=$^{13}C$:$^{12}C$ ratio in Pee Dee Belemnite, the standard.

Table 4 shows measured deviations in the $^{13}C$:$^{12}C$ ratio for some biological products.

TABLE 4

$^{13}C$: $^{12}C$ variations in selected biological products

| Product | $-\delta_p$(‰) | -D(‰)* | References |
|---|---|---|---|
| Plant sugar/starch from atmospheric $CO_2$ | 18-28 | 10-20 | Ivlev |
| Cyanobacterial biomass from marine DIC | 18-31 | 16.5-31 | Goericke et al., Sakata et al. |
| Cyanobacterial lipid from marine DIC | 39-40 | 7.5-40 | Sakata et al. |
| Algal lipid from marine DIC | 17-28 | 15.5-28 | Goericke et al., Abelseon et al. |
| Algal biomass from freshwater DIC | 17-36 | 3-30 | Marty et al. |
| *E. coli* lipid from plant sugar | 15-27 | near 0 | Monson et al. |
| Cyanobacterial lipid from fossil carbon | 63.5-66 | 37.5-40 | — |
| Cyanobacterial biomass from fossil carbon | 42.5-57 | 16.5-31 | — |

*D = discrimination by a biological process in its utilization of $^{12}C$ vs. $^{13}C$ (see text)

Table 2 introduces a new quantity, D. This is the discrimination by a biological process in its utilization of $^{12}C$ vs. $^{13}C$. We define D as follows: $D=(R_p/R_a)-1$.

This quantity is very similar to $\delta_a$ and $\delta_p$, except we now compare the biological product directly to the carbon source rather than to a standard. Using D, we can combine the bias effects of a carbon source and a biological process to obtain the bias of the biological product as compared to the standard. Solving for $\delta_p$, we obtain: $\delta_p=(D)(\delta_a)+D+\delta_a$, and, because $(D)(\delta_a)$ is generally very small compared to the other terms, $\delta_p \approx \delta_a+D$.

For a biological product having a production process with a known D, we may therefore estimate $\delta_p$ by summing $\delta_a$ and D. We assume that D operates irrespective of the carbon source.

This has been done in Table 2 for cyanobacterial lipid and biomass produced from fossil carbon. As shown in the Tables above, cyanobacterial products made from fossil carbon (in the form of, for example, flue gas or other emissions) will have a higher $\delta_p$ than those of comparable biological products made from other sources, distinguishing them on the basis of composition of matter from these other biological products. In addition, any product derived solely from fossil carbon will have a negligible fraction of $^{14}C$, while products made from above-ground carbon will have a $^{14}C$ fraction of approximately $10^{-12}$.

Accordingly, in certain aspects, the invention provides various carbon-based products of interest characterized as $-\delta_p$(‰) of about 63.5 to about 66 and −D(‰) of about 37.5 to about 40.

REFERENCES

1. Goericke, R., Montoya, J. P., and Fry, B. Physiology of isotopic fractionation in algae and cyanobacteria. Chapter 9 in "Stable Isotopes in Ecology and Environmental Science", By K. Lajtha and R. H. Michener, Blackwell Publishing, 1994.

2. Monson, K. D. and Hayes, J. M. Biosynthetic control of the natural abundance of carbon 13 at specific positions within fatty acids in *Escherichia coli*. J. Biol. Chem. 255:11435-41 (1980).
3. Abelseon, P. H. and Hoering, T. C. Carbon isotope fractionation in formation of amino acids by photosynthetic organisms. Proc. Natl. Acad. Sci. 47:623-32 (1961).
4. Sakata, S., Hayes, J. M., McTaggart, A. R., Evans, R. A., Leckrone, K. J., and Togasaki, R. K. Carbon isotopic fractionation associated with lipid biosynthesis by a cyanobacterium: relevance for interpretation of biomarker records. Geochim. Cosmochim. Acta 61:5379-89 (1997).
5. Ivlev, A. A. Carbon isotope effects (13C/12C) in biological systems. Separation Sci. Technol. 36:1819-1914 (20010).
6. Farquhar, G. D., Ehleringer, J. R., and Hubick, K. T. Carbon isotope discrimination and photosynthesis. Annu Rev. Plant Physiol. Plant Mol. Biol. 40:503-37 (1989).
7. Marty, J. and Planas, D. Comparison of methods to determine algal $\delta^{13}C$ in freshwater. Limnol. Oceanogr.: Methods 6:51-63 (2008).
8. Dettman, D. L., Reische, A. K., and K. C. Lohmann. Controls on the stable isotope composition of seasonal growth bands in aragonitic fresh-water bivalves (unionidae). Geochim. Cosmochim. Acta 63:1049-1057 (1999).

All publications and patent documents cited herein are hereby incorporated by reference in their entirety for all purposes to the same extent as if each were so individually denoted.

EXAMPLES

The examples below are provided herein for illustrative purposes and are not intended to be restrictive.

Example 1

Plasmid Construction for *Synechococcus* sp. PCC 7002

Construction of pJB5: The pJB5 base plasmid was designed as an empty expression vector for recombination into *Synechococcus* sp. PCC 7002. Two regions of homology, the Upstream Homology Region (UHR) and the Downstream Homology Region were designed to flank the construct. These 500 bp regions of homology correspond to positions 3301-3800 and 3801-4300 (Genbank Accession NC_005025) for UHR and DHR respectively. The aadA promoter, gene sequence, and terminator were designed to confer spectinomycin and streptomycin resistance to the integrated construct. For expression, pJB5 was designed with the aph2 kanamycin resistance cassette promoter and ribosome binding site (RBS). Downstream of this promoter and RBS, we designed and inserted the restriction endonuclease recognition site for NdeI and EcoRI, as well as the sites for XhoI, BamHI, SpeI and PacI. Following the EcoRI site, the natural terminator from the alcohol dehydrogenase gene from *Zymomonas mobilis* (adhII) terminator was included. Convenient xbaI restriction sites flank the UHR and the DHR allowing cleavage of the DNA intended for recombination from the rest of the vector. pJB5 was constructed by contract synthesis from DNA2.0 (Menlo Park, Calif.).

Construction of pJB5-PdcAdhII The pyruvate decarboxylase (pdc) and alcohol dehydrogenase (adhII) genes were cloned into the pJB5 plasmid with the following procedure. The pdc-adhII genes from *Zymomonas mobilis* (Genbank: DD161475, M15394) were designed with an NdeI site replacing the start of the pdc coding region. Following the pdc gene, we designed two restriction endonuclease sites (XhoI and BamHI). Next, the adhII sequence was designed in whole subsequent to the restriction sites, and finally, the natural adhII terminator was included as well, downstream of an inserted EcoRI site. This construct was constructed by contract synthesis from DNA2.0 (Menlo Park, Calif.) and was inserted by restriction digest with NdeI and EcoRI (New England Biolabs; Ipswitch, Mass.) on both pJB5 and the insert followed by ligation with a Quick Ligation Kit (New England Biolabs; Ipswitch, Mass.). The ligated construct was transformed into The NEB 5-alpha F'Iq Competent *E. coli* (High Efficiency) (New England Biolabs: Ipswitch, Mass.).

pJB5-PdcAdhII(TS): The pyruvate decarboxylase (pdc) from *Zymobacter palmae* (GenBank: AF474145) and alcohol dehydrogenase TS42 (adhII) genes as described in Rellos et al. (1998) "Thermostable variants of *Zymomonas mobilis* alcohol dehydrogenase obtained using PCR-mediated random mutagenesis" Protein Expr Purif 12:61-61) were cloned into the pJB5 plasmid with the following procedure. These genes were designed with an NdeI site replacing the start of the pdc coding region. Following the pdc gene and prior to the adhII gene, a gap is present which includes XhoI and BamHI sites to allow promoters to be inserted later (total length of gap: 39 bp) and the original RBS for adhII from *Z. mobilis*. The adhII (*Z. mobilis*) gene has the original terminator present afterwards, in which an EcoRI site has been placed between the adhII gene and the terminator. Following the terminator, SpeI and PacI sites are present for cloning. This construct was constructed by contract synthesis from DNA2.0 (Menlo Park, Calif.) and was inserted by restriction digest with NdeI and EcoRI (New England Biolabs; Ipswitch, Mass.) on both pJB5 and the insert followed by ligation with a Quick Ligation Kit (New England Biolabs; Ipswitch, Mass.). The ligated construct was transformed into The NEB 5-alpha F'Iq Competent *E. coli* (High Efficiency) (New England Biolabs; Ipswitch, Mass.).

pJB5-Pdc: The pyruvate decarboxylase (pdc) gene was cloned into the pJB5 plasmid with the following procedure. The pJB5-PdcAdhII construct from Example 2, was digested with BamHI and EcoRI (New England Biolabs; Ipswitch, Mass.). The incompatible 5' and 3' DNA overhangs were removed using the Quick Blunting Kit (New England Biolabs, MA), and then ligated using the Quick Ligation Kit (New England Biolabs; Ipswitch, Mass.).

pJB5-AdhII: The alcohol dehydrogenase (adhII) gene was cloned into the pJB5 plasmid with the following procedure. The pJB5-PdcAdhII construct from Example 2, was digested with NdeI and BamHI (New England Biolabs; Ipswitch, Mass.). The incompatible 5' and 3' DNA overhangs were removed using the Quick Blunting Kit (New England Biolabs, MA), and then ligated using the Quick Ligation Kit (New England Biolabs; Ipswitch, Mass.).

pJB5-metE (*E. coli*): The Vitamin B12 independent methionine synthase (metE) gene from *E. coli* (Genbank: NP_418273.1), was cloned into the pJB5 plasmid by the following procedure. A construct was synthesized by contract synthesis by DNA2.0 (Menlo Park, Calif.) to include an NdeI site to replacing the start of the metE gene, and an EcoRI site at the end of the gene. This construct was inserted by restriction digest with NdeI and EcoRI (New England Biolabs; Ipswitch, Mass.) on both pJB5 and the insert followed by ligation with a Quick Ligation Kit (New England Biolabs; Ipswitch, Mass.). The ligated construct was transformed into The NEB 5-alpha F'Iq Competent *E. coli* (High Efficiency) (New England Biolabs: Ipswitch, Mass.).

pJB5-metE (*T. elongates* BP-1): The Vitamin B12-independent methionine synthase (metE) gene from *Thermosynechococcus elongates* BP-1 (Genbank: NP_681881), was cloned into the pJB5 plasmid by the following procedure. A construct was synthesized by contract synthesis by DNA2.0 (Menlo Park, Calif.) to include an NdeI site to replace the start of the metE gene, and an EcoRI site at the end of the gene. This construct was inserted by restriction digest with NdeI and EcoRI (New England Biolabs; Ipswitch, Mass.) on both pJB5 and the insert followed by ligation with a Quick Ligation Kit (New England Biolabs; Ipswitch, Mass.). The ligated construct was transformed into The NEB 5-alpha F'Iq Competent *E. coli* (High Efficiency) (New England Biolabs: Ipswitch, Mass.).

Example 2

Plasmid Construction for *Thermosynechococcus elongatus* BP-1

*Thermosynechococcus elongatus* BP-1 is selected as another exemplary CO2 fixing production host and is modified by engineered nucleic acids to functionally delete certain genes and/or to express, overexpress certain genes.

Four plasmids (pJB18, pJB19, pJB20, and pJB21), all derivatives of pJB5, were constructed to permit homologous recombination into four different loci in the *Thermosynechococcus elongatus* BP-1 genome. Specifically, the 0.5 kb upstream homology (UH) and downstream homology (DH) regions used for *Synechococcus* sp. PCC 7002 homologous recombination in pJB5 were replaced by the following approximately 2.5 kb *T. elongatus* BP-1 (Accession NC_004113) regions: coordinates 831908-834231 (UH) and 834232-836607 (DH) genome for pJB18, 454847-457252 (UH) and 457252-459740 (DH) for pJB19, 481310-483712 (UH) and 483709-486109 (DH) for pJB20, and 787356-789654 (UH) 791080-793494 (DH) for pJB21. The first three homology regions are based on integration sites TS1, TS3, and TS4 described in Onai K. et al. (2004). "Natural transformation of the thermophilic cyanobacterium *Thermosynechococcus elongatus* BP-1: a simple and efficient method for gene transfer." *Mol. Gen. Genomics* 271: 50-59. The last is designed to delete completely the glgA open reading frame, encoding glycogen synthase: The purpose of this deletion is to minimize competing fixed carbon flux towards glycogen once the ethanol-producing genes are integrated into the chromosome.

All *T. elongatus* BP-1 homology regions were generated by PCR using Phusion™ Hot Start High-Fidelity DNA Polymerase (Developed & Manufactured By Finnzymes Oy. Distributed by New England Biolabs, Ipswitch, Mass.) according to manufacturer's instructions. The UH forward PCR primer has a 5'-terminal SbfI restriction site, the UH reverse PCR primer a 5'-terminal NotI restriction site, the DH forward PCR primer a 5'-terminal AscI restriction site, and the DH reverse PCR primer a 5'-terminal FseI restriction site. For pJB18, pJB19, pJB20, and pJB21, the UH region is first inserted into pJB5 via restriction digestion with SbfI and NotI (New England Biolabs; Ipswitch, Mass.) of both vector and PCR-generated insert, followed by with a Quick Ligation Kit (New England Biolabs; Ipswitch, Mass.). The ligated construct is transformed into NEB 5-alpha Competent *E. coli* (High Efficiency) (New England Biolabs: Ipswitch, Mass.). The sequence of the UH region in pHB5 is validated by contract sequencing with GENEWIZ (South Plainfield, N.J.). For pJB18, pJB19, pJB20, and pJB21, the DH region is then inserted into the pJB5-UH region construct exactly as done for the UH region, except that restriction enzymes AscI and FseI are used (New England Biolabs; Ipswitch, Mass.). DH regions are sequence confirmed by contract sequencing with GENEWIZ (South Plainfield, N.J.).

Into each of pJB18, pJB19, pJB20, and pJB21, two different versions of the pyruvate decarboxylase (pdc)/alcohol dehydrogenase (adhII) operons are cloned, creating a set of eight plasmids ready for integration into the *T. elongatus* BP-1 genome. In each case, the selectable marker is the pJB5 aadA gene encoding resistance to spectinomycin and streptomycin. The first version of the operon comprises the pdc and adhII genes from *Zymomonas mobilis* (Genbank: DD161475, M15394) and is designed with an NdeI site covering the start codon of the pdc coding sequence. Following the pdc gene in order are: an XhoI restriction site, a BamHI restriction site, the adhII coding sequence, the natural *Zymomonas mobilis* adhII terminator, and finally an EcoRI restriction site. The second version of the operon, designed to encode relatively more thermostable versions of pyruvate decarboxylase and alcohol dehydrogenase, comprised the pdc gene from *Zymobacter palmae* (GenBank: AF474145) and the adhII mutant TS42 described in Rellos et al., *Protein Expr. Purif.,* 12:61-61 (1998), and is otherwise identical to the first construct in all other ways. Both constructs are made by contract synthesis from DNA2.0 (Menlo Park, Calif.) and are inserted by restriction digest with NdeI and EcoRI (New England Biolabs; Ipswitch, Mass.) into pJB18, pJB19, pJB20, and pJB21, followed by ligation with a Quick Ligation Kit (New England Biolabs; Ipswitch, Mass.). In this way eight pdc-adhII operon plasmids are constructed: pJB22, pJB23, pJB24, and pJB25 containing operon version 1, based on pJB18, pJB19, pJB20, and pJB21, respectively, and pJB26, pJB27, pJB28, and pJB29 containing operon version 2, based on pJB18, pJB19, pJB20, and pJB21, respectively.

In plasmids pJB22, pJB23, pJB24, pJB25, pJB26, pJB27, pJB28, and pJB29, the pdc-adhII operon is expressed by the constitutive $P_{aphII}$ promoter, which is flanked by unique NotI and NdeI restriction sites. These sites permit other constitutive promoters to be cloned in, in lieu of the $P_{aphII}$ promoter, in case that promoter does not afford sufficient expression of the operon when integrated into the genome of *T. elongatus* BP-1. Separate plasmids are constructed (pJB9, pJB10, pJB11, pJB12, pJB13, pJB14, pJB15, pJB16, and pJB17), all made by contract synthesis e.g., DNA2.0 (Menlo Park, Calif.), each bearing one of nine candidate alternative constitutive promoters flanked by NotI and NdeI sites so they can replace the $P_{aphII}$ promoter by standard cloning methods. Seven of those promoters are native *T. elongatus* BP-1 promoters, corresponding to the upstream sequence of the following genes: cpcC, apcA, tsr2142, psaA, rbcL, hsp33, and trnE_UUC and two are *E. coli*-type promoters: $P_{tac}$ (as described in De Boer et al., *Proc Natl Acad USA* 80:21-25 (1983)) and the synthetic $P_{EM7}$ promoter.

Example 3

Engineered Microorganisms Producing Ethanol

Genetically Modified *Synechococcus* sp. PCC 7002: Each of the constructs as described in Example 1 was integrated onto the genome of *Synechococcus* sp. PCC 7002 using the following protocol. *Synechococcus* 7002 was grown for 48 h from colonies in an incubated shaker flask at 30° C. at 1% $CO_2$ to an $OD_{730}$ of 1 in $A^+$ medium described in Frigaard N U et al. (2004) "Gene inactivation in the cyanobacterium *Synechococcus* sp. PCC 7002 and the green sulfur bacterium *Chlorobium tepidum* using in vitro-made DNA constructs and natural transformation" Methods Mol Biol 274:325-340. 500 μL of culture was added to a test-tube with 30 μL of 1-5 μg of DNA prepped from a Qiagen Qiaprep Spin Miniprep Kit (Valencia, Calif.) for each construct. Cells were incubated bubbling in 1% $CO_2$ at approximately 1 bubble every 2 seconds for 4 hours. 200 μL of cells were plated on $A^+$ medium plates with 1.5% agarose and grown at 30° C. for two days in low light. 10 μg/mL of spectinomycin was underplayed on the plates. Resistant colonies were visible in 7-10 days.

Strain Construction and Expression of *Moorella* sp. HUC22-1 AdhA: The sequence for *Moorella* sp. HUC22-1 AdhA has been shown to be an NADP utilizing alcohol dehydrogenase that is also thermostable and preferential for the reduction of acetaldehyde [Inokuma et al., *Arch. Microbiol.,* 188:37-45 (2007)]. While the sequence has not been published, the amino acid similarity to AdhIV from *Moorella thermoacetica* (Accession Number: ABC20211) was 100%. The nucleic acid sequence of AdhIV from *Moorella thermoacetica* (Accession Number: CP000232) was codon optimized for expression and constructed by DNA 2.0 and designated as SEQ ID NO: 1 (the encoded amino acid is SEQ ID NO: 2). The sequence is flanked with CTCGAGTTGGATCC (SEQ ID NO: 28) on the 5' end, which encodes the Xho and BamHI restriction sites, and on the 3' end with TTTCAAAACAGGAATTC (SEQ ID NO: 29) on the 3' end (similar to pJB5-3) which contains an EcoRI site for the purposes of cloning into expression vectors.

The *Moorella* adhA was then cloned downstream of two pyruvate decarboxylase genes, one from *Zymomonas mobilis* (Accession number: AAV89984) and one from *Zymobacter palmae* (Accession Number: AAM49566) to form the expression plasmids pJB136 and pJB133, respectively. As controls, expression plasmids were constructed for the *Z. mobilis* pyruvate decarboxylase gene with the *Z. mobilis* adhII (Accession Number: YP_163331), and the *Z. palmae* pyruvate decarboxylase gene with an improved thermotolerant adhII TS42 [Rellos et al., *Protein Expression and Purification,* 12:61-66 (1998)] to form pJB5-3 and pJB5-4 respectively.

The plasmids pJB5-3, pJB5-4, pJB133, pJB136 were cloned into *Synechococcus* sp. PCC 7002 (JCC1) using standard procedures and designated as JCC136, JCC137, JCC445, JCC446 respectively (Table 5).

TABLE 5

| Host | Integration Construct | Pyruvate decarboxylase | Alcohol Dehydrogenase |
|---|---|---|---|
| JCC136 | pJB5-3 | Z. mobilis pdc | Z. mobilis adhII |
| JCC137 | pJB5-4 | Z. palmae pdc | Z. mobilis adhII TS42 |
| JCC445 | pJB133 | Z. mobilis pdc | Moorella adhA |
| JCC446 | pJB136 | Z. mobilis pdc | Moorella adhA |

JCC1, JCC136, JCC137, JCC445, JCC446 were grown on $A^+$ media plates (1.5% agar) with 100 ug/mL spectinomycin for transgenic strains. A single colony was grown in 10 mL A+ with 100 ug/mL spectinomycin in a test tube immersed in a 37 C bath with 1% CO2 bubbled through. Cultures were grown to $OD_{730nm}$ 5.0 or higher (Molecular Devices Spectramax M2e; previously determined that an $OD_{730nm}$ of 1 is equal to ~0.3 g CDW), and then spun down (21,000 RCF, 20 C, 5 min), resuspended in fresh A+ media to original concentration, and then appropriately back-diluted to $OD_{730nm}$ 0.2 in 25 mL $A^+$ in a baffled 125 mL shaker flask. Approximately 1 mL of culture was taken for each time point (0, 6, 24, 48, 72 hours post-dilution; 6 hour time point not plotted for time spacing reasons), $OD_{730nm}$ was recorded (appropriately diluted to give reading between 0.04 and 0.4, which was previously determined to be most accurate range on the Spectramax M2e). Samples were immediately spun down at 4 C for 10 min at 21,000 RCF. Supernatant was placed in a new tube, and frozen at −80 C until ready for analysis.

Supernatant of each time point was analyzed for ethanol and acetaldehyde by use of an Agilent 7890 Gas Chromatograph equipped with a headspace analyzer and a flame ionization detector (Agilent) using a J&W Scientific DB-ALC1 (Catalog Number: 123-9134; length: 30 m, Inner Diameter, 0.320 mm, Film Thickness: 1.80 um). 100 uL of each samples was subjected to headspace analysis. Controls were measured for A+ alone, and as well as from serial dilution of standards for ethanol and acetaldehyde obtained from Sigma to obtain a calibration curve.

To measure the optical densities, ethanol and acetaldehyde concentrations, cultures were backdiluted from $OD_{730nm}$ 5 or greater to a starting $OD_{730nm}$ and timepoints were taken at 0, 24, 48, and 72 hours post-dilution.

Figure 11:
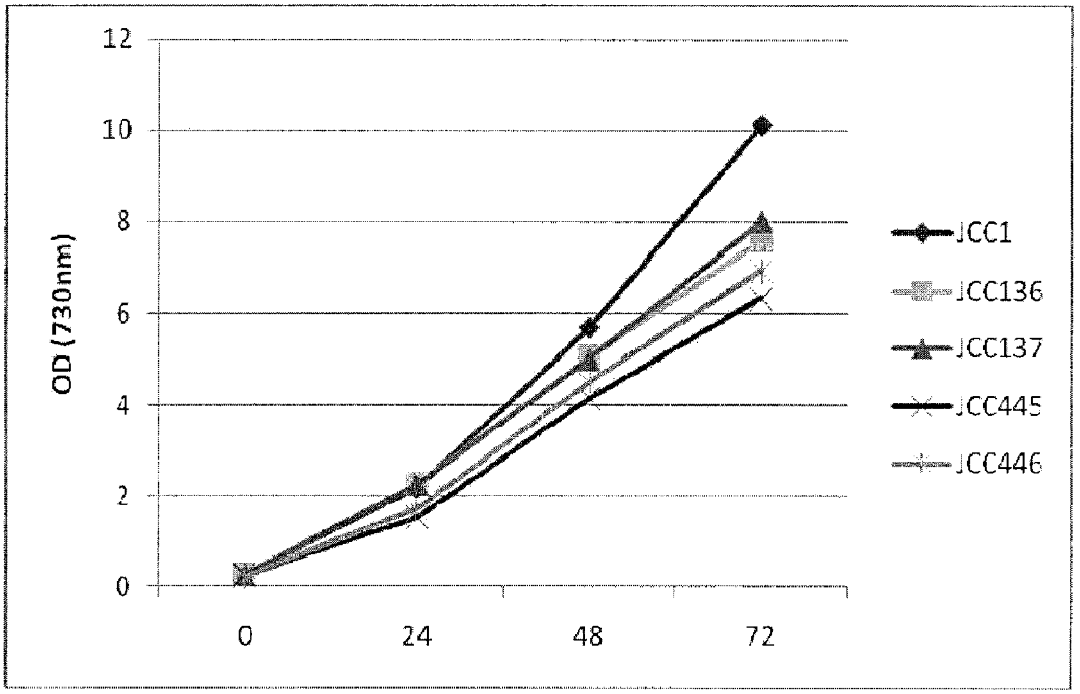
FIG. 11 graphically illustrates optical density of select ethanologens over time.

Optical densities of wildtype and various transgenic *Synechococcus* sp. cultures are shown (FIG. 11). The graph shows plots of $OD_{730nm}$ measurements at each timepoint. Resulting OD measurements are shown Table 6.

TABLE 6

| | OD (730 nm) | | | |
|---|---|---|---|---|
| Time | 0 | 24 | 48 | 72 |
| JCC1 | 0.257 | 2.19 | 5.7 | 10.1 |
| JCC136 | 0.259 | 2.26 | 5.06 | 7.6 |
| JCC137 | 0.263 | 2.265 | 5.02 | 8 |
| JCC445 | 0.246 | 1.52 | 4.16 | 6.35 |
| JCC446 | 0.227 | 1.71 | 4.52 | 6.95 |

Ethanol concentrations of cultures in the supernatant are plotted showing increased ethanol concentrations with respect to time in various in transgenic *Synechococcus* species cultures (FIG. 12). Notably, higher ethanol concentration was measured in JCC445, the strain transformed with *Moorella* adhA at 72 hours (Table 7).

TABLE 7

| | EtOH (mg/L) | | | |
|---|---|---|---|---|
| | 0 | 24 | 48 | 72 |
| JCC1 | 0 | 0 | 1.704728 | 5.880188 |
| JCC136 | 0 | 63.00976 | 140.7334 | 252.8226 |
| JCC137 | 0 | 72.02925 | 137.0422 | 256.4378 |
| JCC445 | 0 | 14.03474 | 153.5205 | 296.761 |
| JCC446 | 0 | 16.06255 | 125.6418 | 249.6592 |

Additionally, decreased acetaldehyde concentrations were observed at various timepoints in the strains transformed with *Moorella* adhA (FIG. 13 and Table 8).

TABLE 8

| | Acetaldehdye (mg/L) | | | |
|---|---|---|---|---|
| | 0 | 24 | 48 | 72 |
| JCC1 | 0 | 0 | 0.411352 | 02.362828 |
| JCC136 | 0 | 14.20144 | 34.95365 | 36.49536 |
| JCC137 | 0 | 19.80197 | 36.05125 | 35.83849 |
| JCC445 | 0 | 9.455919 | 10.82248 | 13.57957 |
| JCC446 | 0 | 8.368128 | 9.07078 | 12.32025 |

At later timepoints, the strains transformed with *Moorella* adhA (JCC445 and JCC446) show marked increases in the ratio of ethanol to acetaldehyde as compared to the *Z. mobilis* based alcohol dehydrogenases as shown in cultures over time (FIG. 14 and Table 9).

TABLE 9

| | EtOH/Acetaldehdye | | | |
|---|---|---|---|---|
| | 0 | 24 | 48 | 72 |
| JCC1 | N/A | N/A | 4.144204 | 16.20655 |
| JCC136 | N/A | 4.436856 | 4.026287 | 6.927526 |
| JCC137 | N/A | 3.637479 | 3.801316 | 7.155373 |
| JCC445 | N/A | 1.484228 | 14.18532 | 21.85348 |
| JCC446 | N/A | 1.919491 | 13.85137 | 20.26414 |

Figure 15:
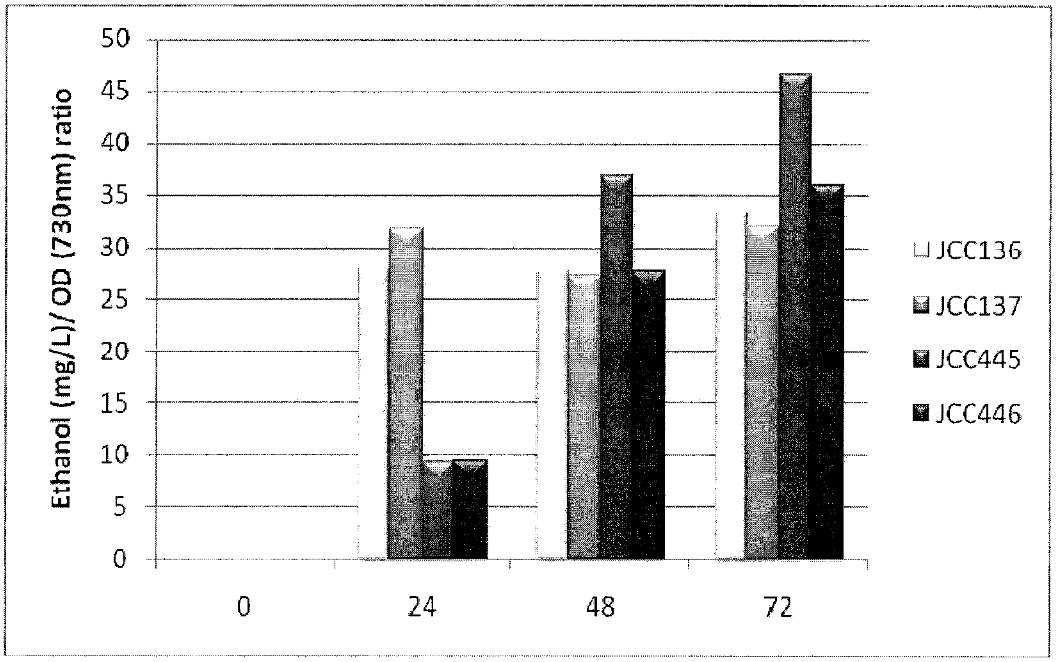
FIG. 15 graphically illustrates ratios of ethanol concentration to OD (730 nm) of cultures in the supernatant over time.

FIG. 15 depicts ethanol to $OD_{730nm}$ ratios of cultures over time. Plotted are the ratios of ethanol concentration to $OD_{730nm}$ in the supernatant at each timepoint. The ratio of the strains transformed with *Z. mobilis* adh (JCC136 and JCC137) quickly arrive at a steady state whereas, the ratio of the strains transformed with *Moorella* adhA constructs (JCC445 and JCC446) increase over time (Table 10).

TABLE 10

| | EtOH/OD (mg/L/OD) | | | |
|---|---|---|---|---|
| | 0 | 24 | 48 | 72 |
| JCC1 | 0 | 0 | 0.299075 | 0.582197 |
| JCC136 | 0 | 27.88043 | 27.81293 | 33.26613 |
| JCC137 | 0 | 31.80099 | 27.29924 | 32.05472 |
| JCC445 | 0 | 9.233379 | 36.90395 | 46.73402 |
| JCC446 | 0 | 9.393303 | 27.79687 | 35.92218 |

Genetically Modified *Thermosynechococcus elongatus* BP-1: From Example 2, pJB22, pJB23, pJB24, pJB25, pJB26, pJB27, pJB28, and pJB29 are integrated into the chromosome of *T. elongatus* BP-1 by homologous recombination using the transformation method detailed in Onai K. et al. (2004). "Natural transformation of the thermophilic cyanobacterium *Thermosynechococcus elongatus* BP-1: a simple and efficient method for gene transfer." *Mol. Gen. Genomics* 271: 50-59. The selection antibiotics used are spectinomycin plus streptomycin.

Example 4

Engineered Microorganisms Producing Butanol

The enzyme beta-ketothiolase (*R. eutropha* phaA) (EC 2.3.1.16) converts 2 acetyl-CoA to acetoacetyl-CoA and CoA. Acetoacetyl-CoA reductase (*R. eutropha* phaB) (EC 1.1.1.36) generates 3-hydroxybutyryl-CoA from acetoacetyl-CoA and NADPH. Enoyl-CoA hydratase (*E. coli* maoC) (EC 4.2.1.{17,55}) generates crotonyl-CoA from 3-hydroxybutyryl-CoA. Butyryl-CoA dehydrogenase (*C. acetobutylicum* bcd) (EC 1.3.99.2) generates butyryl-CoA and NAD(P)H from crotonyl-CoA. Butyrate CoA-transferase (*R. eutropha* pct) (EC 2.8.3.1) generates butyrate and acetyl-CoA from butyryl-CoA and acetate. Aldehyde dehydrogenase (*E. coli* adhE) (EC 1.2.1.{3,4}) generates butanal from butyrate and NADH. Alcohol dehydrogenase (*E. coli* adhE) (EC 1.1.1.{1, 2}) generates 1-butanol from butanal and NADH, NADPH. Production of 1-butanol is conferred by the engineered host cell by expression of the above enzyme activities.

Example 5

Alkane Flux Increasers

At least one of the following enzyme activities are selected and modified in the host organism. Acetyl-CoA carboxylase (*E. coli* accABCD) (EC 6.4.1.2, AAN73296) converts acetyl-CoA and CO2 to malonyl-CoA. Acyl-CoA synthase (*E. coli* fadD) (EC 2.3.1.86) converts fatty acid and CoA to acyl-CoA. The enzymes TGL2 and LipA (*S. cerevisiae* triacylglycerides lipase) (EC 3.1.1.3, AN CAA98876) produces triacylglycerides from fatty acids and glycerol. Lipase (*S. cerevisiae* LipA) (EC 3.1.1.3, CAA89087) also produces triacylglycerides from fatty acids and glycerol. and also functions as a suppressor of fabA. Mutation of *E. coli* K12 plsB D311E (AAC77011) removes limitation on the pool of acyl-CoA in the host organism. *E. coli* fabR (NP_418398), a repressor of fatty acid biosynthesis, is deleted for increased unsaturated fatty acid production (Zhang et al., J. Biol. Chem. 277: pp. 15558, 2002).

Example 6

Specific Length Fatty Acid Production

To produce a specific carbon chain length at least one of the following enzyme activities is modified in the host organism. Thioesterases (EC 3.1.2.14) generate acyl-ACP from fatty acid and ACP. The enzyme *E. coli* tesA (AAC73596, P0ADA1) is usually knocked down for an alternate fatty acid C-18:1 thioesterase. One or more of the following is expressed or attenuated depending on desired fatty acid length production: *A. thaliana* fatA (NP_189147, NP 193041) *Bradyrhizobium japonicum* fatA, a C-18:1 thioesterase (CAC39106); *Cuphea hookeriana* fatA, C-18:1 thioesterase (AAC72883); *Arabidopsis thaliana* fatB, C-16:1 thioesterase (CAA85388); *Cuphea hookeriana* fatB2, C-8:0 to C-10:0 thioesterase (Q39513); *Cuphea hookeriana* fatB3 C-14:0 to C-16:0 thioesterase (AAC49269; *Cinnamonum camphorum* fatB C-14:0 thioesterase (Q39473); *Umbellularia california* fatB C-12:0 thioesterase (Q41635).

Example 7

Unsaturated Fatty Acid Increase

Overexpression of *E. coli* fabM (DAA05501) may increase unsaturated fatty acid production (trans-2, cis-3-decenoyl-ACP isomerase). Controlled expression of *S. pneumoniae* fabK (NP_357969) may also increase in unsaturated fatty acid production (trans-2-enoyl-ACP reductase II). Additionally, *E. coli* fabI (NP_415804) (trans-2-enoyl-ACP reductase) is attenuated or deleted for increased unsaturated fatty acid production. Overexpression of fabB resulted in the production of a significant percentage of unsaturated fatty acids (de Mendoza et al., *J. Biol. Chem.,* 258:2098-101 (1983)).

Example 8

Unsaturated Fatty Acid Ester

Overexpression of *E. coli* sfa (AAN79592, AAC44390)-suppressor of fabA, *E. coli* fabB (EC 3.2.1.41, BAA16180) (B-ketoacyl-ACP synthase I), secG null mutant suppressors (cold shock proteins) such as *E. coli* gnsA (ABD18647.1) and *E. coli* gnsB (AAC74076.1) may increase production of unsaturated fatty acids. Genes similar to *E. coli* fabF (YP_852193) are attenuated to increase percentage of C16:1 produced.

Example 9

Conversion of Fatty Aldehyde to Alkane

Decarbonylases convert fatty aldehyde to alkane and CO. For example, *A. thaliana* cer1 (NP_171723) or *Oryza sativa* cer1 (AAD29719) is expressed.

Example 10

Conversion of Fatty Alcohol to Alkane

Terminal alcohol oxidoreductase, e.g., *Vibrio furnissii* M1 may convert fatty alcohol to alkane acyl terminal alcohol and NADPH to alkanes.

Example 11

Branched Production Alkanes

Step 1 involves expression of a branched-chain amino acid aminotransferase such as *E. coli* ilvE (EC2.6.1.42, YP_026247), *Lactococcus lactis* ilvE (EC 2.6.1.42, AAF24406), *Pseudomonas putida* ilvE (EC 2.6.1.42, NP_745648), *Streptomyces coelicolor* ilvE (EC 2.6.1.42, NP_629657).

Step 2 involves expression of oxidative decarboxylation of α-ketoacids to branched chain acyl-CoA, such as *Streptomyces coelicolor* bkdA1 (EC 1.2.4.4, NP_628006) E1α (decarboxylase component), *S. coelicolor* bkdB2 (EC 1.2.4.4, NP_628005) E1β (decarboxylase component), *S. coelicolor* bkdA3 (EC 1.2.4.4, NP_638004) E2 (dihydrolipoyl transacylase); or *S. coelicolor* bkdA2 (EC 1.2.4.4, NP_733618) E1α (decarboxylase component), *S. coelicolor* bkdB2 (EC 1.2.4.4, NP_628019) E1β (decarboxylase component), *S. coelicolor* bkdC2 (EC 1.2.4.4, NP_628018) E2 (dihydrolipoyl transacylase); or *S. avermitilis* bkdA (EC 1.2.4.4, BAC72074) E1a (decarboxylase component), *S. avermitilis* bkdB (EC 1.2.4.4, BAC72075) E1β (decarboxylase component), *S. avermitilis* bkdC (EC 1.2.4.4, BAC72076) E2 (dihydrolipoyl transacylase); *S. avermitilis* bkdF (EC1.2.4.4, BAC72088) E1α (decarboxylase component), *S. avermitilis* bkdG (EC 1.2.4.4, BAC72089) E1β (decarboxylase component), *S. avermitilis* bkdH (EC 1.2.4.4, BAC72090) E2 (dihydrolipoyl transacylase); *B. subtilis* bkdAA (EC 1.2.4.4, NP_390288) E1α (decarboxylase component), *B. subtilis* bkdAB (EC 1.2.4.4, NP_390288) E1β (decarboxylase component), *B. subtilis* bkdB (EC 1.2.4.4, NP_390288) E2 (dihydrolipoyl transacylase); or *P. putida* bkdA1 (EC 1.2.4.4, AAA65614) E1α (decarboxylase component), *P. putida* bkdA2 (EC 1.2.4.4, AAA65615) E1β (decarboxylase component), *P. putida* bkdC (EC 1.2.4.4, AAA65617) E2 (dihydrolipoyl transacylase); and *E. coli* lpd (EC 1.8.1.4, NP_414658) E3 (dihydrolipoyl dehydrogenase).

If the native fatty acid synthase cannot use the branched acyl-CoAs, fabH (EC 2.3.1.41) β-ketoacyl-ACP (acyl carrier protein) synthase III with branched chain acyl CoA specificity can be expressed WITH ACP. Another approach is to express, with ACP, FabF (EC 2.3.1.41) β-ketoacyl-ACP synthase II with branched chain acyl CoA specificity.

Alternatively, fabH is expressed with bkd genes (EC 1.2.4.4.) (Denoya et al. J. Bacteriol 177: pp. 3504, 1995), which consist of E1α/β (decarboxylase), E2 (dihydrolipoyl transacylase) and E3 (dihydrolipoyl dehydrogenase) subunits, which are similar to pyruvate and α-ketoglutarate dehydrogenase complexes.

To form branched chain acyl-CoA one or more of the following genes are expressed: *Streptomyces coelicolor* fabH1 NP_626634; *S. coelicolor* ACP NP_626635; *S. coelicolor* fabF NP_626636; *Streptomyces avermitilis* fabH3 NP_823466; *S. avermitilis* fabC3 NP_823467; *S. avermitilis* fabF NP_823468; *Bacillus subtilis* fabH_A NP_389015; *B. subtilis* fabH_B NP_388898; *B. subtilis* ACP NP_389474; *B. subtilis* fabF NP_389016; *Stenotrophomonas maltophilia* SmalDRAFT_0818 ZP_01643059; *S. maltophilia* SmalDRAFT_0821 ZP_01643063; *S. maltophilia* SmalDRAFT_0822 ZP_01643064; *Legionella pneumophila* fabH YP_123672; *L. pneumophila* ACP YP_123675; and *L. pneumophila* fabF YP_123676.

Other branched alkane production genes which can be expressed include *S. coelicolor* ccr (EC 1.1.19, NP_630556) crotonyl-CoA reductase, *S. coelicolor* icmA (EC 5.4.99.2, NP_629554) isobuturyl-CoA mutase large subunit, and *S. coelicolor* icmB (EC 5.4.99.13, NP_630904) isobuturyl-CoA mutase small subunit; or *Streptomyces cinnamonensis* ccr (EC 1.1.19, AAD53915) crotonyl-CoA reductase, *S. cinnamonensis* icmA (EC 5.4.99.2, AAC08713) isobuturyl-CoA mutase large subunit, and *S. cinnamonensis* icmB (EC 5.4.99.13, AJ246005) isobuturyl-CoA mutase small subunit.

Step 3 includes to the three genes above ccr, icmA and icmB expressing branched alkanes, an alcohol reductase activity *A. baylyi* acr1 expressed with bkd operon, which yields isopentanol, isobutanol or 2-methyl butanol.

Similarly, expression of genes associated with the genes above, *A. baylyi* acyl alcohol reductase, express with ccr/icm genes pathways above, yields isobutanol.

Example 12

Production of Fatty Acids with Genes in Host which May Interfere with Branch FAS To increase branched FAS, lower expression fabH (EC 2.3.1.41) β-ketoacyl-ACP synthase III or lower expression fabF (EC 2.3.1.41) β-ketoacyl-ACP synthase II.

Example 13

Production of ω-Cyclic Fatty Acids

Genes needed to be expressed which provide the cyclic precursor cyclohexylcarbonyl-CoA, and can be expressed with the branch-tolerant FAS genes include, for example, bkdC, lpd, fabH, ACP, fabF, fabH1, ACP, fabF, fabH3, fabC3, fabF, fabH_A, fabH_B, ACP.

Example 14

Ansatrienin Cluster

Express 2-cyclohexenylcarbonyl CoA isomerase *Streptomyces collinus* ansJK (AF268489), *S. collinus* ansL (AF268489), 1-cyclohexenylcarbonyl CoA reductase *S. collinus* chcA (U72144), and acyl CoA isomerase *S. collinus* chcB (AF268489).

Example 15

Phoslactomycin Cluster

The following genes are co-expressed with chcB from *S. collinus, S. coelicolor* or *S. avermitilis*: express 5-enolpyruvylshikimate-3-phosphate synthase from *Streptomyces* sp. HK803 plmJK (AAQ84158), acyl-CoA dehydrogenase from *Streptomyces* sp. HK803 plmL (AAQ84159), enoyl-(ACP) reductase from *Streptomyces* sp. HK803 chcA (AAQ84160), 2,4-dienoyl-CoA reductase *Streptomyces* sp. HK803 plmM (AAQ84161), and acyl CoA isomerase from *S. coelicolor* chcB/caiD (NP__629292).

Example 16

Fatty Acid/Alkane Export

Express alkane transporter such as *Rhodococcus erythopolis* ansP (AAN73268), cer5, ABC transporter such as *A. thalania* At1g51500 (AY734542), multi-drug efflux protein *E. coli* acrAB (NP__414996.1, NP__414995.1), efflux protein *E. coli* tolC (NP__417507.2), multi-drug efflux protein *E. coli* AcrEF (NP__417731.1, NP__417732.1), *T. elongatus* BP-1 t111618, (NP__682408.1), *T. elongatus* BP-1 t111619 (NP__682409.1), *T. elongatus* BP-1 t110139 (NP__680930.1), mammalian fatty acid transport protein (FATP) from *D. melanogaster, C. elegans*, fatty acid transport protein (FATP) from *M. tuberculosis*, mammalian fatty acid transport protein (FATP) from *S. cerevisiae*, transporter *Acinetobacter* sp. H01-N.

Example 17

Biodiesel-Like Biosynthesis

A cyanobacterium strain is transformed with the plasmids carrying a wax synthase gene from *A. baylyi* (EC: 2.3.175), a thioesterase gene from *Cuphea hookeriana* (EC AAC72883) and a fadD gene from *E. coli*. This recombinant strain is grown at optimal temperatures under certain conditions in suitable media. The cells are separated from the spent medium by centrifugation. The cell pellet is re-suspended and the cell suspension and the spent medium are then extracted with ethyl acetate. The resulting ethyl acetate phases from the cells suspension and the supernatant are subjected to GC-MS analysis. The fatty acid esters are quantified using commercial palmitic acid ethyl ester as the reference. Fatty acid esters are also made using the methods described herein except that methanol, or isopropanol is added to the fermentation media and the expected fatty acid esters are produced.

Wax synthase (EC 2.3.1.75) generates acyl ester from acyl-CoA and terminal acyl-OH. Acetyl transferase (EC 2.3.1.84) converts alcohol and acetyl-CoA to acetic ester and CoA. The following are exemplary genes to be expressed:

wst9 from *Fundibacter jadensis* DSM 12178 wshn from *Acinetobacter* sp. H01-N wsadp1 from *Acinetobacter* baylyi ADP 1 mWS from *H. sapiens* mWS from *Mus musculus* (Q6E1M8)

SAAT from *Fragaria xananassa* mpAAT from *Malus xdomestica*

JjWS from *Simmondsia chinensis*

Additional genes for the production of biodiesel are set forth in Table 11, below:

TABLE 11

| Producing organism | Notes | GenBank: gene | Genbank: protein |
|---|---|---|---|
| *E. coli* | carboxy transferase, alpha subunit | NC_000913.2 | NP_414727 |
| *E. coli* | biotin carboxyl carrier protein (BCCP) | NC_000913.2 | NP_417721 |
| *E. coli* | biotin carboxylase | NC_000913.2 | NP_417722 |
| *E. coli* | caboxytransferase, beta subunit | NC_000913.2 | NP_416819 |
| *Synechococcus* sp. JA-2-3B'a(2-13) | accA from thermophilic cyanobacterium | NTC_007776 | |
| *Synechococcus* sp. JA-2-3B'a(2-13) | accB from thermophilic cyanobacterium | NC_007776 | |
| *Synechococcus* sp. JA-2-3B'a(2-13) | accC from thermophilic cyanobacterium | NC_007776 | |
| *Synechococcus* sp. JA-2-3B'a(2-13) | accD from thermophilic cyanobacterium | NC_007776 | |
| *Cuphea hookeriana* | C-8:0 to C-10:0 thioesterase | U39834.1 | AAC49269 |
| *Umbellularia california* | C-12:0 thioesterase | M94159.1 | Q41635 |
| *Cinnamonum camphorum* | C-14:0 thiocstcrasc | U17076.1 | Q39473 |
| *E. coli* | C-18:1 thioesterase | NC_000913 | NP_415027 |
| *E. coli* | flexible Synthetase | NC_000913 | NP_416319.1 |
| *Trichodesmium etythraeum* IMS101 | best blast match of 7002 acyl-CoA Synthetase | NC_008312 | YP_722779 |
| *Synechococcus* sp. JA-2-3B'a(2-13) | putative fatty acid-CoA ligase from thermophile | NC_007776 | YP_478389.1 |

TABLE 11-continued

| Producing organism | Notes | GenBank: gene | Genbank: protein |
|---|---|---|---|
| *Acinetobacter baylyi* ADP1 | acyl-CoA to aldehyde (host to OH) known range C14 and higher but possibly to C8-NADPH | U77680.1 | AAC45217 |
| *Synechococcus* sp. JA-2-3B'a(2-13) | homology to acrl from cyano-bacterial thermophile | NC_007776 | YP_476452.1 |
| *Simmondsia chinensis* | acyl-CoA to fatty alcohol via aldehyde (2 NADPH) native range C20 to C22, can handle C16-C18 | AF149917 | AAD38039.1" |
| *Rubrobacter xylanophilus* DSM 9941 | bacterial analog of jojoba FAR from thermophile | NC_008148.1 | YP_644868 |
| *Acinetobacter* sp. M-1 | thermostable fatty aldehyde reductase, C2-C14 (NADPH) | AB047854 | BAB12270.1 |
| *Arabidopsis thaliana* | Note: plant transmembrane protein, C18-C32 | NM_100101.3 | NP_171723 |
| *Thermosynechococcus elongatus* BP-1 | sterol desaturase family protein; E(cer1) = 1e−07 | | NP_682707 |
| *Parvularcula bermudensis* HTCC2503 | COG3000 Sterol desaturase, E(ccr1) = 1c−08 | NZ_AAMU01000002.1 | ZP_01017596 |
| *Pedobacter* sp. BAL39 | sterol desaturase family protein, E(cer1) = 1e−08 | NZ_ABCM01000018.1 | ZP_01885831 |
| *Fragaria x ananassa* | Note: modified to remove NcoI site for *E. coli* exp. Functioned as wax synthase, not acetyl transferase | AF193789 | AAG13130.1 |
| *Acinetobacter baylyi* ADP1 | can make smaller waxes like octyl octanoate as can SAAT | AF529086.1 | AAO17391.1 |

Genes and Plasmids: The *E. coli* thioesterase tesA gene with the leader sequence targeting the removed (Genbank # NC__000913, ref: Chot and Cronan, 1993), the *E. coli* acyl-CoA synthetase fadD (Genbank # NC__000913, ref: Kameda and Nunn, 1981) and the wax synthase (=wax) from *Acinetobacter baylyi* strain ADPI (Genbank # AF529086.1, ref: Stöveken et al. 2005) was purchased from DNA 2.0 following codon optimization, checking for secondary structure effects, and removal of any unwanted restriction sites (NdeI, XhoI, BamHI, NgoMIV, NcoI, SacI, BsrGI, AvrII, BmtI, MluI, EcoRI, SbfI, NotI, SpeI, XbaI, PacI, AscI, FseI). These genes were received on pJ201 vectors and assembled into a three gene operon (tesA-fadD-wax, SEQ ID NO: 3) with flanking NdeI-EcoRI sites on the recombination vector pJB5 under the control of the PaphII kanamycin resistance cassette promoter. Another plasmid was constructed where the PaphII promoter was replaced with a Ptrc promoter under the control of a lacIq repressor (SEQ ID NO: 4). A control plasmid with only tesA under the control of the PaphII promoter was also prepared. The Joule plasmid numbers for these three plasmids are pJB494, pJB532, and pJB413, respectively.

The pJB5 base vector was designed as an empty expression vector for recombination into *Synechococcus* sp. PCC 7002. Two regions of homology, the Upstream Homology Region (UHR) and the Downstream Homology Region (DHR) were designed to flank the construct. These 500 bp regions of homology correspond to positions 3301-3800 and 3801-4300 (Genbank Accession NC__005025) for UHR and DHR respectively. The aadA promoter, gene sequence, and terminator were designed to confer spectinomycin and streptomycin resistance to the integrated construct. For expression, pJB5 was designed with the aph2 kanamycin resistance cassette promoter and ribosome binding site (RBS). Downstream of this promoter and RBS, we designed and inserted the restriction endonuclease recognition site for NdeI and EcoRI, as well as the sites for SpeI and PacI. Following the EcoRI site, the natural terminator from the alcohol dehydrogenase gene from *Zymomonas mobilis* (adhII) terminator was included. Convenient xbaI restriction sites flank the UHR and the DHR allowing cleavage of the DNA intended for recombination from the rest of the vector. The pJB5 vector was constructed by contract synthesis from DNA2.0 (Menlo Park, Calif.).

Strain Construction: The constructs as described above were integrated onto the plasmid pAQ1 in *Synechococcus* sp. PCC 7002 using the following protocol. *Synechococcus* 7002 was grown for 48 h from colonies in an incubated shaker flask at 37° C. at 2% $CO_2$ to an $OD_{730}$ of 1 in $A^+$ medium described in Frigaard et al., *Methods Mol. Biol.,* 274:325-340 (2004). 450 μL of culture was added to a epi-tube with 50 μL of 5 μg of plasmid DNA digested with xbal ((New England Biolabs; Ipswitch, Mass.)) that was not purified following restriction digest. Cells were incubated in the dark for four hours at 37° C. The entire volume cells was plated on $A^+$ medium plates with 1.5% agarose and grown at 37° C. in a lighted incubator (40-60 μE/m2/s PAR, measured with a LI-250A light meter (LI-COR)) for about 24 hours. 25 μg/mL of spectinomycin was underlayed on the plates. Resistant colonies were visible in 7-10 days after further incubation, and recombinant strains were confirmed by PCR using internal and external primers to check insertion and confirm location of the genes on pAQ1 in the strains (Table 12).

TABLE 12

Joule Culture Collection (JCC) numbers of the *Synechococcus* sp. PCC 7002 recombinant strains with gene insertions on the native plasmid pAQ1

| JCC # | Promoter | Genes | Marker |
|---|---|---|---|
| JCC879 | PaphII | — | aadA |
| JCC750 | PaphII | tesA | aadA |
| JCC723 | PaphII | tesA-fadD-wax | aadA |
| JCC803 | lacIq Ptrc | tesA-fadD-wax | aadA |

Ethyl Ester Production culturing conditions: One colony of each of the four strains (Table 12) was inoculated into 10 mls of A+ media containing 50 μg/ml spectinomycin and 1% ethanol (v/v). These cultures were incubated for about 4 days in a bubble tube at 37° C. sparged at approximately 1-2 bubbles of 1% $CO_2$/air every 2 seconds in light (40-50 μE/m2/s PAR, measured with a LI-250A light meter (LI-COR)). The cultures were then diluted so that the following day they would have $OD_{703}$ of 2-6. The cells were washed with 2×10 ml JB 2.1/spec200, and inoculated into duplicate 28 ml cultures in JB 2.1/spec200+1% ethanol (v/v) media to an $OD_{730}$=0.07. IPTG was added to the JCC803 cultures to a final concentration of 0.5 mM. These cultures were incubated in a shaking incubator at 150 rpm at 37° C. under 2% $CO_2$/air and continuous light (70-130 μE m2/s PAR, measured with a LI-250A light meter (LI-COR)) for ten days. Water loss through evaporation was replaced with the addition of sterile Milli-Q water. 0.5% (v/v) ethanol was added to the cultures to replace loss due to evaporation every 48 hours. At 68 and 236 hours, 5 ml and 3 ml of culture were removed from each flask for ethyl ester analysis, respectively. The $OD_{730}$s reached by the cultures is given in Table 13.

TABLE 13

The $OD_{730}$s reached by the *Synechococcus* sp. PCC 7002 recombinant strains at timepoints 68 and 236 h

| Time point | JCC879 #1 | JCC87 9#2 | JCC75 0#1 | JCC750 #2 | JCC723 #1 | JCC723 #2 | JCC803 #1 | JCC803 #2 |
|---|---|---|---|---|---|---|---|---|
| 68 h | 3.6 | 4.0 | 4.6 | 5.0 | 6.6 | 6.0 | 5.4 | 5.8 |
| 236 h | 21.2 | 18.5 | 19.4 | 20.9 | 22.2 | 21.4 | 17.2 | 17.7 |

The culture aliquots were pelleted using a Sorvall RC6 Plus superspeed centrifuge (Thermo Electron Corp) and a F13S-14X50CY rotor (5000 rpm for 10 min). The spend media supernatant was removed and the cells were resuspended in 1 ml of Milli-Q water. The cells were pelleted again using a benchtop centrifuge, the supernatant discarded and the cell pellet was stored at −80° C. until analyzed for the presence of ethyl esters.

Detection and quantification of ethyl esters in strains: Cell pellets were thawed and 1 ml aliquots of acetone (Acros Organics 326570010) containing 100 mg/L butylated hydroxytoluene (Sigma-Aldrich B1378) and 50 mg/L ethyl valerate (Fluka 30784) were added. The cell pellets were mixed with the acetone using a Pasteur pipettes and vortexed twice for 10 seconds (total extraction time of 1-2 min). The suspensions were centrifuged for 5 min to pellet debris, and the supernatants were removed with Pasteur pipettes and subjected to analysis with a gas chromatograph using flame ionization detection (GC/FID).

An Agilent 7890A GC/FID equipped with a 7683 series autosampler was used to detect the ethyl esters. One μL of each sample was injected into the GC inlet (split 5:1, pressure: 20 psi, pulse time: 0.3 min, purge time: 0.2 min, purge flow: 15 mL/min) and an inlet temperature of 280° C. The column was a HP-5MS (Agilent, 30 m×0.25 mm×0.25 μm) and the carrier gas was helium at a flow of 1.0 mL/min. The GC oven temperature program was 50° C., hold one minute; 10°/min increase to 280° C.; hold ten minutes. The GC/MS interface was 290° C., and the MS range monitored was 25 to 600 amu. Ethyl myristate [retention time (rt): 17.8 min], ethyl palmitate (rt: 19.8 min) and ethyl stearate (rt: 21.6 min) were identified based on comparison to a standard mix of C4-C24 even carbon saturated fatty acid ethyl esters (Supelco 49454-U). Ethyl oleate (rt: 21.4 min) was identified by comparison with an ethyl oleate standard (Sigma Aldrich 268011). These identifications were confirmed by GC/MS (see following Methyl Ester Production description for details). Calibration curves were constructed for these ethyl esters using the commercially available standards, and the concentrations of ethyl esters present in the extracts were determined and normalized to the concentration of ethyl valerate (internal standard).

Figure 20:
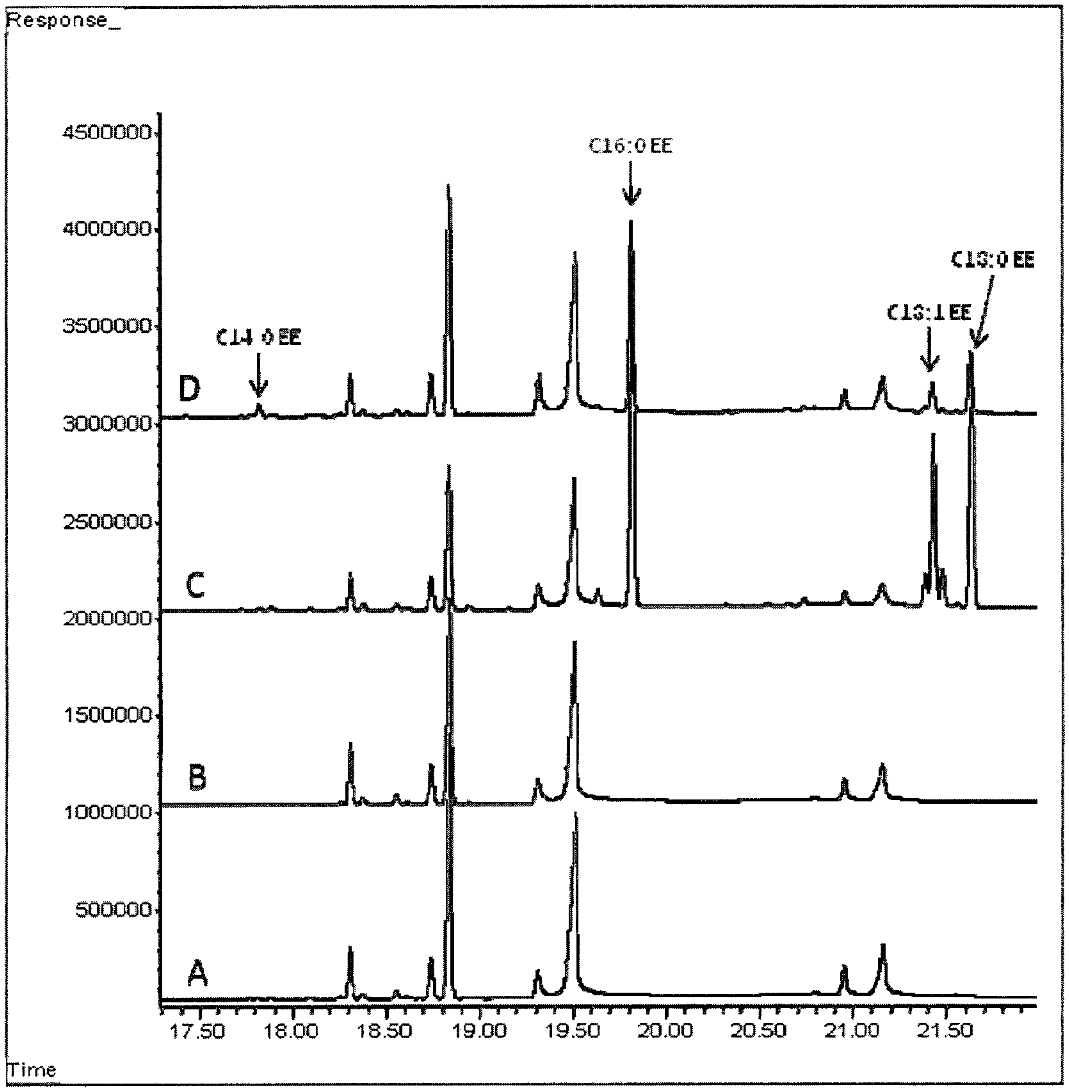
FIG. 20 depicts representative GC/FID chromatograms of strains analyzed for the presence of ethyl esters. The peaks for ethyl myristate, ethyl palmitate, ethyl oleate and ethyl stearate are indicated. (A) JCC879 (resistance marker) 236 h timepoint flask #1; (B) JCC750 (PaphII-tesA) 236 h timepoint flask #1; (C) JCC803 (lacIq Ptrc-tesA-fadD-wax) 236 h timepoint flask #1; (D) JCC723 (PaphII-tesA-fadD-wax) 236 h timepoint flask #1.

Four different ethyl esters were found in the extracts of JCC723 and JCC803 (Table 14). In general, JCC803 produced 2-10× the amount of each ethyl ester than JCC723, but ethyl myristate was only produced in low quantities of 1 mg/L or less for all these cultures. No ethyl esters were found in the extracts of JCC879 or JCC750, indicating that the strain cannot make ethyl esters naturally and expression of only tesA is not enough to confer production of ethyl esters (FIG. 20).

TABLE 14

Amounts of respective ethyl esters found in the cell pellet extracts of JCC723 given as mg/L of culture

| Sample | C14:0 ethyl ester | C16:0 ethyl ester | C18:1 ethyl ester | C18:0 ethyl ester |
|---|---|---|---|---|
| JCC723 #1 68 h | 0.08 | 0.34 | 0.22 | 0.21 |
| JCC723 #2 68 h | 0.12 | 1.0 | 0.43 | 0.40 |
| JCC803 #1 68 h | 0.45 | 6.6 | 1.4 | 0.74 |
| JCC803 #2 68 h | 0.63 | 8.6 | 2.0 | 0.94 |
| JCC723 #1 236 h | 1.04 | 15.3 | 2.1 | 4.5 |
| JCC723 #2 236 h | 0.59 | 9.0 | 1.3 | 3.7 |
| JCC803 #1 236 h | 0.28 | 35.3 | 13.4 | 19.2 |
| JCC803 #2 236 h | 0.49 | 49.4 | 14.9 | 21.2 |

Methyl Ester Production Culturing conditions: One colony of JCC803 (Table 1) was inoculated into 10 mls of A+ media containing 50 μg/ml spectinomycin and 1% ethanol (v/v). This culture was incubated for 3 days in a bubble tube at 37° C. sparged at approximately 1-2 bubbles of 1% $CO_2$/air every 2 seconds in light (40-50 μE/m2/s PAR, measured with a LI-250A light meter (LI-COR)). The culture was innoculated into two flasks to a final volume of 20.5 ml and $OD_{730}$=0.08 in A+ media containing 200 μg/ml spectinomycin and 0.5 mM IPTG with either 0.5% methanol or 0.5% ethanol (v/v). These cultures were incubated in a shaking incubator at 150 rpm at 37° C. under 2% $CO_2$/air and continuous light (70-130 μE m2/s PAR, measured with a LI-250A light meter (LI-COR)) for three days. Water loss through evaporation was replaced with the addition of sterile Milli-Q water. 5 ml of these cultures ($OD_{730}$=5-6) were analyzed for the presence of ethyl or methyl esters.

Detection of ethyl- or methyl-esters: Cell pellets were thawed and 1 ml aliquots of acetone (Acros Organics 326570010) containing 100 mg/L butylated hydroxytoluene (Sigma-Aldrich B 1378) and 50 mg/L ethyl valerate (Fluka 30784) were added. The cell pellets were mixed with the acetone using a Pasteur pipettes and vortexed twice for 10 seconds (total extraction time of 1-2 min). The suspensions were centrifuged for 5 min to pellet debris, and the supernatants were removed with Pasteur pipettes and subjected to analysis with a gas chromatograph using mass spectral detection (GC/MS).

An Agilent 7890A GC/5975C E1-MS equipped with a 7683 series autosampler was used to measure the ethyl esters. One μL of each sample was injected into the GC inlet using pulsed splitless injection (pressure: 20 psi, pulse time: 0.3 min, purge time: 0.2 min, purge flow: 15 mL/min) and an inlet temperature of 280° C. The column was a HP-5MS (Agilent, 30 m×0.25 mm×0.25 μm) and the carrier gas was helium at a flow of 1.0 mL/min. The GC oven temperature program was 50° C., hold one minute; 10°/min increase to 280° C.; hold ten minutes. The GC/MS interface was 290° C., and the MS range monitored was 25 to 600 amu. Compounds indicated by peaks present in total ion chromatograms were identified by matching experimentally determined mass spectra associated with the peaks with mass spectral matches found by searching in a NIST 08 MS database.

Figure 21:
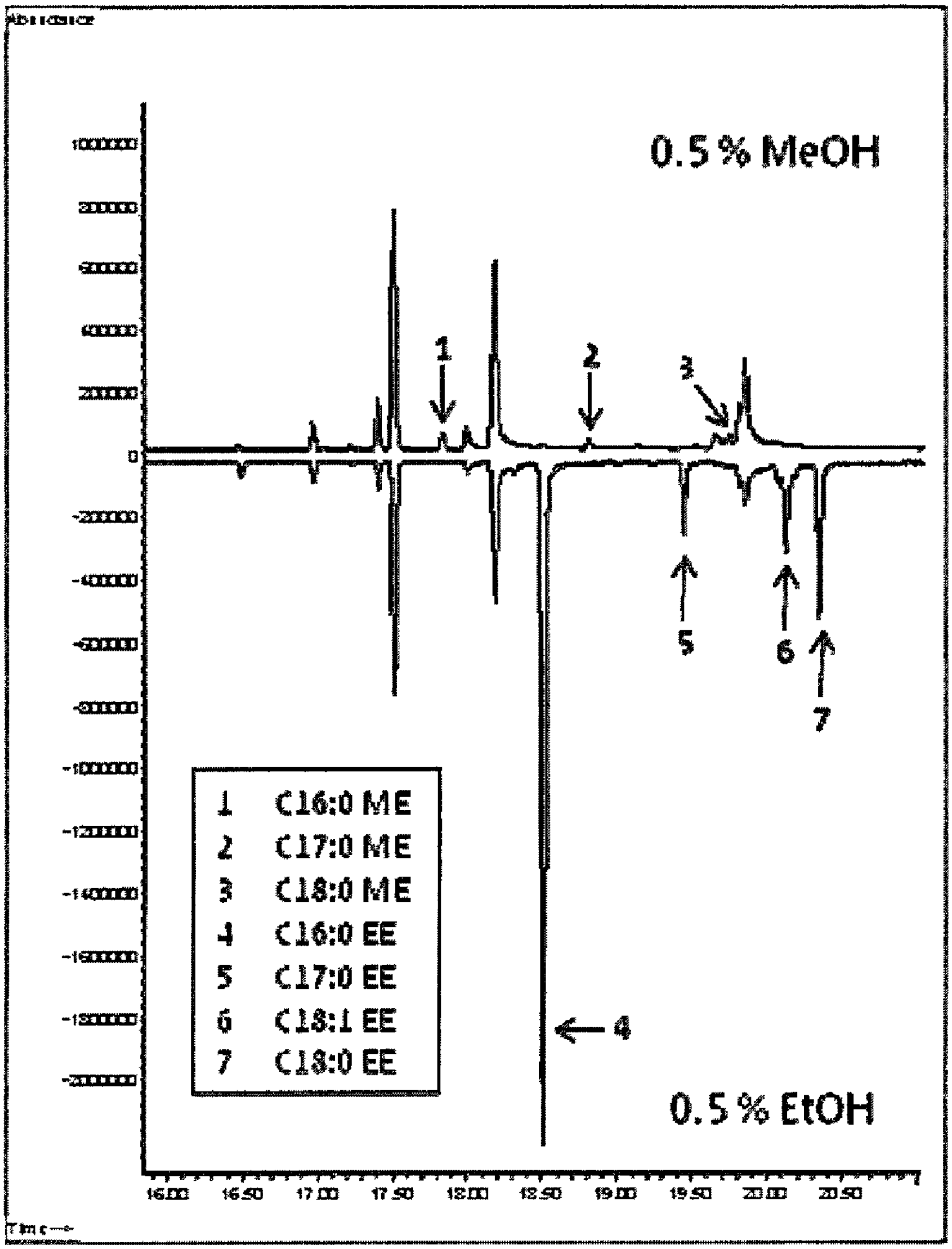
FIG. 21 depicts a GC/MS chromatogram overlay comparing cell pellet extracts of JCC803 incubated with either methanol (top trace) or ethanol (bottom traces). The peaks due to methyl esters (MEs) or ethyl esters (EEs) are labeled.

The culture of JCC803 incubated with ethanol contained ethyl palmitate [retention time (rt): 18.5 min], ethyl heptadecanoate (rt: 19.4 min), ethyl oleate (rt: 20.1 min) and ethyl stearate (rt: 20.3 min). No ethyl esters were detected in the strain incubated with methanol. Instead, methyl palmitate (rt: 17.8 min), methyl heptadecanoate (rt: 18.8 min) and methyl stearate were found (FIG. 21). This strain apparently has the capability to make both methyl and ethyl esters depending on alcohol used. The wax synthase gene used in this strain is known to have a very broad substrate specificity (Stöveken et al. 2005; Kalscheuer et al. 2006a; Kalscheuer et al. 2006b), and therefore JCC803 could utilize a wide variety of alcohols to produce various fatty acid esters.

REFERENCES

Cho, H. and Cronan, J. E. 1993. *Escherichia coli* thioesterase I, molecular cloning and sequencing of the structural gene and identification as a periplasmic enzyme. The Journal of Biological Chemistry 268: 9238-9245.

Kalscheuer, R., Stölting, T. and Steinbüchel, A. 2006a. Microdiesel: *Escherichia coli* engineered for fuel production. Microbiology 152: 2529-2536.

Kalscheuer, R., Stöveken, T., Luftman, H., Malkus, U., Reichelt, R. and Steinbüchel, A. 2006b. Neutral lipid biosynthesis in engineered *Escherichia coli*: jajoba oil-like wax esters and fatty acid butyl esters. Applied and Environmental Microbiology 72: 1373-1379.

Kameda, K. and Nunn, W. D. 1981. Purification and characterization of the acyl Coenzyme A synthetase from *Escherichia coli*. The Journal of Biological Chemistry 256: 5702-5707.

Stöveken, T., Kalscheuer, R., Malkus, U., Reichelt, R. and Steinbüchel, A. 2005. The wax ester synthase/acyl coenzyme A: diacylglycerol acyltransferase from *Acinetobacter* sp. strain ADP1: characterization of a novel type of acyltransferase. Journal of Bacteriology 187:1369-1376.

Example 18

Fatty Alcohol Producers

Acyl-CoA reductases (EC 1.2.1.50) convert acyl-CoA and NADPH to fatty alcohol and CoA. Examples of genes to express include: bfar from *Bombyx mori* (Q8R079); acr1 from *Acinetobacter baylyi* ADP1 (AAC45217); jjfar from *Simmondsia chinensis*; an unspecified acyl-CoA reductase from *Triticum aestivum*; mfar1 from *Mus musculus*; mfar2 from *Mus musculus*; acrM1 from *Acinetobacter* sp. M1; and hfar from *H. sapiens*.

Example 19

Engineered Microorganisms Producing Octane

To produce a particular alkane such as octane, several genes as identified in FIG. 1 are introduced in a selected microorganism. The enzyme acetyl-CoA:ACP transacylase (*E. coli* fabH) (EC 2.3.1.38) generates acetyl-ACP+CoA from acetyl-CoA and ACP. Acetyl-CoA carboxylase (*E. coli* accBCAD) (EC 6.4.1.2) generates malonyl-CoA from acetyl-CoA, ATP and CO2. Malonyl-CoA:ACP transacylase (*E. coli* fabD) (EC 2.3.1.39) generates malonyl-ACP and CoA from malonyl-CoA and ACP. 3-ketoacyl-ACP synthase (*E. coli* fabB) (EC 2.3.1.41) generates CO2 and 3-ketoacyl-ACP from acyl-ACP and malonyl-ACP. 3-Ketoacyl-ACP reductase (*E. coli* fabG) (EC 1.1.1.100) generates 3-hydroxyacyl-ACP from 3-ketoacyl-ACP and NADPH. 3-hydroxyacyl-ACP dehydratase (*E. coli* fabA) (EC 4.2.1.60) generates enoyl-ACP from 3-hydroxyacyl-ACP. Enoyl-ACP reductase (*E. coli* fabI) (EC 1.3.1. {9,10}) generates acyl-ACP from enoyl-ACP and NADH, NADPH. Acyl-ACP hydrolase (*S. cerevisiae* fall) (EC 3.1.2.14) generates fatty acid and ACP from acyl-ACP. Several aldehyde dehydrogenase found in *P. aeruginosa* (EC 1.2.1.{3,4}) generate octanal from octanoate and NADH, NADPH. Alcohol dehydrogenase (*Z. mobilis* adhI) (EC 1.1.1.{1,2}) generates 1-octanol from octanal and NADH, NADPH. Alkane 1-monooxygenase (*P. fluorescens* alkB) (EC 1.14.15.3) then generates n-octane, NAD(P)H and O2 from 1-octanol. Production of n-octane confers engineered host cell expression of the above enzyme activities.

Example 20

Production of Isoprenoids

To generate a strain of cyanobacteria for the production of 3-methyl-but-3-en-1-ol and 3-methyl-but-2-en-1-ol, plasmids are generated by inserting a genomic DNA fragment of *Synnechococcus* sp. PCC 7002 comprising the coding sequence of the nudF gene and upstream genomic sequences into a vector.

Synechococcus 7002 is grown for 48 h from colonies in an incubated shaker flask at 30° C. at 1% $CO_2$ to an $OD_{730}$ of 1 in $A^+$ medium described in Frigaard et al., *Methods Mol. Biol.* 274:325-340 (2004). 500 μL of culture is added to a test-tube with 30 μL of 1-5 μg of DNA prepped from a Qiagen Qiaprep Spin Miniprep Kit (Valencia, Calif.) for each construct. Cells were incubated bubbling in 1% $CO_2$ at approximately 1 bubble every 2 seconds for 4 hours. 200 μL of cells were plated on $A^+$ medium plates with 1.5% agarose and grown at 30° C. for two days in low light. 10 μg/mL of spectinomycin was underplayed on the plates. Resistant colonies were visible in 7-10 days. The cultures are grown overnight by shaking on a rotary shaker. The $OD_{600}$ of each culture is measured, and a sample is removed. To each removed sample, ethyl acetate is added, and the sample is vortexed. A portion of the upper ethyl acetate phase is transferred to a clean glass vial for analysis by gas chromatography-mass spectrometry.

The samples are analyzed on a GC/MS. A 1 μL sample is separated on the GC using a DB-5 column (Agilent Technologies, Inc., Palo Alto, Calif.) and helium carrier gas. The oven cycle for each sample is 60° C. for 3 minutes, increasing temperature at 60° C./minute to a temperature of 300° C., and a hold at 300° C. for 2 minutes. The total run time is 9 minutes. The resolved samples are analyzed by a mass-selective detector along with previously measured retention time of 3-methyl-3-buten-1-ol and 3-methyl-2-buten-1-ol mass spectra using this GC protocol.

The 3-methyl-3-buten-1-ol and isoamyl alcohol can be blended respectively with a California Reformulated Gasoline Blendstock for Oxygen Blending (CARBOB) to form various mixtures having an oxygen content of 2 wt %, 2.7 wt. % or 3.5 wt. %. Similarly, 1-butanol, ethanol, methyl tertiary-butyl ether (MTBE) and ethyl tertiary-butyl ether (ETBE) can also be blended respectively with CARBOB to form various mixtures having an oxygen content of 2 wt %, 2.7 wt. % or 3.5 wt. %. The API gravity values, research octane numbers, motor octane numbers, anti-knock indexes, vapor pressure data, net heats of combustion, water tolerance data, and vapor-liquid ratio of the mixtures are tested.

Example 21

Engineered Microorganisms Producing Terephthalate 2-dehydro-3-deoxyphosphoheptonate aldolase *E. coli* aroF (EC 2.5.1.54) generates 3-deoxy-D-arabino-heptulosonate-7-P from PEP and D-erythrose-4-P. 3-dehydroquinate synthase *E. coli* aroB (EC 4.2.3.4) generates 3-dehydroquinate from 3-deoxy-D-arabino-heptulosonate-7-P. 3-dehydroquinate dehydratase *E. coli* aroD (EC 4.2.1.10) generates 3-dehydro-shikimate from 3-dehydroquinate. 3-dehydroshikimate dehydratase from *Acinetobacter* sp. ADP1 quiC (EC 4.2.1.n) generates protocatechuate from 3-dehydro-shikimate. β-ketoadipyl-CoA synthase from *Rhodococcus* sp. RHA1 pcaF (EC 2.3.1.174) generates β-ketoadipyl-CoA and CoA from acetyl-CoA and succinyl-CoA. β-ketoadipate CoA-transferase from *Pseudomonas putida* pcaIJ (EC 2.8.3.6) generates β-ketoadipate and succinyl-CoA from β-ketoadipyl-CoA and succinate. 3-oxoadipate enol-lactone hydrolase *Rhodococcus* sp. RHA1 pcaL EC 3.1.1.24 generates β-ketoadipate enol lactone from β-ketoadipate. 4-carboxymuconolactone decarboxylase *Rhodococcus* sp. RHA1 pcaL (EC 4.1.1.44) generates γ-carboxy-muconolactone from β-ketoadipate enol lactone and CO2. γ-carboxy-cis,cis-muconate cycloisomerase *Rhodococcus* sp. RHA1 pcaB (EC 5.5.1.2) generates β-carboxy-cis,cis-muconate from γ-carboxy-muconolactone. Protocatechuate 3,4-dioxygenase from *Rhodococcus* sp. RHA1 pcaGH (EC 1.13.11.3) generates protocatechuate from β-carboxy-cis,cis-muconate. Protocatechuate 1,2-cis-dihydrodiol dehydrogenase *Rhodococcus* sp. RHA1 tpaC (EC 1.3.1.n) generates DDT from protocatechuate, CO2 and NADPH. Terephthalate 1,2-dioxygenase *Rhodococcus* sp. RHA1 tpaAB (EC 1.14.12.15) converts DDT to terephthalate, NADH and O2.

Example 22

Engineered Microorganisms Producing 1,3-Propanediol

The enzyme sn-glycerol-3-P dehydrogenase *S. cerevisiae* dar1 (EC 1.1.1. {8,94}) generates sn-glycerol-3-P from dihydroxyacetone-P and {NADH, NADPH}. sn-glycerol-3-phosphatase *S. cerevisiae* gpp2 (EC 3.1.3.21) generates glycerol from sn-glycerol-3-P. glycerol dehydratase *K. pneumonia* dhaB1-3 (EC 4.2.1.30) generates 3-hydroxypropanal from glycerol. 1,3-propanediol oxidoreductase *K. pneumonia* dhaT (EC 1.1.1.202) converts 3-hydroxypropanal and NADH to 1,3-propanediol.

Example 23

Engineered Microorganisms Producing 1,4-butanediol

Figure 8:
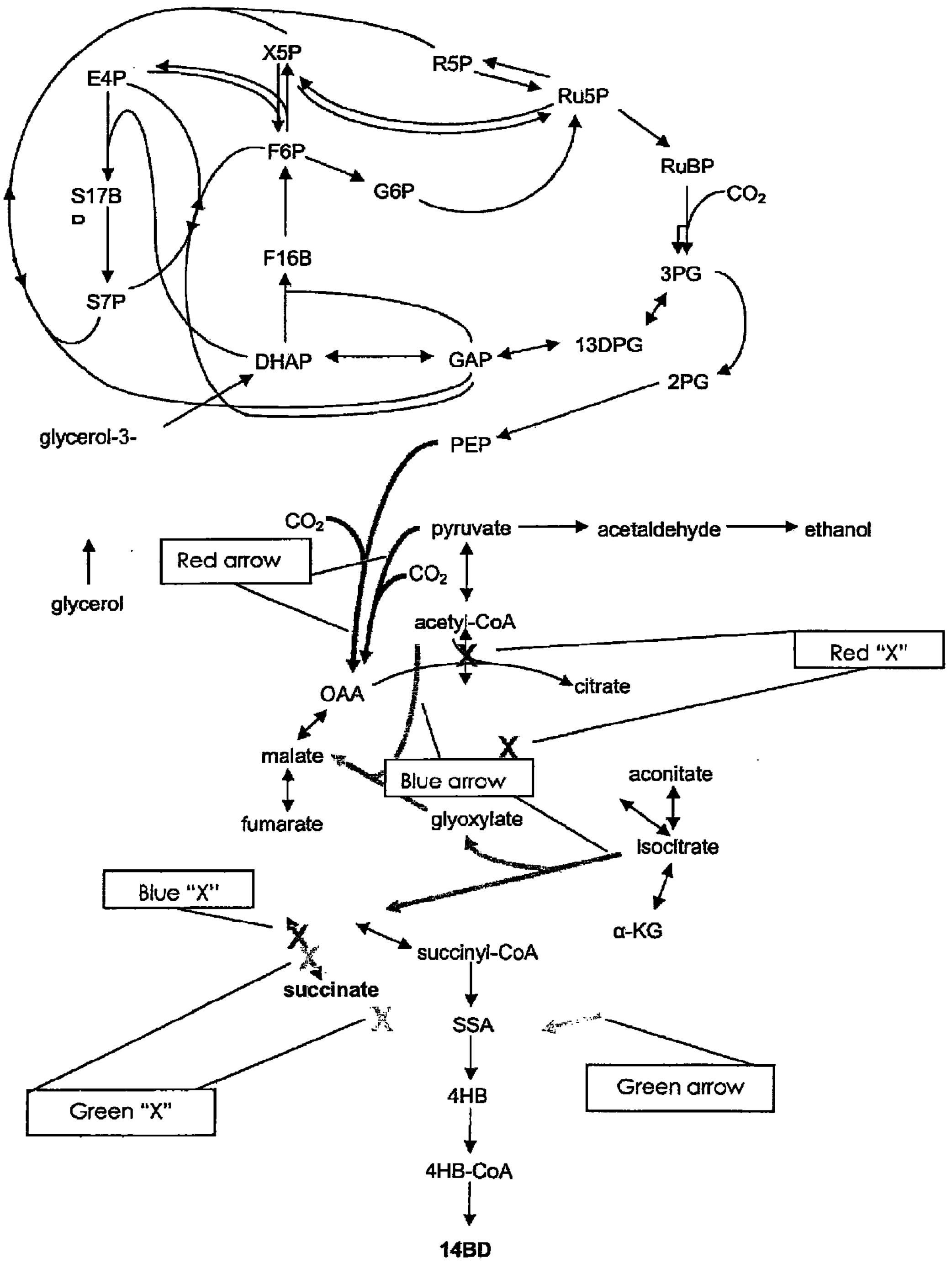
FIG. 8 provides a schematic of pathways to produce butanediol from succinate.

Succinyl-CoA dehydrogenaseC. *Kluyveri* sucD (EC 1.2.1.n) generates succinic from succinyl-CoA and NADPH. 4-hydroxybutyrate dehydrogenase *A. thaliana* ghbdh (EC 1.1.1.2) generates 4-hydroxybutyrate from succinic semialdehyde and NADPH. Glutamate dehydrogenase *E. coli* gdhA (EC 1.4.1.4) generates glutamate from α-ketoglutarate, NH3 and NADPH. Glutamate decarboxylase *E. coli* gadA (EC 4.1.1.15) generates 4-aminobutyrate and CO2 from glutamate. 4-aminobutyrate transaminase *E. coli* gabT (EC 2.6.1.19) generates glutamate and succinic semialdehyde from 4-aminobutyrate and α-ketoglutarate. Aldehyde dehydrogenase *E. coli* aldH (EC 1.1.1.n) generates 4-hydroxybutanal from 4-hydroxybutyrate and NADH. 1,3-propanediol oxidoreductase *K. pneumonia* dhaT (EC 1.1.1.202) generates 1,4-butanediol from 4-hydroxybutanal and NADH. This scheme is illustrated in FIG. 8. FIG. 8 also illustrates genes that can be knocked out (if already present in a host cell) to improve efficiency of 1,4-butanediol synthesis. Those genes are identified by the "Xs." Genes to be overexpressed are indicated in FIG. 8 by the colored arrows.

Example 24

Engineered Microorganisms Producing PHB

Beta-ketothiolase (*R. eutropha* phaA) (EC 2.3.1.16) converts 2 acetyl-CoA to acetoacetyl-CoA and CoA. Acetoacetyl-CoA reductase (*R. eutropha* phaB) (EC 1.1.1.36) generates 3-hydroxybutyryl-CoA from acetoacetyl-CoA and NADPH. PHA synthase (*R. eutropha* phaC) generates PHB and CoA from 3-hydroxybutyryl-CoA.

Production of Polyhydroxybutyrate (PHB): PHB is produced in nature by microorganisms as a carbon reservoir, usually under conditions of carbon sufficiency and limitation of some other nutrient. PHB is synthesized inside the cell in all known cases, not secreted into the medium. PHB is derived from acetyl-CoA in a three-step enzymatic pathway consisting of acetyl-CoA:acetyl-CoA C-acetyltransferase (EC 2.3.1.9), which converts two molecules of acetyl-CoA to one molecule of acetoacetyl-CoA and one molecule of free CoA; (R)-3-hydroxyacyl-CoA:NADP+ oxidoreductase (EC 1.1.1.36), which reduces acetoacetyl-CoA to (R)-3-hydroxybutyryl-CoA at the expense of NADPH; and polyhydroxyalkanoate synthase (EC 2.3.1.–), which polymerizes units of (R)-3-hydroxybutyryl-CoA by adding each to the growing chain and liberating free CoA.

Microorganisms that naturally produce PHB also have the capacity to degrade it, via one or more poly[(R)-3-hydroxybutanoate]hydrolase (EC 3.1.1.75) enzymes, more commonly referred to as depolymerases. These enzymes are expressed or activated to access stored carbon and energy upon occurrence of the appropriate conditions, such as carbon limitation. Expression of the PHB pathway in a non-natural producer often leads to irreversible accumulation of PHB because the non-natural producer lacks depolymerase activity.

Methods of Detecting PHB: Intracellular PHB can be measured by solvent extraction and esterification of the polymer from whole cells. Typically, lyophilized biomass is extracted with methanol-chloroform with 10% HCl as a catalyst. The chloroform dissolves the polymer, and the methanol esterifies it in the presence of HCl. The resulting mixture is extracted with water to remove hydrophilic substances, and the organic phase is analyzed by GC.

Engineered Microorganisms Producing PHB: The phaCAB operon from Ralstonia eutropha H16 is expressed in the recombinant host under control of an appropriate promoter. Examples of such promoters include the aphII, cpcB, cI, and lacIq-trc promoters. The operon is placed on pAQ1, pAQ7, or at a suitable site on the chromosome by homologous recombination.

Construction of pJB528: The DNA sequence encoding the PHB operon of Ralstonia eutropha H16 (phaCAB) was obtained from GenBank (NC008313, *Ralstonia eutropha* H16 chromosome 1). The individual genes (gene locus tags H16_A1437, H16_A1438, and H16_A1439) were each codon-optimized for expression in *E. coli*. The genes were then recast into an operon in the form phaCAB, but with convenient restriction sites between the genes. This optimized phaCAB operon was obtained by contract synthesis from DNA 2.0 (Menlo Park, Calif.). The phaCAB operon was designed with an NdeI site including part of the start codon and an EcoRI site after the stop codon. This construct was removed from its backbone vector by restriction digest with NdeI and EcoRI and inserted by ligation into pAQ1 insertion vector pJB496 (SEQ ID NO: 5) that had been digested with the same enzymes. The ligated construct, pJB528, was transformed into *E. coli* CopyCutter (Epicentre; Madison, Wis.). Subsequent transformation into *E. coli* NEB5α (New England Biolabs; Ipswich, Mass.) gave intracellular PHB granules which were apparent by visual inspection with light microscopy.

Example 25

Engineered Microorganisms Producing Acrylate

Enoyl-CoA hydratase (*E. coli* paaF) (EC 4.2.1.17) converts 3-hydroxypropionyl-CoA to acryloyl-CoA. Acrylate CoA-transferase (*R. eutropha* pct) (EC 2.8.3.n) generates acrylate+acetyl-CoA from acryloyl-CoA and acetate.

Example 26

Engineered Microorganisms Producing ϵ-Caprolactone

Acetyl-CoA:ACP transacylase *E. coli* fabH (EC 2.3.1.38) generates acetyl-ACP and CoA from acetyl-CoA and ACP. Acetyl-CoA carboxylase *E. coli* accBCAD (EC 6.4.1.2) generates malonyl-CoA acetyl-CoA, ATP and CO2. Malonyl-CoA:ACP transacylase *E. coli* fabD (EC 2.3.1.39) generates malonyl-ACP and CoA from malonyl-CoA and ACP. 3-ketoacyl-ACP synthase *E. coli* fabB (EC 2.3.1.41) generates CO2 and 3-ketoacyl-ACP from acyl-ACP and malonyl-ACP. 3-ketoacyl-ACP reductase *E. coli* fabG (EC 1.1.1.100) generates 3-hydroxyacyl-ACP from 3-ketoacyl-ACP and NADPH. 3-hydroxyacyl-ACP dehydratase *E. coli* fabA (EC 4.2.1.60) generates enoyl-ACP from 3-hydroxyacyl-ACP. Enoyl-ACP reductase *E. coli* fabI (EC 1.3.1.{9,10}) generates acyl-ACP from enoyl-ACP and {NADH, NADPH}. Acyl-ACP hydrolase *S. cerevisiae* FAS1 (EC 3.1.2.14) generates fatty acid and ACP from acyl-ACP. Fatty-acid monooxygenase *P. oleovorans* alkB (EC 1.14.15.3) generates ω-hydroxyalkanoate from fatty acid, NADPH and O2. An 1,6-lactonase (EC 3.1.1.n) converts 6-hydroxyhexanoate to ϵ-caprolactone.

Example 27

Engineered Microorganisms Producing Isoprene 1-deoxy-D-xylulose-5-phosphate synthase *E. coli* dxs (EC 2.2.1.7) generates 1-deoxy-D-xylulose-5-P and CO2 from pyruvate and D-glyceraldehyde-3-P. 1-deoxy-D-xylulose-5-phosphate reductoisomerase *E. coli* dxr (EC 1.1.1.267) generates 2-C-methyl-D-erythritol-4-P from 1-deoxy-D-xylulose-5-P+NADPH. 2-C-methyl-D-erythritol 4-phosphate cytidylyltransferase *E. coli* ispD (EC 2.7.7.60) generates 4-(cytidine-5'-PP)-2-C-methyl-D-erythritol from CTP+2-C-methyl-D-erythritol 4-P. 4-(cytidine 5'-diphospho)-2-C-methyl-D-erythritol kinase *E. coli* ispE (EC 2.7.1.148) generates 2-P-4-(cytidine 5'-PP)-2-C-methyl-D-erythritol from ATP and 4-(cytidine-5'-PP)-2-C-methyl-D-erythritol. 2-C-methyl-D-erythritol-2,4-cyclodiphosphate synthase *E. coli* ispF (EC 4.6.1.12) generates 2-C-methyl-D-erythritol-2,4-cyclo-PP+CMP from 2-P-4-(cytidine 5'-PP)-2-C-methyl-D-erythritol. 4-hydroxy-3-methylbut-2-en-1-yl diphosphate synthase *E. coli* ispG (EC 1.17.4.3) generates (E)-4-hydroxy-3-methylbut-2-en-1-yl-PP from 2-C-methyl-D-erythritol-2,4-cyclo-PP. 4-hydroxy-3-methylbut-2-enyl diphosphate reductase *E. coli* ispH (EC 1.17.1.2) generates isopentenyl-PP and NADP from (E)-4-hydroxy-3-methylbut-2-en-1-yl-PP and NADPH. 4-hydroxy-3-methylbut-2-enyl diphosphate reductase *E. coli* ispH (EC 1.17.1.2) generates dimethylallyl-PP+NADP from (E)-4-hydroxy-3-methylbut-2-en-1-yl-PP and NADPH. Isopentenyl-diphosphate Δ-isomerase *E. coli* idi (EC 5.3.3.2) converts dimethylallyl-PP to isopentenyl-PP.

Example 28

Engineered Microorganisms Producing Rubber

Rubber is produced by cis-polyprenylcistransferase from *H. brasiliensis* (EC 2.5.1.20), which converts isopentenyl-PP to rubber.

Example 29

Engineered Microorganisms Producing Lactate

Lactate dehydrogenase *E. coli* ldhA (EC 1.1.1.28) converts NADH and pyruvate to D-lactate.

Example 30

Engineered Microorganisms Producing DHA

DHA kinase *C. freundii* dhaK (EC 2.7.1.29) converts dihydroxyacetone and ATP to dihydroxyacetone-P.

Example 31

Engineered Microorganisms Producing 3-Hydroxypropionate

Figure 5:
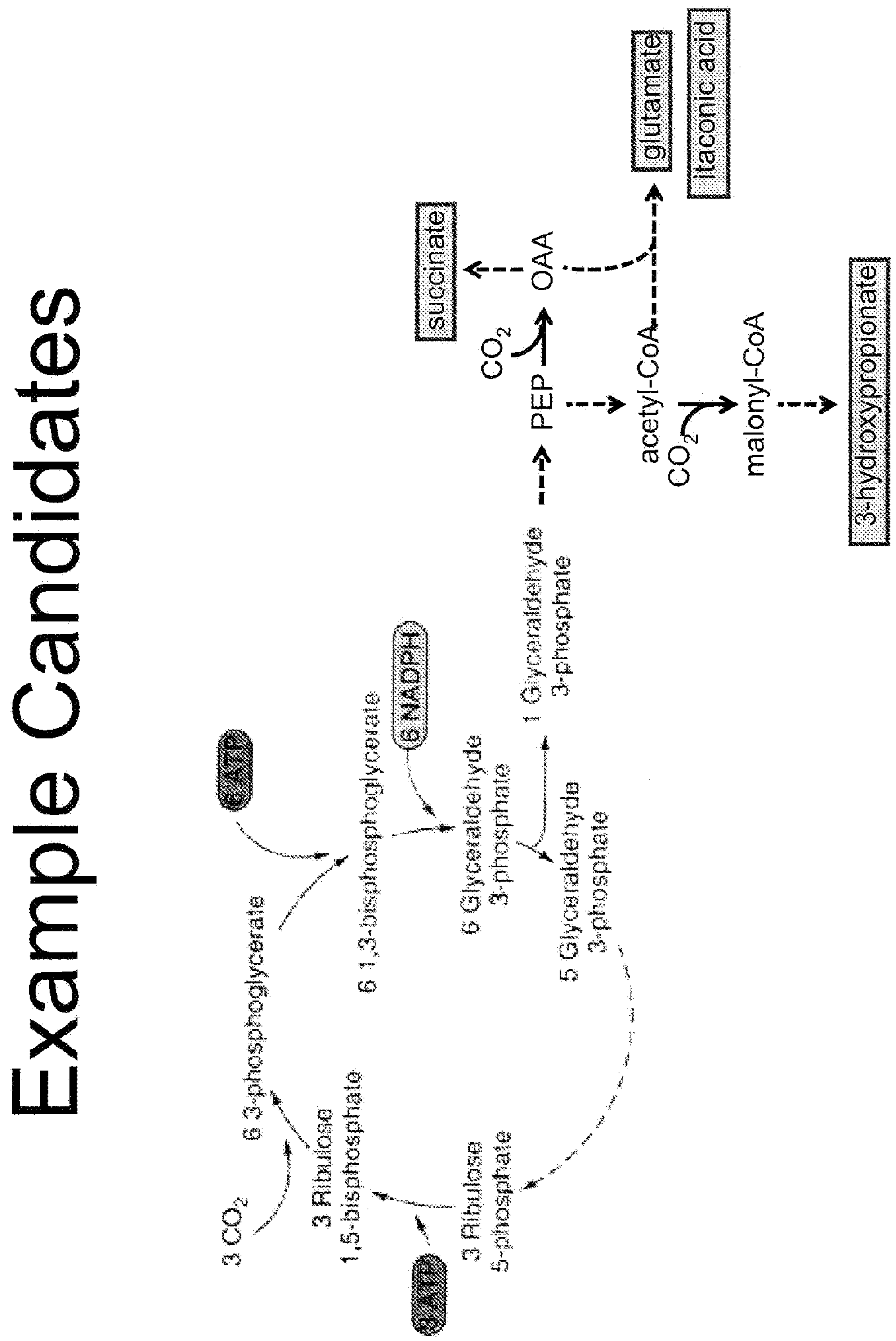
FIG. 5 provides an example of pathways to produce several different chemicals: succinate, glutamate, itaconic acid and 3-hydroxypropionate.

Acetyl-CoA carboxylase *E. coli* accBCAD (EC 6.4.1.2) generates malonyl-CoA from acetyl-CoA, ATP and CO2 (see, e.g., the pathway shown in FIG. 5). The bifunctional malonyl-CoA reductase from *C. aurantiacus* (EC 1.2.1.18, 1.1.1.59) converts malonyl-CoA and 2 NADPH to 3-hydroxypropionate and CoA.

Example 32

Engineered Microorganisms Producing γ-Valerolactone

The enzyme 2-oxobutyrate synthase from *C. pasteurianum* (EC 1.2.7.2) converts propionyl-CoA, CO2 and 2 Fdred to 2-oxobutanoate, CoA and 2 FDox. The enzyme 2-ethylmalate synthase from *S. cerevisiae* (EC 2.3.3.6) generates (R)-2-ethylmalate+CoA from 2-oxobutanoate and acetyl-CoA. Aconitase analog generates 3-carboxy-4-hydroxypentanoate from (R)-2-ethylmalate. Isocitrate dehydrogenase analog converts 3-carboxy-4-hydroxypentanoate to levulinate. Acetoacetyl-CoA reductase analog *R. eutropha* ler generates 4-hydroxypentanoate from levulinate and NAD(P)H. 1,4-lactonase from *R. norvegicus* (EC 3.1.1.25) generates γ-valerolactone from 4-hydroxypentanoate.

Alternatively, acetyl-CoA carboxylase *E. coli* accBCAD (EC 6.4.1.2) converts acetyl-CoA, ATP and CO2 to malonyl-CoA. The bifunctional malonyl-CoA reductase from *C. aurantiacus* (EC 1.2.1.18, 1.1.1.59) converts malonyl-CoA and 2 NADPH to 3-hydroxypropionate and CoA. The enoyl-CoA hydratase *E. coli* paaF (EC 4.2.1.17) generates acryloyl-CoA from 3-hydroxypropionyl-CoA. Acyl-CoA dehydrogenase *A. thaliana* At3G06810 (EC 1.3.99.3) generates propionyl-CoA from acryloyl-CoA and FADH2. Beta-ketothiolase *R. eutropha* bktB (EC 2.3.1.16) generates 3-ketovaleryl-CoA and CoA from propionyl-CoA and acetyl-CoA. Acetoacetyl-CoA reductase *R. eutropha* phaB (EC 1.1.1.36) generates (R)-3-hydroxyvaleryl-CoA from 3-ketovaleryl-CoA and NADPH. 3-hydroxybutyryl-CoA dehydratase *X. axonopodis* crt (EC 4.2.1.55) generates 3-pentenoyl-CoA from (R)-3-hydroxyvaleryl-CoA. Vinylacetyl-CoA Δ-isomerase *C. difficile* abfD (EC 5.3.3.3) generates 4-hydroxypentanoyl-CoA from 3-pentenoyl-CoA. 4-hydroxybutyryl-CoA transferase *C. kluyveri* orfZ (EC 2.8.3.n) converts 4-hydroxypentanoyl-CoA and acetate to acetyl-CoA and 4-hydroxypentanoate. 1,4-lactonase from *R. norvegicus* (EC 3.1.1.25) generates γ-valerolactone from 4-hydroxypentanoate.

Example 33

Engineered Microorganisms Producing Lysine

Aspartate aminotransferase *E. coli* aspC (EC 2.6.1.1) generates L-aspartate and α-ketoglutarate from oxaloacetate and L-glutamate. Aspartate kinase *E. coli* lysC (EC 2.3.3.14) generates L-aspartyl-4-P from L-aspartate and ATP. Aspartate semialdehyde dehydrogenase *E. coli* asd (EC 1.2.1.11) generates NADPH+L-aspartyl-4-phosphate from L-aspartate-semialdehyde. Dihydrodipicolinate synthase *E. coli* dapA (EC 4.2.1.52) generates L-2,3-dihydrodipicolinate from pyruvate and L-aspartate-semialdehyde. Dihydrodipicolinate reductase *E. coli* dapB (EC 1.3.1.26) generates tetrahydrodipicolinate from L-2,3-dihydrodipicolinate and NADPH. Tetrahydrodipicolinate succinylase *E. coli* dapD (EC 2.3.1.117) generates N-succinyl-2-amino-6-ketopimelate and CoA from tetrahydrodipicolinate and succinyl-CoA. N-succinyldiaminopimelate-aminotransferase *E. coli* argD (EC 2.6.1.17) generates α-ketoglutarate and N-succinyl-L,L-2,6-diaminopimelate from L-glutamate and N-succinyl-2-amino-6-ketopimelate. N-succinyl-L-diaminopimelate desuccinylase *E. coli* dapE (EC 3.5.1.18) generates L,L-diaminopimelate and succinate from N-succinyl-L,L-2,6-diaminopimelate. Diaminopimelate epimerase *E. coli* dapF (EC 5.1.1.7) generates meso-diaminopimelate from L,L-diaminopimelate. Diaminopimelate decarboxylase *E. coli* lysA (EC 4.1.1.20) generates L-lysine and CO2 from meso-diaminopimelate.

Alternatively, in lieu of dapD (EC 2.3.1.117), argD (EC 2.6.1.17), dapE (EC 3.5.1.18); LL-diaminopimelate aminotransferase *A. thaliana* At4g33680 (EC 2.6.1.83) is used to generate L,L-diaminopimelate and L-glutamate from tetrahydrodipicolinate and α-ketoglutarate. Homocitrate synthase *S. cerevisiae* lys21 (EC 2.3.3.14) generates homocitrate and CoA from acetyl-CoA and α-ketoglutarate. Homoaconitase *S. cerevisiae* lys4, lys3 (EC 4.2.1.36) generates homoisocitrate from homocitrate and homo-cis-aconitate. Homoisocitrate dehydrogenase *S. cerevisiae* lys12, lys11, lys10 (EC 1.1.1.87) generates 2-oxoadipate and CO2+NADH from homoisocitrate. 2-aminoadipate transaminase *S. cerevisiae* ARO8 (EC 2.6.1.39) generates L-2-aminoadipate and α-ketoglutarate from 2-oxoadipate and L-glutamate. 2-aminoadipate reductase *S. cerevisiae* lys2, lys5 (EC 1.2.1.31) generates L-2-aminoadipate 6-semialdehyde from L-2-aminoadipate and NAD(P)H. Aminoadipate semialdehyde-glutamate reductase *S. cerevisiae* lys9, lys13 (EC 1.5.1.10) generates N6-(L-1,3-Dicarboxypropyl)-L-lysine and NADP from L-glutamate and L-2-aminoadipate 6-semialdehyde and NADPH. Lysine-2-oxoglutarate reductase *S. cerevisiae* lys1 (EC 1.5.1.7) generates L-lysine and α-ketoglutarate and NADH from N6-(L-1,3-dicarboxypropyl)-L-lysine.

Example 34

Engineered Microorganisms Producing Serine

Phosphoglycerate dehydrogenase *E. coli* serA (EC 1.1.1.95) generates 3-phosphonooxypyruvate and NADH from 3-P-D-glycerate. Phosphoserine transaminase *E. coli* serC (EC 2.6.1.52) generates 3-phosphonooxypyruvate+L-glutamate from ortho-P-L-serine+α-ketoglutarate. Phosphoserine phosphatase *E. coli* serB (EC 3.1.3.3) converts ortho-P-L-serine to L-serine.

Example 35

Engineered Microorganisms Producing Aspartate

Aspartate aminotransferase *E. coli* aspC (EC 2.6.1.1) converts oxaloacetate and L-glutamate to L-aspartate and α-ketoglutarate.

Example 36

Engineered Microorganisms Producing Sorbitol

Sorbitol (from F6P) Glucose-6-phosphate isomerase *E. coli* pgi (EC 5.3.1.9) converts D-β-fructose-6-P to D-α-glucose-6-P.

Phosphoglucomutase *E. coli* pgm (EC 5.4.2.2) converts D-α-glucose-6-P to D-α-glucose-1-P. Glucose-1-phosphatase *E. coli* agp (EC 3.1.3.10) converts D-α-glucose-1-P to D-α-glucose.

Alternatively, aldose-1-epimerase *E. coli* galM (EC 5.1.3.3) converts D-β-glucose to D-α-glucose. Polyol dehydrogenase *S. cerevisiae* GRE3 (EC 1.1.1.21) generates D-sorbitol from D-α-glucose and NADPH.

Example 37

Engineered Microorganisms Producing Ascorbate

Alpha-D-glucose-6-phosphate ketol-isomerase *A. thaliana* PGI1 (EC 5.3.1.9) generates β-D-fructose-6-P from D-α-glucose-6-P. D-Mannose-6-phosphate ketol-isomerase *A. thaliana* din9 (EC 5.3.1.8) converts β-D-fructose-6-P to D-mannose-6-P. D-Mannose 6-phosphate 1,6-phosphomutase *A. thaliana* atpmm (EC 5.4.2.8) converts D-mannose-6-P to D-mannose-1-P. Mannose-1-phosphate guanylyltransferase *A. thaliana* cyt (EC 2.7.7.22) converts D-mannose-1-P to GDP-mannose. GDP-mannose 3,5-epimerase *A. thaliana* gene (EC 5.1.3.18) converts GDP-mannose to GDP-L-galactose. Galactose-1-phosphate guanylyltransferase *A. thaliana* VTC2 (EC 2.7.n.n) converts GDP-L-galactose to L-galactose-1-P. L-galactose 1-phosphate phosphatase *A. thaliana* VTC4 (EC 3.1.3.n) converts L-galactose-1-P to L-galactose. L-galactose dehydrogenase *A. thaliana* At4G33670 (EC 1.1.1.122) converts L-galactose to L-1,4-galactonolactone and NADH. L-galactonolactone oxidase *S. cerevisiae* ATGLDH (EC 1.3.3.12) converts L-1,4-galactonolactone and O2 to ascorbate and H2O2. A catalase *E. coli* katE (EC 1.11.1.6) (2H2O2=>O2) converts hydrogen peroxide to oxygen.

Example 38

Engineered Microorganisms Producing Cephalosporin

Homocitrate synthase *S. cerevisiae* lys21 (EC 2.3.3.14) converts acetyl-CoA and α-ketoglutarate to homocitrate and CoA.

Homoaconitase *S. cerevisiae* lys4, lys3 (EC 4.2.1.36) generates homocitrate or homo-cis-aconitate or homoisocitrate. Homoisocitrate dehydrogenase *S. cerevisiae* lys12, lys11, lys10 (EC 1.1.1.87) generates 2-oxoadipate and CO2 and NADH from homoisocitrate. 2-aminoadipate transaminase *S. cerevisiae* aro8 (EC 2.6.1.39) converts 2-oxoadipate and L-glutamate to L-2-aminoadipate and α-ketoglutarate. Phosphoglycerate dehydrogenase *E. coli* serA (EC 1.1.1.95) converts 3-P-D-glycerate to 3-phosphonooxypyruvate and NADH. Phosphoserine transaminase *E. coli* serC (EC 2.6.1.52) converts ortho-β-L-serine and α-ketoglutarate to 3-phosphonooxypyruvate and L-glutamate. Phosphoserine phosphatase *E. coli* serB (EC 3.1.3.3) converts ortho-P-L-serine to L-serine. Serine O-acetyltransferase *A. thaliana* AtSerat2; 1 (EC 2.3.1.30) converts acetyl-CoA and L-serine to CoA and O-acetyl-L-serine. Cysteine synthase *A. thaliana* At1G55880 (EC 2.5.1.47) converts O-acetyl-L-serine to L-cysteine and acetate. Acetolactate synthase *E. coli* ilvN, ilvB (EC 2.2.1.6) converts pyruvate to CO2 and 2-acetolactate. Acetohydroxyacid isomeroreductase *E. coli* ilvC (EC 1.1.1.86) converts 2-acetolactate and NADPH to 2,3-dihydroxyisovalerate. Dihydroxyacid dehydratase *E. coli* ilvD (EC 4.2.1.9) converts 2,3-dihydroxyisovalerate to 2-ketoisovalerate. Valine transaminase *E. coli* ilvE (EC 2.6.1.42) converts 2-ketoisovalerate and L-glutamate to α-ketoglutarate and L-valine. ACV synthetase *A. variabilis* Ava_1613 (EC 6.3.2.26) converts 3 ATP, L-2-aminoadipate, L-cysteine and L-valine to N-[L-5-amino-5-carboxypentanoyl]-L-cysteinyl-D-valine. Isopenicillin-N synthase *A. variabilis* Ava_5009 (EC 1.21.3.1) converts N-[L-5-amino-5-carboxypentanoyl]-L-cysteinyl-D-valine and O2 to isopenicillin-N. Isopenicillin-N epimerase *M. xanthus* cefD (EC 5.1.1.17) converts isopenicillin-N to penicillin-N. Cephalosporin biosynthesis expandase/hydroxylase *C. acremonium* cefEF (EC 1.14.20.1, 1.14.11.26) converts penicillin-N, 2α-ketoglutarate and 2 O2 to deacetylcephalosporin C, 2 succinate and 2 CO2. Deacetylcephalosporin-C acetyltransferase *C. acremonium* cefG (EC 2.3.1.175) then generates CoA and cephalosporin C from acetyl-CoA and deacetylcephalosporin C.

Example 39

Engineered Microorganisms Producing Isopentenol 1-deoxy-D-xylulose-5-phosphate synthase *E. coli* dxs (EC 2.2.1.7) converts pyruvate and D-glyceraldehyde-3-P to 1-deoxy-D-xylulose-5-P and CO2. 1-deoxy-D-xylulose-5-phosphate reductoisomerase *E. coli* dxr (EC 1.1.1.267) converts 1-deoxy-D-xylulose-5-P and NADPH to 2-C-methyl-D-erythritol-4-P. 2-C-methyl-D-erythritol 4-phosphate cytidylyltransferase *E. coli* ispD (EC 2.7.7.60) converts CTP and 2-C-methyl-D-erythritol 4-P to 4-(cytidine-5'-PP)-2-C-methyl-D-erythritol. 4-(cytidine 5'-diphospho)-2-C-methyl-D-erythritol kinase *E. coli* ispE (EC 2.7.1.148) converts ATP and 4-(cytidine-5'-PP)-2-C-methyl-D-erythritol to 2-P-4-(cytidine 5'-PP)-2-C-methyl-D-erythritol. 2-C-methyl-D-erythritol 2,4-cyclodiphosphate synthase *E. coli* ispF (EC 4.6.1.12) converts 2-P-4-(cytidine 5'-PP)-2-C-methyl-D-erythritol to 2-C-methyl-D-erythritol-2,4-cyclo-PP and CMP. 4-hydroxy-3-methylbut-2-en-1-yl diphosphate synthase *E. coli* ispG (EC 1.17.4.3) convert 2-C-methyl-D-erythritol-2,4-cyclo-PP to (E)-4-hydroxy-3-methylbut-2-en-1-yl-PP. 4-hydroxy-3-methylbut-2-enyl diphosphate reductase *E. coli* ispH (EC 1.17.1.2) convert (E)-4-hydroxy-3-methylbut-2-en-1-yl-PP and NADPH to isopentenyl-PP. 4-hydroxy-3-methylbut-2-enyl diphosphate reductase *E. coli* ispH (EC 1.17.1.2) converts (E)-4-hydroxy-3-methylbut-2-en-1-yl-PP and NADPH to dimethylallyl-PP. Isopentenyl-diphosphate Δ-isomerase *E. coli* idi (EC 5.3.3.2) converts dimethylallyl-PP to isopentenyl-PP. Isopentenyl-PP pyrophosphatase converts isopentenyl-PP to isopentenol. Isopentenol dikinase converts isopentenyl-PP to isopentenol and ATP. Hydroxymethylglutaryl-CoA synthase *S. cerevisiae* erg13 (EC 2.3.3.10) converts acetyl-CoA and acetoacetyl-CoA to (S)-3-hydroxy-3-methylglutaryl-CoA and CoA. Hydroxymethylglutaryl-CoA reductase *S. cerevisiae* hmg2 (EC 1.1.1.34) converts (R)-mevalonate and CoA to (S)-3-hydroxy-3-methylglutaryl-CoA and 2 NADPH. Mevalonate kinase *S. cerevisiae* erg12 (EC 2.7.1.36) converts ATP and (R)-mevalonate to (R)-5-P-mevalonate. Phosphomevalonate kinase *S. cerevisiae* erg8 (EC 2.7.4.2) converts ATP and (R)-5-P-mevalonate to (R)-5-PP-mevalonate. Diphosphomevalonate decarboxylase *S. cerevisiae* mvd1 (EC 4.1.1.33) converts ATP and (R)-5-PP-mevalonate to isopentenyl-PP and CO2.

Example 40

Engineered Microorganisms Producing Lanosterol 1-deoxy-D-xylulose-5-phosphate synthase *E. coli* dxs (EC 2.2.1.7) converts pyruvate and D-glyceraldehyde-3-P to 1-deoxy-D-xylulose-5-P and CO2. 1-deoxy-D-xylulose-5-phosphate reductoisomerase *E. coli* dxr (EC 1.1.1.267) converts 1-deoxy-D-xylulose-5-P and NADPH to 2-C-methyl-D-erythritol-4-P. 2-C-methyl-D-erythritol 4-phosphate cytidylyltransferase *E. coli* ispD (EC 2.7.7.60) converts CTP and 2-C-methyl-D-erythritol 4-P to 4-(cytidine-5'-PP)-2-C-methyl-D-erythritol. 4-(cytidine 5'-diphospho)-2-C-methyl-D-erythritol kinase *E. coli* ispE (EC 2.7.1.148) converts ATP and 4-(cytidine-5'-PP)-2-C-methyl-D-erythritol to 2-P-4-(cytidine 5'-PP)-2-C-methyl-D-erythritol. 2-C-methyl-D-erythritol 2,4-cyclodiphosphate synthase *E. coli* ispF (EC 4.6.1.12) converts 2-P-4-(cytidine 5'-PP)-2-C-methyl-D-erythritol to 2-C-methyl-D-erythritol-2,4-cyclo-PP and CMP. 4-hydroxy-3-methylbut-2-en-1-yl diphosphate synthase *E. coli* ispG (EC 1.17.4.3) converts 2-C-methyl-D-erythritol-2,4-cyclo-PP to (E)-4-hydroxy-3-methylbut-2-en-1-yl-PP. 4-hydroxy-3-methylbut-2-enyl diphosphate reductase *E. coli* ispH (EC 1.17.1.2) converts (E)-4-hydroxy-3-methylbut-2-en-1-yl-PP and NADPH to isopentenyl-PP. 4-hydroxy-3-methylbut-2-enyl diphosphate reductase *E. coli* isp (EC 1.17.1.2) converts (E)-4-hydroxy-3-methylbut-2-en-1-yl-PP+NADPH=dimethylallyl-PP. Isopentenyl-diphosphate Δ-isomerase *E. coli* idi (EC 5.3.3.2) converts dimethylallyl-PP to isopentenyl-PP. Geranylgeranyl pyrophosphate synthase *Synechocystis* sp. PCC6803 crtE (EC 2.5.1.29) converts dimethylallyl-PP and 2 isopentenyl-PP to farnesyl-PP. Squalene synthase *Synechocystis* sp. PCC6803 s110513 (EC 2.5.1.21) converts 2 farnesyl-PP and NADPH to squalene. Squalene monooxygenase *S. cerevisiae* erg1 (EC 1.14.99.7) converts squalene, NADPH and O2 to (S)-squalene-2,3-epoxide. Lanosterol synthase *S. cerevisiae* ERG7 (EC 5.4.99.7) converts (S)-squalene-2,3-epoxide to lanosterol.

Example 41

Engineered Microorganisms Producing Omega-3 DHA

To engineer microorganisms producing omega-3 DHA, the necessary genes are pfaABCDE, some of which are multi-functional. Acetyl-CoA:ACP transacylase *S. pneumatophori* (EC 2.3.1.38) converts acetyl-CoA and ACP to acetyl-ACP+CoA. Acetyl-CoA carboxylase *E. coli* (EC 6.4.1.2) converts acetyl-CoA, ATP and CO2 to malonyl-CoA. Malonyl-CoA:ACP transacylase *E. coli* (EC 2.3.1.39) converts malonyl-CoA and ACP to malonyl-ACP and CoA. 3-ketoacyl-ACP synthase *E. coli* (EC 2.3.1.41) converts acyl-ACP and malonyl-ACP to CO2 and 3-ketoacyl-ACP. 3-ketoacyl-ACP reductase *E. coli* (EC 1.1.1.100) converts 3-ketoacyl-ACP and NADPH to 3-hydroxyacyl-ACP. 3-hydroxyacyl-ACP dehydratase *E. coli* (EC 4.2.1.60) converts 3-hydroxyacyl-ACP to enoyl-ACP. Enoyl-ACP reductase *E. coli* (EC 1.3.1.{9,10}) converts enoyl-ACP and {NADH, NADPH} to acyl-ACP. Desaturase *S. pneumatophori* (EC 1.14.19.n) converts m:n fatty acid, NADPH and O2 to m:(n+1) fatty acid. Acyl-ACP hydrolase *S. cerevisiae* FAS1 (EC 3.1.2.14) acyl-ACP to fatty acid and ACP.

Example 42

Engineered Microorganisms Producing Lycopene 1-deoxy-D-xylulose-5-phosphate synthase *E. coli* dxs (EC 2.2.1.7) converts pyruvate and D-glyceraldehyde-3-P to 1-deoxy-D-xylulose-5-P and CO2. 1-deoxy-D-xylulose-5-phosphate reductoisomerase *E. coli* dxr (EC 1.1.1.267) converts 1-deoxy-D-xylulose-5-P and NADPH to 2-C-methyl-D-erythritol-4-P. 2-C-methyl-D-erythritol 4-phosphate cytidylyltransferase *E. coli* ispD (EC 2.7.7.60) converts CTP and 2-C-methyl-D-erythritol 4-P to 4-(cytidine-5'-PP)-2-C-methyl-D-erythritol. 4-(cytidine 5'-diphospho)-2-C-methyl-D-erythritol kinase *E. coli* ispE (EC 2.7.1.148) converts ATP+4-(cytidine-5'-PP)-2-C-methyl-D-erythritol to 2-P-4-(cytidine 5'-PP)-2-C-methyl-D-erythritol. 2-C-methyl-D-erythritol 2,4-cyclodiphosphate synthase *E. coli* ispF (EC 4.6.1.12) converts 2-P-4-(cytidine 5'-PP)-2-C-methyl-D-erythritol to 2-C-methyl-D-erythritol-2,4-cyclo-PP and CMP. 4-hydroxy-3-methylbut-2-en-1-yl diphosphate synthase *E. coli* ispG (EC 1.17.4.3) converts 2-C-methyl-D-erythritol-2,4-cyclo-PP to (E)-4-hydroxy-3-methylbut-2-en-1-yl-PP. 4-hydroxy-3-methylbut-2-enyl diphosphate reductase *E. coli* ispH (EC 1.17.1.2) converts (E)-4-hydroxy-3-methylbut-2-en-1-yl-PP and NADPH to isopentenyl-PP. 4-hydroxy-3-methylbut-2-enyl diphosphate reductase *E. coli* ispH (EC 1.17.1.2) converts (E)-4-hydroxy-3-methylbut-2-en-1-yl-PP and NADPH to dimethylallyl-PP. Isopentenyl-diphosphate Δ-isomerase *E. coli* idi (EC 5.3.3.2) converts dimethylallyl-PP to isopentenyl-PP. Geranylgeranyl pyrophosphate synthase *Synechocystis* sp. PCC6803 crtE (EC 2.5.1.29) converts dimethylallyl-PP and 2 isopentenyl-PP to farnesyl-PP. Geranylgeranyl pyrophosphate synthase *Synechocystis* sp. PCC6803 crtE (EC 2.5.1.29) converts isopentenyl-PP and farnesyl-PP to (all trans)-geranylgeranyl-PP. Phytoene synthase *Synechocystis* sp. PCC6803 crtB (EC 2.5.1.32) converts 2 geranylgeranyl-PP to phytoene. Phytoene oxidoreductase *Synechocystis* sp. PCC6803 crtI (EC 1.14.99.n phytoene, 2 NADPH and 2 O2 to ζ-carotene. ζ-carotene oxidoreductase *Synechocystis* sp. PCC6803 crtQ-2 (EC 1.14.99.30) converts ζ-carotene, 2 NADPH and 2 O 2 to lycopene.

Example 43

Engineered Microorganisms Producing Itaconate

Figure 7:
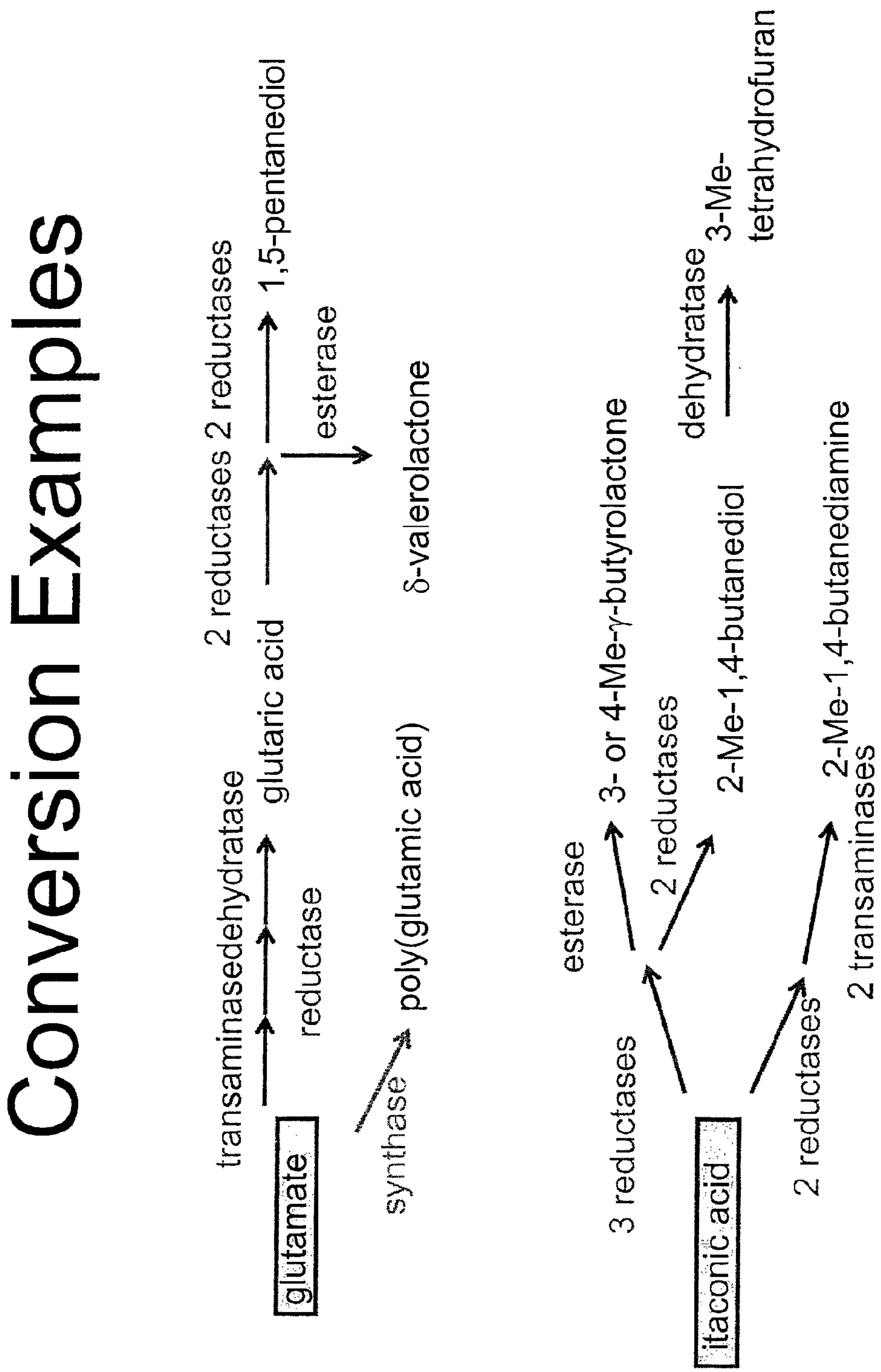
FIG. 7 provides a schematic of glutamate or itaconic acid conversion to various chemicals.

Aconitate decarboxylase from *A. terreus* (EC 4.1.1.6) converts cis-aconitate to itaconate and CO2. Itaconate can subsequently be converted to various other carbon-based products of interest, e.g., according to the scheme presented in FIG. 7.

Example 44

Engineered Microorganisms Producing 1,3-Butadiene or Glutamate

Succinyl-CoA dehydrogenase *C. kluyveri* sucD (EC 1.2.1.n) converts succinyl-CoA and NADPH to succinic semialdehyde and CoA. 4-hydroxybutyrate dehydrogenase *A. thaliana* ghbdh (EC 1.1.1.2) converts succinic semialdehyde and NADPH to 4-hydroxybutyrate. Glutamate dehydrogenase *E. coli* gdhA (EC 1.4.1.4) converts α-ketoglutarate, NH3 and NADPH to glutamate. Glutamate decarboxylase *E. coli* gadA (EC 4.1.1.15) converts glutamate to 4-aminobutyrate and CO2. 4-aminobutyrate transaminase *E. coli* gabT (EC 2.6.1.19) converts 4-aminobutyrate and α-ketoglutarate to glutamate and succinic semialdehyde. Aldehyde dehydrogenase *E. coli* aldH (EC 1.1.1.n) converts 4-hydroxybutyrate and NADH to 4-hydroxybutanal. 1,3-propanediol oxidoreductase *K. pneumonia* dhaT (EC 1.1.1.202) 4-hydroxybutanal and NADH to 1,4-butanediol. Alcohol dehydratase (EC 4.2.1.n) converts 1,4-butanediol to 1,3-butadiene.

Example 45

Engineered Microorganisms Producing Propylene

Acetyl-CoA carboxylase *E. coli* accBCAD (EC 6.4.1.2) converts acetyl-CoA, ATP and CO2 to malonyl-CoA. A bifunctional malonyl-CoA reductase *C. aurantiacus* (EC 1.2.1.18, 1.1.1.59) converts malonyl-CoA and 2 NADPH to 3-hydroxypropionate and CoA. 3-hydroxypropionyl-CoA transferase *C. kluyveri* orfZ (EC 2.8.3.n) converts 3-hydroxypropionate and acetyl-CoA to 3-hydroxypropionyl-CoA and acetate. 3-hydroxypropionyl-CoA dehydratase *C. aurantiacus* (EC 4.2.1.17) converts 3-hydroxypropionyl-CoA to acryloyl-CoA. Acryloyl-CoA reductase *C. aurantiacus* (EC 1.3.1.n) converts acryloyl-CoA and NADPH to propionyl-CoA. Propionyl CoA-transferase *R. eutropha* pct (EC 2.8.3.1) converts propionyl-CoA and acetate to acetyl-CoA and propionate. Aldehyde dehydrogenase *E. coli* adhE (EC 1.2.1.{3,4}) converts propionate and NADPH to propanal. Alcohol dehydrogenase *E. coli* adhE (EC 1.1.1.{1,2}) converts propanal and NADPH to 1-propanol. Alcohol dehydratase (EC 4.2.1.n) converts 1-propanol to propylene.

Example 46

Engineered Microorganisms Producing Succinate, Citrate, Glutamate, Malate

From glyceraldehydes 3-phosphate (GAP), NAD+ and Pi, triosephosphate dehydrogenase converts GAP to 1,3-bisphosphoglycerate, NADH and H+. Phosphoglycerate kinase converts 1,3-bisphosphoglycerate and ADP to 3-P-glycerate and ATP. Mutase converts 3-P-glycerate to 2-P-glycerate. Enolase converts 2-P-glycerate to phosphoenolpyruvate (PEP) and H2O. Phosphoenolpyruvate carboxylase then converts PEP to oxaloacetate (OAA). OAA is converted to succinate in one of two ways. OAA, H2O and acetyl-CoA are converted to citrate and CoASH by citrate synthase, which converts to H2O and cis-aconitate, an enzyme-bound intermediate, which is subsequently converted to succinate by isocitrate lyase. Alternatively, cis-aconitate and H2O is converted to isocitrate by aconitase. Isocitrate and NADP+ are converted to oxalosuccinate, NADPH and H+ by isocitrate dehydrogenase. Oxalosuccinate is then converted to α-ketoglutarate and CO2 by isocitrate dehydrogenase. α-ketoglutarate, NAD+ and CoASH are converted to succinyl-CoA, CO2, NADH and H+ by α-ketoglutarate dehydrogenase. Succinate thiokinase convert succinyl-CoA, ADP and Pi to succinate, ATP and CoASH.

Figure 6:
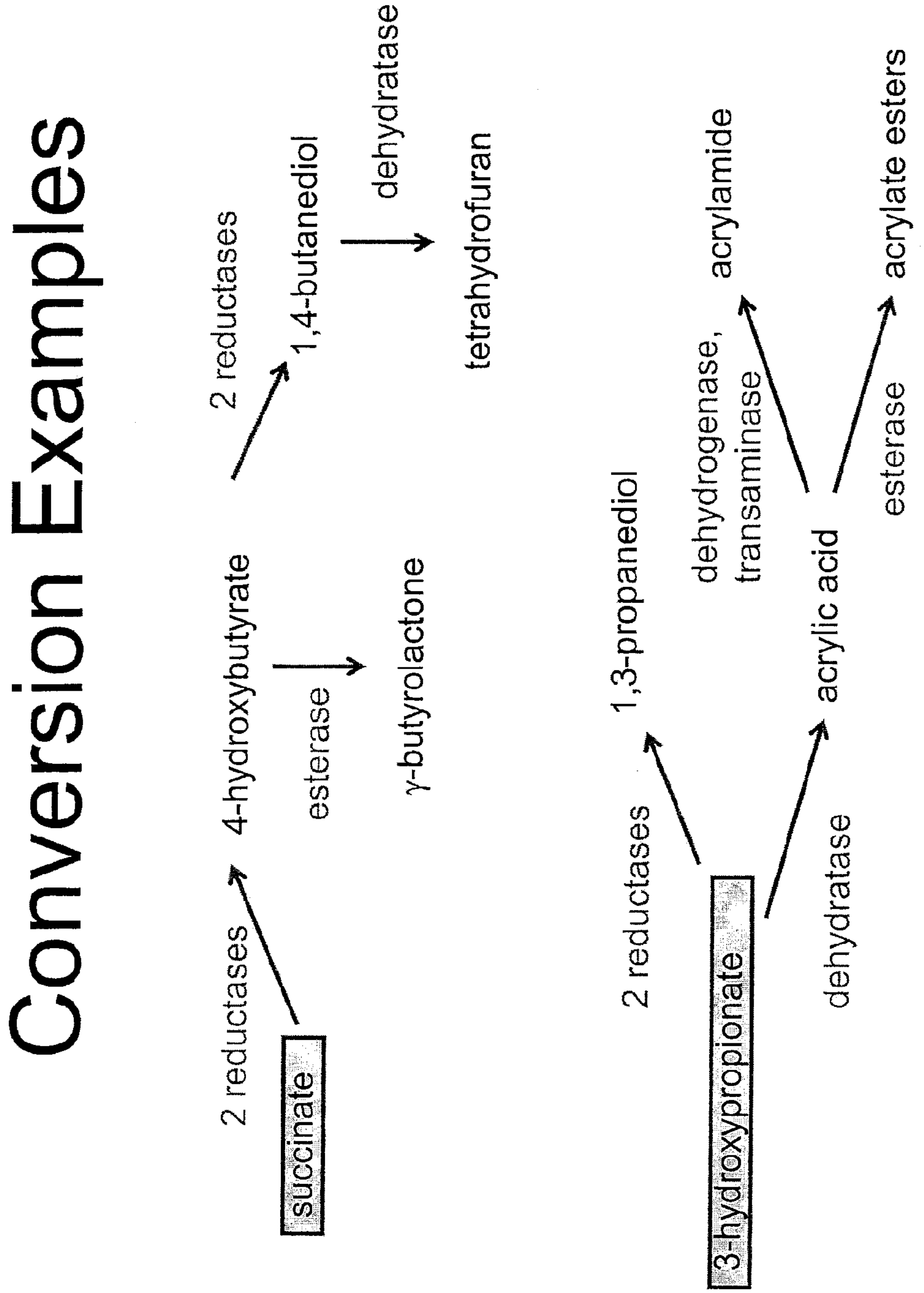
FIG. 6 provides a schematic to convert succinate or 3-hydroxypropionate to various chemicals.

In those microorganisms where the above chemicals are already part of central metabolism, they are engineered to export the chemicals from the cells. Under some conditions such as anaerobic fermentation, succinate can build up in cells due to repression of the citric acid cycle. Once this occurs, one or more members of a family of enzymes known as C4-dicarboxylate carriers serve to export succinate from cells into the media. Janausch et al., *Biochimica et Biophysica Acta* 1553:39-56 (2002); Kim et al., *J. Bacteriol*, March 2007, p. 1597-1603. In certain aspects of the invention, succinate can be coverted to various other chemicals as illustrated in, e.g., FIG. 6.

Example 47

Analytical Methods to Detect 3-hpa

Colorimetric: To obtain standard curves, 0-6 μmol of freshly distilled acrolein (Fluka, Buchs, Switzerland) is added to 6 ml of distilled water. Then, 4.5 ml of DL-tryptophan (Fluka) solution (0.01 M solution in 0.05 M HCl, stabilized with a few drops of toluene) and 18 ml of 37% HCl are added immediately. For 3-HPA quantification, a 1-ml sample is mixed with 0.75 ml of DL-tryptophan solution and 3 ml of HCl 37%. Mixtures containing samples and standards are incubated for 20 min in a water bath at 37° C. and the optical density is measured at 560 nm (OD560). 3-HPA samples are diluted with distilled water before mixing with reagents to ensure a final OD560<1. This method is shown to allow a precise quantification of 3-HPA using acrolein as a standard (Lüthi-Peng et al. 2002a, b). The same tryptophan solution is used for the standard curves and all 3-HPA quantifications and reported data are means for duplicate analyses. Appl Microbiol Biotechnol (2005) 68: 467-474

GC-MS: To determine the polyester content of the bacteria, 3 to 5 mg of lyophilized cell material is subjected to methanolysis in the presence of 3 or 15% (v/v) sulfuric acid according to Brandl et al. (1988). Under these conditions the intracellular poly(3-hydroxyalkanoates) are degraded to their constituent 3-hydroxaylkanoic acid methyl esters. The methyl esters are assayed by gas chromatography with a Perkin-Elmer 8420 gas chromatograph equipped with a Permaphase PEG 25 Mx capillary column (25 m by 0.32 ram, Bodenseewerk Perkin Elmer, Uberlingen, FRG) and a flame ionization detector. A 2-1a1 portion of the organic phase is analyzed after split injection (split ratio 1:40), and helium (35 cm/min) is used as a carrier gas. The temperatures of the injector and detector are 230° C. and 275° C., respectively. For efficient separation of the different 3-hydroxyalkanoic acid methyl esters the following temperature program is used: 120° C. for 5 min, temperature ramp of 8° C. per rain, 180° C. for 12 min. Calibration is performed with synthesized methyl esters of standard 3-hydroxyalkanoic acids with 4 to 12 carbon atoms (Brandl et al. 1988). Under these conditions the retention times of the different 3-hydroxyalkanoic acid methyl esters are as described recently (Timm et al. 1990). The total amount of PHA per cell dry weight is determined by summing the absolute amounts of all hydroxyalkanoate monomers detected. Arch Microbiol (1991) 155:415-421.

To determine the polymer content of lyophilized whole cells, approximately 4 mg of these cells is reacted in a small screw-cap test tube with a solution containing 1 ml of chloroform, 0.85 ml of methanol, and 0.15 ml of sulfuric acid for 140 min at 100° C. in a thermostat-equipped oil bath (3; Lageveen, dissertation). This method degrades the intracellular PHA by methanolysis to its constituent β-hydroxycarboxylic acid methyl esters. After the reaction, 0.5 ml of distilled water is added and the tube is shaken vigorously for 1 min. After phase separation, the organic phase (bottom layer) is removed and transferred to a small screw-cap glass vial. Samples are stored in the freezer at −70° C. until further analysis. The methyl esters are assayed by gas chromatography (GC) with a Perkin-Elmer 8500 gas chromatograph equipped with a Durabond-Carbowax-M15 megabore capillary column (CR note: similar to DB-Wax column) (15 m by 0.54 mm; J & W Scientific) and a flame ionization detector. A 2-μl portion of the organic phase is analyzed after splitless injection. Helium (17 ml/min) is used as the carrier gas. The temperatures of the injector and detector are 230 and 275° C., respectively. A temperature program is used which efficiently separated the different, hydroxyalkanoic acid methyl esters (80° C. for 4 min; temperature ramp of 8° C. per min; 160° C. for 6 min). Under these conditions, the retention times of the different, B-hydroxyalkanoic acid methyl ester standards are as follows (min): C-4, 4.22; C-5, 5.82; C-6, 7.40; C-7, 9.19; C-8, 10.71; C-10, 13.46; C-11, 14.81; C-12, 16.61 (C-x represents the P-hydroxyalkanoic acid methyl ester with a chain length of x carbon atoms).

Example 48

Analytical Methods to Detect 1,3-PDL

The presence of 1,3-PDL determined by gas chromatography using a HP 5890A equipped with a FID, a wide-bore column DB-5 (CR note: identical resin to HP-5) (15 m×530 μm I.D.) with a film thickness of 1.5 μm. The instrumental conditions for calibration and assays are as follows: helium, hydrogen and air flow-rates were 8.5, 30 and 400 ml min-1, respectively; the injector port temperature is 220° C.; the detector temperature was 260° C. The column is temperature-programmed from 40 to 220° C. as follows: the initial temperature (40° C.) is held for 5 min, the temperature is then increased from 40 to 150° C. at 5° C. min-1, and held for 1 min at 150° C., and then increased from 150 to 220° C. at 10° C. min-1. Samples are diluted 10 times with distilled water prior to injection. See, e.g., *Appl. Microbiol. Biotechnol.,* 59:289-296 (2002).

Example 49

Analytical Methods to Detect Succinate

Organic acids and glucose concentrations are determined by using a Hewlett-Packard HPLC (HP 1090 series II) equipped with a UV monitor (210 nm) and refractive index detector. Products are separated by using a Bio-Rad HPX-87H column (10_1 injection) with 4 mM H2SO4 as the mobile phase (0.4 ml_min__1, 45° C.). Reference: T. B. Causey et al., *PNAS* 100: 825-832 (2003).

Example 50

Analytical Methods to Detect Lipids

FAME analysis coupled with direct injection GC/EI-MS quantification. Two example protocols:

4.5 ml of *E. coli* culture are acidified with 200 uL acetic acid, supplemented with 0.1 mg of pentadecanoic acid as an internal standard, and partitioned by adding 1:1 CHCl3: MeOH. The organic layer is evaporated to near dryness, resuspended in 1 ml 5% H2SO4 in MeOH, and incubated at 90 C for 2 h. The FAMEs are extracted with 300 uL Hexanes after addition of 0.9% wt/vol NaCl in H20. E1 GC-MS is performed on 1 uL of the Hexanes solution.

A different protocol that has been proposed to be "most-efficient" for lipid-producing bacteria involving treating freeze-dried cells at 90° C. for 60 min in the 3 ml mixture 10/1/1 v/v methanol/conc HCl/chloroform. 1 ml water is then added, and the methyl esters are extracted by vortexing 3× with 2 ml 4/1 hexane/chloroform. (J. Microbiol. Meth. 2000, 43, 107).

From 2 different cyanobacteria: Freshly harvested algal pellets (8 g) are boiled in 5 mL of isopropanol for 2 min to inhibit the lipase activity and are then dried under nitrogen gas. The dried pellet is homogenized in chloroform-methanol (1:2 vol/vol) to achieve a final volume of 15 mL with 0.01% BHT added as an antioxidant in the lipid extraction solvent system. Lipid extract is centrifuged for 5 min at 2000 g to remove cell debris. A total of 0.8 mL of distilled water is added the to supernatant, followed by 5 mL of chloroform and 5 mL of 0.88% potassium chloride in a separating funnel to achieve a chloroform-methanol-water ratio of 1:1:0.9. The mixture is shaken vigorously for 5 min and allowed to separate for 30 min. The solvent phase is collected and concentrated under nitrogen gas. The dried lipid extract is redissolved in 5.0 mL of chloroform and used for quantitative determination of different class of lipids. Fatty acid methyl esters are prepared for gas chromatograph (GC) analysis according to the protocol of Christie (20). The internal standard (1 mM heptadecenoic acid) is added to the lipid sample and is subjected to methanolysis in the presence of methanoic-HCl at 68-708° C. for 2 h. The methyl esters are extracted with three successive portions of hexane and treated with 5 mL of saturated solution of sodium bicarbonate and washed with 5 mL of distilled water. The upper (hexane) solution is evaporated to dryness in a water bath at 35-408° C. with the help of nitrogen gas. The methyl esters are placed in a small volume of fresh hexane and 2 IL of sample was injected into the injector port of the gas chromatograph (GC-Nucon). Photochemistry and Photobiology, 2006, 82: 702-710.

Example 51

Analytical Methods to Detect Amino Acids

From Waters website, supposedly the industry-standard amino acid dev/HPLC fluorescent detector combination: as described on the Waters website under /WatersDivision/ContentD.asp?watersit=JDRS-5LTH9Q&WT.sv1=1.

Derivitization: The AccQTag Method is based on a derivatizing reagent developed specifically for amino acid analysis. Waters AccQFluor Reagent (6-aminoquinolyl-N-hydroxysuccinimidyl carbamate, or ACQ) is an N-hydroxysuccinimide-activated hetrocyclic carbamate, a new class of amine-derivatizing compounds. Waters AccQFluor Reagent is a highly reactive compound, 6-aminoquinolyl-N-hydroxysuccinimidyl carbamate (AQC), which forms stable derivatives with primary and secondary amino acids in a matter of seconds. The derivatives are easily separated by reversed phase HPLC using Waters AccQTag Amino Acid Analysis System in less than 35 minutes. Excess reagent is consumed during the reaction to form aminoquinoline (AMQ). AMQ has significantly different spectral properties than any of the derivatized amino acids, which allows programming a detector wavelength that maximizes the spectral emission response of the derivatives while minimizing the response of the AMQ. Detection limits for AQC-derivatized amino acids range from 38 to 320 fmol. Fluorescence detection with 250 nm excitation, 395 nm emission or less sensative UV detection at 248 nm.

GC-MS method: The labeling patterns of extracellular alanine, valine, and lysine are determined by GC-MS after conversion into t-butyl-dimethylsilyl (TBDMS) derivates with dimethyl-t-butyl-silyl-trifluororo-acetamide. For this purpose, 100 μl of cultivation supernatant is lyophilized. The freeze-dried residue is resuspended in 40 μl of dimethylformamide (0.1% pyridine) and 40 μl of N-methyl-t-butyldimethylsilyltrifluoroacetamide (Machcrcy and Nagel, Easton, Pa.) and incubated at 80° C. for 1 h. GC-MS analysis is carried out on a Hewlett-Packard 5890 series II gas chromatograph connected to a Hewlett-Packard 5971 quadrupole mass selective detector (Agilent Technologies, Waldbronn, Germany) with electron impact ionization at 70 eV, and an RTX-5MS column (95% dimethyl-5% diphenylpolysiloxane; 30 m; 320-μm inside diameter; Restek, Bellefonte, Pa.) is used with a column head pressure of 70 kPa and helium as the carrier gas. The column temperature is initially kept at 120° C. for 5 min, subsequently increased by 10° C./min up to 270° C., and maintained at that temperature for 4 min. Other temperature settings are 270° C. (inlet), 280° C. (interface), and 280° C. (quadrupole). For analysis, 1 μl of sample is injected. TBDMS-derivatized alanine, valine, and lysine eluted after 7, 12, and 22 min, respectively. All compounds exhibited a high signal intensity for a fragment ion obtained by a mass loss of m-57 from the parent radical due to release of a t-butyl group from the derivatization residue. The fragment ions thus contain the entire carbon skeleton of the corresponding analyte.

In order to increase the sensitivity, the mass isotopomer fractions m, m+1, and m+2 are quantified by selective ion monitoring of the corresponding ion cluster at m/z 260 to 262 (TBDMS-alanine), m/z 288 to 290 (TBDMS-valine), and m/z 431 to 433 (TBDMS-lysine). All measurements are carried out in triplicate. Ref: Applied and Environmental Microbiology, December 2002, p. 5843-5859, Vol. 68, No. 12. See Journal of Bioscience and Bioengineering 2006, 102: 413-424, APPLIED AND ENVIRONMENTAL MICROBIOLOGY, June 2007, p. 3859-3864 for other GC/MS analysis on extended set of amino acids, all but cysteine, tryptophan, glutamine and asparagines.

Example 52

Analytical Methods to Detect Lipids

General photosynthetic pigment analysis (ex carotenoids) Cyanobacterial cells are collected after centrifugation of culture at 8000 g for 15 min. The supernatant is discarded and the pellet of algal cells is dried in lyophilizer (Snijders, Holland). A total of 0.1 g of lyophilized algal cells are extracted in 1 mL 80% vol/vol methanol in a homogenizer at 48 C under dim light, followed by centrifugation at 6000 g for 10 min at 48° C. The samples are filtered through a 0.2 um filter before HPLC analysis. The pigments are separated by HPLC with a reverse-phase column (Waters Spherisorb ODS, 25 lm 34.6 mm 3250 mm) (CR note: Agilent suggests trying Zorbax SB-C18 column as substitute, 884950-567) and a PDA detector (Waters 2996) according to the method described by Sharma and Hall. A total of 20 μL of filtered sample is injected into the HPLC. The gradient for separation is 0-100% ethyl acetate in acetonitrile-water (9:1 vol/vol) over 25 min with flow rate of 1.2 mL/min. The quantity of pigments is calculated from peak area value using b-carotene as an external standard. Identification of pigments is performed by comparison of the retention time against standard values and analysis of the spectral profile of individual peaks with a PDA detector in the range of 400-700 nm. Photochemistry and Photobiology, 2006, 82: 702-710.

Example 53

Analytical Methods to Detect Lipids Phycobilisomes

Quantifying Phycocyanin, Allophycocyanin, Phycoerythrin

Cell samples are concentrated by centrifugation for 15 min at 6000 g, 0.1 g pellet is resuspended in 5 mL of 20 mM sodium acetate buffer (pH 5.5) and cells are broken using sonicator (Bandelin UW 2200, Germany) at 50% power with 9 cycles for 1 min. Phycobilisomes are precipitated by incubation with 1% streptomycin sulphate (wt/vol) for 30 min at 48 C and re collected by centrifugation at 8000 g for 30 min at 48 C. The amount of phycocyanin, allophycocyanin and phycoerythrin are calculated according to the methods of Liotenberg et al. (15). Photochemistry and Photobiology, 2006, 82: 702-710.

Example 54

Analytical Methods to Detect Erythromycin A

Bioassay and HPLC

The titers of erythromycin produced by the industrial *Saccharopolyspora erythraea* strain are determined using a conventional bioassay with commercially available erythromycin (Sigma) as a standard. Portions (20 ml) of test medium (5 g peptone 1-1, 3 g beef extract 1-1, 3 g K2HPO4 1-1, and 15 g agar 1-1) are poured into Petri dishes (90 mm). Once the medium is solidified, a second layer consisting of 5-ml test medium with 0.1% of a *Bacillus puinilus* [CMCC(B)63 202] is plated. ErA and its genetically engineered derivatives are extracted from culture broth and determined by HPLC according to Tsuji and Goetz (1978). Ref: Yong Wang et al. Improved production of erythromycin A by expression of a heterologous gene encoding S-adenosylmethionine synthetase. Appl Microbiol Biotechnol (2007) 75:837-842.

A new HPLC-UV method for the determination of the impurity profile of erythromycin is developed. In contrast to the liquid chromatography described in the European Pharmacopoeia the analysis could be performed at a temperature of 25° C. Erythromycin samples are analysed on an end-capped RP phase with cyanopropyl groups on the surface using gradient elution with 32 mM potassium phosphate buffer pH 8.0 and acetonitrile/methanol (75:25). The liquid chromatography for erythromycin is performed on an Agilent System 1100 LC (Böblingen, Germany) consisting of a vacuum degasser, a binary pumping system forming a high pressure gradient by a static mixer (delay volume of 600-900A, an autosampler, a thermostated column compartment, an UV-visible diode array detector (detection wavelength 215 nm) and a LC 3D ChemStation equipped with HP Kayak XM600 and 3DSoftware (Version 8.04). As a stationary phase, a Nucleodur CN-RP column (5 μm, 250 mm×4.0 mm i.d.) (Macherey-Nagel, Düren, Germany) is used See, e.g., Deubel et al., *Journal of Pharmaceutical and Biomedical Analysis,* 43:493-498 (2007).

Example 55

Engineered Microorganisms Producing Ethylene

Alcohol dehydratase (EC 4.2.1.n) converts ethanol to ethylene. Table 15, below, presents a list of alcohol dehydatases and their natural substrates.

TABLE 15

| EC Aumber(s) | Natural substrate |
|---|---|
| 4.2.1.2 | malate |
| 4.2.1.3, 4.2.1.4 | citrate |
| 4.2.1.11 | 2-phospho-D-glycerate |
| 4.2.1.17, 4.2.1.55 | 3-hydroxybutyryl-CoA |
| 4.2.1.33 | 3-isopropylmalate |
| 4.2.1.34, 4.2.1.35 | {(R),(S)}-2-methylmalate |
| 4.2.1.54 | lactoyl-CoA |
| 4.2.1.58 | 3-hydroxybutyryl-ACP |
| 4.2.1.60 | 3-hydroxydecanoyl-CoA |
| 4.2.1.68 | L-fuconate |
| 4.2.1.74 | hydroxyacyl-CoA |
| 4.2.1.79 | methylcitrate |

Genes encoding ethylene-forming enzymes (EfE) from various sources, e.g., *Pseudomonas syringae* pv. *Phaseolicola* D13182, *P. syringae* pv. *Pisi* AF 101061, *Ralstonia solanacearum* AL646053, may be expressed in microorganisms.

Construction of pJB5-efe_rs: The DNA sequence from the ethylene-forming enzyme of *Ralstonia solanacearum* (efe_rs) was obtained from Genbank (AL646053, (SEQ ID NO: 6); protein: CAD18680.1) and codon-optimized for *E. coli* (SEQ ID NO: 7). For examples of codon optimization of genes for *E. coli*, see Chandler et al., *Mol. Plant,* 1:285-94

(2008); Xue et al., *Enzyme and Microbial Technol.* 42:58-64 (2007); and Chun et al., *J Biol Chem.,* 282:17486-500 (2007). All conflicting restriction sites used in the pJB5 vector for cloning were removed from the gene to aid cloning experiments. This optimized gene was obtained by contract synthesis from DNA 2.0 (Menlo Park, Calif.). The efe_rs gene was designed with an NdeI site including part of the start codon and an EcoRI site after the stop codon. This gene was inserted by restriction digest with NdeI and EcoRI (New England Biolabs; Ipswitch, Mass.) on both pJB5 and the insert followed by ligation with a Quick Ligation Kit (New England Biolabs; Ipswitch, Mass.). The ligated construct was transformed into The NEB 5-alpha F'Iq Competent *E. coli* (High Efficiency) (New England Biolabs: Ipswitch, Mass.).

Example 56

Engineered Microorganisms Producing Ethylene with pJB5-efe_rs

Genetically Modified *Synechococcus* sp. PCC 7002 (7002/efe_rs): The construct as described in Example 55 was integrated onto the genome of *Synechococcus* sp. PCC 7002 (Synechococcus 7002 or 7002) using the following protocol. *Synechococcus* 7002 was grown for 48 h from colonies in an incubated shaker flask at 30° C. at 2% $CO_2$ to an $OD_{730}$ of 1 in $A^+$ medium described in Frigaard N U et al. (2004) "Gene inactivation in the cyanobacterium *Synechococcus* sp. PCC 7002 and the green sulfur bacterium *Chlorobium tepidum* using in vitro-made DNA constructs and natural transformation" Methods Mol Biol 274:325-340. 900 μL of culture was added to a test-tube with 50 μL of 10 μg of DNA digested with xbaI ((New England Biolabs; Ipswitch, Mass.) and added to cells without further purification. DNA was prepped from a Qiagen Qiaprep Spin Miniprep Kit (Valencia, Calif.) for each construct. Cells were incubated in the dark for four hours at 37° C. 100 μL of cells were plated on $A^+$ medium plates with 1.5% agarose and grown to 30° C. for two days in low light. 10 μg/mL of spectinomycin was underlayed on the plates. Resistant colonies were visible in 7-10 days. 500 μL of cells remaining from the incubation with digested DNA were added to 20 ml A+ cultures and bubbled with 1% $CO_2$ at approximately 1 bubble every 2 seconds for 24 h in the light. After 2 h, 2 ml of the culture was transferred into 20 ml of A+ media containing 10 μg/mL spectinomycin. After five days, the culture turned green and 1 ml was passaged into 25 μg/mL spectinomycin and bubbled with 1% $CO_2$ at approximately 1 bubble every 2 seconds for 24 h in the light. After a period of 18 hours, the cells had achieved an $OD_{730}$=7.4 (dry weight 1.6 g/L). 1 ml of this culture was placed in a 10 ml headspace vial (Agilent Technologies) and 1 ml of a 7002 wild type culture was placed into another 10 ml headspace vial as a control. The two cultures were incubated in a shaking incubator in the light for 1 h. The cultures were then killed by incubating them at 80° C. for 5 min and analyzed for the presence of ethylene.

Measurement of Ethylene by Headspace Gas Chromatography with Flame Ionization Detection Headspace-gas chromatography with flame-ionization detection (headspace GC-FID) can be used to analyze gases that are emitted from a liquid or solid sample that is contained inside an airtight vial capped with a septum. A sample of gas is obtained by puncturing the septum with a syringe needle and then injecting the gas sample into a temperature-controlled GC column. The mixture and subsequently its individual components are carried through the column by a pressurized inert carrier gas that is flowing at a constant flow rate. Because different components of the mixture traverse the column at different rates, they elute from the end of the column at different times. When they emerge, they immediately enter the FID where a hydrogen flame ionizes them. This ionization yields a quantifiable electric current which correlates with the amount of substance being ionized. Components can be identified by the amount of time they stay in the column. This time is called the retention time.

Ethylene produced by a bacterial culture was analyzed. Because of ethylene's extremely low molecular weight (28.05) and minimal polarity, analysis of it by headspace GC requires that an appropriate column be used to separate it from other components in a gaseous mixture being subjected to headspace analysis. For this analysis, a J&W HP-PLOT/Q capillary column with a length of 30 meters, a diameter of 0.53 mm, and a coating having a thickness of 40 micrometers was installed in a gas chromatograph (Agilent 7890A). The carrier gas was helium flowing at a rate of 4.2 ml/minute. The column temperature was maintained at 60° C. The GC inlet where samples are injected into the column was maintained at 150° C. with a split ratio of 20. The portion of the FID where the components first elute from the column was maintained at 250° C.

Although headspace analysis can be done manually as described above, here an automated system (Agilent G1888) was used. The vial was temperature equilibrated in an isothermal oven at 50° C. for 2 minutes without shaking. Subsequently the sample loop, which was maintained at 60° C., was filled for 0.15 minutes and equilibrated for 0.1 minutes. Then the gas sample was transferred to the GC injection port for 0.5 minutes through a transfer line maintained at 70° C.

Figure 9:
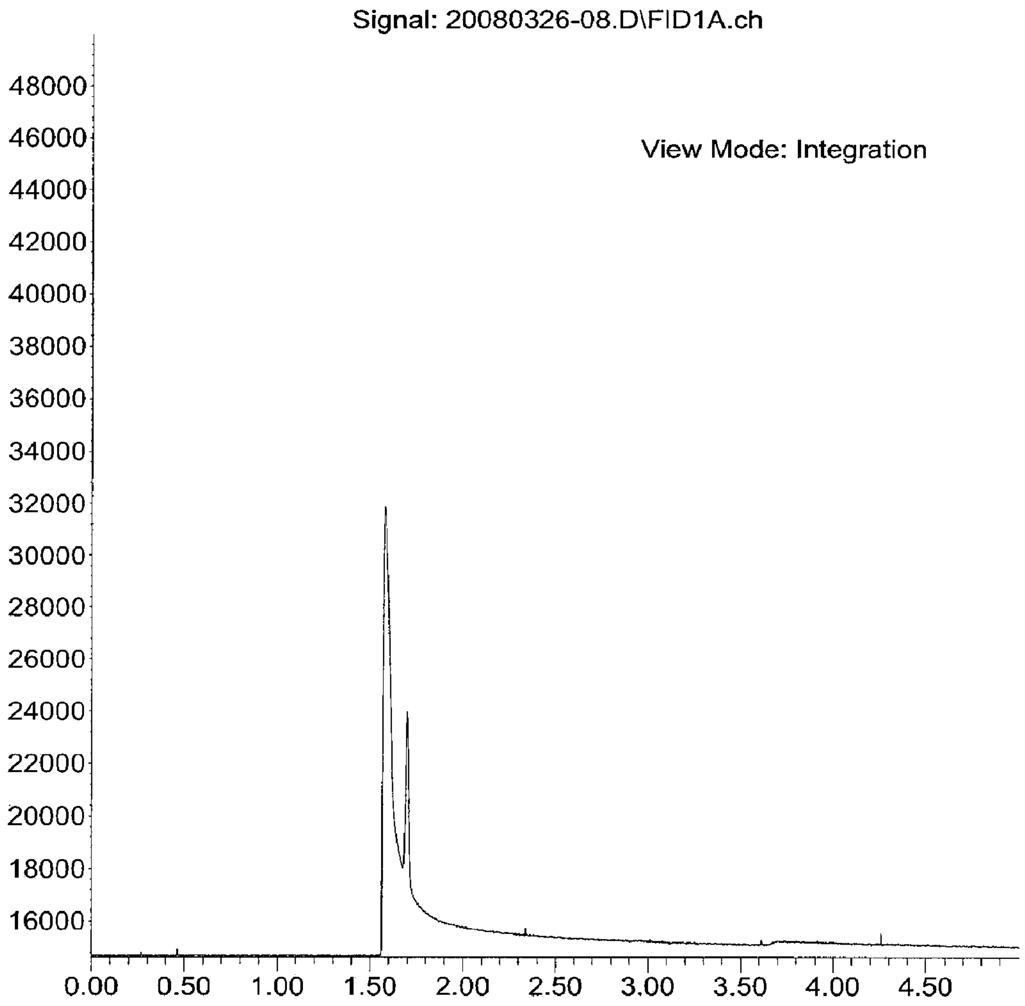
FIG. 9 shows the GC/FID chromatogram of the control *Synechococcus* 7002 strain.
Figure 10:
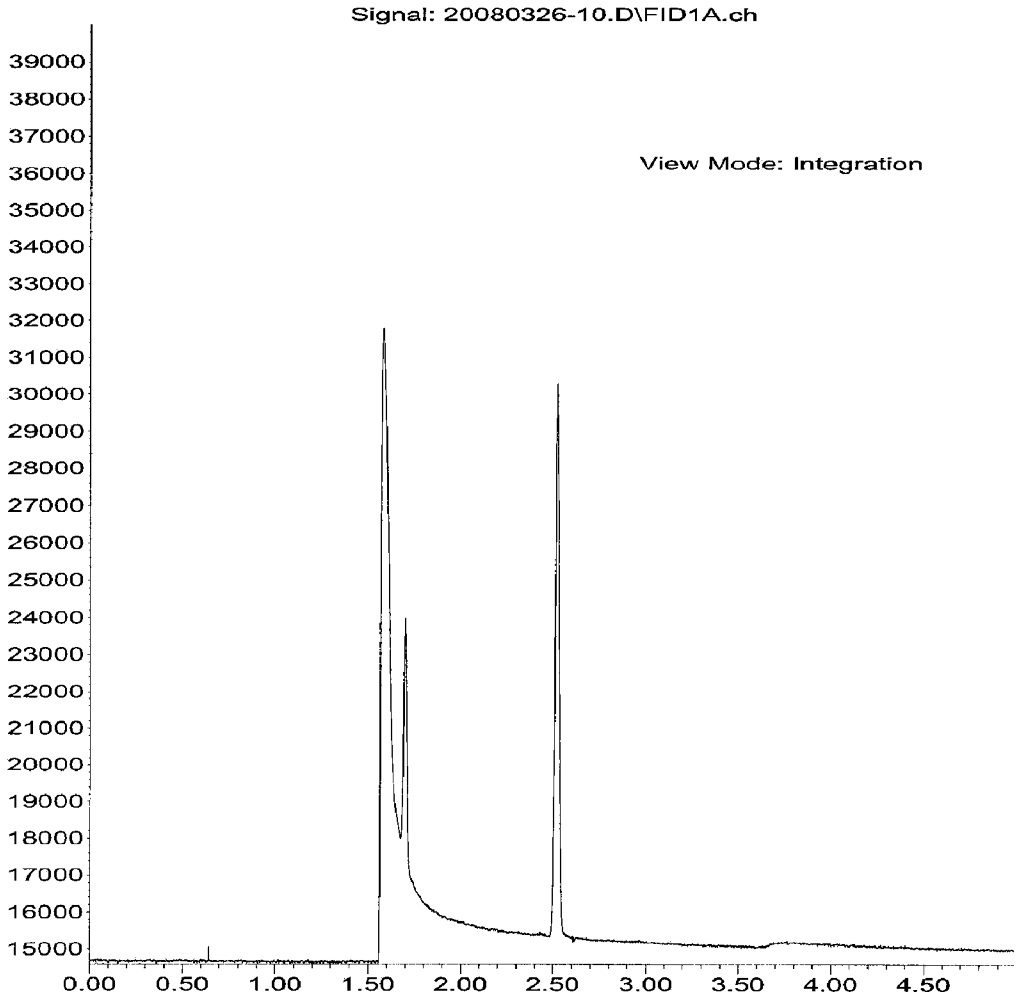
FIG. 10 shows the GC/FID chromatogram of the 7002/efe_rs recombinant strain.

Ethylene eluted from the column with a retention time of 2.52 minutes. This is in extremely good agreement with the retention time reported by the column manufacturer (i.e., J&W) of 2.41 minutes using the same conditions. The approximate amount of ethylene in the vials containing 7002/efe_rs was 0.75 nanomoles/vial. FIG. 9 shows the GC/FID chromatogram of the control 7002 strain. FIG. 10 shows the GC/FID chromatogram of the 7002/efe_rs recombinant strain Ethylene was quantified by using multiple headspace extraction [Kolb et al., *Static Headspace-Gas Chromatography,* $2^{nd}$ Ed, John Wiley & Sons (2006), pp. 45-49] and the FID molar response factor (RF) for ethylene. The molar RF for ethylene was extrapolated from the molar response factors for 1-hexene, 1-heptene and 1-octene [Ackman, *J Gas Chromatography,* 6 (1968) 497]. The response factors for those three compounds were measured using multiple headspace extraction.

Example 57

Engineered Microorganisms Producing Glucose pJB336 was constructed in the following manner A synthetic DNA kan cassette (DNA2.0) was subcloned via flanking PacI and AscI restriction sites into vector pJB303. This kan cassette comprises a promoter, active in both *E. coli* and JCC1, driving expression of gene aph that confers resistance to kanamycin in both organisms. pJB303 contains a synthetic DNA region (DNA2.0) comprising an upstream homology region (UHR) and a downstream homology region (DHR) flanking a multiple cloning region that includes PacI and AscI sites. The UHR corresponds to coordinates 1615342 to 1615841, the DHR to coordinates 1617346 to 1617845, of the JCC1 genome (Genbank Accession NC_010475), respectively. The UHR and DHR mediate homologous recombinational integration of heterologous DNA flanked by these regions into the JCC1 chromosome. In the case of SfiI-linearized pJB336, recombination occurs in such a way that the JCC1 glgA1 gene encoding glycogen synthase 1 (SYNPCC7002_A1532; Genbank Accession YP_001734779) is deleted, and replaced by a kan cassette. The SfiI-flanked DNA sequence contained within pJB336 is shown as SEQ ID NO: 8.

pJB342 was constructed in the following manner A synthetic DNA spec cassette (DNA2.0) was subcloned via flanking PacI and AscI restriction sites into vector pJB301, creating vector pJB330. This spec cassette comprises a promoter, active in both *E. coli* and JCC1, driving expression of gene aadA that confers resistance to spectinomycin and streptomycin in both organisms. pJB301 contains a synthetic DNA region (DNA2.0) comprising an upstream homology region (UHR) and a downstream homology region (DHR) flanking a multiple cloning region that includes PacI and AscI sites. The UHR corresponds to coordinates 2207877 to 2208376, the DHR to coordinates 2209929 to 2210428, of the JCC1 genome (Genbank Accession NC_010475), respectively; the UHR and DHR mediate homologous recombinational integration of heterologous DNA flanked by these regions into the JCC1 chromosome. In parallel with the construction of pJB330, a synthetic TPT gene (DNA2.0) was subcloned via flanking NdeI and EcoRI restriction sites into vector pJB168, creating vector pJB171. TPT encodes a phosphate/triose-phosphate antiport translocator (UniProt Q9ZSR7) from *Arabidopsis thaliana* [Flügge U-I., *Ann. Rev. Plant Physiol. Plant Mol. Biol.* 50:27-45 (1999)], and was codon-optimized for expression in *E. coli*, checking for secondary structure effects and removing restriction sites that were of utility in construct assembly strategies; the first seventy-seven amino acids encoding the chloroplastic signal peptide were removed. This gene was selected as it encodes a non-glucose transporter gene and thus serves as a negative control for assessing sugar transport. pJB168 contains a synthetic DNA region (DNA2.0) comprising the *E. coli* lacI gene, encoding the LacI repressor and driven by a $lacI^q$ promoter, upstream of a LacI-repressed, IPTG-inducible $P_{trc}$ promoter; in pJB171, this promoter controls expression of TPT. Via NotI and SpeI restriction sites, the lacI/$P_{trc}$-TPT fragment of pJB171 was then subcloned between the UHR and spec cassette of pJB330 to create plasmid pJB342. In the ease of SfiI-linearized pJB342, recombination occurs in such a way that the JCC1 glgA2 gene encoding glycogen synthase 2 (SYNPCC7002_A2125; Genbank Accession YP_001735362) is deleted, and replaced by a lacI/$P_{trc}$-TPT/spec cassette. The SfiI-flanked DNA sequence contained within pJB342 is SEQ ID NO: 9.

pJB345 was constructed in the following manner A synthetic yihX gene (DNA2.0) was subcloned via flanking NdeI and EcoRI restriction sites into vector pJB168, creating vector pJB179. yihX encodes an α-D-glucose-1-phosphatase (UniProt P0A8Y3) from *Escherichia coli* K12 (Kuznetsova E et al. (2006). Genome-wide Analysis of Substrate Specificities of the *Escherichia coli* Haloacid Dehalogenase-like Phosphatase Family. *J. Biol. Chem.* 281:36149-36161). A synthetic GLUT1 gene (DNA2.0) was subcloned via flanking MfeI and SpeI restriction sites into vector pJB179 (digested with EcoRI and SpeI), creating vector pJB185. GLUT1 encodes glucose transporter GLUT-1 (UniProt P11166) from *Homo sapiens* (Zhao F-Q and Keating A F (2007). Functional Properties and Genomics of Glucose Transporters. *Current Genomics* 8:113-128), and was codon-optimized for expression in *E. coli*, checking for secondary structure effects and removing restriction sites that were of utility in construct assembly strategies. In plasmid pJB185, a yihX-GLUT1 operon was thus placed under the control of the $P_{trc}$ promoter, itself regulated by the upstream lacI gene. Via NotI and SpeI restriction sites, the lacI/$P_{trc}$-yihX-GLUT1 fragment of pJB185 was then subcloned between the UHR and spec cassette of pJB330 to create plasmid pJB345. In the case of SfiI-linearized pJB345, recombination occurs in such a way that the JCC1 glgA2 gene encoding glycogen synthase 2 is deleted, and replaced by a lacI/$P_{trc}$-yihX-GLUT1/spec cassette. The SfiI-flanked DNA sequence contained within pJB345 is shown as SEQ ID NO: 10.

pJB348 was constructed in the following manner A synthetic glf gene (DNA2.0) was subcloned via flanking MfeI and SpeI restriction sites into vector pJB179 (digested with EcoRI and SpeI), creating vector pJB188. glf encodes glucose facilitated diffusion transporter Glf (UniProt P21906) from *Zymomonas mobilis* [Weisser P et al., *J. Bacteriol.* 177: 3351-3354 (1995)], and was codon-optimized for expression in *E. coli*, checking for secondary structure effects and removing restriction sites that were of utility in construct assembly strategies. In plasmid pJB188, a yihX-glf operon was thus placed under the control of the $P_{trc}$ promoter, itself regulated by the upstream lacI gene. Via NotI and SpeI restriction sites, the lacI/$P_{trc}$-yihX-glf fragment of pJB188 was then subcloned between the UHR and spec cassette of pJB330 to create plasmid pJB348. In the case of SfiI-linearized pJB348, recombination occurs in such a way that the JCC1 glgA2 gene encoding glycogen synthase 2 is deleted, and replaced by a lacI/$P_{trc}$-yihX-glf/spec cassette. The SfiI-flanked DNA sequence contained within pJB348 is shown as SEQ ID NO: 11.

Strain Construction: The UHR/DHR-flanked segments of pJB336, pJB342, pJB345, and pJB348 were integrated into the chromosome of JCC1 (pJB336) or JCC475 (pJB342, pJB345, and pJB348) in the following manner. Consider the JCC1 transformation first. A culture of JCC1 was grown in A+ medium to an $OD_{730}$ of ~1 in a shaking incubator (Infors) at 37° C. in an atmosphere of 2% $CO_2$ at 150 rpm. 0.5 ml of this culture was incubated with ~5 μg SfiI-digested plasmid pJB336—used without purification following the digest—for four hours at 37° C. in a low light (~2 μE $m^{-2}$ $sec^{-1}$ photosynthetically active radiation (PAR)) environment in a shaking incubator (250 rpm). The cell-DNA mixture was concentrated to 50 μl and plated in its entirety onto an $A^+$ agar plate, which was subsequently incubated at 37° C. in a photoincubator (Percival; ~50 μE $m^{-2}$ $sec^{-1}$ PAR) for approximately 24 hours in the absence of $CO_2$ enrichment. At this point, kanamycin was underlaid to a final post-diffusion concentration in the agar of 25 μg $ml^{-1}$, so as to select for integrants. Kanamycin-resistant colonies were visible after approximately five days, at which point the plates was transferred to a 37° C. photoincubator (Percival; ~50 μE $m^{-2}$ $sec^{-1}$ PAR) with a 1% $CO_2$ atmosphere, and incubated for a further two days.

To fully segregate recombinants, a small population (10-20) of kanamycin-resistant colonies from this initial plate was streaked onto an A+ 50 μg $ml^{-1}$ kanamycin plate, and grown as above; a small population (10-20) of kanamycin-resistant colonies from this second plate was then streaked onto an A+ 75 μg $ml^{-1}$ kanamycin plate, and grown as above. Genomic DNA was prepared from a single candidate JCC475 colony from this third plate and checked for complete segregation by PCR. For pJB336 and all other constructs, this involved checking for the presence of (i) the upstream recombinant junction, (ii) the downstream recombinant junction, and (iii) the heterologous gene(s), and the absence of the deleted wild-type gene (glgA1 or glgA2). Transformation of pJB342, pJB345, and pJB348 into JCC475 was carried out as described above except that kanamycin was included in all plates to maintain selection for the glgA1::kan disruption in JCC475, and spectinomycin was used as the selective antibiotic—first at 25 μg $ml^{-1}$, then at 50 μg $ml^{-1}$, and finally at 75 μg $ml^{-1}$.

In this way, the ΔglgA1::kan ΔglgA2::spec JCC1-derived strains shown in Table 16 were constructed:

TABLE 16

ΔglgA1::kan ΔglgA2::spec JCC1-derived recombinant strains used for sugar production

| Strain | Parent Strain | Transforming DNA | Integration locus | Promoter | Heterologous gene(s) | Marker(s) |
|---|---|---|---|---|---|---|
| JCC475 | JCC1 (*Synechococcus* sp. PCC 7002) | pJB336 | ΔglgA1 | — | — | Kan |
| JCC342c (control) | JCC475 | pJB342 | ΔglgA2 | lacI/$P_{trc}$ | TPT | kan, spec |
| JCC543, JCC545 | JCC475 | pJB345 | ΔglgA2 | lacI/$P_{trc}$ | yihX-GLUT1 | kan, spec |
| JCC547 | JCC475 | pJB348 | ΔglgA2 | lacI/$P_{trc}$ | yihX-glf | kan, spec |

In reference to the above table, JCC543 and JCC545 represent independently isolated colonies from the final segregation plate; two were selected to assess the genotypic reproducibility of any sugar production phenotype that emerged. JCC543, JCC545, and JCC547 were completely and faithfully segregated as determined by PCR in that they yielded the expected upstream junction, downstream junction, and heterologous gene(s) amplicons, as well as lack of an amplicon corresponding to glgA2-internal sequence (unlike JCC1). While JCC342c failed, as anticipated, to give an amplicon corresponding to glgA2, it yielded only the downstream junction amplicon, indicating that while glgA2 had been successfully deleted in this strain and the spec cassette was in the expected location relative to the DHR, the lacI/$P_{trc}$-TPT region had been somehow corrupted, most likely due to the toxicity of even small levels of TPT expression. Despite this, JCC342c, by virtue of being ΔglgA1::kan ΔglgA2::spec and having been made in the same way and at the same time as JCC543, JCC545, and JCC547, served as an ideal negative control for determining whether these three strains were able to export, or augment export of, sugar(s) into the medium. Note that all strains, because they lack all genes encoding glycogen synthases, were designed to be unable to produce glycogen.

Sugar Production: Glucose was assayed in the culture medium of JCC342c, JCC543, JCC545, and JCC547 both enzymatically and by gas chromatography mass spectrometry (GC-MS). These two methods, which give concordant results, are treated separately below.

Enzymatic assay: A single colony of each of JCC342c, JCC543, JCC545, and JCC547 was inoculated into 10 ml A+ medium containing 75 μg/ml kanamycin and 75 μg/ml spectinomycin. These cultures were incubated at 37° C. for approximately three days, slowly and continuously bubbled with air enriched with 1% $CO_2$ in ~50 μE $m^{-2}$ $sec^{-1}$ PAR. Cells were washed twice with 10 ml A+ medium containing 75 μg/ml kanamycin, 75 μg/ml spectinomycin, and 0.5 mM IPTG, and seeded into 30 ml cultures of the same medium at an initial $OD_{730}$ of 0.07. These cultures were incubated in a shaking photoincubator (Infors) at 150 rpm at 37° C. for 15 days in a 2% $CO_2$ atmosphere and continuous light (~100 μE $m^{-2}$ $sec^{-1}$ PAR). Water lost by evaporation was replaced every two days with the appropriate volumes of sterile Milli-Q water. 0.2 ml of culture was sampled on days 7, 11, 12, and 15; cells were pelleted by centrifugation, and the culture supernatant was frozen at −20° C. until ready to be assayed for glucose. Culture supernatants were all assayed at the same time.

The Maltose and Glucose Assay Kit (Biovision; catalog number K618-100) was used to determine the concentration of glucose in culture supernatant. In a flat-bottomed 96-well plate well, 10 μl of culture supernatant was mixed with 86 μl Glucose Assay Buffer (GAB; K618-100-1), 2 μl DMSO-dissolved Glucose Probe (K618-100-2), and 2 μl GAB-dissolved Glucose Enzyme Mix (K618-100-5). These 100 μl reaction mixtures were incubated for 1 hour at 37° C. in the dark. $OD_{570}$ was then measured using a microplate reader (SpectraMax). To relate $OD_{570}$ to absolute D-glucose concentrations, at the same time as the above reactions mixtures were being assembled, 10 μl of solutions of known concentrations of D-glucose from 0 to 54 mg $liter^{-1}$ dissolved in A+ medium were assayed in the same fashion. The $OD_{570}$ measurements for the culture supernatants were thereby converted to D-glucose concentrations.

As shown in Table 17, JCC543 and JCC545, the replicate ΔglgA1::kan ΔglgA2::lacI-$P_{trc}$-yihX-GLUT1-spec strains, produced five times more glucose than the control ΔglgA1::kan ΔglgA2::spec JCC342c strain, when all three cultures were at a comparable cell density ($OD_{730}$ 13-15). JCC547, the ΔglgA1::kan ΔglgA2::lacI-$P_{trc}$-yihX-glf-spec strain, grew significantly more slowly than the other three strains, failing to grow beyond $OD_{730}$ 9.6 during the course of the experiment; at this $OD_{730}$, the culture supernatant of JCC547 had a glucose concentration comparable to that of JCC342c.

TABLE 17

Glucose produced in the culture media of JCC342c, JCC547, JCC543, and JCC545 as determined by an enzymatic assay

| Strain | Genotype | Cell Density ($OD_{730}$) | Glucose in Culture Medium (mg/liter) |
|---|---|---|---|
| JCC342c | ΔglgA1::kan ΔglgA2::spec | 15.0 | 9 |
| JCC547 | ΔglgA1::kan ΔglgA2::lacI-$P_{trc}$-yihX-glf-spec | 9.6 | 6 |
| JCC543 | ΔglgA1::kan ΔglgA2::lacI-$P_{trc}$-yihX-GLUT1-spec | 13.1 | 52 |
| JCC545 | ΔglgA1::kan ΔglgA2::lacI-$P_{trc}$-yihX-GLUT1-spec | 13.8 | 53 |

GC-MS assay: In a separate growth experiment to the one described in the Enzymatic Assay section, a single colony of each of JCC342c, JCC543, JCC545, and JCC547 was inoculated into 10 ml A+ medium containing 75 μg/ml kanamycin and 75 μg/ml spectinomycin. These cultures were incubated at 37° C. for approximately three days, slowly and continuously bubbled with air enriched with 1% $CO_2$ in ~50 μE $m^{-2}$ $sec^{-1}$ PAR. Cells were washed twice with 10 ml A+ medium containing 75 μg/ml kanamycin, 75 μg/ml spectinomycin, and 0.5 mM IPTG, and seeded into 30 ml cultures of the same medium at an initial $OD_{730}$ of 0.05. These cultures were incubated in a shaking photoincubator (Infors) at 150 rpm at 37° C. for 8 days in a 2% $CO_2$ atmosphere and continuous light (~100 μE $m^{-2}$ $sec^{-1}$ PAR). Two milliliters of culture was sampled on the final day. Cells were pelleted by centrifugation, and the culture supernatant was filtered through a 0.2 μm filter to remove any remaining cells. 0.9 ml of filtered culture supernatant was lyophilized overnight in preparation of derivatization for GC-MS.

Lyophilized residue was partially dissolved in 200 μl of anhydrous pyridine by vigorous vortexing to which was added 1.0 ml of silylating reagent (BSA+TMCS+TMSI, 3:2:3; Supelco, Bellefonte, Pa.). Mixtures were subjected to substantial vortexing and then placed at 70° C. for two hours with occasional vortexing. After cooling to room temperature, the derivatized sample was transferred to a glass autosampler vial in preparation for GC-MS analysis using an Agilent 7890A GC equipped with a 5975C electron-impact MS. 1.0 μl of derivatized sample was injected into the GC with a 7683 automatic liquid sampler equipped with a 10 μl syringe. The GC inlet temperature was 280° C. and a split ratio of 5 was used. The capillary column was an Agilent HP-5MS (30 m×0.25 mm×0.25 μm). The carrier gas was helium at a flow rate of 1.0 ml $min^{-1}$. The GC oven temperature program was 50° C., hold 1 min; 10° C. $min^{-1}$ to 280° C., hold 10 min. The GC-MS interface temperature was 290° C., the mass spectrometer source temperature was 230° C. and the quadrupole temperature was 150° C. The mass range was 25-1000 amu. Sugar peaks present in the total ion chromatograms were identified by their retention times by using authentic standards (Sigma-Aldrich) and by searching an NIST MS database (2008 version).

Figure 16:
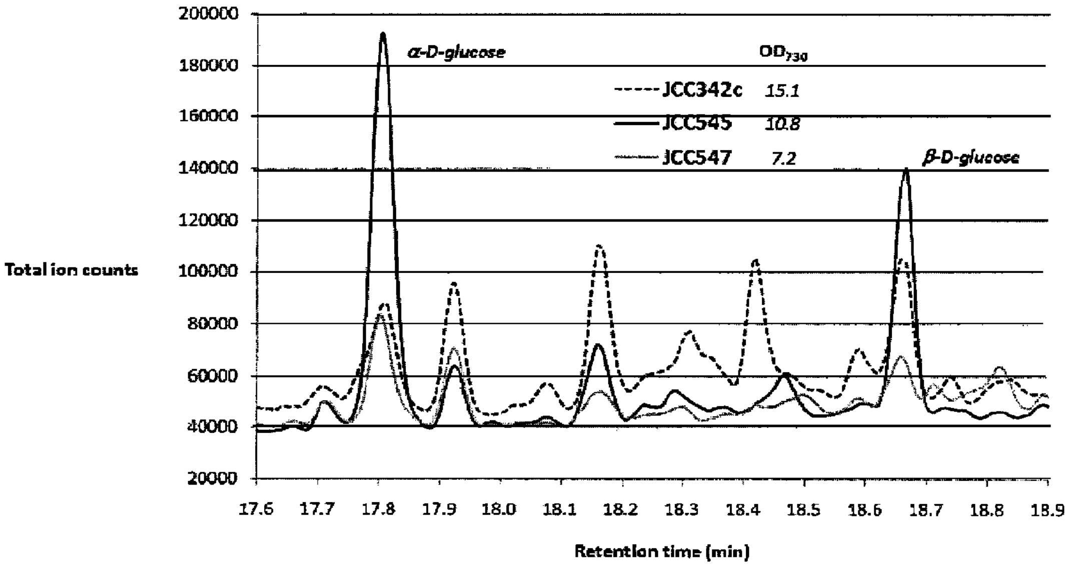
FIG. 16 depicts a total ion chromatograph for JCC342c, JCC545, and JCC547 in the retention time window during which TMS-derivatized α-D-glucose and β-D-glucose elute. The JCC543 trace has been omitted for clarity.

As shown in Table 18, JCC543 and JCC545 had produced over twice as much glucose than the control JCC342c strain, despite the former being at lower cell density ($OD_{730}$ 9.7 and 10.8) than the latter ($OD_{730}$ 15.1). JCC547 produced basal amounts of glucose. FIG. 16 shows the total ion chromatogram (TIC) for JCC342c, JCC545, and JCC547 in the retention time window during which TMS-derivatized α-D-glucose and β-D-glucose elute, from which the combined peak areas in Table 18 were derived.

TABLE 18

Glucose produced in the culture media of JCC342c, JCC547, JCC543, and JCC545, as determinedby total ion chromatogram peak areas for glucose seen by GC-MS analysis

| Strain | Genotype | Cell Density ($OD_{730}$) | Combined TIC peak area for α- and β-D-glucose |
|---|---|---|---|
| JCC342c | ΔglgA1::kan ΔglgA2::spec | 15.1 | 2341996 |
| JCC547 | ΔglgA1::kan ΔglgA2::lacI-$P_{trc}$-yihX-glf-spec | 7.2 | 1581200 |
| JCC543 | ΔglgA1::kan ΔglgA2::lacI-$P_{trc}$-yihX-GLUT1-spec | 9.7 | 5827988 |
| JCC545 | ΔglgA1::kan ΔglgA2::lacI-$P_{trc}$-yihX-GLUT1-spec | 10.8 | 6114673 |

These GC-MS data corroborate the independent enzymatic assay data reported in the previous section, namely that the $P_{trc}$-yihX-GLUT1 cassette, but not the $P_{trc}$-yihX-glf cassette in JCC547, resulted in significantly higher glucose production than observed in an isogenic control strain.

Figure 17:
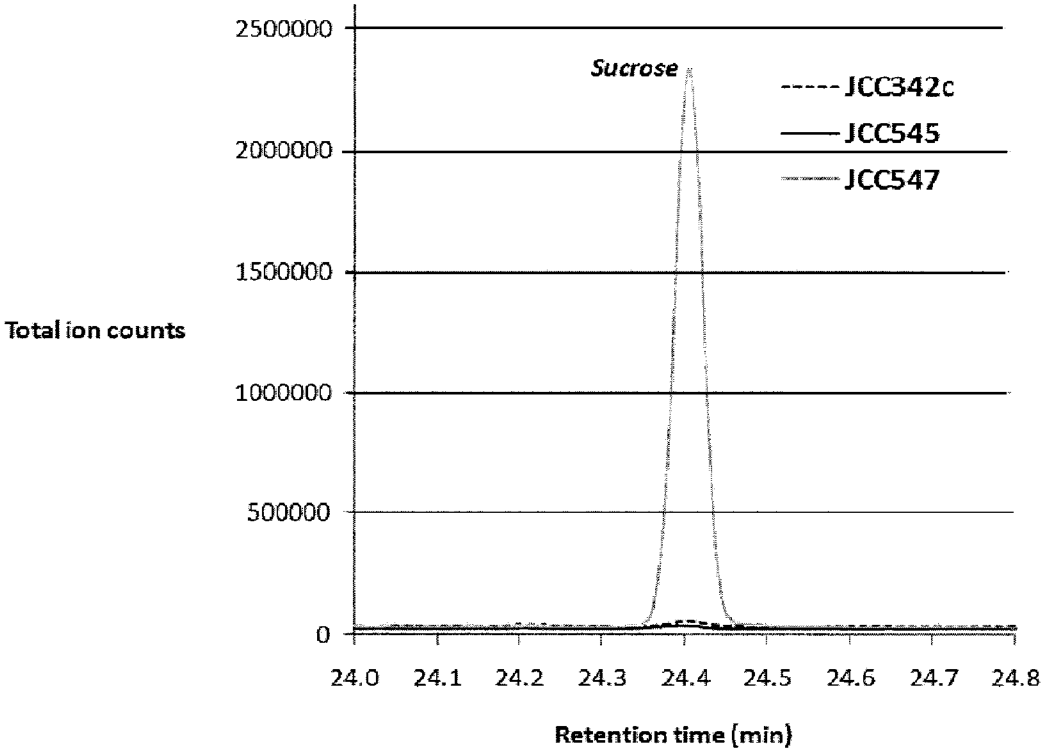
FIG. 17 depicts a total ion chromatograph for JCC342c, JCC545, and JCC546 in the retention time window during which TMS-derivatized sucrose elute. Cell densities were as indicated in FIG. 16. The JCC543 trace has been omitted for clarity.

Although GC-MS analysis indicated only basal levels of glucose were present in the growth medium of JCC547, it was apparent that there were several other ion chromatogram peaks only present, or present with larger areas, in this strain and not in JCC342c, JCC543, or JCC545. One of these peaks was positively identified as sucrose based on authentic standard analysis, as shown in Table 19 and FIG. 17. Based on the concentration of sucrose used in the authentic standard analysis, and assuming that the TIC peak area observed scales linearly with this known sucrose concentration, it was estimated that the JCC547 culture medium contained approximately 600 mg $liter^{-1}$ sucrose, approximately 100 times that seen in JCC342c, JCC543, or JCC545. No maltose was observed in any of the four strains' culture media.

TABLE 19

Sucrose produced in the culture media of JCC342c, JCC547, JCC543, and JCC545, as determined by extracted ion chromatogram peak areas for the m/z 361 diagnostic disaccharide ion seen by GC-MS analysis

| Strain | Genotype | Extracted ion chromatogram (EIC) peak area for sucrose (m/z = 361 ion) |
|---|---|---|
| JCC342c | ΔglgA1::kan ΔglgA2::spec | 63632 |
| JCC547 | ΔglgA1::kan ΔglgA2::lacI-$P_{trc}$-yihX-glf-spec | 8892575 |
| JCC543 | ΔglgA1::kan ΔglgA2::lacI-$P_{trc}$-yihX-GLUT1-spec | 50666 |
| JCC545 | ΔglgA1::kan ΔglgA2::lacI-$P_{trc}$-yihX-GLUT1-spec | 53940 |

The $P_{trc}$-yihX-glf cassette in JCC547 therefore resulted in significantly higher sucrose production than observed in an isogenic control strain. A possible reason for this is that the Glf transporter is able to mediate the export of sucrose that is naturally synthesized, and otherwise maintained, within the cell. There are no reports of Glf being able to mediate transport of disaccharides such as sucrose. Glf has been reported as being able to mediate transport of glucose and, to a much lesser degree, fructose. However, the notion of Glf-mediated disaccharide export was supported by the GC-MS analysis of the culture medium of JCC547. As mentioned above, GC-MS indicated several ion chromatogram peaks that were only present, or present with larger areas, in this strain and not in JCC342c, JCC543, or JCC545. Consistent with these peaks representing disaccharides, many of these peaks were characterized by a dominant m/z 361 ion, which is diagnostic of TMS-derivatized disaccharides [Molnár-Perl et al., *Chem. Maier. Sci.,* 45:321-327 (1997)], as shown in Table 20. Because none of the authentic disaccharide standards that were used eluted at the times indicated in the table above, none of these corresponding peaks could be identified with certainty. However, given the presence of the m/z 361 ion in all, it is highly likely that these peaks represent disaccharide or disaccharide-like molecules, most likely synthesized naturally within the cell.

TABLE 20

Disaccharide and/or disaccharide-like molecules produced by JCC547, as determined by extracted ion chromatogram peak areas for the m/z 361diagnostic disaccharide ion seen by GC-MS analysis*

| | | EIC peak area for diagnostic m/z = 361 ion at the following elution times (min) | | | | | | | |
|---|---|---|---|---|---|---|---|---|---|
| Strain | Genotype | 20.41 | 21.30 | 21.84 | 21.98 | 22.07 | 22.15 | 22.56 | 22.77 |
| JCC342c | ΔglgA1::kan ΔglgA2::spec | 0 | 0 | 0 | 0 | 0 | 0 | 0 | 0 |
| JCC547 | ΔglgA1::kan ΔglgA2::lacI-$P_{trc}$-yihX-glf-spec | 60635 | 64499225 | 193663 | 46991 | 114604 | 91013 | 65186 | 14880 |
| JCC543 | ΔglgA1 ::kan ΔglgA2::lacI-$P_{trc}$-yihX-GLUT1-spec | 0 | 0 | 0 | 0 | 0 | 0 | 0 | 0 |
| JCC545 | ΔglgA1::kan ΔglgA2::lacI-$P_{trc}$-yihX-GLUT1-spec | 0 | 0 | 0 | 0 | 0 | 0 | 0 | 0 |

*These peaks have not been associated definitively with defined chemicaspecies

Example 58

Engineered Microorganisms Producing Maltose with Amylase Expressing Plasmids Construction of amylase expressing plasmids: The DNA sequence of the amylase genes of *Gylcine max* (AMY_gm), *Bacillus cereus* (AMY_bc), and the transporter genes from *Arabidopsis thaliana* (MEX1) and *Escherichia coli* (setA) were obtained from Genbank. The codon sequences were optimized for *E. coli*. The codon-optimized sequences and amino acid sequences for BAA34650 (SEQ TD NO: 12 and SEQ ID NO:13, respectively), CAA50551 (SEQ ID NO: 14 and SEQ ID NO: 15, respectively), AAF04350 (SEQ ID NO: 16 and SEQ ID NO: 17, respectively), and YP_025293 (SEQ ID NO: 18 and SEQ ID NO: 19, respectively) are provided herein. The DNA sequence of aphII, amt2, and trc promoters were obtained from Genbank and codon-optimized for *E. coli* (SEQ ID NO: 20, SEQ ID NO: 21 and SEQ ID NO: 22, respectively). The trc promoter was engineered with an upstream $lacI^q$ gene that is constitutively expressed. For examples of codon optimization of genes for *E. coli*, see Chandler et al., "Characterization of Gibberellin receptor mutants of Barley (*Hordeum vulgare* L.)", *Mol. Plant* 2008 1:285-94; Xue et al., Improved production of p-hydroxycinnamic acid from tyrosine using a novel thermostable phenylalanine/tyrosine ammonia lyase enzyme, *Enzyme and Microbial Technol.* 2007 42:58-64.; and Chun et al., Electron transport pathway for a *Streptomyces* cytochrome P450: cytochrome P450 105D5-catalyzed fatty acid hydroxylation in *Streptomyces coelicolor* A3(2). *J Biol Chem.* 2007 282:17486-500. These optimized genes were obtained by contract synthesis from DNA 2.0 (Menlo Park, Calif.). In addition, plasmids containing two 750 bp regions of homology designed to remove the native glgB (pJB315) or the restriction site (pJB318) from *Synechococcus* sp. PCC 7002 were obtained by contract synthesis from DNA 2.0 (Menlo Park, Calif.). Using pJB315 and pJB318 as vectors, the constructs were engineered by performing 4 sequential clonings: insertion of aadA using PacI and I AscI, insertion of the amylase/transporter cassette using NdeI and EcoRI, insertion of the promoter-cat cassette with NotI and NdeI, and removal of the cat gene using SfiI. All restriction and ligation enzymes were obtained from New England Biolabs (Ipswich, Mass.). Ligated constructs were transformed into either NEB 5-α, competent *E. coli* (High Efficiency) (New England Biolabs: Ipswich, Mass.) or Copy Cutter EPI400 competent *E. coli* (Epicentre Biotechnologies: Madison, Wis.).

Genetically Modified *Synechococcus* sp. PCC 7002 (7002/amylase_transporter): The constructs as described above were integrated onto the genome of *Synechococcus* sp. PCC 7002 (Synechococcus 7002 or 7002) using the following protocol. *Synechococcus* 7002 was grown in an incubated shaker flask at 37° C. at 1% $CO_2$ to an $OD_{730}$ of 1.2 in $A^+$ medium described in Frigaard N U et al., *Methods Mol. Biol.,* 274:325-340 (2004). 1000 μL of culture was added to a test-tube with 50 μL of 2 μg of DNA digested with XbaI (New England Biolabs; Ipswich, Mass.) and added to cells without further purification. DNA was prepped from a Qiagen Qiaprep Spin Miniprep Kit (Valencia, Calif.) for each construct. Cells were incubated in the dark for two hours at 37° C. The entire volume of cells were plated on $A^+$ medium plates with 1.5% agarose and grown to 37° C. in a lighted incubator (40-60 μE/m2/s PAR, measured with a LI-250A light meter (LI-COR)) for approximately 24 hours. 25 μg/mL of spectinomycin was underlayed on the plates. After further incubation, resistant colonies became visible in 5 days. One colony from each of the 18 cultures (JCC724-741) was restreaked onto $A^+$ medium plates with 1.5% agarose and 50 μg/mL spectinomycin. Colonies from these plates were then inoculated into 5 ml of A+ media containing 25 μg/ml spectinomycin. This culture was incubated in a bubble tube at 37° C. sparged at approximately 1-2 bubbles of 1% $CO_2$/air every 2 seconds in light (40-50 μE/m2/s PAR, measured with a LI-250A light meter (LI-COR)). Strains containing amylase-transporter constructs under constitutive expression were harvested at $OD_{730}$ ranging from 1.04 to 9.44. Strains containing amylase-transporter constructs under trc expression were incubated to $OD_{730}$ between 3.76 and 8.15. 1 mL of these uninduced cultures was harvested. The remaining cultures were diluted to $OD_{730}$ of 1, induced with 0.05 mM IPTG, and incubated for 24 hours. To harvest cells, cultures were spun for 1 minute at 14800 rpm. The supernatant was subsequently submitted for GC/MS analysis.

Measurement of maltose by gas chromatography: Samples were partially dissolved in 300 μL anhydrous pyridine (Sigma Aldrich; St Louis Mo.) before adding 1.0 mL of silylation reagent (BSA+TMCS+TMSI 3:2:3 (Supelco; Bellefonte Pa.)). After each addition, samples were subjected to vigorous vortexing. Samples were then heated at 70° C. for two hours, cooled, transferred to autosampler vials, and measured with the GC/MS. Retention time in minutes of α-maltose and β-maltose were identified by their mass spectra and their retention times.

Figure 18:
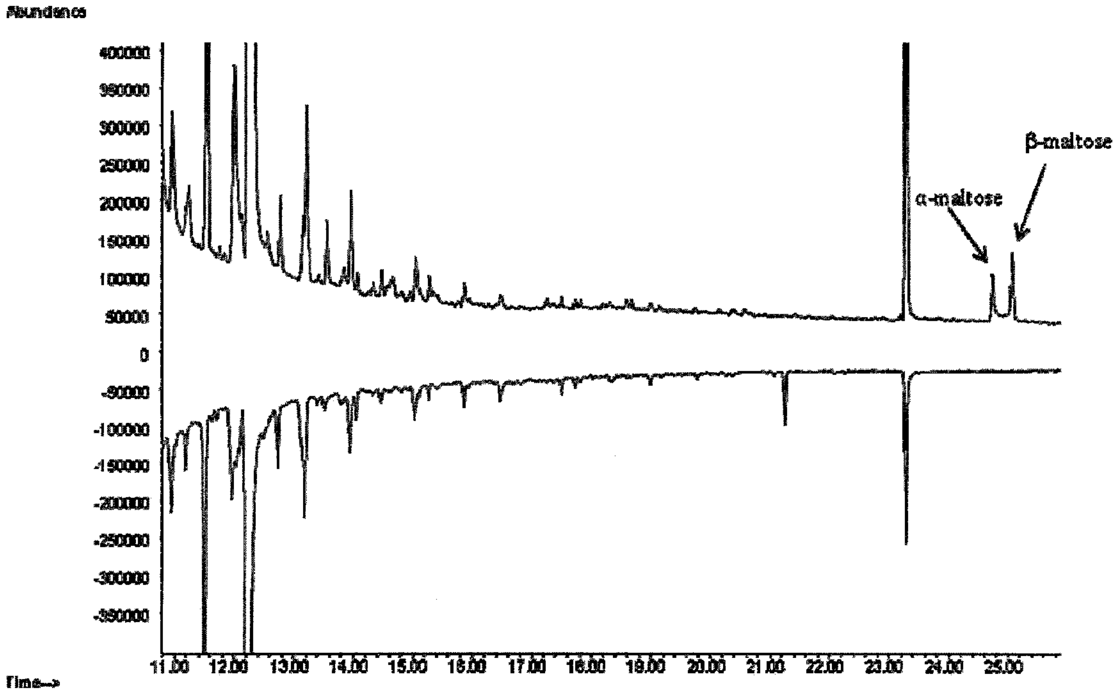
FIG. 18 shows representative GC/MS chromatograms of JCC738 (top trace) and JCC724 (bottom trace) analyzed for the presence of maltose. The peaks for α-maltose and β-maltose are indicated.

An Agilent 7890A GC/5975C ELMS equipped with a 7683 series autosampler was used to detect maltose. The GC inlet was set to a split ratio of 5.0 and the inlet temperature was set to 280° C. 1 μL of sample was injected into a HP-5MS column (Agilent, 30 m×0.25 mm×0.25 μm). The carrier gas was helium. The GC oven temperature program was 50° C., hold one min; 10°/min increase to 280° C., hold ten min. The GC-MS interface was set to 290° C., and the MS mass range was 25 to 1000 amu. Peaks present in the total-ion chromatograms were identified by retention time analysis and by searching the NIST MS Search database version 2.0 (2008) with the associated mass spectra. Retention times in minutes of α-maltose (24.73 min) and β-maltose (25.06 min) were determined with authentic standards from Fluka and are represented in FIG. 18.

Maltose was detected in JCC726, 729, 735, and 738 (FIG. 19). Maltose was produced only in strains in which expression of the amylase-transporter operon was controlled by the trc promoter.

Example 59

Engineered Methanogenesis Pathway

A host cell of interest is engineered to produce methane. Preferably, a host is selected or engineered to have methanogenic properties.

TABLE 21

| Enzyme | EC No. | Example Organism, gene(s) |
|---|---|---|
| formylmethanofuran dehydrogenase | 1.2.99.5 | *Methanosarcina acetivorans* fmdEFACDB |
| formylmethanofuran-tetrahydromethanopterin formyltransferase | 2.3.1.101 | *Methanosarcina acetivorans* ftr |
| methenyltetrahydromethanopterin cyclohydrolase | 3.5.4.27 | *Methanosarcina acetivorans* mch |
| methylenetetrahydromethanopterin dehydrogenase | 1.5.99.9 | *Methanosarcina acetivorans* mer |
| 5,10-methylenetetrahydromethanopterin reductase | 1.5.99.11 | *Methanococcus maripaludis* hmd |
| tetrahydromethanopterin S-methyltransferase | 2.1.1.86 | *Methanosarcina acetivorans* mtrHGFABCDE |
| methyl-coenzyme M reductase | 2.8.4.1 | *Methanosphaera stadtmanae* mrtBGA |
| heterodisulfide reductase | 1.8.98.1 | *Methanococcus aeolicus* Maeo_0307 |
| coenzyme F420 hydrogenase | 1.12.98.1 | *Methanococcus maripaludis* frcBGDA |

Example 60

Engineered Acetogenesis Pathway

A host cell of interest is engineered to produce acetate. Preferably, the host cell is selected or engineered to have acetogenic properties.

TABLE 22

| Enzyme | EC No. | Example Organism, gene(s) |
|---|---|---|
| Phosphotransacetylase | 2.3.1.8 | *Escherichia coli* pta |
| Acetate kinase | 2.7.2.1 | *Escherichia coli* ackA |
| formate dehydrogenase | 1.2.1.2 | *Escherichia coli* fdhF |

TABLE 22-continued

| Enzyme | EC No. | Example Organism, gene(s) |
|---|---|---|
| formyltetrahydrofolate synthetase | 6.3.4.3 | *Clostridium acetobutylicum* CAC3201 |
| 5,10-methylenetetrahydrofolate cyclohydrolase | 3.5.4.9 | *Escherichia coli* folD (bifunctional) |
| 5,10-methylenetetrahydrofolate dehydrogenase | 1.5.1.5 | *Escherichia coli* folD (bifunctional) |
| methylenetetrahydrofolate reductase [NAD(P)H] | 1.5.1.20 | *Arabidopsis thaliana* MTHFR1 |
| Methyltransferase | 2.1.1.— | *Clostridium thermoaceticum* |
| Carbon monoxide dehydrogenase | 1 .2.99.2 | *Clostridium beijerinckii* Cbei_3020 |
| Hydrogenase | — | *Escherichia coli* hycDCFGBE |

Example 61

Engineered Reductive TCA Cycle

A host cell of interest is engineered to have a reductive TCA cycle. Preferably, the host cell is selected or engineered to have photosynthetic properties.

TABLE 22

| Enzyme | EC No. | Example Organism, gene(s) |
|---|---|---|
| PEP carboxylase | 4.1.1.31 | *Escherichia coli* ppc |
| α-ketoglutarate synthase | 1.2.7.3 | *Campylobacter jejuni* oorDABC |
| aconitase | 4.2.1.3 | *Escherichia coli* acnB |
| isocitrate dehydrogenase (NADP+) | 1.1.1.42 | *Escherichia coli* icd |
| citrate-ATP lyase | 2.3.3.8 | *Arabidopsis thaliana* ACLB-1 |
| fumarate reductase | 1.3.99.1 | *Escherichia coli* frdDCBA |
| fumarate hydratase | 4.2.1.2 | *Escherichia coli* fumCAB |
| malate dehydrogenase | 1.1.1.37 | *Escherichia coli* mdh |
| succinate-CoA ligase (ADP-forming) | 6.2.1.5 | *Escherichia coli* sucCD |
| pyruvate:ferredoxin oxidoreductase | 1.2.7.1 | *Clostridium kluyveri* porB |
| PEP synthetase | 2.7.9.2 | *Escherichia coli* pps |

Example 62

Engineered Calvin Cycle

A host cell of interest is engineered to have a Calvin cycle. Preferably, the host cell is selected or engineered to have photosynthetic properties.

TABLE 23

| Enzyme | EC No. | Example Organism, gene(s) |
|---|---|---|
| D-ribulose-1,5-bisphosphate carboxylase | 4.1.1.39 | *Arabidopsis thaliana* rbcL, ATS1A, ATS1B, ATS2B |
| phosphoketolase | 4.1.2.9 | *Pseudomonas putida* Pput_2459 |
| fructose-bisphosphate aldolase | 4.1.2.13 | *Escherichia coli* fbaBA |
| transketolase | 2.2.1.1 | *Escherichia coli* tktBA |
| fructose-bisphosphatase | 3.1.3.11 | *Escherichia coli* fbp |
| sedoheptulose-bisphosphatase | 3.1.3.37 | *Arabidopsis thaliana* SBPASE |
| triose-phosphate isomerase | 5.3.1.1 | *Escherichia coli* tpiA |
| glyceraldehyde-3-phosphate dehydrogenase (NADP+) (phosphorylating); | 1.2.1.13 | *Arabidopsis thaliana* GAPA |
| ribose-5-phosphate isomerase | 5.3.1.6 | *Escherichia coli* rpiA |
| ribulose-phosphate 3-epimerase | 5.1.3.1 | *Escherichia coli* rpe |
| phosphoglycerate kinase | 2.7.2.3 | *Escherichia coli* pgk |
| phosphoribulokinase | 2.7.1.19 | *Arabidopsis thaliana* PRK |

Example 63

Engineered 3-HPA Cycle

A host cell of interest is engineered to have a 3-HPA cycle. Preferably, the host cell is selected or engineered to have photosynthetic properties.

TABLE 24

| Enzyme | EC No. | Example Organism, gene(s) |
|---|---|---|
| Acetyl-CoA carboxylase | 6.4.1.2 | Chloroflexus aurantiacus |
| malonatescmialdchyde dehydrogenase (NADP-acylating) | 1.2.1.18 | Chloroflexus aurantiacus |
| 3-hydroxypropionate dehydrogenase (NADP+) | 1.1.1.— | Chloroflexus aurantiacus |
| 3-hydroxypropionate-CoA ligase | 6.2.1.— | Chloroflexus aurantiacus |
| acryloyl-CoA hydratase | 4.2.1.— | Chloroflexus aurantiacus |
| acryloyl-CoA reductase (NADPH) | 1.3.1.— | Chloroflexus aurantiacus |
| propionyl-CoA carboxylase | 6.4.1.3 | Chloroflexus aurantiacus |
| methylmalonyl-CoA epimerase | 5.1.99.1 | Chloroflexus aurantiacus |
| methylmalonyl-CoA mutase | 5.4.99.2 | Chloroflexus aurantiacus |
| succinyl-CoA:malate CoA-transferase | 2.8.3.— | Chloroflexus aurantiacus |
| succinate dehydrogenase (physiological acceptor unknown) | 1.3.99.1 | Chloroflexus aurantiacus |
| fumarate hydratase | 4.2.1.2 | Chloroflexus aurantiacus |
| malyl-CoA lyase | 4.1.3.24 | Chloroflexus aurantiacus |
| ribulose-1,5-bisphosphate carboxylase | 4.1.1.39 | Chloroflexus aurantiacus |
| CO dehydrogenase/acetyl-CoA synthase | 1.2.99.2 | Chloroflexus aurantiacus |
| pyruvate synthase | 1.2.7.1 | Chloroflexus aurantiacus |
| 2-oxoglutarate synthase | 1.2.7.3 | Chloroflexus aurantiacus |
| ATP citrate (pro-3s)-lyase | 4.1.3.8 | Chloroflexus aurantiacus |
| phosphoribulokinase | 2.7.1.19 | Chloroflexus aurantiacus |
| malate-CoA ligase | 6.2.1.9 | Chloroflexus aurantiacus |
| succinate-CoA ligase | 6.2.1.3 | Chloroflexus aurantiacus |
| isocitrate lyase | 4.1.3.1 | Chloroflexus aurantiacus |

Example 64

Engineered 3HP/4HB Cycle

A host cell of interest is engineered to have a 3HP/4HB cycle (Berg et al., Science 318:1782 (2007)). In more preferred embodiments, the Calvin Cycle is removed and the 3HP/4HB Cycle is engineered into the host. Preferably, the host cell is selected or engineered to have photosynthetic properties.

TABLE 25

| Enzyme | Example Organism, gene(s) |
|---|---|
| acetyl-CoA carboxylase | Metallosphaera sedula |
| malonyl-CoA reductase (NADPH) | Metallosphaera sedula |
| malonate semialdehyde reductase (NADPH) | Metallosphaera sedula |
| 3-hydroxypropionyl-CoA synthetase (AMP-forming) | Metallosphaera sedula |
| 3-hydroxypropionyl-CoA dehydratase | Metallosphaera sedula |
| acryloyl-CoA reductase (NADPH) | Metallosphaera sedula |
| propionyl-CoA carboxylase | Metallosphaera sedula |
| methylmalonyl-CoA epimerase | Metallosphaera sedula |
| methylmalonyl-CoA mutase | Metallosphaera sedula |
| succinyl-CoA reductase (NADPH) | Metallosphaera sedula |
| succinate semialdehyde reductase (NADPH) | Metallosphaera sedula |
| 4-hydroxybutyryl-CoA synthetase (AMP-forming) | Metallosphaera sedula |
| 4-hydroxybutyryl-CoA dehydratase | Metallosphaera sedula |
| crotonyl-CoA hydratase | Metallosphaera sedula |
| 3-hydroxybutyryl-CoA dehydrogenase (NAD+) | Metallosphaera sedula |
| acetoacetyl-CoA b-ketothiolas | Metallosphaera sedula |
| pyruvate synthase | Metallosphaera sedula |

Example 65

Engineered Limonene Production

A host cell of interest is engineered to produce limonene. Preferably, the host cell is selected or engineered to have photosynthetic properties. In more preferred embodiments, the Calvin Cycle is removed and the 3HP/4HB Cycle is engineered into the host.

TABLE 26

| Enzyme | EC # | Product |
|---|---|---|
| Mevalonate pathway to (R)- or (S)-limonene | | |
| (4S)-limonene synthase | 4.2.3.16 | (S)-limonene (piney) |
| (R)-limonene synthase | 4.2.3.20 | (R)-limonene (citrus) |
| geranyl-diphosphate synthase | 2.5.1.1 | geranyl-PP |
| isopentenyl-diphosphate Delta-isomerase | 5.3.3.2 | dimethylallyl-P |
| diphosphomevalonate decarboxylase | 4.1.1.33 | isopentenyl-PP |
| phosphomevalonate kinase | 2.7.4.2 | mevalonate-5-PP |
| mevalonate kinase | 2.7.1.36 | mevalonate-5-P |
| 3-hydroxy-3-methylglutaryl-CoA reductase | 1.1.1.34 | mevalonate |
| Non-mevalonate pathway to (R)- or (S)-limonene | | |
| (4S)-limonene synthase | 4.2.3.16 | (S)-limonene (piney) |
| (R)-limonene synthase | 4.2.3.20 | (R)-limonene (citrus) |
| geranyl-diphosphate synthase | 2.5.1.1 | geranyl-PP |
| isopentenyl-diphosphate Delta-isomerase | 5.3.3.2 | dimethylallyl-P |
| 4-hydroxy-3-methylbut-2-enyl diphosphate reductase | 1.17.1.2 | isopentenyl-PP |
| 4-hydroxy-3-methylbut-2-en-1-yl diphosphate synthase | 1.17.4.3 | 1-hydroxy-2-methyl-2-butenyl-4-diphosphate |
| 2-C-methyl-D-erythritol 2,4-cyclodiphosphate synthase | 4.6.1.12 | 2-C-methyl-D-erythritol-2,4-cyclodiphosphate |
| 4-(cytidine 5'-diphospho)-2-C-methyl-D-erythritol kinase | 2.7.1.148 | 2-phospho-4-(cytidine 5'-diphospho)-2-C-methyl-D-erythritol |
| 2-C-methyl-D-erythritol 4-phosphate cytidylyltransferase | 2.7.7.60 | 4-(cytidine 5'-diphospho)-2-C-methyl-D-erythritol |
| 1-deoxy-D-xylulose-5-phosphate reductoisomerase | 1.1.1.267 | 2-C-methyl-D-erythritol-4-P |
| 1-deoxy-D-xylulose-5-phosphate synthase | 2.2.1.7 | 1-deoxy-D-xylulose-5-P |

Example 66

Enhanced Secretion of Fatty Acid Esters

Cloning of fadL and construction of vectors for expressing fadL in cyanobacteria: fadL (SEQ ID NO: 24) was generated by PCR from Escherichia coli (Migula) strain genomic DNA (ATCC # 700926) using Phusion™ Hot Start High-Fidelity DNA Polymerase (Developed & Manufactured By Finnzymes Oy and distributed by New England Biolabs, Ipswitch, Mass.)) according to manufacturer's instructions.

The forward primer (fadl_FP) used in this reaction contains a 5' NdeI restriction site and the reverse primer (fadl_RP) contains a 5' EcoRI restriction site. Amplified DNA was subsequently purified by gel electrophoresis followed by agarose purification using the Qiagen gel extraction kit protocol (Qiagen). Purified DNA product and vector pJB41 (a vector based on the DNA 2.0 pJ204 vector containing NdeI and EcoRI cloning sites) were both digested with NdeI (New England Biolabs; Ipswitch, Mass.) and EcoRI (New England Biolabs; Ipswitch, Mass.) followed by ligation overnight using T4 ligase (New England Biolabs; Ipswitch, Mass.). The ligated construct was transformed into NEB EPI400 Copy-Cutter competent *E. coli* (New England Biolabs: Ipswitch, Mass.). Colonies were subsequently grown in LB media and screened for insert by PCR using the same primers as above. The selected construct was validated by sequence verification GENEWIZ (South Plainfield, N.J.).

This fadL insert was cloned into a recombination vector suitable for insertion into *Synechococcus* sp. 7002 containing several elements. An upstream homology region (UHR; see, e.g., SEQ ID NO: 26) and a downstream homology region (DHR; see, e.g., SEQ ID NO:26) is present in the fadL insert allowing recombination into pAQ7 (pAQ7 plasmid sequence, see Genbank # CP000957). The homology regions flank a multiple cloning site (mcs) and a kanamycin cassette which provides resistance in both *E. coli* and *Synechococcus* sp. 7002. An XbaI site present upstream of the UHR and downstream of the DHR allows linearization of the fadL insert to facilitate transformation and integration into the host organism.

Several variants bearing fadL under different strength promoters have been prepared. One such promoter (amt1 from JCC160) is presented in SEQ ID NO: 26. Other variants that have been constructed include constructs with fadL under the control of *Thermosynechococcus elongatus* BP-1 promoters such as tsr2142 or psaA.

Assessment of fadL expression constructs. The fadL constructs will be integrated onto pAQ7 of the engineered Synechococcus strain JCC803 (pAQ1: lacIq Ptrc-tesA-fadD-wax synthase-aadA) using the following protocol. The strain will be grown from colonies in an incubated shaker flask at 37° C. at 2% $CO_2$ to an $OD_{730}$ of 1 in $A^+$ medium supplemented with 200 mg/L spectinomycin. 500 μL of culture will be added to a microcentrifuge tube with 50 μL of 1-5 μg of DNA prepped from a Qiagen Qiaprep Spin Miniprep Kit (Valencia, Calif.) for each construct after digesting with xbal (New England Biolabs; Ipswitch, Mass.). Cells will be incubated in the dark at 37° C. for four hours in a shaking incubator. 200 μL of cells will be plated on $A^+$ medium plates with 1.5% agarose and 100 μg/ml spectinomyin and incuated at 37° C. for 24 h under light. 50 μg/mL of kanamycin will be underlayed on the plates, and resistant colonies will be visible in 7-10 days.

Expression and secretion of ethyl ester in strains containing the fadL expression constructs will be measured and compared as described in, e.g., Example 17, herein. In addition, cultures will be partitioned with an organic solvent such as isooctane or ethyl acetate, and the organic solvent partition will be analyzed by GC/MS as detailed in example 17 to detect and quantify esters present in the media. Other techniques known to those skilled in the art may also be used to measure the amount of ethyl ester secreted into the medium.

Different levels of expression and/or secretion may be desired, depending on the particular environment and/or purpose for the expression and/or secretion. A variety of constructs effecting a range of expression levels is therefore desirable. In addition to fadL from *E. coli*, other transporters including the CER5 wax transporter from *A. thaliana* (Q9C8K2; SEQ ID NO: 23) and XylN from *Pseudomonas putida* (Q8VMI2; SEQ ID NO:25) will be incorporated into constructs and their enhancing effects on ethyl ester secretion will be measured. In certain embodiments, two or more distinct transporters may be incorporated into a single strain to achieve levels of biofuel secretion that are greater than the levels achieved using a single transporter. In addition, recombinant transporters may be modified or mutated to modulate (increase or decrease) the level of secretion achieved, or to alter the specificity of the transporter(s) such that the transport of additional types of molecules is increased or decreased relative to the unmodified form of the transporter. Such modified transporters may have amino acid sequences that are at least 80%, 85%, 90%, 95%, 96%, 97%, 98%, or 99% identical to the transporters disclosed herein. Other promoters in addition to those mentioned above may be used in this context, including apcA, EM7, tRNA-Glu, lacIq-Ptrc, nblA, hsp33, rbcL, cpcC, cpcB, rpsU, PaphII, Pci and nirA. As with the transporter sequences, modifications may be made to any of the promoter sequences to modulate the level of expression of the transporters under their control.

Example 67

Enhanced Ethanol Production

This Example provides an illustration of how ethanol production in an engineered organism can be improved and made more efficient by modifying the expression levels and/or identity of enzymes involved in ethanol production. Specifically, a series of pAQ7 Δldh targeting plasmids were constructed containing *Moorella* alcohol dehydrogenase (adh) genes under the control of different strength promoters. These plasmids were transformed into JCC445 (see Table 5) and the resulting strains were examined for ethanol production. Transformation of JCC445 by several different plasmids was shown to enhance production of ethanol but only one plasmi, PcI_adhAM, resulted in increased levels of ethanol accompanied by a concomitant decrease in acetaldehyde levels.

Strain Construction:

TABLE 27

| Strain | Host + | Plasmid (pAQ7-derived) |
|---|---|---|
| JCC445 + 773 | JCC445 + 773 | Δldh_kan_PaphII_adhAM |
| JCC445 + 782 (aka JCC1005) | JCC445 + 782 | Δldh_kan_PcI_adhAM (SEQ ID NO: 27) |

Four μg of the plasmid DNA was digested with XmaI and used to transform 400 μl of JCC445 ($OD_{730}$=1.15) using the transformation protocol described herein. The entire transformation mix was plated onto A agar plates and incubated at 37 C (~50 μE) in air. After 24 hours the plates were underplated with kanamycin to a final concentration of 50 μg/ml and incubated as above. After 5 days background growth was diminished and $Km^R$ colonies began to be visible, at which point the plates were transferred to 37 C (~50 μE)+1% $CO_2$. After 3 days, two $Km^R$ colonies from each transformation were streaked onto $A^{+Km50Sp100}$ agar plates for single colony isolation. Streaked plates were incubated for 4 days at 37 C (~50 μE) in air and then transferred to 37 C (~50 μE)+1% $CO_2$ for an additional 3 days.

Figure 22:
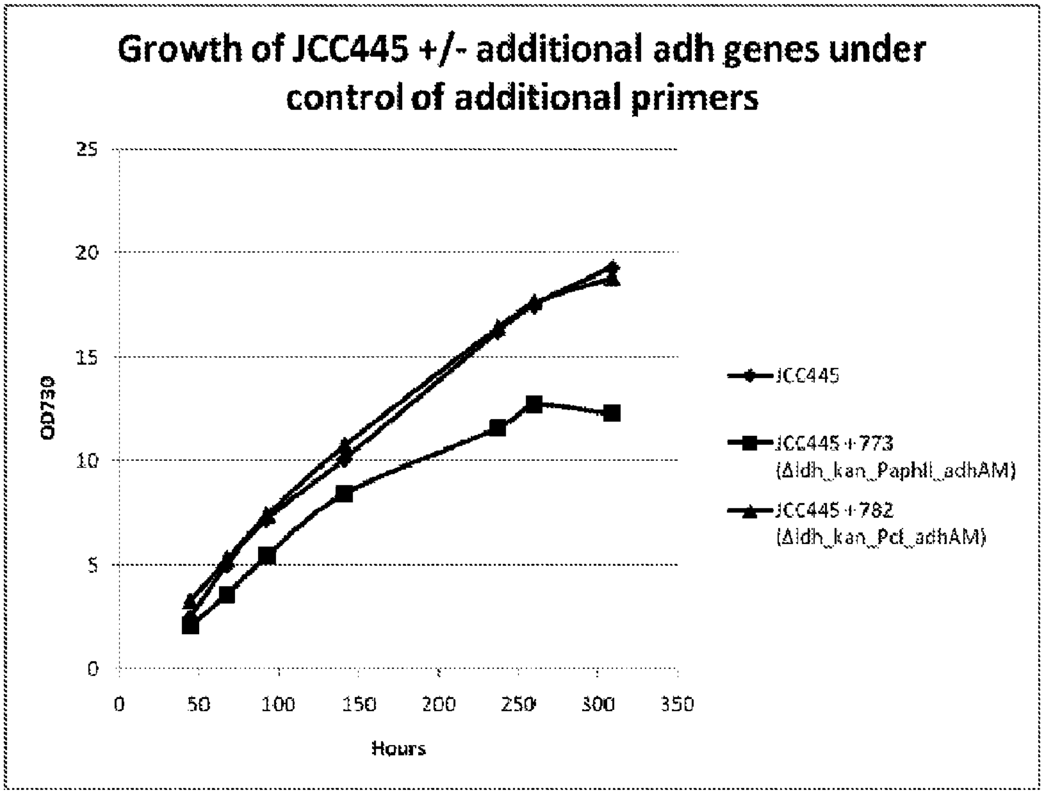
FIG. 22 depicts growth curves (OD/time) of strain JCC445, and a variant strain expressing an additional alcohol dehydrogenase gene from a plasmid.
Figure 23:
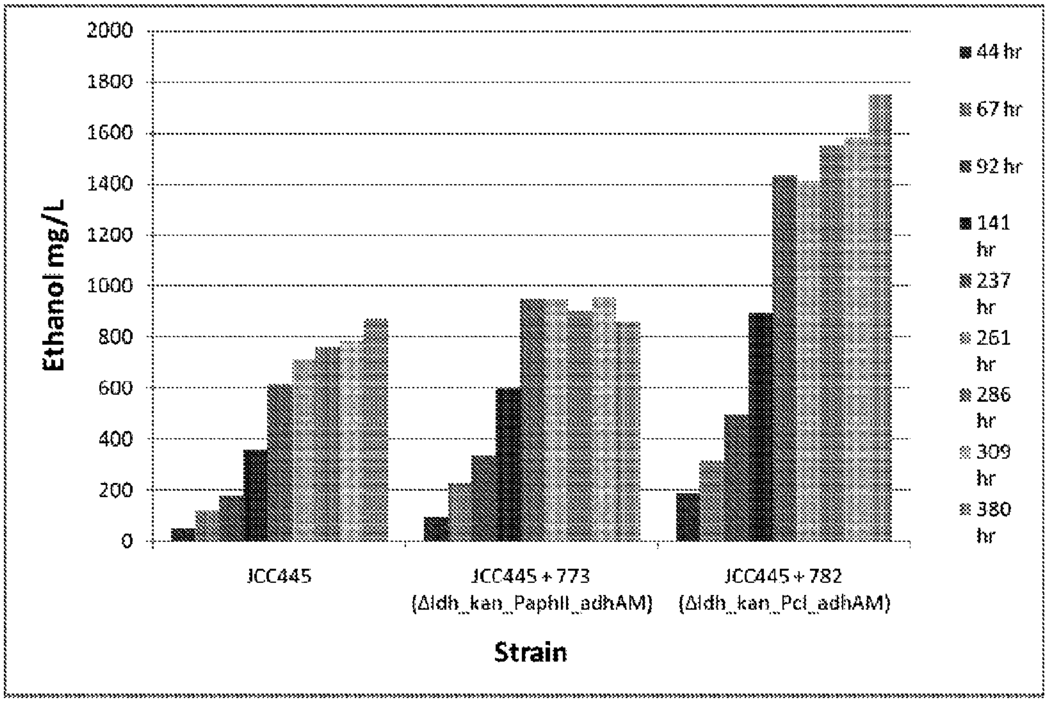
FIG. 23 depicts ethanol production (mg/L) at various time points by JCC445, and variant strains expressing an alcohol dehydrogenase gene from a plasmid.
Figure 24:
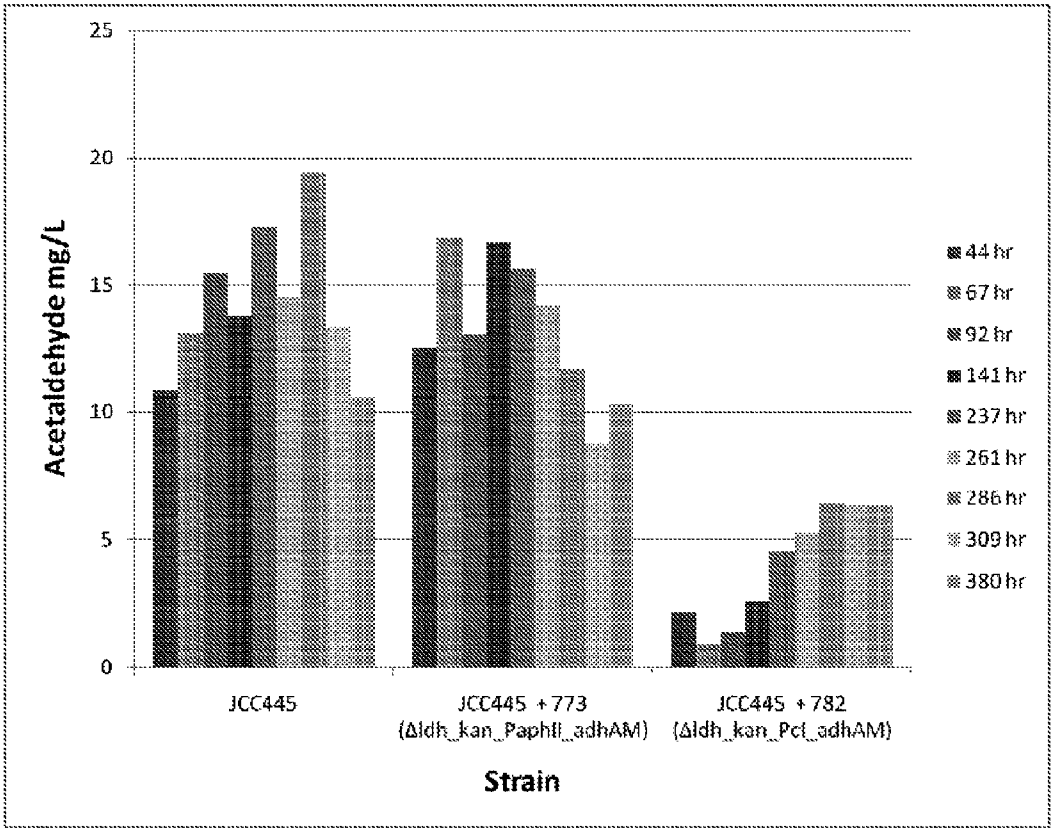
FIG. 24 depicts acetaldehyde production (mg/L) at various time points by JCC445, and variant strains expressing an alcohol dehydrogenase gene form a plasmid.

Batch Ethanol in Flasks: A single colony of one clone from the original streak plate from each transformation was inoculated into 5 ml $A^{+Km50Sp100}$ broth in a 16 mM×150 mM plastic-capped culture tube and incubated in the Infors incubator (37 C, 150 rpm, 2% $CO_2$) at a ~60° angle. After 3 days the cultures were transferred into foam-plugged 125-ml Erlenmeyer flasks containing 30 ml JB2.1$^{Km50Sp100}$ to an $OD_{730}$=~0.1. The initial weight of each flask culture was determined so that sterile $dH_2O$ could be added at sampling times to account for evaporation. At each sampling point, 300 µl of culture was removed and the cultures were replenished with an equal amount of fresh JB2.1 medium. At roughly 24 hour intervals, samples were taken for growth rate and ethanol/acetaldehyde determinations. $OD_{730}$ measurements and derived growth curves are shown FIG. 22. The levels of ethanol and acetaldehyde in the media were determined as described herein and the data is presented in FIG. 23 and FIG. 24, respectively.

As can be seen from the Figures, the levels of ethanol were highest in JCC445+782, where additional $adhA_M$ is expressed under the control of the lambda cI promoter. The cumulative levels of ethanol produced by this strain were approximately 4 g/L. At any given time point, the measured levels of ethanol were substantially higher than those measured in JC445 or JCC445+773, in some cases nearly twice as high. In addition, the same strain produced only 50% (or less) acetaldehyde compared to JC445 or JCC445+773 (expressing $adhA_M$ under the control of the PaphII promoter). Thus, this Example demonstrates not only that enhanced levels of ethanol and reduced levels of toxic intermediates can result from alterations to promoters controlling $adhA_M$ expression, but also provides a specific example of an engineered cyanobacteria (JCC445+773) with enhanced ethanol producing capabilities.

All publications, patent documents and sequences referred to herein are hereby incorporated by reference in their entirety for all purposes to the same extent as if each were so individually denoted.

What is claimed is:

1. A method for the biogenic production of ethanol, comprising: culturing an engineered cyanobacterium in a culture medium in the presence of light and $CO_2$, wherein said cyanobacterium comprises a recombinant pyruvate decarboxylase gene and at least one recombinant alcohol dehydrogenase gene, wherein said recombinant pyruvate decarboxylase gene and at least one recombinant alcohol dehydrogenase gene belong to distinct operons wherein the expression of said recombinant alcohol dehydrogenase gene is increased relative to the expression of said recombinant pyruvate decarboxylase gene, and wherein the amount of ethanol released into said culture medium by said engineered organism is equal to or greater than 10 mg/L/hr.

2. The method of claim 1, wherein said engineered cyanobacterium comprises a first copy and a second copy of said recombinant alcohol dehydrogenase gene, and wherein said first and second copies of said recombinant alcohol dehydrogenase gene belong to distinct operons.

3. The method of claim 2, wherein said recombinant pyruvate decarboxylase gene and said second copy of said recombinant alcohol dehydrogenase gene are part of the same operon.

4. The method of claim 2, wherein the expression of at least one copy of said alcohol dehydrogenase gene is operably linked to a lambda cI promoter.

5. The method of claim 2, wherein said first and second copies of said recombinant alcohol dehydrogenase genes are encoded by distinct plasmids.

6. The method of claim 1, wherein the activity of alcohol dehydrogenase encoded by said recombinant alcohol dehydrogenase is varied by controlling the level of a co-factor required by alcohol dehydrogenase.

7. The method of claim 1, wherein the measured level of acetaldehyde released into said culture medium by said engineered organism is less than 7 mg/L after 10 days of culture.

8. The method of claim 1, wherein the measured level of ethanol released into said culture medium by said engineered organism is at least 1750 mgs/L.

9. The method of claim 1, wherein the measured concentration (mg/ml) of ethanol released into said culture medium by said engineered organism is at least 100 fold higher than the measured level of acetaldehyde in said culture medium.

10. The method of claim 1, wherein said cyanobacterium is a thermophilic cyanobacterium.

11. The method of claim 1, wherein said recombinant alcohol dehydrogenase gene encodes an alcohol dehydrogenase which is from *Moorella* species.

* * * * *